United States Patent
Malcolm et al.

(10) Patent No.: US 9,580,409 B2
(45) Date of Patent: Feb. 28, 2017

(54) MODULATORS OF OPIOID RECEPTORS AND METHODS OF USE THEREOF

(71) Applicant: Sunovion Pharmaceuticals Inc., Marlborough, MA (US)

(72) Inventors: Scott Malcolm, Southborough, MA (US); Carrie Bowen, Uxbridge, MA (US); Laurence Melnick, Watertown, MA (US); Linghong Xie, Southborough, MA (US)

(73) Assignee: SUNOVION PHARMACEUTICALS, INC., Marlborough, MA (US)

( * ) Notice: Subject to any disclaimer, the term of this patent is extended or adjusted under 35 U.S.C. 154(b) by 0 days.

(21) Appl. No.: 14/352,294

(22) PCT Filed: Nov. 7, 2012

(86) PCT No.: PCT/US2012/063795
§ 371 (c)(1),
(2) Date: Apr. 16, 2014

(87) PCT Pub. No.: WO2013/070659
PCT Pub. Date: May 16, 2013

(65) Prior Publication Data
US 2014/0288050 A1    Sep. 25, 2014

Related U.S. Application Data

(60) Provisional application No. 61/556,686, filed on Nov. 7, 2011.

(51) Int. Cl.
| | | |
|---|---|---|
| *C07D 403/04* | (2006.01) |
| *C07D 401/14* | (2006.01) |
| *C07D 403/14* | (2006.01) |
| *C07D 487/04* | (2006.01) |
| *C07D 487/14* | (2006.01) |
| *C07D 498/04* | (2006.01) |
| *C07D 471/04* | (2006.01) |
| *C07D 405/14* | (2006.01) |
| *C07D 487/10* | (2006.01) |
| *C07D 491/10* | (2006.01) |
| *A61K 31/4178* | (2006.01) |
| *A61K 31/4184* | (2006.01) |
| *A61K 31/4196* | (2006.01) |
| *A61K 31/437* | (2006.01) |
| *A61K 31/4439* | (2006.01) |
| *A61K 31/454* | (2006.01) |
| *A61K 31/501* | (2006.01) |
| *A61K 31/551* | (2006.01) |
| *A61K 31/553* | (2006.01) |

(52) U.S. Cl.
CPC ......... *C07D 403/04* (2013.01); *A61K 31/4178* (2013.01); *A61K 31/4184* (2013.01); *A61K 31/4196* (2013.01); *A61K 31/437* (2013.01); *A61K 31/4439* (2013.01); *A61K 31/454* (2013.01); *A61K 31/501* (2013.01); *A61K 31/551* (2013.01); *A61K 31/553* (2013.01); *C07D 401/14* (2013.01); *C07D 403/14* (2013.01); *C07D 405/14* (2013.01); *C07D 471/04* (2013.01); *C07D 487/04* (2013.01); *C07D 487/10* (2013.01); *C07D 487/14* (2013.01); *C07D 491/10* (2013.01); *C07D 498/04* (2013.01)

(58) Field of Classification Search
CPC ... C07D 403/04; C07D 401/14; C07D 403/14; C07D 487/04; C07D 487/14; C07D 498/04
USPC ...................................... 548/306.1
See application file for complete search history.

(56) References Cited

U.S. PATENT DOCUMENTS

2009/0163545 A1* 6/2009 Goldfarb ............... A61K 31/122
514/312

FOREIGN PATENT DOCUMENTS

| EP | 0666258 A1 | 8/1995 |
| EP | 1652429 A1 | 5/2006 |
| EP | 1031573 | 3/2008 |
| SU | 687070 A1 | 9/1979 |
| WO | WO 00/39089 A1 | 7/2000 |
| WO | WO 2004/043949 A1 | 5/2004 |
| WO | WO 2006/044497 A2 | 4/2006 |
| WO | WO 2008/024311 A2 | 2/2008 |
| WO | WO 2008/085509 A1 | 7/2008 |
| WO | WO 2010/151799 A2 | 12/2010 |

OTHER PUBLICATIONS

Chemical Abstracts Registry No. 137-45-1, indexed in the Registry file on STN CAS Online Nov. 16, 1984.*
Chemical Abstracts Registry No. 5860-48-0, indexed in the Registry file on STN CAS Online Nov. 16, 1984.*
Chemical Abstracts Registry No. 459138-26-2, indexed in the Registry file on STN CAS Online Oct. 4, 2002.*
Chemical Abstracts Registry No. 880443-45-8, indexed in the Registry file on STN CAS Online Apr. 14, 2006.*
Chemical Abstracts Registry No. 880448-15-7, indexed in the Registry file on STN CAS Online Apr. 14, 2006.*
Chemical Abstracts Registry No. 885189-94-6, indexed in the Registry file on STN CAS Online May 22, 2006.*
Chemical Abstracts Registry No. 914216-98-1, indexed in the Registry file on STN CAS Online Nov. 29, 2006.*

(Continued)

*Primary Examiner* — Laura L. Stockton
(74) *Attorney, Agent, or Firm* — Heslin Rothenberg Farley & Mesiti P.C.

(57) ABSTRACT

Provided herein are compounds and methods of synthesis thereof. The compounds provided herein are useful for the treatment, prevention, and/or management of various disorders, such as pain, neurological disorders, psychiatric disorders, and neuromuscular disorders. Compounds provided herein modulate the activity of opioid receptor (e.g., μ-opioid receptor) in the central nervous system or the periphery. Pharmaceutical formulations containing the compounds and their methods of use are also provided herein.

22 Claims, No Drawings

(56) References Cited

OTHER PUBLICATIONS

Chemical Abstracts Registry No. 927969-90-2, indexed in the Registry file on STN CAS Online Mar. 23, 2007.*
Chemical Abstracts Registry No. 880443-39-0, indexed in the Registry file on STN CAS Online Apr. 14, 2006.*
Chemical Abstracts Registry No. 1031962-56-7, indexed in the Registry file on STN CAS Online Jul. 1, 2008.*
Volovenko et al., Ukrainskii Khimicheskii Zhurnal (Russian Edition), 1985, 51(2), pp. 205-209.*
An English translation of Volovenko et al., Ukrainskii Khimicheskii Zhurnal (Russian Edition), 1985, 51(2), pp. 205-209.*
PubChem CID 11131059—National Center for Biotechnology Information. PubChem Compound Database; CID=11131059, http://pubchem.ncbi.nlm.nih.gov/summary/summary.cgi?cid=11131059 (accessed Aug. 26, 2015), create date Oct. 26, 2006.*
PubChem CID 15536149—National Center for Biotechnology Information. PubChem Compound Database; CID=15536149, http://pubchem.ncbi.nlm.nih.gov/summary/summary.cgi?cid=15536149 (accessed Aug. 26, 2015), create date Feb. 10, 2007.*
PubChem CID 2378316—National Center for Biotechnology Information. PubChem Compound Database; CID=2378316, http://pubchem.ncbi.nlm.nih.gov/summary/summary.cgi?cid=2378316 (accessed Aug. 26, 2015), create date Jul. 15, 2005.*
PubChem CID 16228873—National Center for Biotechnology Information. PubChem Compound Database; CID=16228873, http://pubchem.ncbi.nlm.nih.gov/summary/summary.cgi?cid=16228873 (accessed Aug. 26, 2015), create date Jul. 30, 2007.*
PubChem CID 20216643—National Center for Biotechnology Information. PubChem Compound Database; CID=20216643, http://pubchem.ncbi.nlm.nih.gov/summary/summary.cgi?cid=20216643 (accessed Aug. 26, 2015), create date Dec. 5, 2007.*
PubChem CID 22021212—National Center for Biotechnology Information. PubChem Compound Database; CID=22021212, http://pubchem.ncbi.nlm.nih.gov/summary/summary.cgi?cid=22021212 (accessed Aug. 26, 2015), create date Dec. 5, 2007.*
Chemical Abstracts Registry No. 907554-55-6, indexed in the Registry file on STN CAS Online Sep. 19, 2006.*
Chemical Abstracts Registry No. 62019-60-7, indexed in the Registry file on STN CAS Online Nov. 16, 1984.*
Chemical Abstracts Registry No. 380347-68-2, indexed in the Registry file on STN CAS Online Jan. 3, 2002.*
Chemical Abstracts Registry No. 327081-30-1, indexed in the Registry file on STN CAS Online Mar. 14, 2001.*
Chemical Abstracts Registry No. 380393-94-2, indexed in the Registry file on STN CAS Online Jan. 3, 2002.*
Volovenko et al., Chemistry of Heterocyclic Compounds (New York, NY, United States) (Translation of Khimiya Geterotsiklicheskikh Soedinenii), 2002, 38(3), pp. 324-330.*
Volovenko et al., Collection of Czechoslovak Chemical Communications, 2002, 67(3), pp. 365-372.*
Resnyanskaya et al. {Chemistry of Heterocyclic Compounds (New York, NY, United States) (Translation of Khimiya Geterotsiklicheskikh Soedinenii), 2000, vol. Date 1999, 35(10), pp. 1230-1236.*
Watanabe et al., Chemical & Pharmaceutical Bulletin, 1975, 23(11), pp. 2598-2604.*
Chemical Abstracts Registry No. 37465-83-1, indexed in the Registry file on STN CAS Online Nov. 16, 1984.*
Sakan et al., Bulletin of the Chemical Society of Japan, 1972, 45(5), pp. 1485-1491.*
Volovenko Ju M et al., "Interaction of phenyl acetonitrile with esters of alpha-aryl aminocarbonic acids", Dopovidi Akaoemii Nauk Ukrains'Ko RSR. Seria B. Geologiageofizika Himia Ta Biologia, No. 7, Jan. 1, 1978, pp. 619-621, XP009182712.
Henning H-G et al., "Heterocyclensynthesen mit 5-Phenylisoxazoliumsalzen; Synthase von 1H-2-Benzoylmethylen-2,3,6,7-tetrahydro-3,6,7, 7-tetramethyl-pyrrolo 3,4-dpyrimidin-4,5-dion", Zeitschrift Fuer Chemie, vol. 28, No. 9, 1988 , pp. 334-335, XP009182700.
Auzzi et al., "Synthesis of 2-[1 ,2-dihydropyrazol-4-y1]-1,3,4-thiadiazole derivatives as potential microbial agents", IL Farmaco, vol. 45, No. 1, 1990, pp. 81-92, XP009182705.
Boberg F et al., "Ueber 1,2-Dithia-Cyclopentene, Xviii- 3-Amino-4-Aryl-Pyrazolinone-(5) Aus 5-Amin0-4-Aryl-1 ,2-Dithiacyclopentenonen-(3)", Justus Liebigs Annalen Oer Chemie, vol. 734, 1970, pp. 173-179, XP009182707.
Yu. M. Volovenko et al., "Synthesis and Properties of 6-Amino-7-hetaryi-5-R-5H-pyrrolo[2,3-b]pyrazine-2,3-dicarbonitriles.", Cheminform, vol. 34, No. 1, Jan. 7, 2003, XP055170747.
Alexander D. Tereshchenko et al., "A Facile Route to Pyrrolo[3',4':3,4]pyrido[1,2-a]benzimidazoles, Novel Heterocyclic Derivatives", Synthesis, No. 3, 2004, pp. 373-376, XP055170748.
Chowdhury FA et al., "One-Pot Synthesis of Azabicyclic Peroxides from Tetramic Acid Derivatives by Manganese(III)-Mediated Oxidative [2+2+2] Cycloaddition", Tetrahedron Letters, vol. 39, No. 43, Oct. 22, 1998, pp. 7931-7934, XP004137845.
Folkes A et al., "Design, Synthesis and In Vitro Evaluation of Potent, Novel, Small Molecule Inhibitors of Plasminogen Activator Inhibitor-1", Bioorganic & Medicinal Chemistry Letters, vol. 12, 2002, pp. 1063-1066, XP002368302.
Zaharan M A et al., "Some reactions with ketene dithioacetals. Part I. Synthesis of antimicrobial pyrazolo[1,5-a]pyrimidines via the reaction of ketene dithioacetals and 5-aminopyrazoles", IL Farmaco, vol. 56, No. 4, Apr. 1, 2001, pp. 277-283, XP002243487.
Galal H. Elgemeie et al., "-Acetals and Their Reactions with Nucleophiles", Synthetic Communications, vol. 33, No. 4, Jan. 4, 2003, pp. 555-562, XP055170761.
R. Glatthard et al., "2-Substituierte 1-Phenyl-3-sulfonamido-3-pyrazolin-5-one; ber Pyrazole, 3. Mitteilung", Helvetica Chimica ACTA, vol. 47, No. 1, 1964, pp. 132-144, XP055170805.
A. V. Tverdokhlebov et al., "Synthesis of 1-R-2-amino-3[2-(benz)azolyl]-4(5H)-ketopyrroles", Chemistry of Heterocyclic Compounds, vol. 34, No. 1, 1998, pp. 44-50, XP055170736.
Yu. M. Volovenko et al., "ChemInform Abstract: Synthesis of 5-Amino-1-aryl-4-(4-aryl-1,3-thiazol-2-yl)-2,3-dihydro-1H-pyrrol-3-ones", Cheminform, vol. 33, No. 21, May 28, 2002, XP0055170738.
Nemazanyi A et al., "Synthesis of 3-amino-4-heteroaryl-1(2H)isoquinolones based on condensed isoquinolones with a bridgehead nitrogen atom", Chemistry of Heterocyclic Compounds, No. 1, 1992, pp. 86-88, XP002977626.
Resnyanskaya E V et al., "Interaction of 2-(2-Azahetaryl)-3-oxo-4-chlorobutane nitriles with esters of aromatic amino acids", Chemistry of Heterocyclic Compounds, vol. 35, No. 10, 1999, pp. 1230-1236, XP002516619.
Anton Tverdokhlebov et al., "Synthesis of Masked 2-Amino-4,5-dihydro-4-oxopyrrole-3-carboxaldehydes", Synthesis, vol. 2007, No. 12, Jun. 1, 2007, pp. 1811-1818, XP055188007.
Lauren M Junker et al., "High-Throughput Screens for SmallMolecule Inhibitors of Pseudomonas Aeruginosa Biofilm Development: Supplementary Materials Table 1: Structures and EC", Antimicrobial Agents and Chemotherapy, vol. 51, No. 10, Jun. 30, 2007 (Jun. 30, 2007), pp. S1-S8, XP055188064.
Palin R et al., "Synthesis and SAR studies of 3-phenoxypropyl piperidine analogues as ORL1 (NOP) receptor agonists", Bioorganic & Medicinal Chemistry Letters, Pergamon, Amsterdam, NL, vol. 15, No. 3, pp. 589-593, XP027882802, Feb. 2005.
Extended European search report, mailed on May 21, 2015 in connection with EP 12848416.9.
Mercader et al., 2011, "Synthesis of site-heterologous heptens for high-affinity anti-pyraclostrobin antibody generation," Organic and Biomolecular Chemistry, 9(5): 1443-1453 (2011).
Zhang et al., 2000, "Nonpeptide endothelin antagonists: from lower affinity pyrazol-5-ols to higher affinity pyrazole-5-carboxylic acids," Bioorganic and Medicinal Chemistry Letters, 10(12): 1351-1355 (2000).

(56) References Cited

OTHER PUBLICATIONS

Henning H-G et al., "Heterocyclensynthesen mit 5-Phenylisoxazoliumsalzen; Synthase von 1H-2-Benzoylmethylen-2,3,6,7-tetrahydro-3,6,7, 7-tetramethyl-pyrrolo 3,4-dpyrimidin-4,5-dion", Zeitschrift Fuer Chemie, vol. 28, No. 9, 1988, pp. 334-335, XP009182700, (English translation of title, no abstract available).
R. Glatthard et al., "2-Substituierte 1-Phenyl-3-sulfonamido-3-pyrazolin-5-one; ber Pyrazole, 3. Mitteilung", Helvetica Chimica ACTA, vol. 47, No. 1, 1964, pp. 132-144, XP055170805, (English translation of abstract).
Nemazanyi A et al., "Synthesis of 3-amino-4-heteroaryl-1(2H)isoquinolones based on condensed isoquinolones with a bridgehead nitrogen atom", Chemistry of Heterocyclic Compounds, No. 1, 1992, pp. 86-88, XP002977626, (English translation of abstract).
CAS RN 288-13-1, STN entry date Nov. 16, 1984.
CAS RN 64532-07-6, STN entry date Nov. 16, 1984.
CAS RN 857492-62-7, STN entry date Jul. 28, 2005.

\* cited by examiner

MODULATORS OF OPIOID RECEPTORS AND METHODS OF USE THEREOF

This application is a U.S. national stage application of International Patent Application No. PCT/US2012/063795, filed Nov. 7, 2012, which claims the benefit of U.S. Provisional Application No. 61/556,686, filed Nov. 7, 2011, each of which is incorporated by reference herein in its entirety.

I. FIELD

Provided herein are compounds useful for treating disorders relating to opioid receptors, such as, e.g., a neurological disorder or pain, compositions comprising the compounds, and methods of use thereof.

II. BACKGROUND

Chronic pain remains a challenge in medical science. Chronic pain is a common complaint in patients who have undergone surgical procedures or who suffer from long term illnesses, such as, e.g., cancer, nerve injury, arthritis, or heart diseases. Existing therapeutic agents for treating chronic pain are often unsatisfactory because of side effects accompanying the treatment. For example, opiates at high doses are apt to produce sedation, respiratory depression, and tolerance, which severely limit their use.

Generally, acute pain is of limited duration and rapidly subsides after removing the triggering stimuli. Acute pain due to the stimulation of intact nociceptors has a protective warning function to preserve physical integrity—the subsequent responses to avoid pain provide protection from injury. Chronic pain typically does not possess this protective function, resulting in a pain disorder. Chronic pain may be subdivided into at least two major groups. Pathophysiological nociceptor pain, including, e.g., chronic inflammatory pain, is caused by stimulation of intact nociceptors, after, for example, tissue trauma. By contrast, neuropathic pain arises from damages to nerves themselves.

The changeover from acute pain to chronic pain may occur within hours. Pain treatment during and following surgery may be affected by this. Acute pain may become chronic, both peripherally and in the CNS, by pathophysiological processes subsequent to tissue damage, for example, after surgery. The association of tissue damage, acute postoperative pain, and development of chronic pain has been investigated. It is possible to regard the severity of acute pain as a predictive factor for the duration of chronic pain. Thus, satisfactory treatment of acute pain is desired.

One issue in combating pain is the side effects of known analgesics, such as, respiratory depression caused by opioids. Since the side effects occasionally result in fatalities in patients having just undergone surgery, pain medications are often not given in sufficient quantity to combat pain satisfactorily. Because of respiratory depression and other known side effects, opiates are often used to an inadequate extent in treating severe pain, for example, in cancer patients. In addition, the risk of respiratory depression occurring after administration of opiates is higher in older people than in younger people. For example, the risk of developing respiratory depression rises distinctly in people of 60 years of age or older.

Thus, there is an urgent need for new therapeutic agents for the treatment of pain, such as, severe pain, with less adverse events than traditional analgesics.

III. SUMMARY

In one embodiment, provided herein are compounds of formula (I), or a pharmaceutically acceptable salt thereof:

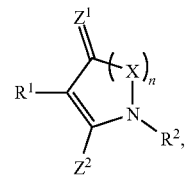

wherein $Z^1$, $Z^2$, $R^1$, $R^2$, X and n are defined herein elsewhere. The compounds are useful in modulating the activity of opioid receptors, such as, μ-opioid receptors. In certain embodiments, the compounds provided herein are agonists of μ-opioid receptors. In certain embodiments, the compounds provided herein are useful for treating pain, such as, severe pain, with less adverse event or side effect than traditional analgesics (e.g., traditional opioid analgesics).

Also provided herein are compositions and dosage forms comprising compounds provided herein. Compositions and dosage forms provided herein may comprise one or more additional active ingredients.

Also provided herein are methods for the treatment, prevention, and/or management of various disorders mediated by opioid receptors, such as, μ-opioid receptors, using compounds and compositions provided herein. Also provided herein are uses of compounds and compositions provided herein in the manufacture of a medicament for the treatment, prevention, and/or management of one or more disorders provided herein. Also provided herein are compounds and compositions for use in the treatment, prevention, and/or management of one or more disorders provided herein. Disorders that may be treated, prevented, and/or managed include, a neurological disorder, pain, or diarrhea. Such neurological disorders include, but are not limited to, a neurodegenerative disease, a neuropsychiatric disease, fibromyalgia, or an affective disorder. Such pain includes, but is not limited to, migraine, inflammatory pain, neuropathic pain, acute pain, chronic pain, severe pain, postoperative pain, acute thermal hyperalgesia, mechanical allodynia, visceral pain, or pain associated with other diseases, such as, arthritis, heart diseases, cancer, and diabetes. In one embodiment, the methods provided herein comprise administering a compound provided herein, or a pharmaceutically acceptable salt thereof, to a subject in need thereof. In one embodiment, the methods provided herein comprise administering a composition provided herein to a subject in need thereof. In one embodiment, a compound provided herein, or a pharmaceutically acceptable salt thereof, or a composition provided herein, is administered orally, parenterally, or topically. In one embodiment, a compound provided herein, or a pharmaceutically acceptable salt thereof, or a composition provided herein, is co-administered with a second active agent.

In one embodiment, provided herein is a method of modulating the activity of an opioid receptor. In one embodiment, provided herein is a method of modulating the activity of a μ-opioid receptor. In one embodiment, provided herein is a method of increasing the activity of an opioid receptor. In one embodiment, provided herein is a method of increasing the activity of a μ-opioid receptor. In one embodiment, provided herein is a method of reducing the activity of an opioid receptor. In one embodiment, provided herein is a method of reducing the activity of a μ-opioid receptor. The method comprises contacting an opioid receptor (e.g., μ-opioid receptor) with a compound provided herein. In some embodiments, the method comprises contacting an opioid receptor with an agonist. In some embodiments, the method comprises contacting an opioid receptor with a positive allosteric modulator. In some embodiments, the method comprises contacting an opioid receptor with an antagonist. In some embodiments, the method comprises contacting an opioid receptor with a negative allosteric modulator. In one embodiment, the method comprises contacting a cell with a compound provided herein. In an exemplary embodiment, the cell is a brain cell, such as, for example, a neuronal cell or a glial cell. In an exemplary embodiment, the cell is a neuronal cell in the periphery. In an exemplary embodiment, the cell is a neuronal cell in the central nervous system.

IV. DETAILED DESCRIPTION

Unless defined otherwise, all technical and scientific terms used herein generally have the same meaning as commonly understood by one of ordinary skill in the art to which this disclosure belongs. All publications and patents referred to herein are incorporated by reference herein in their entireties.

A. DEFINITIONS

As used in the specification and the accompanying claims, the indefinite articles "a" and "an" and the definite article "the" include plural as well as singular referents, unless the context clearly dictates otherwise.

As used herein, and unless otherwise indicated, the term "alkyl" refers to a linear or branched saturated monovalent hydrocarbon radical, wherein the alkyl may be optionally substituted with one or more substituents. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or a branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl, isopropyl), butyl (including all isomeric forms, e.g., n-butyl, isobutyl, t-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is optionally substituted as described herein elsewhere. In some embodiments, the alkyl is optionally substituted with one or more halo.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" also encompasses radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenyl is optionally substituted as described herein elsewhere. In some embodiments, the alkenyl is optionally substituted with one or more halo.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted with one or more substituents. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—CCH) and propargyl (—CH$_2$CCH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is optionally substituted as described herein elsewhere. In some embodiments, the alkynyl is optionally substituted with one or more halo.

As used herein, and unless otherwise specified, the term "cycloalkyl" refers to a cyclic fully or partially saturated bridged and/or non-bridged hydrocarbon radical or ring system, which may be optionally substituted with one or more substituents. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl. In certain embodiments, the cycloalkyl is optionally substituted as described herein elsewhere. In some embodiments, the cycloalkyl is optionally substituted with one or more halo.

As used herein, and unless otherwise specified, the term "heteroalkyl" refers to a stable straight or branched chain, consisting of the stated number of carbon atoms and from one or more, in one embodiment, one to three, heteroatoms selected from the group consisting of O, N, Si, and S, and wherein the nitrogen and sulfur atoms are optionally oxidized and the nitrogen heteroatom can optionally be quaternized. In one embodiment, the heteroatom(s) O and N can be placed at any interior position of the heteroalkyl group. In one embodiment, the heteroatom(s) S and Si can be placed at any position of the heteroalkyl group (e.g., interior or terminal position), including the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Up to two heteroatoms can be consecutive, such as, for example, —CH$_2$—NH—O—CH$_3$ and —CH$_2$—O—Si(CH$_3$)$_3$. In certain embodiments, the heteroalkyl is optionally substituted as described herein elsewhere. In some embodiments, the heteroalkyl is optionally substituted with one or more halo.

As used herein, and unless otherwise specified, the term "alkoxyl" or "alkoxy" refers to a stable straight or branched chain, or cyclic hydrocarbon radical, or combinations thereof, consisting of the stated number of carbon atoms and from one or more, in one embodiment, one to three, O atoms, wherein at least one O atom is at the position where the alkoxyl or alkoxy group is attached to the remainder of the molecule. Examples of alkoxyl include, but are not limited to, —O—CH$_3$, —O—CF$_3$, —O—CH$_2$—CH$_3$, —O—CH$_2$—CH$_2$—CH$_3$, —O—CH—(CH$_3$)$_2$, and —O—CH$_2$—CH$_2$—O—CH$_3$. In one embodiment, the alkoxyl is optionally substituted as described herein elsewhere. In some embodiments, the alkoxyl is optionally substituted with one or more halo.

As used herein, and unless otherwise specified, the term "aminoalkyl" or "alkylamino" refers to a stable straight or branched chain, or cyclic hydrocarbon radical, or combinations thereof, consisting of the stated number of carbon atoms and from one or more, in one embodiment, one to three, N atoms, wherein at least one N atom is at the position where the aminoalkyl or alkylamino group is attached to the remainder of the molecule. Examples of aminoalkyl include, but are not limited to, —NH—CH$_3$, —N(CH$_3$)$_2$, —NH—CH$_2$—CH$_3$, —N(CH$_3$)—CH$_2$—CH$_3$, —NH—CH—(CH$_3$)$_2$, and —NH—CH$_2$—CH$_2$—N(CH$_3$)$_2$. In one embodiment, the aminoalkyl is optionally substituted as described herein elsewhere. In some embodiments, the aminoalkyl is optionally substituted with one or more halo.

As used herein, and unless otherwise specified, the term "aryl" refers to an optionally substituted monocyclic or multicyclic radical or ring system that contains at least one aromatic hydrocarbon ring. In certain embodiments, the aryl has from 6 to 20, from 6 to 15, or from 6 to 10 ring atoms. Examples of aryl groups include, but are not limited to, phenyl, naphthyl, fluorenyl, azulenyl, anthryl, phenanthryl, pyrenyl, biphenyl, and terphenyl. In certain embodiments, aryl also refers to bicyclic, tricyclic, or tetracyclic carbon rings, where one of the rings is aromatic and the other(s) of the rings may be saturated, partially unsaturated, or aromatic, for example, dihydronaphthyl, indenyl, indanyl, or tetrahydronaphthyl (tetralinyl). In certain embodiments, aryl may be a bicyclic, tricyclic, or tetracyclic ring system, where at least one of the rings is aromatic and one or more of the ring(s) is/are saturated or partially unsaturated containing one or more heteroatoms independently selected from O, S, and N. In certain embodiments, the aryl is optionally substituted with one or more substituents as described herein elsewhere.

As used herein, and unless otherwise specified, the term "arylalkyl" or "aralkyl" refers to a monovalent alkyl group substituted with aryl. An example of aralkyl includes, but is not limited to, benzyl. In certain embodiments, both alkyl and aryl may be optionally substituted with one or more substituents as described herein elsewhere.

As used herein, and unless otherwise specified, the term "heteroarylalkyl" or "heteroaralkyl" refers to a monovalent alkyl group substituted with heteroaryl. In certain embodiments, both alkyl and heteroaryl may be optionally substituted with one or more substituents as described herein elsewhere.

As used herein, and unless otherwise specified, the term "heteroaryl" refers to an optionally substituted monocyclic or multicyclic radical or ring system which contains at least one aromatic ring having one or more heteroatoms independently selected from O, S, and N. In one embodiment, each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, heteroaryl also refers to bicyclic, tricyclic, or tetracyclic rings, where one of the rings is aromatic having one or more heteroatoms independently selected from O, S, and N, and the other(s) of the rings may be saturated, partially unsaturated, or aromatic and may be carbocyclic or contain one or more heteroatoms independently selected from O, S, and N. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents as described herein elsewhere.

As used herein, and unless otherwise specified, the term "heterocycloalkyl" or "heterocyclyl" refers to an optionally substituted monocyclic or multicyclic radical or ring system which contains at least one non-aromatic ring having one or more heteroatoms independently selected from O, S, and N. In certain embodiments, the heterocyclyl or heterocycloalkyl group has from 3 to 20, from 3 to 15, from 3 to 10, from 3 to 8, from 4 to 7, or from 5 to 6 ring atoms. In certain embodiments, the heterocyclyl or heterocycloalkyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, the ring carbon atoms may be optionally substituted with oxo, and some rings may be partially or fully saturated, or aromatic. The heterocycloalkyl or heterocyclyl may be attached to the main structure at a heteroatom or a carbon atom which results in the creation of a stable compound. Examples include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, when the heterocyclyl or heterocycloalkyl ring contains one or more O, the heterocyclyl or heterocycloalkyl may also be referred to as "cycloalkoxyl." In certain embodiments, the heterocyclyl or heterocycloalkyl is optionally substituted with one or more substituents as described herein elsewhere.

As used herein, and unless otherwise specified, the term "halogen", "halide" or "halo" refers to fluorine, chlorine, bromine, and iodine.

As used herein, and unless otherwise specified, the term "hydrogen" encompasses proton ($^1$H), deuterium ($^2$H), tritium ($^3$H), and/or mixtures thereof. In a compound described herein, one or more positions occupied by hydrogen may be enriched with deuterium and/or tritium. Such isotopically enriched analogs may be prepared from suitable isotopically labeled starting material obtained from a commercial source or prepared using known literature procedures.

As used herein, and unless otherwise specified, the atoms of the compounds provided herein are meant to represent any stable or radioactive isotope of that atom. In certain embodiments, a compound provided herein encompasses all possible isotopic variants of that compound. For example, as used herein, and unless otherwise specified, hydrogen encompasses proton ($^1$H), deuterium ($^2$H), tritium ($^3$H), and/or mixtures thereof. In one embodiment, when a position is designated as "H" or "hydrogen", the position is understood to have hydrogen at its natural isotopic composition. In one embodiment, when a position is designated as "H" or "hydrogen", the position is understood to have hydrogen at an isotopically enriched composition, i.e., an isotopic composition other than the natural isotopic composition of that atom. In one embodiment, the compounds provided herein optionally comprise deuterium at one or more positions where hydrogen atoms are present, and wherein the deuterium composition of the atom or atoms is other than the natural isotopic composition. In one embodiment, the compounds provided herein optionally comprise isotopes for other elements at one or more positions, including but not limited to, $^{13}$C, $^{14}$C, $^{33}$S, $^{34}$S, $^{36}$S, $^{15}$N, $^{17}$O, and/or $^{18}$O, and wherein the isotopic composition of the atom or atoms is other than the natural isotopic composition.

As used herein, and unless otherwise specified, the term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^1$H), deuterium ($^2$H), tritium ($^3$H), carbon 11 ($^{11}$C), carbon 12 ($^{12}$C), carbon 13 ($^{13}$C), carbon-14, ($^{14}$O), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, for example, or any carbon can be $^{13}$C, for example, or any nitrogen can be $^{15}$N, for example, or any oxygen can be $^{18}$O, for example, where feasible according to the judgment of one of skill. In certain embodiments, an "isotopic variant" of a compound contains unnatural proportions of deuterium (D).

As used herein, and unless otherwise specified, the term "optionally substituted" is intended to mean that a group, such as an alkyl, alkenyl, alkynyl, cycloalkyl, heteroalkyl, alkoxyl, aminoalkyl, aryl, aralkyl, heteroaralkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—NO$_2$), oxo (=O), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) R$^b$ and R$^c$ together with the N atom to which they are attached form heteroaryl or heterocyclyl, optionally substituted with one or more, in one embodiment, one, two, three, or four, substituents $Q^1$. As used herein, all groups that can be substituted are "optionally substituted," unless otherwise specified.

In one embodiment, each $Q^1$ is independently selected from the group consisting of (a) cyano, halo, oxo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

As used herein, and unless otherwise specified, the term "pharmaceutically acceptable salts" refers to salts prepared from pharmaceutically acceptable non-toxic acids, including inorganic acids and organic acids; or from pharmaceutically acceptable non-toxic bases, including inorganic bases and organic bases.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

In certain embodiments, as used herein, and unless otherwise specified, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

As used herein, and unless otherwise specified, the terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

As used herein, and unless otherwise specified, the terms "drug" and "therapeutic agent" refer to a compound, or a pharmaceutical composition thereof, which is administered to a subject for treating, preventing, managing, or ameliorating one or more symptoms of a condition, disorder, or disease.

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, "amelioration" of the symptoms of a particular disorder by administration of a particular pharmaceutical composition refers to any lessening, whether permanent or temporary, lasting or transient, that can be attributed to or associated with the administration of the composition.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human.

As used herein, and unless otherwise specified, the term "opioid receptor ligand" or "opioid ligand" refers to any compound, which binds to an opioid receptor. Unless otherwise specified, the opioid receptor includes, but is not limited to μ-opioid receptor. Ligands include endogenous ligands for a given opioid receptor as well as naturally occurring opiates, drug molecules, and other compounds, such as synthetic molecules known to bind to a particular opioid receptor. In some embodiments, the ligand is an allosteric modulator. In one embodiment, the ligands include those labeled with one or more radioisotopes, such as tritium or $^{11}C$, or otherwise (e.g., fluorescently) labeled. In some embodiments, the ligand is a positron-emission tomography (PET) ligand. In some embodiments, it is within the abilities of the skilled person to select an appropriate ligand, for example, an agonist or an antagonist, for a given opioid receptor.

As used herein, and unless otherwise specified, the term "neurological disorder" refers to any condition of the central or peripheral nervous system of a mammal. The term "neurological disorder" includes, but is not limited to, neurodegenerative diseases (e.g., Alzheimer's disease, Parkinson's disease, Huntington's disease, levodopa-induced dyskinesia, and amyotrophic lateral sclerosis), neuropsychiatric diseases (e.g., schizophrenia and anxiety, such as general anxiety disorder), and affective disorders (e.g., depression, anxiety, and attention deficit disorder). Exemplary neurological disorders include, but are not limited to, MLS (cerebellar ataxia), Down syndrome, multi-infarct dementia, status epilecticus, contusive injury (e.g., spinal cord injury and head injury), viral infection induced neurodegeneration, (e.g., AIDS, encephalopathies), epilepsy, benign forgetfulness, closed head injury, sleep disorder, depression (e.g., major depressive disorder, dysthymia, and bipolar depressive disorder), anxiety, dementias, movement disorder, seizure, convulsion, psychosis, schizophrenia, alcoholism, substance abuse, obsessive-compulsive disorder, post-traumatic stress disorder, eating disorder, fibromyalgia, and the like. "Neurological disorder" also includes any condition associated with the disorder. For instance, a method of treating a neurodegenerative disorder includes methods of treating loss of memory and/or loss of cognition associated with a neurodegenerative disorder. An exemplary method would also include treating or preventing loss of neuronal function characteristic of neurodegenerative disorder. In one embodiment, "neurological disorder" also includes any disease or condition that is implicated, at least in part, in opioid receptor (e.g., μ-opioid receptor) activities.

As used herein, and unless otherwise specified, the terms "psychosis," "schizophrenia," "obsessive-compulsive disorder," "substance abuse," "anxiety," "eating disorder," "migraine," and other CNS disorders or neurological disorders described herein elsewhere are used herein in a manner consistent with their accepted meanings in the art. See, e.g., *Diagnostic and Statistical Manual of Mental Disorders*, 4$^{th}$ Ed., American Psychiatric Association (1997) (DSM-IV™).

As used herein, and unless otherwise specified, the term "affective disorder" includes depression, attention deficit disorder, attention deficit disorder with hyperactivity, bipolar and manic conditions, and the like. The terms "attention deficit disorder" (ADD) and "attention deficit disorder with hyperactivity" (ADDH), or attention deficit/hyperactivity disorder (AD/HD), are used herein in accordance with the accepted meanings as found in the *Diagnostic and Statistical Manual of Mental Disorders*, 4$^{th}$ Ed., American Psychiatric Association (1997) (DSM-IV™).

As used herein, and unless otherwise specified, the term "depression" includes all forms of depression including, but not limited to, major depressive disorder (MDD), bipolar disorder, seasonal affective disorder (SAD), dysthymia, and treatment resistant depression. "Major depressive disorder" is used herein interchangeably with "unipolar depression" and "major depression." "Depression" may also include any condition commonly associated with depression, such as all forms of fatigue (e.g., chronic fatigue syndrome) and cognitive deficits.

As used herein, and unless otherwise specified, the term "convulsion" refers to a neurological disorder and is used interchangeably with "seizure," although there are many types of seizure, some of which have subtle or mild symptoms instead of convulsions. Seizures of all types may be caused by disorganized and sudden electrical activity in the brain. In some embodiments, convulsions are a rapid and uncontrollable shaking during which the muscles contract and relax repeatedly.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

As used herein, and unless otherwise specified, the term "pain" refers to an unpleasant sensory and emotional experience. The term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (see, e.g., Harrison's Principles of Internal Medicine, pp. 93-98 (Wilson et al., eds., 12th ed. 1991); Williams et al., J. of Med. Chem. 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In addition, the term "pain" includes pain resulting from dysfunction of the nervous system: organic pain states that share clinical features of neuropathic pain and possible common pathophysiology mechanisms, but are not initiated by an identifiable lesion in any part of the nervous system.

The term "somatic pain," as used herein, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

The term "neuropathic pain," as used herein, refers to a heterogeneous group of neurological conditions that result from damage to the nervous system. The term also refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis, and is also encompassed by the term. Other types of pain that are meant to be included in the definition of neuropathic pain include, but are not limited to, pain from neuropathic cancer pain, HIV/AIDS induced pain, phantom limb pain, and complex regional pain syndrome.

The term also encompasses the common clinical features of neuropathic pain including, but not limited to, sensory loss, allodynia (non-noxious stimuli produce pain), hyperalgesia and hyperpathia (delayed perception, summation, and painful after sensation). Pain is often a combination of nociceptive and neuropathic types, for example, mechanical spinal pain and radiculopathy or myelopathy.

As used herein, and unless otherwise specified, the term "acute pain" refers to the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. The term also refers to pain which is marked by short duration or sudden onset.

As used herein, and unless otherwise specified, the term "chronic pain" encompasses the pain occurring in a wide range of disorders, for example, trauma, malignancies and chronic inflammatory diseases such as rheumatoid arthritis. Chronic pain may last more than about six months. In addition, the intensity of chronic pain may be disproportionate to the intensity of the noxious stimulus or underlying process. The term also refers to pain associated with a chronic disorder, or pain that persists beyond resolution of an underlying disorder or healing of an injury, and that is often more intense than the underlying process would predict. It may be subject to frequent recurrence.

As used herein, and unless otherwise specified, the term "inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. The term also refers to pain which is produced as a symptom or a result of inflammation or an immune system disorder.

As used herein, and unless otherwise specified, the term "visceral pain" refers to pain which is located in an internal organ.

As used herein, and unless otherwise specified, the term "mixed etiology pain" refers to pain that contains both inflammatory and neuropathic components.

As used herein, and unless otherwise specified, the term "dual mechanism pain" refers to pain that is amplified and maintained by both peripheral and central sensitization.

As used herein, and unless otherwise specified, the term "causalgia" refers to a syndrome of sustained burning, allodynia, and hyperpathia after a traumatic nerve lesion, often combined with vasomotor and sudomotor dysfunction and later trophic changes. As used herein, and unless otherwise specified, the term "central pain" refers to pain initiated by a primary lesion or dysfunction in the central nervous system.

As used herein, and unless otherwise specified, the term "hyperesthesia" refers to increased sensitivity to stimulation, excluding the special senses.

As used herein, and unless otherwise specified, the term "hyperpathia" refers to a painful syndrome characterized by an abnormally painful reaction to a stimulus, especially a repetitive stimulus, as well as an increased threshold. It may occur with allodynia, hyperesthesia, hyperalgesia, or dysesthesia.

As used herein, and unless otherwise specified, the term "dysesthesia" refers to an unpleasant abnormal sensation, whether spontaneous or evoked. In certain embodiments, dysesthesia include hyperalgesia and allodynia.

As used herein, and unless otherwise specified, the term "hyperalgesia" refers to an increased response to a stimulus that is normally painful. It reflects increased pain on suprathreshold stimulation.

As used herein, and unless otherwise specified, the term "allodynia" refers to pain due to a stimulus that does not normally provoke pain.

As used herein, and unless otherwise specified, the term "Diabetic Peripheral Neuropathic Pain" (DPNP), also called diabetic neuropathy, DN or diabetic peripheral neuropathy), refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

As used herein, and unless otherwise specified, the term "Post-Herpetic Neuralgia", also called "Postherpetic Neuralgia (PHN)", refers to a painful condition affecting nerve fibers and skin. Without being limited by a particular theory, it is a complication of shingles, a second outbreak of the varicella zoster virus (VZV), which initially causes chickenpox.

As used herein, and unless otherwise specified, the term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

As used herein, and unless otherwise specified, the term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

As used herein, and unless otherwise specified, the term "Phantom Limb Pain" refers to pain appearing to come from where an amputated limb used to be. Phantom limb pain can also occur in limbs following paralysis (e.g., following spinal cord injury). "Phantom Limb Pain" is usually chronic in nature.

As used herein, and unless otherwise specified, the term "Trigeminal Neuralgia (TN)" refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

As used herein, and unless otherwise specified, the term "Complex Regional Pain Syndrome (CRPS)," formerly known as Reflex Sympathetic Dystrophy (RSD), refers to a chronic pain condition whose key symptom is continuous, intense pain out of proportion to the severity of the injury, which gets worse rather than better over time. The term encompasses type 1 CRPS, which includes conditions caused by tissue injury other than peripheral nerve, and type 2 CRPS, in which the syndrome is provoked by major nerve injury, and is sometimes called causalgia.

B. COMPOUNDS

In one embodiment, provided herein is a compound of formula (I):

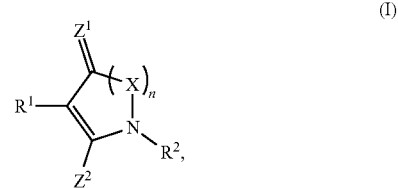

(I)

or a pharmaceutically acceptable salt thereof, wherein $R^1$ is (i) hydrogen, halo, or cyano; or (ii) alkyl, alkenyl, heteroalkyl, alkoxyl, aminoalkyl, cycloalkyl, heterocyclyl, aryl, heteroaryl, aralkyl, or heteroaralkyl, each of which is optionally substituted; or (iii) —C(O)OR$^3$, —C(O)NR$^3$R$^4$, or —C(NR$^3$)NR$^3$R$^4$;

$R^2$ is (i) hydrogen; or (ii) alkyl, alkenyl, heteroalkyl, cycloalkyl, heterocyclyl, aryl, heteroaryl, aralkyl, or heteroaralkyl, each of which is optionally substituted;

$Z^1$ is =O, =S, =NR$^3$, or =CR$^5$R$^6$;

$Z^2$ is hydrogen, halo, cyano, —NR$^3$R$^4$, —SR$^3$, —OR$^3$, or optionally substituted alkyl;

each occurrence of X is independently CR$^7$R$^8$, C=CR$^7$R$^8$, or NR$^9$;

n is 1, 2, or 3;

each occurrence of R$^3$ and R$^4$ is independently (i) hydrogen; or (ii) alkyl, alkenyl, heteroalkyl, cycloalkyl, heterocyclyl, aryl, heteroaryl, aralkyl, or heteroaralkyl, each of which is optionally substituted; or (iii) when R$^3$ and R$^4$ are attached to the same nitrogen, R$^3$ and R$^4$ together with the nitrogen atom to which they are attached form an optionally substituted 3- to 8-membered heterocyclyl or heteroaryl ring; or (iv) when R$^3$ and R$^4$ are attached to the same nitrogen, one of R$^3$ and R$^4$ is OH and the other is hydrogen;

each occurrence of R$^5$ and R$^6$ is independently (i) hydrogen, halo, or cyano; or (ii) alkyl, alkenyl, heteroalkyl, alkoxyl, aminoalkyl, cycloalkyl, heterocyclyl, aryl, heteroaryl, aralkyl, or heteroaralkyl, each of which is optionally substituted; or (iii) when R$^5$ and R$^6$ are attached to the same carbon, R$^5$ and R$^6$ together with the carbon atom to which they are attached form an optionally substituted 3- to 8-membered heterocyclyl, heteroaryl, aryl, or cycloalkyl ring;

each occurrence of R$^7$ and R$^8$ is independently (i) hydrogen, halo, or cyano; or (ii) alkyl, alkenyl, heteroalkyl, alkoxyl, aminoalkyl, cycloalkyl, heterocyclyl, aryl, heteroaryl, aralkyl, or heteroaralkyl, each of which is optionally substituted; or (iii) —OR$^3$, —C(O)OR$^3$, —C(O)NR$^3$R$^4$, or —C(O)R$^3$; or (iv) when R$^7$ and R$^8$ are attached to the same carbon, R$^7$ and R$^8$ together with the carbon atom to which they are attached form an optionally substituted 3- to 8-membered heterocyclyl, heteroaryl, aryl, or cycloalkyl ring; and each occurrence of R$^9$ is independently (i) hydrogen, halo, or cyano; or (ii) alkyl, alkenyl, heteroalkyl, alkoxyl, aminoalkyl, cycloalkyl, heterocyclyl, aryl, heteroaryl, aralkyl, or heteroaralkyl, each of which is optionally substituted;

optionally (i) $Z^1$ and one occurrence of $R^7$, $R^8$, or $R^9$ together with the atoms to which they are attached form an optionally substituted heterocyclyl, heteroaryl, aryl, or cycloalkyl ring; (ii) $Z^1$ and $R^1$ together with the atoms to which they are attached form an optionally substituted heterocyclyl, heteroaryl, aryl, or cycloalkyl ring; (iii) $Z^2$ and $R^1$ together with the atoms to which they are attached form an optionally substituted heterocyclyl, heteroaryl, aryl, or cycloalkyl ring; (iv) $Z^2$ and $R^2$ together with the atoms to which they are attached form an optionally substituted heterocyclyl or heteroaryl ring; or (v) $R^2$ and one occurrence of $R^7$, $R^8$, or $R^9$ together with the atoms to which they are attached form an optionally substituted heterocyclyl or heteroaryl ring.

In another embodiment, provided herein is a compound of formula (II):

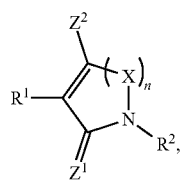

(II)

or a pharmaceutically acceptable salt thereof, wherein $R^1$ is (i) hydrogen, halo, or cyano; or (ii) alkyl, alkenyl, heteroalkyl, alkoxyl, aminoalkyl, cycloalkyl, heterocyclyl, aryl, heteroaryl, aralkyl, or heteroaralkyl, each of which is optionally substituted; or (iii) —C(O)OR$^3$, —C(O)NR$^3$R$^4$, or —C(NR$^3$)NR$^3$R$^4$;

$R^2$ is (i) hydrogen; or (ii) alkyl, alkenyl, heteroalkyl, cycloalkyl, heterocyclyl, aryl, heteroaryl, aralkyl, or heteroaralkyl, each of which is optionally substituted;

$Z^1$ is =O, =S, =NR$^3$, or =CR$^5$R$^6$;

$Z^2$ is hydrogen, halo, cyano, —NR$^3$R$^4$, —SR$^3$, —OR$^3$, or optionally substituted alkyl;

each occurrence of X is independently CR$^7$R$^8$, C=CR$^7$R$^8$, or NR$^9$;

n is 1, 2, or 3;

each occurrence of $R^3$ and $R^4$ is independently (i) hydrogen; or (ii) alkyl, alkenyl, heteroalkyl, cycloalkyl, heterocyclyl, aryl, heteroaryl, aralkyl, or heteroaralkyl, each of which is optionally substituted; or (iii) when $R^3$ and $R^4$ are attached to the same nitrogen, $R^3$ and $R^4$ together with the nitrogen atom to which they are attached form an optionally substituted 3- to 8-membered heterocyclyl or heteroaryl ring; or (iv) when $R^3$ and $R^4$ are attached to the same nitrogen, one of $R^3$ and $R^4$ is OH and the other is hydrogen;

each occurrence of $R^5$ and $R^6$ is independently (i) hydrogen, halo, or cyano; or (ii) alkyl, alkenyl, heteroalkyl, alkoxyl, aminoalkyl, cycloalkyl, heterocyclyl, aryl, heteroaryl, aralkyl, or heteroaralkyl, each of which is optionally substituted; or (iii) when $R^5$ and $R^6$ are attached to the same carbon, $R^5$ and $R^6$ together with the carbon atom to which they are attached form an optionally substituted 3- to 8-membered heterocyclyl, heteroaryl, aryl, or cycloalkyl ring;

each occurrence of $R^7$ and $R^8$ is independently (i) hydrogen, halo, or cyano; or (ii) alkyl, alkenyl, heteroalkyl, alkoxyl, aminoalkyl, cycloalkyl, heterocyclyl, aryl, heteroaryl, aralkyl, or heteroaralkyl, each of which is optionally substituted; or (iii) —OR$^3$, —C(O)OR$^3$, —C(O)NR$^3$R$^4$, or —C(O)R$^3$; or (iv) when $R^7$ and $R^8$ are attached to the same carbon, $R^7$ and $R^8$ together with the carbon atom to which they are attached form an optionally substituted 3- to 8-membered heterocyclyl, heteroaryl, aryl, or cycloalkyl ring; and each occurrence of $R^9$ is independently (i) hydrogen, halo, or cyano; or (ii) alkyl, alkenyl, heteroalkyl, alkoxyl, aminoalkyl, cycloalkyl, heterocyclyl, aryl, heteroaryl, aralkyl, or heteroaralkyl, each of which is optionally substituted;

optionally (i) $Z^2$ and one occurrence of $R^7$, $R^8$, or $R^9$ together with the atoms to which they are attached form an optionally substituted heterocyclyl, heteroaryl, aryl, or cycloalkyl ring; (ii) $Z^2$ and $R^1$ together with the atoms to which they are attached form an optionally substituted heterocyclyl, heteroaryl, aryl, or cycloalkyl ring; (iii) $Z^1$ and $R^1$ together with the atoms to which they are attached form an optionally substituted heterocyclyl, heteroaryl, aryl, or cycloalkyl ring; (iv) $Z^1$ and $R^2$ together with the atoms to which they are attached form an optionally substituted heterocyclyl or heteroaryl ring; or (v) $R^2$ and one occurrence of $R^7$, $R^8$, or $R^9$ together with the atoms to which they are attached form an optionally substituted heterocyclyl or heteroaryl ring.

In one embodiment, provided herein is a compound of formula (Ia), or a pharmaceutically acceptable salt thereof, wherein $R^1$, $R^2$, $Z^1$, $Z^2$, and X are defined herein elsewhere.

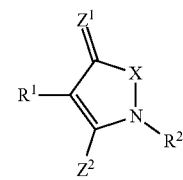

(Ia)

In another embodiment, provided herein is a compound of formula (IIa), or a pharmaceutically acceptable salt thereof, wherein $R^2$, $R^2$, $Z^1$, $Z^2$, and X are defined herein elsewhere.

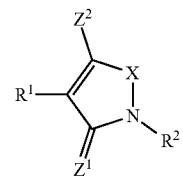

(IIa)

Provided below are further embodiments of compounds of the present disclosure, including a compound of formula (I), (II), (Ia), (Ib), (Ib-1), (Ib-2), (Ic), (Ic-1), (Id), (Id-1), (Id-2), (Ie), (If), (IIa), (IIb), (IIc), or (III) provided herein. Various embodiments of X, $Z^1$, $Z^2$, $R^1$, $R^2$, $R^3$, $R^4$, $R^5$, $R^6$, $R^7$, $R^8$, $R^9$, $R^{10}$, $R^{11}$, $R^{12}$, m, k, and/or n provided herein may be applied to formula (I), (II), (Ia), (Ib), (Ib-1), (Ib-2), (Ic), (Ic-1), (Id), (Id-1), (Id-2), (Ie), (If), (IIa), (IIb), (IIc), or (III), and any of the combinations are encompassed by this disclosure and specifically disclosed herein.

In one embodiment, n is 1. In one embodiment, n is 2. In one embodiment, n is 3. In one embodiment, n is 1 or 2. In one embodiment, n is 2 or 3.

In one embodiment, $Z^1$ is =O or =NR$^3$. In specific embodiments, $R^3$ is H or optionally substituted methyl (e.g., CH$_3$ or CF$_3$).

In specific embodiments, $Z^1$ is =O, =NH, or =NCH$_3$.

In one embodiment, $Z^2$ is H, halo, cyano, —NR$^3$R$^4$, or —OR$^3$. In one embodiment, $Z^2$ is —NR$^3$R$^4$ or —OR$^3$. In one embodiment, $Z^2$ is OH. In other embodiments, $Z^2$ is not OH. In one embodiment, $Z^2$ is NH$_2$. In other embodiments, $Z^2$ is not NH$_2$. In one embodiment, $Z^2$ is NHCH$_3$. In one embodiment, $Z^2$ is N(CH$_3$)$_2$. In one embodiment, $Z^2$ is —NH—OH. In one embodiment, $Z^2$ is —NR$^3$R$^4$, wherein R$^4$ is H or optionally substituted (C$_1$-C$_4$)alkyl (e.g., CH$_3$, CF$_3$, or Et), and R$^3$ is defined herein. In specific embodiments, R$^3$ is H, optionally substituted (C$_1$-C$_4$)alkyl (e.g., CH$_3$, CF$_3$, Et, Pr, Bu, CH$_2$-cycloalkyl, CH$_2$CH$_2$-cycloalkyl, CH$_2$-alkoxyl, CH$_2$CH$_2$-alkoxyl, CH$_2$-aminoalkyl, CH$_2$CH$_2$-aminoalkyl, CH$_2$CH=CH$_2$, CH$_2$Ph, or CH$_2$-dimethoxyphenyl), or optionally substituted aryl (e.g., phenyl). In one embodiment, R$^4$ is H or optionally substituted methyl (e.g., CH$_3$ or CF$_3$). In one embodiment, when R$^3$ and R$^4$ are attached to the same nitrogen, R$^3$ and R$^4$ together with the nitrogen atom to which they are attached form an optionally substituted heteroaryl or heterocyclyl ring. In one embodiment, R$^3$ and R$^4$ together form an optionally substituted heteroaryl ring (e.g., imidazolyl or pyrrolyl). In one embodiment, R$^3$ and R$^4$ together form an optionally substituted heterocyclyl ring (e.g., pyrrolidinyl or dihydropyrrolyl).

In specific embodiments, $Z^2$ is NH$_2$, NHMe, NHEt, NHnPr, NHiPr, NHPh, NHOH, NHCH$_2$Cyclopropyl, NHCH$_2$Cyclobutyl, NHCH$_2$Ph, NHCH$_2$CH=CH$_2$, NHCH$_2$CH$_2$OMe, or N(Me)$_2$, each of which is optionally substituted; or NHCH$_2$Ph, wherein Ph is optionally substituted (e.g., optionally substituted with one or more halo, cyano, Me, OMe, CF$_3$, or OCF$_3$, for example, 3,5-dimethoxyphenyl). In specific embodiments, $Z^2$ is OH. In specific embodiments, $Z^2$ is —NH—OH. In specific embodiments, $Z^2$ is an optionally substituted heterocyclyl (e.g., $Z^2$ is —NR$^3$R$^4$, wherein R$^3$ and R$^4$ together form an optionally substituted heterocyclyl or heteroaryl ring), including, but not limited to:

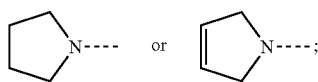

wherein each of which is optionally substituted with one or more substituents provided herein.

In one embodiment, R$^1$ is hydrogen, halo, or cyano.

In one embodiment, R$^1$ is —C(O)OR$^3$, —C(O)NR$^3$R$^4$, or —C(NR$^3$)NR$^3$R$^4$. Specific examples of R$^1$ include, but are not limited to:

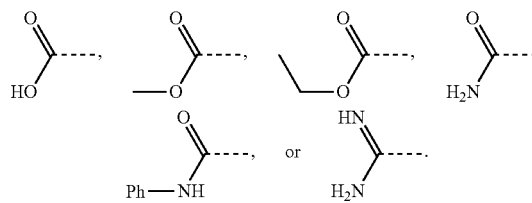

In one embodiment, R$^1$ is an optionally substituted aryl or heteroaryl. In one embodiment, R$^1$ is an optionally substituted aryl (e.g., phenyl). In one embodiment, R$^1$ is an optionally substituted 5- to 10-membered heteroaryl (e.g., benzimidazolyl). Specific examples of R$^1$ include, but are not limited to:

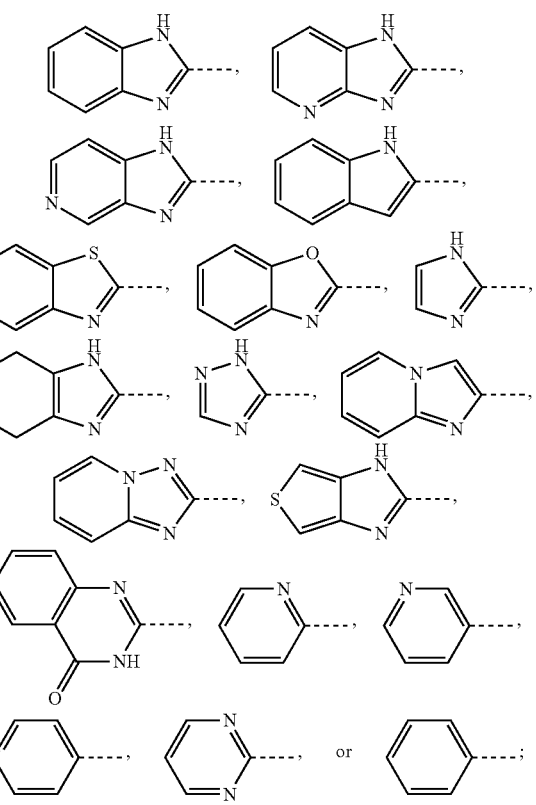

wherein each of which is optionally substituted with one or more substituents provided herein (e.g., halo, cyano, CH$_3$, CF$_3$, Et, Ph, allyl, benzyl, CH$_2$-cycloalkyl, OCH$_3$, OCF$_3$, OEt, OPh, OH, or NMe$_2$).

In specific embodiments, R$^1$ is an optionally substituted benzimidazolyl. Specific examples of R$^1$ include, but are not limited to:

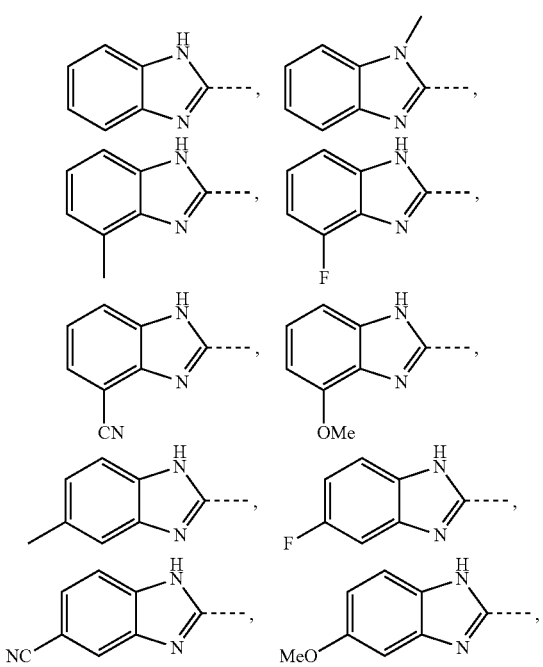

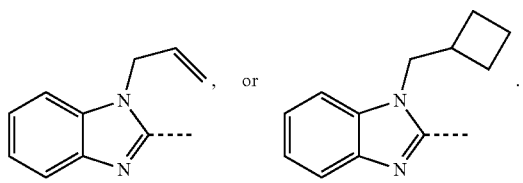

In specific embodiments, R¹ is an optionally substituted imidazolyl. Specific examples of R¹ include, but are not limited to:

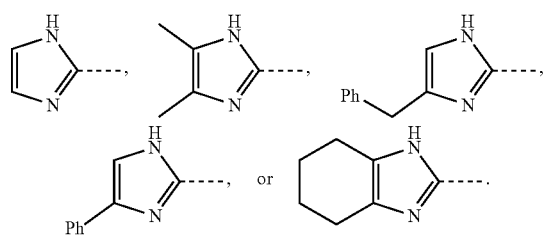

In specific embodiments, R¹ is an optionally substituted triazolyl. Specific examples of R¹ include, but are not limited to:

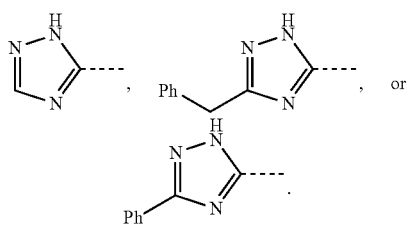

In one embodiment, R² is hydrogen, optionally substituted alkyl, optionally substituted cycloalkyl, optionally substituted aralkyl, optionally substituted aryl, optionally substituted heteroaryl, or optionally substituted heterocyclyl.

In one embodiment, R² is hydrogen.

In one embodiment, R² is optionally substituted alkyl. In one embodiment, R² is optionally substituted $(C_1-C_4)$alkyl (e.g., methyl, ethyl, propyl, or butyl, each of which is optionally substituted with one or more substituents provided herein, e.g., optionally substituted with methoxy). In one embodiment, R² is optionally substituted aralkyl (e.g., benzyl or phenethyl, each of which is optionally substituted with one or more substituents provided herein, e.g., optionally substituted with methoxy, e.g., R² is $CH_2$-dimethoxyphenyl or $CH_2CH_2$-dimethoxyphenyl). In one embodiment, R² is optionally substituted with methyl. In one embodiment, R² is optionally substituted with isopropyl. Specific examples of R² include, but are not limited to:

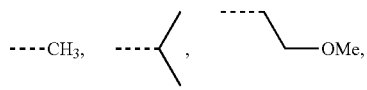

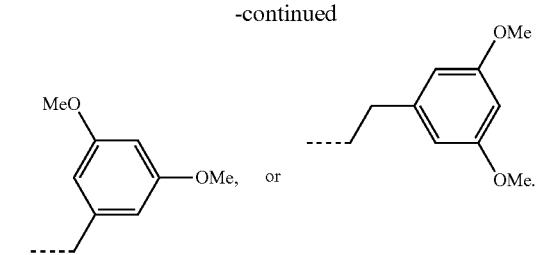

In one embodiment, R² is optionally substituted heterocyclyl. In one embodiment, R² is optionally substituted 5- to 12-membered heterocyclyl. Specific examples of R² include, but are not limited to:

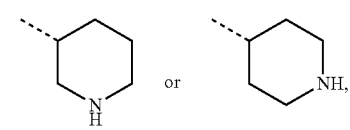

wherein each of which is optionally substituted with one or more substituents provided herein (e.g., optionally substituted with alkyl, acyl, or sulfonyl).

In one embodiment, R² is optionally substituted cycloalkyl. In one embodiment, R² is optionally substituted 3- to 7-membered cycloalkyl (e.g., cyclobutyl, which is optionally substituted with one or more substituents provided herein).

In one embodiment, R² is optionally substituted aryl or heteroaryl. In one embodiment, R² is optionally substituted aryl (e.g., phenyl or naphthyl). In one embodiment, R² is optionally substituted heteroaryl. In one embodiment, R² is optionally substituted 5- to 10-membered heteroaryl (e.g., pyridyl, pyrimidinyl, pyridazinyl, imidazolyl, or pyrazolyl). Specific examples of R² include, but are not limited to:

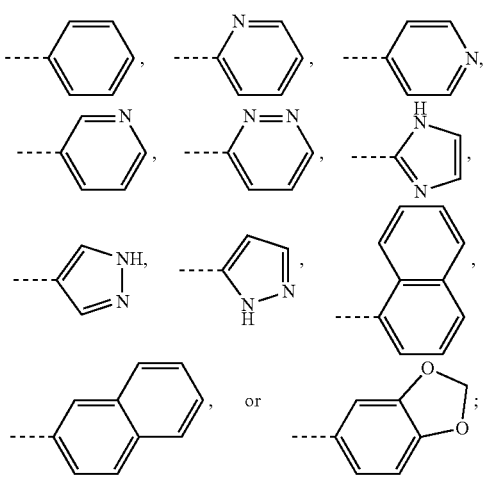

wherein each of which is optionally substituted with one or more substituents provided herein (e.g., optionally substituted with halo, cyano, $CH_3$, $CF_3$, Et, Pr, Bu, Ph, allyl, benzyl, $OCH_3$, $OCF_3$, OEt, OPr, OBu, OPh, OH, or $NMe_2$).

In specific embodiments, R² is an optionally substituted phenyl. In one embodiment, R² is phenyl substituted with one or more substituents. In one embodiment, R² is phenyl substituted with two or more substituents. In one embodiment, when $R^2$ is phenyl substituted with two or more substituents, at least two of the substituents are the same. In one embodiment, when $R^2$ is phenyl substituted with two or more substituents, the substituents are the different. In one embodiment, $R^2$ is 3- and 5-disubstituted phenyl. In one embodiment, $R^2$ is 2- and 5-disubstituted phenyl. In one embodiment, $R^2$ is 2- and 4-disubstituted phenyl. In one embodiment, $R^2$ is 3- and 4-disubstituted phenyl. In one embodiment, $R^2$ is 2-substituted phenyl. In one embodiment, $R^2$ is 3-substituted phenyl. In one embodiment, $R^2$ is 4-substituted phenyl. In specific embodiments, at least one substituent of the phenyl is a methoxy. In specific embodiments, at least one substituent of the phenyl is $OCF_3$. In specific embodiments, two substituents of the phenyl are $OCH_3$. In specific embodiments, $R^2$ is 3,5-disubstituted phenyl, wherein at least one of the substituents is selected from halo, OH, $CH_3$, $OCH_3$, $OCF_3$, Et, and OEt; and the other substituent is provided herein elsewhere. In specific embodiments, $R^2$ is 3,5-disubstituted phenyl, wherein the substituents may be the same or different, and each substituent is independently selected from halo, OH, $CH_3$, $OCH_3$, $OCF_3$, Et, and OEt. In specific embodiments, $R^2$ is 3,5-disubstituted phenyl, wherein at least one of the substituents is $OCH_3$, and the other substituent is provided herein elsewhere. Specific examples of $R^2$ include, but are not limited to:

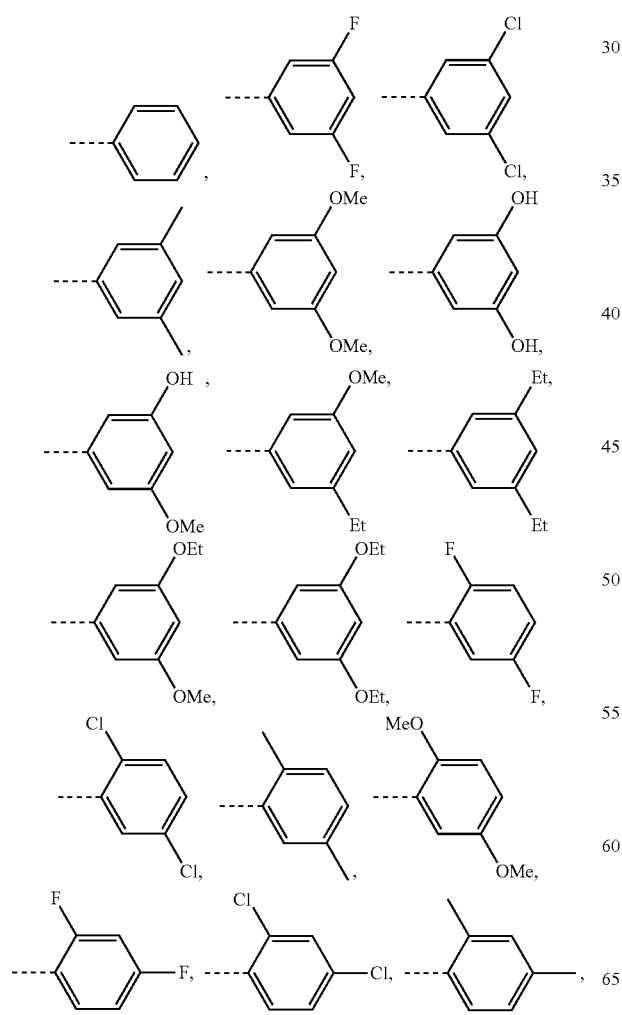

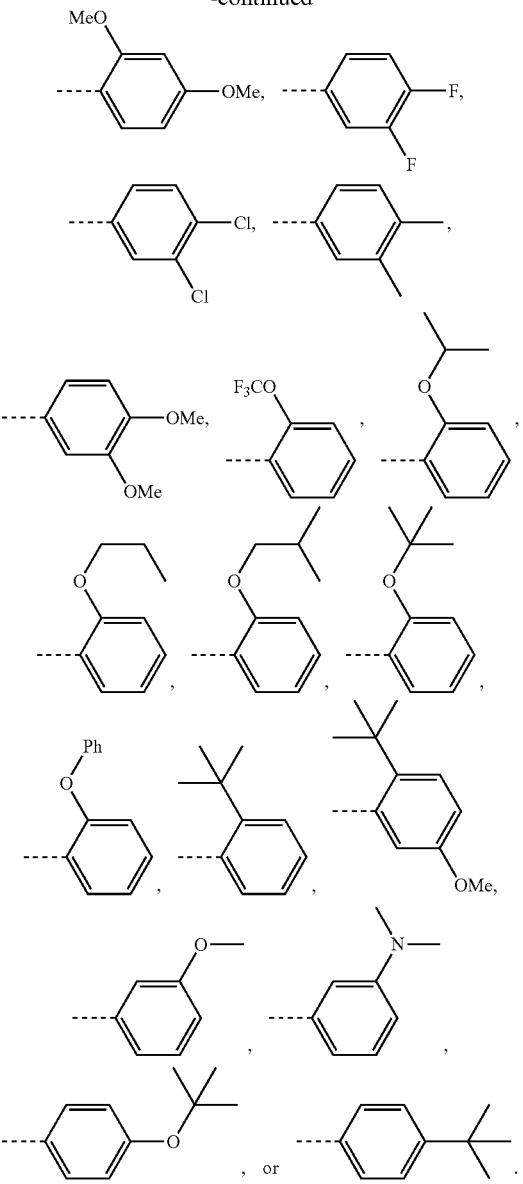

In specific embodiments, $R^2$ is:

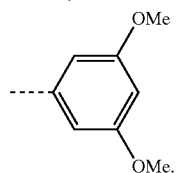

In some embodiments, $R^2$ is:

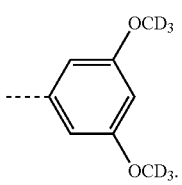

In specific embodiments, $R^2$ is an optionally substituted pyridyl. Specific examples of $R^2$ include, but are not limited to:

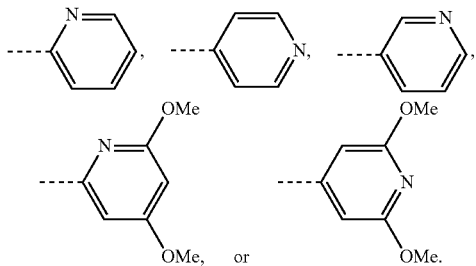

In one embodiment, X is $NR^9$. In one embodiment, $R^9$ is hydrogen, optionally substituted alkyl, optionally substituted cycloalkyl, optionally substituted heterocyclyl, optionally substituted aryl, or optionally substituted heteroaryl. In one embodiment, $R^9$ is H. In one embodiment, $R^9$ is optionally substituted ($C_1$-$C_4$)alkyl (e.g., methyl, ethyl, propyl, or butyl, each of which is optionally substituted with one or more substituents provided herein, e.g., optionally substituted with hydroxy, methoxy, or amido).

In one embodiment, $R^9$ is optionally substituted aryl (e.g., phenyl optionally substituted with one or more substituents provided herein, e.g., optionally substituted with hydroxy, methoxy, or amido). In one embodiment, $R^9$ is optionally substituted ($C_3$-$C_7$)cycloalkyl (e.g., optionally substituted with one or more substituents provided herein, e.g., optionally substituted with hydroxy, methoxy, or amido). In one embodiment, $R^9$ is optionally substituted heterocyclyl (e.g., optionally substituted with one or more substituents provided herein, e.g., optionally substituted with hydroxy, methoxy, or amido). Specific examples of $R^9$ include, but are not limited to, Me, nPr, iPr, $CH_2CH_2OH$, $CH_2CH_2OMe$, $CH_2CH_2NHC(O)Me$, $CH_2CH_2CH_2OH$, Ph, cyclobutyl, or oxetanyl, each of which is optionally substituted; for example, 3,5-dimethoxyphenyl).

In one embodiment, X is $CR^7R^8$. In specific embodiments, X is $CH_2$. In specific embodiments, X is CHMe, In specific embodiments, X is $CMe_2$.

In one embodiment, X is $C=CR^7R^8$. In specific embodiments, X is $C=CH_2$.

In one embodiment, $R^7$ is H, optionally substituted methyl, or optionally substituted ethyl (e.g., Me, Et, or $CH_2OH$), and $R^8$ is defined herein. In one embodiment, $R^7$ is H, Me, or Et, and $R^8$ is defined herein. In one embodiment, $R^7$ is H, and $R^8$ is defined herein. In one embodiment, $R^7$ is optionally substituted methyl, and $R^8$ is defined herein. In one embodiment, $R^7$ is Me, and $R^8$ is defined herein. In one embodiment, $R^7$ is optionally substituted ethyl, and $R^8$ is defined herein. In one embodiment, $R^7$ is Et, and $R^8$ is defined herein. In one embodiment, $R^7$ is —$OR^3$ (e.g., —OH or —OMe), and $R^8$ is defined herein.

In one embodiment, $R^8$ is hydrogen, —$OR^3$ (e.g., OH or OMe), —$C(O)OR^3$ (e.g., COOH COOMe, or COOEt), —$C(O)R^3$ (e.g., C(O)H or C(O)Me), optionally substituted alkyl (e.g., ($C_1$-$C_4$)alkyl optionally substituted with one or more substituents, including, halo, optionally substituted aryl, optionally substituted heterocyclyl, optionally substituted heteroaryl, $OR^3$, $NR^3R^4$, $C(O)R^3$, $C(O)OR^3$, $C(O)NR^3R^4$, or $NR^3C(O)R^4$, wherein $R^3$ and $R^4$ are defined herein), optionally substituted aryl (e.g., optionally substituted phenyl, such as, phenyl, hydroxyphenyl, methoxyphenyl, or dimethoxyphenyl), or optionally substituted heteroaryl (e.g., optionally substituted furanyl).

Specific examples of $R^8$ include, but are not limited to: H, Me, Et, nPr, iPr, Ph, furanyl, —$CH_2$-furanyl, —$CH_2Cl$, —$CH_2NH_2$, —$CH_2OH$, —$CH_2OMe$, —$CH_2CH_2NH_2$, —$CH_2CH_2OH$, —$CH_2CH_2OMe$, —$CH_2CH_2CH_2NH_2$, —$CH_2CH_2CH_2OH$, —$CH_2CH_2CH_2OMe$, —$CH_2CH_2CH_2CH_2NH_2$, —$CH_2CH_2CH_2CH_2OH$, —$CH_2CH_2CH_2CH_2OMe$, —$CH_2NHC(O)CH_3$, —$CH_2NHC(O)Ph$, —$CH_2NHC(O)CH_2CH_3$, —$CH_2NHC(O)CH_2OCH_3$, —$CH_2N(CH_3)C(O)CH_3$, —$CH_2N(CH_3)C(O)Ph$, —$CH_2N(CH_3)C(O)CH_2CH_3$, —$CH_2N(CH_3)C(O)CH_2OCH_3$, —$CH_2CH_2NHC(O)CH_3$, —$CH_2CH_2NHC(O)Ph$, —$CH_2CH_2NHC(O)CH_2CH_3$, —$CH_2CH_2NHC(O)CH_2OCH_3$, —$CH_2CH_2N(CH_3)C(O)CH_3$, —$CH_2CH_2N(CH_3)C(O)Ph$, —$CH_2CH_2N(CH_3)C(O)CH_2CH_3$, —$CH_2CH_2N(CH_3)C(O)CH_2OCH_3$, —$CH_2CH_2N(CH_3)_2$, —$CH_2CH_2Ph$, —$CH_2CH_2OPh$, —$CH_2CH_2NHPh$, —$CH_2CH_2$-morpholinyl, —$CH_2CH_2$-pyrrolidinyl, —$CH_2CH_2$-imidazolyl, —$CH_2CH_2$-phthalimidyl, —$CH_2CH(OH)CH_3$, —$CH_2COOH$, —$CH_2CONH_2$, —$CH_2CONHCH_3$, —$CH_2CONHCH_2CH_3$, —$CH_2C(O)CH_3$, —OH, —OMe, —COOH, —COOMe, —COOEt, —$C(O)H$, or —$C(O)Me$, each of which is optionally substituted; for example, an optionally substituted Ph, such as, 3-hydroxyphenyl, 4-hydroxyphenyl, or 3,5-dimethoxyphenyl.

In one embodiment, when $R^7$ and $R^8$ are attached to the same carbon, $R^7$ and $R^8$ together with the carbon atom to which they are attached form an optionally substituted 3- to 8-membered heterocyclyl, heteroaryl, aryl, or cycloalkyl ring (e.g., a cycloalkyl or heteroalkyl ring, for example, a cyclopropyl, cyclobutyl, cyclopentyl, cyclohexyl, oxetanyl, azetidinyl, tetrahydrofuranyl, pyrrolidinyl, tetrahydropyranyl, or piperidinyl ring, each of which is optionally substituted). Examples of optional substituents of the 3- to 8-membered heterocyclyl, heteroaryl, aryl, or cycloalkyl ring include, but are not limited to, one or more halo, cyano, OH, =O, $OR^3$, $NR^3R^4$, $C(O)OR^3$, $C(O)NR^3R^4$, $C(O)R^3$, $NR^4C(O)R^3$, $S(O)R^3$, $S(O)_2R^3$, $S(O)_2NR^3R^4$, or optionally substituted ($C_1$-$C_4$)alkyl. In one embodiment, X is $CR^7R^8$, and $R^7$ and $R^8$ form an optionally substituted spiral ring. In another embodiment, X is $C=CR^7R^8$, and $R^7$ and $R^8$ form an optionally substituted exo-cyclic ring to the double bond. Specific examples of $CR^7R^8$ include, but are not limited to:

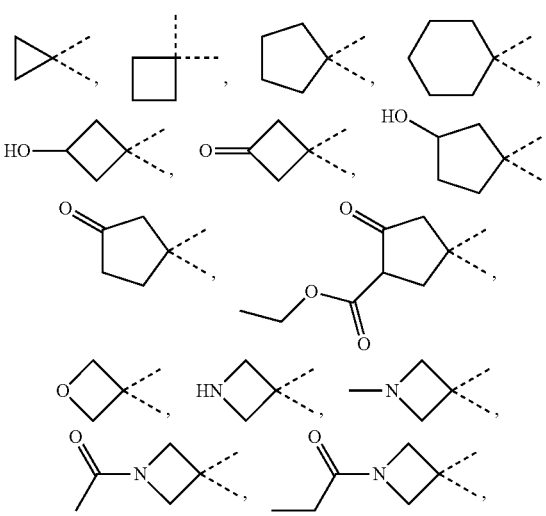

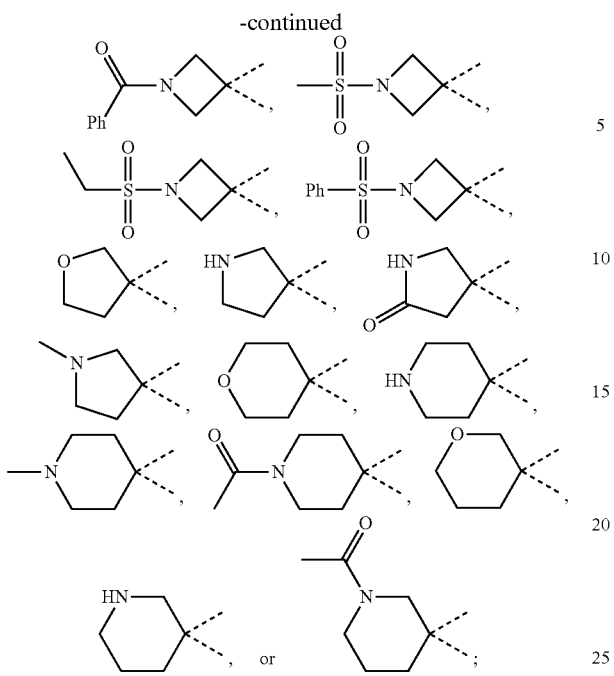

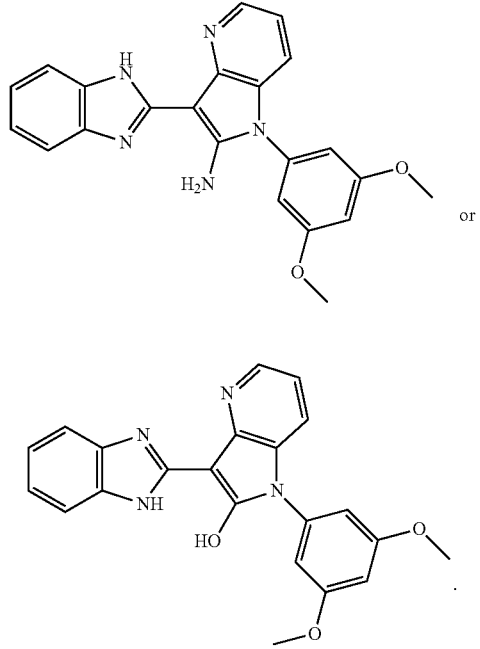

wherein the dashed bonds represent attachment point to the rest of the molecule; for example, when X is C=CR$^7$R$^8$, the dashed bonds are taken together to be a double bond; when X is CR$^7$R$^8$, the dashed bonds are part of the central ring of the molecule.

In specific embodiments, R$^3$ is H, optionally substituted (C$_1$-C$_6$)alkyl, optionally substituted (C$_1$-C$_6$)heteroalkyl, or optionally substituted phenyl. In specific embodiments, R$^4$ is H, optionally substituted (C$_1$-C$_6$)alkyl, optionally substituted (C$_1$-C$_6$)heteroalkyl, or optionally substituted phenyl. In specific embodiments, R$^3$ is H, optionally substituted methyl, or optionally substituted ethyl. In specific embodiments, R$^3$ is H, methyl, or ethyl. In specific embodiments, R$^4$ is H, optionally substituted methyl, or optionally substituted ethyl. In specific embodiments, R$^4$ is H, methyl, or ethyl. In some embodiments, R$^3$ is optionally substituted methyl or optionally substituted ethyl. In some embodiments, R$^4$ is optionally substituted methyl or optionally substituted ethyl. In some embodiments, R$^3$ is methyl or ethyl. In some embodiments, R$^4$ is methyl or ethyl.

In some embodiments, R$^3$ is not H. In some embodiments, R$^4$ is not H. In some embodiments, R$^3$ and R$^4$ are not both H.

In some embodiments, Z$^2$ is not NH$_2$. In one embodiment, Z$^2$ is not OH.

In one embodiment, Z$^1$ and one occurrence of R$^7$, R$^8$, or R$^9$ together with the atoms to which they are attached form an optionally substituted heterocyclyl, heteroaryl, aryl, or cycloalkyl ring. In one embodiment, when Z$^1$ is =NR$^3$, the R$^3$ and R$^7$ together with the atoms to which they are attached form an optionally substituted heterocyclyl or heteroaryl ring. In one embodiment, when Z$^1$ is =NR$^3$, the R$^3$ and R$^8$ together with the atoms to which they are attached form an optionally substituted heterocyclyl or heteroaryl ring. In one embodiment, when Z$^1$ is =NR$^3$, the R$^3$ and R$^9$ together with the atoms to which they are attached form an optionally substituted heterocyclyl or heteroaryl ring. Specific examples include, but are not limited to:

In one embodiment, Z$^1$ and R$^1$ together with the atoms to which they are attached form an optionally substituted heterocyclyl, heteroaryl, aryl, or cycloalkyl ring. In one embodiment, when Z$^1$ is =NR$^3$, the R$^3$ and R$^1$ together with the atoms to which they are attached form an optionally substituted heterocyclyl or heteroaryl ring.

In one embodiment, Z$^2$ and R$^1$ together with the atoms to which they are attached form an optionally substituted heterocyclyl, heteroaryl, aryl, or cycloalkyl ring. In one embodiment, when Z$^2$ is —NR$^3$R$^4$, the R$^3$ and R$^1$ together with the atoms to which they are attached form an optionally substituted heterocyclyl or heteroaryl ring. Specific examples include, but are not limited to:

In one embodiment, $Z^2$ and $R^2$ together with the atoms to which they are attached form an optionally substituted heterocyclyl or heteroaryl ring. In one embodiment, when $Z^2$ is $-NR^3R^4$, the $R^3$ and $R^2$ together with the atoms to which they are attached form an optionally substituted heterocyclyl or heteroaryl ring. Specific examples include, but are not limited to:

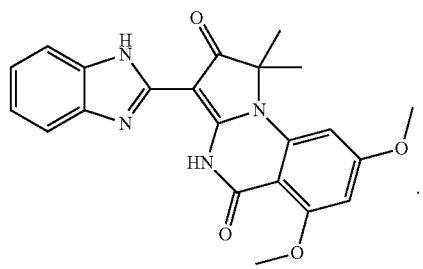 [SMILES: COc1cc(OC)c2c(c1)N1C(=C(c3nc4ccccc4[nH]3)C(=O)C1(C)C)NC2=O]

In one embodiment, $R^2$ and one occurrence of $R^7$, $R^8$, or $R^9$ together with the atoms to which they are attached form an optionally substituted heterocyclyl or heteroaryl ring. In one embodiment, $R^2$ and $R^7$ together with the atoms to which they are attached form an optionally substituted heterocyclyl or heteroaryl ring. In one embodiment, $R^2$ and $R^8$ together with the atoms to which they are attached form an optionally substituted heterocyclyl or heteroaryl ring. In one embodiment, $R^2$ and $R^9$ together with the atoms to which they are attached form an optionally substituted heterocyclyl or heteroaryl ring. Specific examples include, but are not limited to:

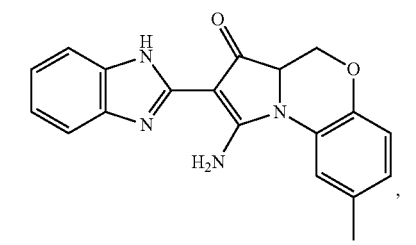

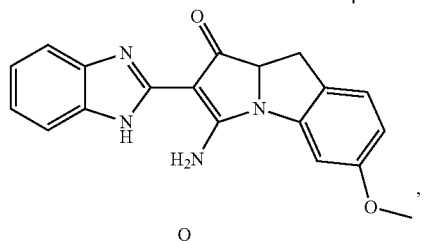

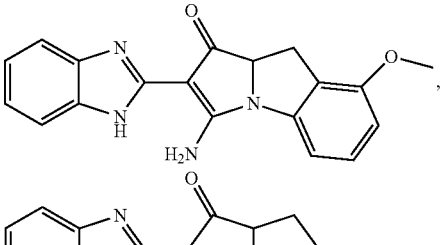

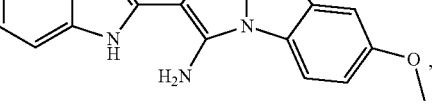

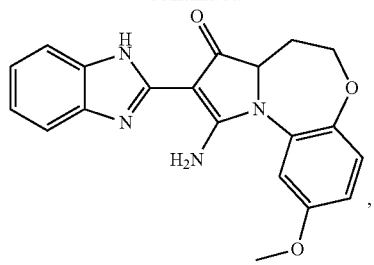

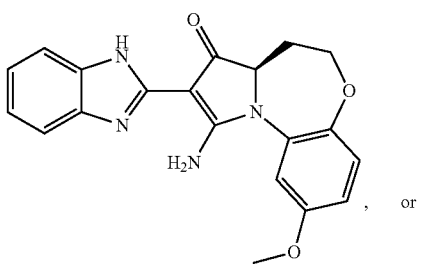

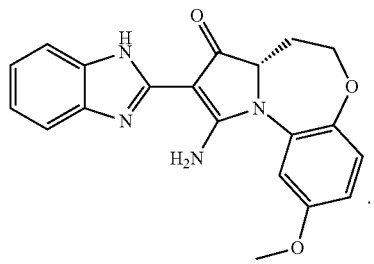

In one embodiment, provided herein is a compound of formula (Ib):

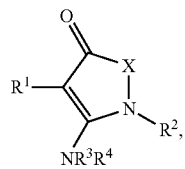

(Ib)

or a pharmaceutically acceptable salt thereof, wherein $R^1$, $R^2$, $R^3$, $R^4$, and X are defined herein elsewhere.

In one embodiment, X is $CR^7R^8$, wherein $R^7$ and $R^8$ are each independently H or optionally substituted alkyl. Specific examples include, but are not limited to:

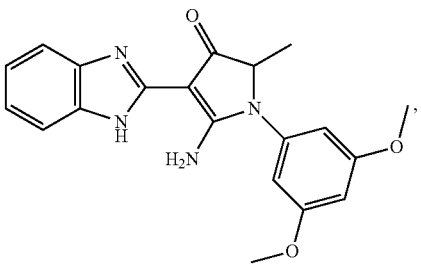

31
-continued
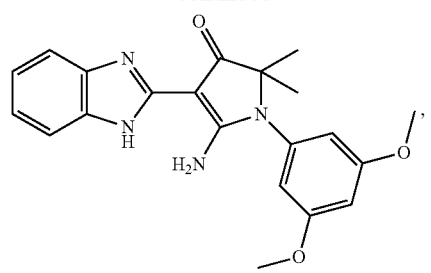
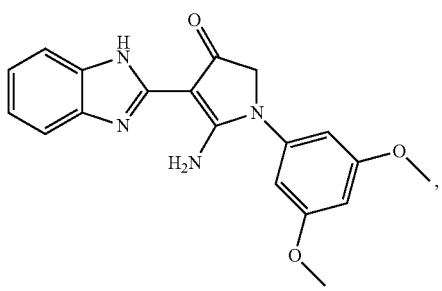
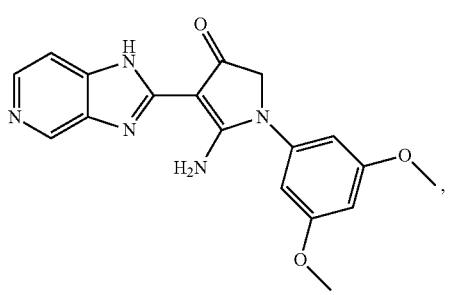
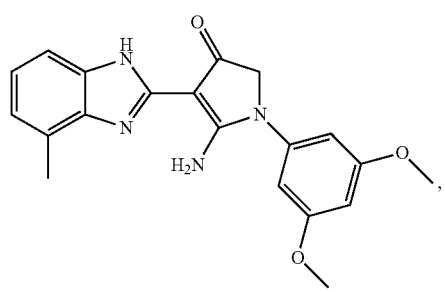
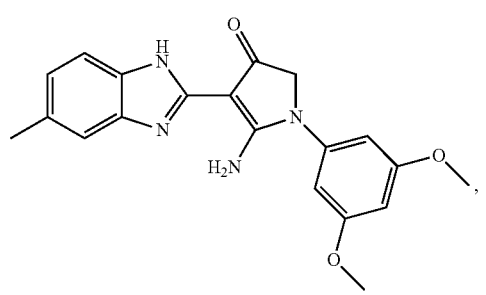
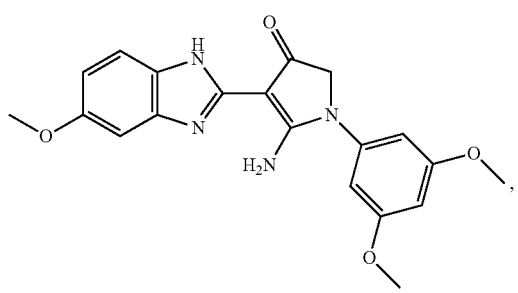
32
-continued
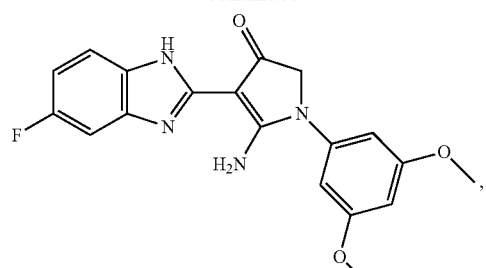
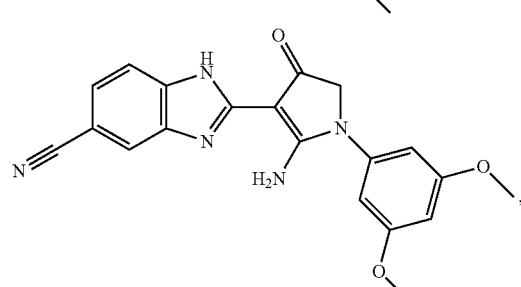
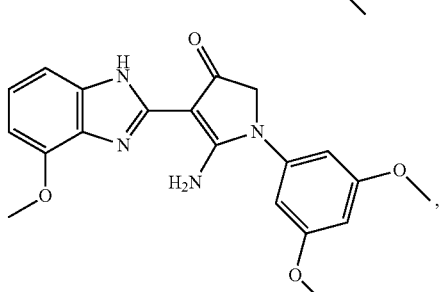
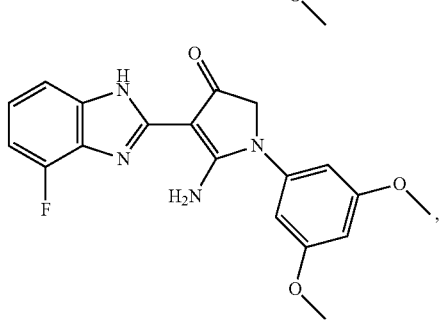
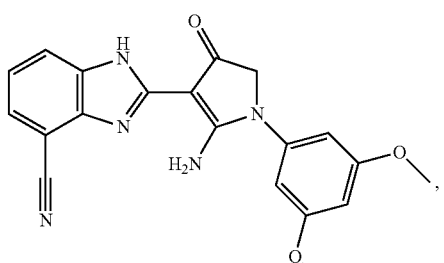
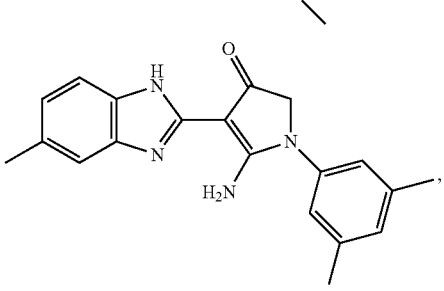

33
-continued
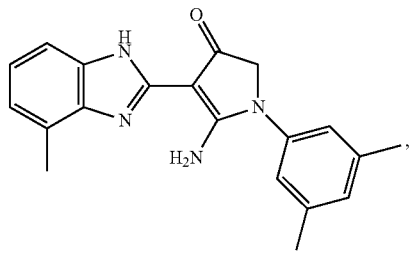
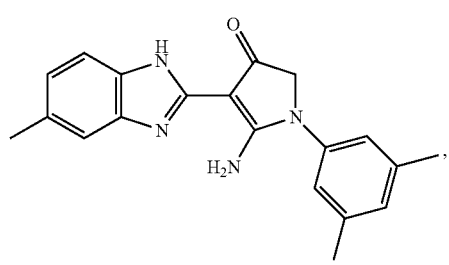
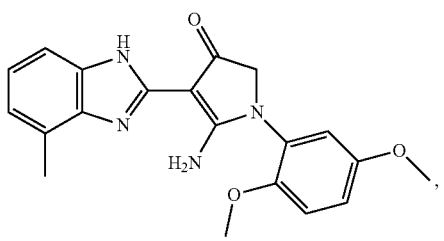
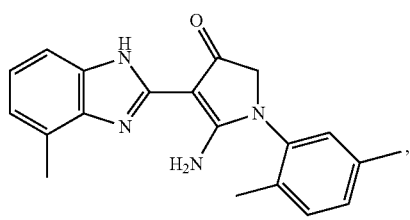
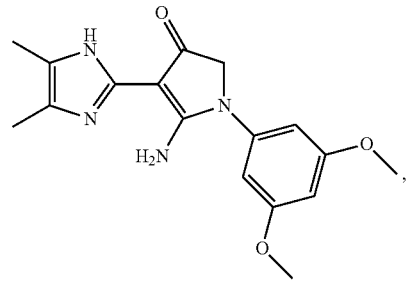
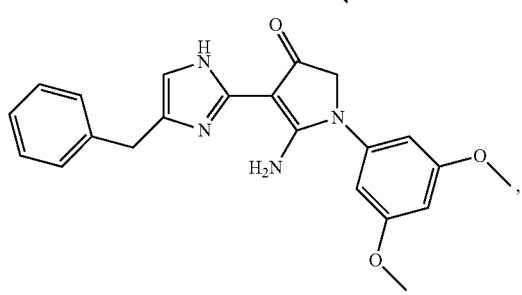
34
-continued
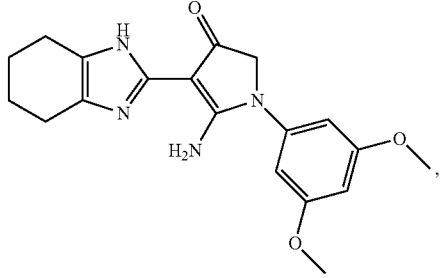
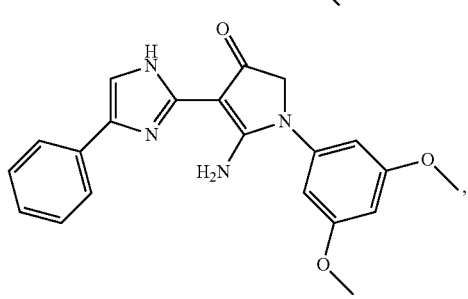
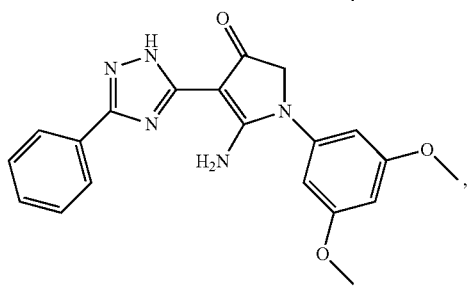
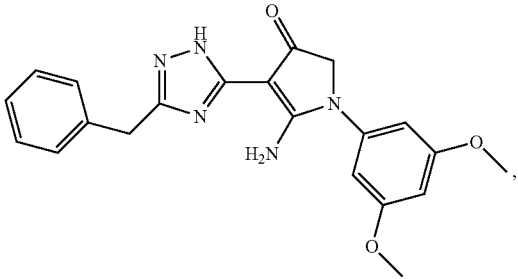
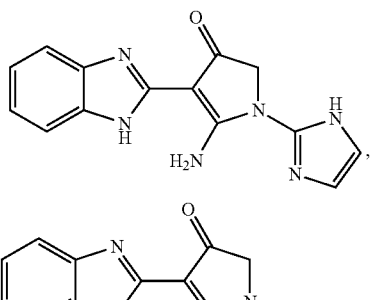
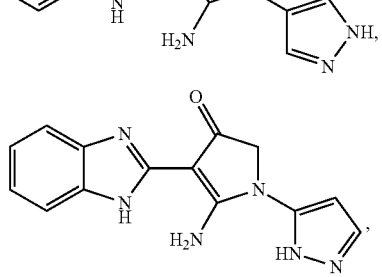

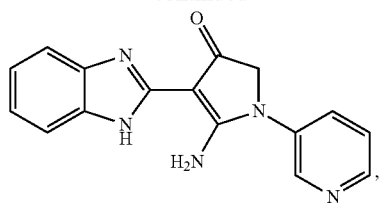
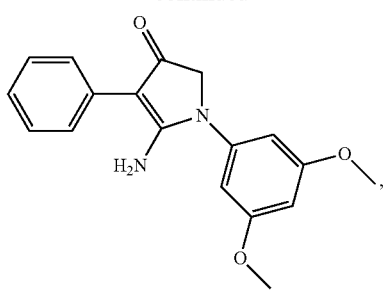
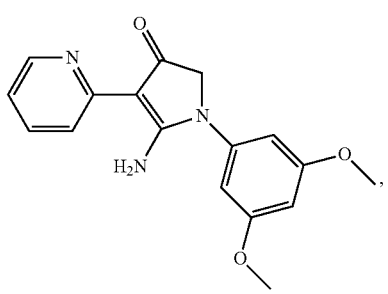
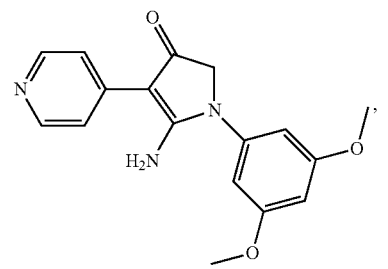
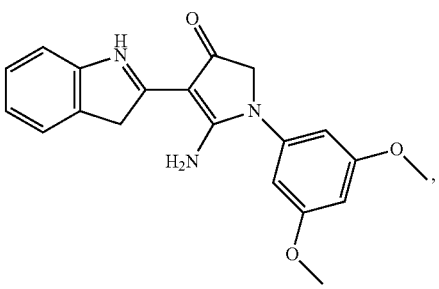
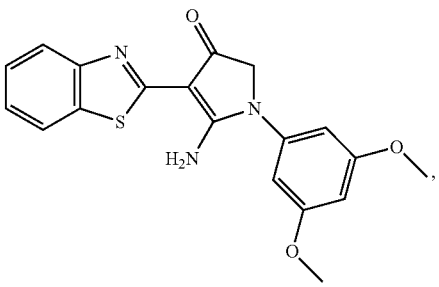
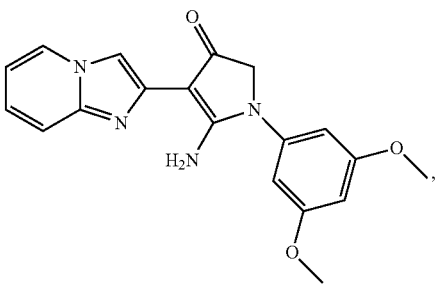

37
-continued
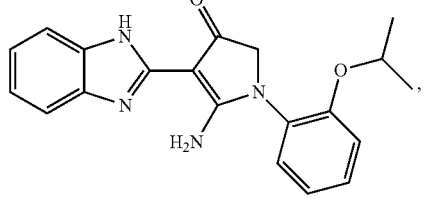
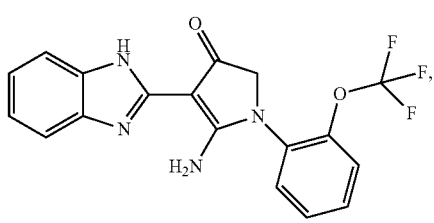
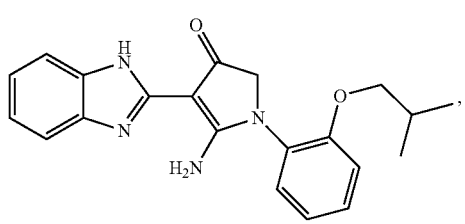
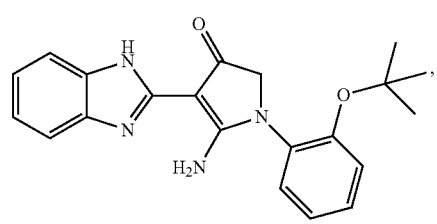
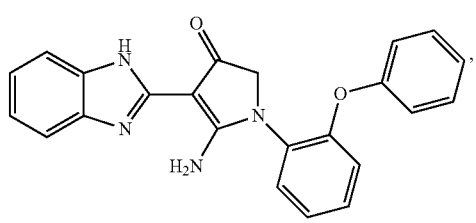
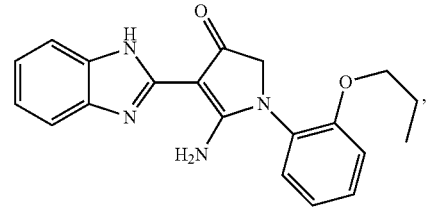
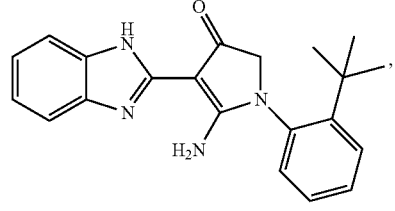
38
-continued
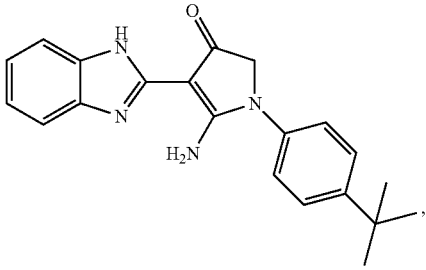
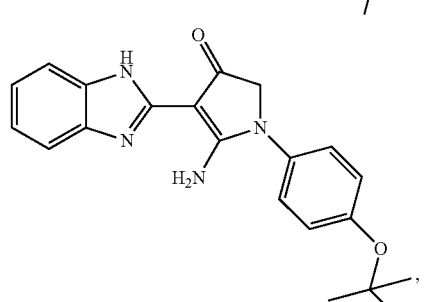
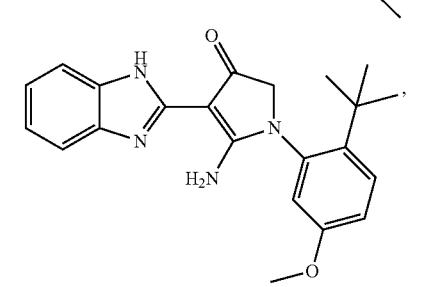
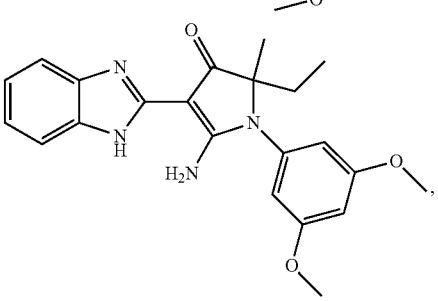
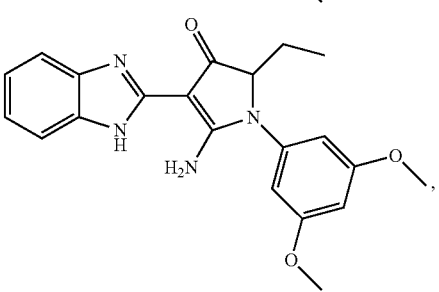
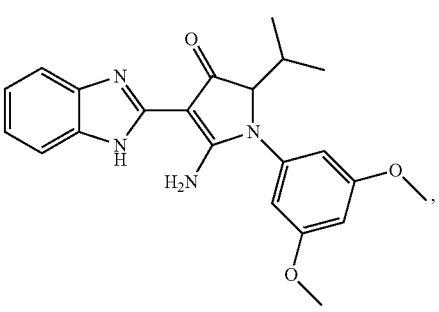

-continued
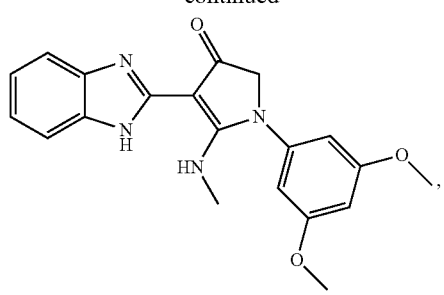
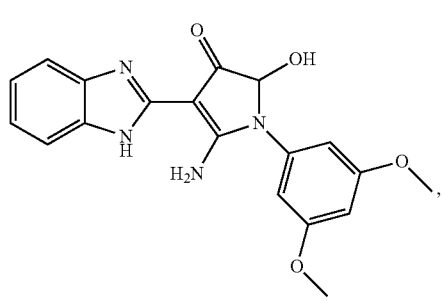
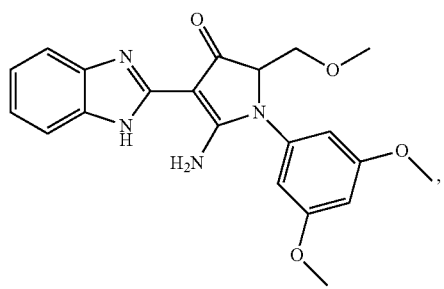
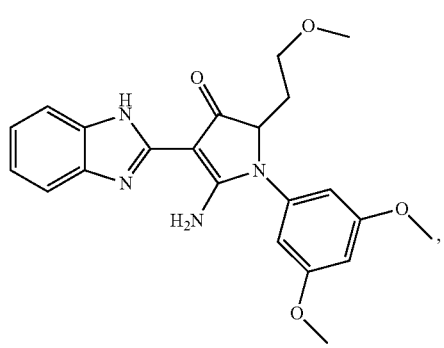
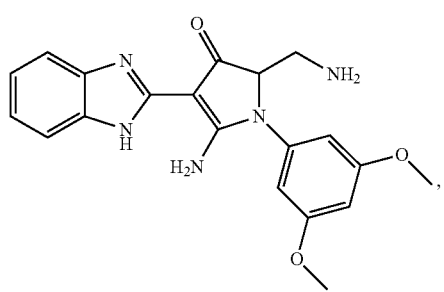
-continued
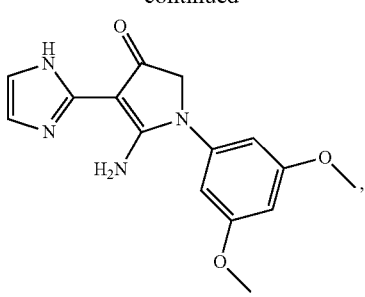
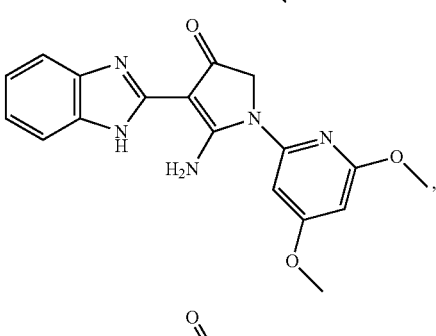
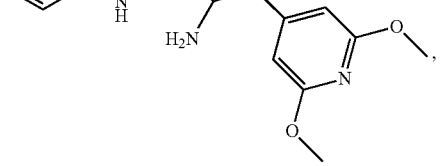
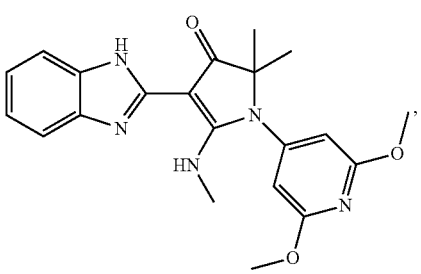
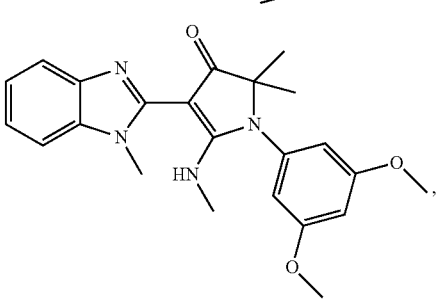
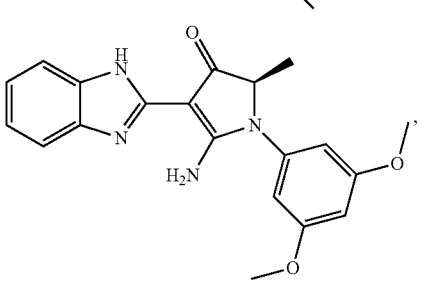

-continued

-continued
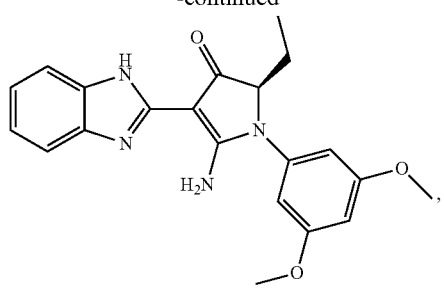
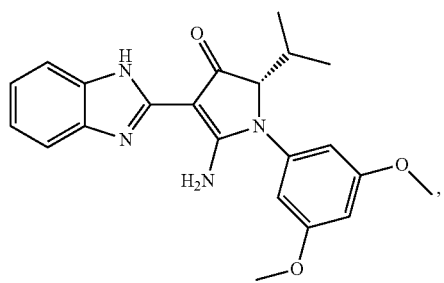
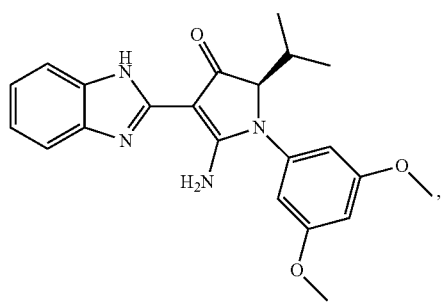
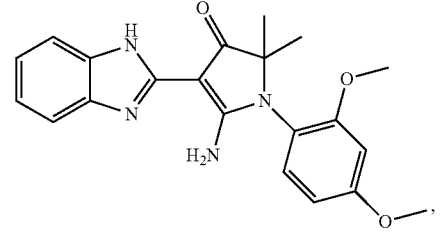
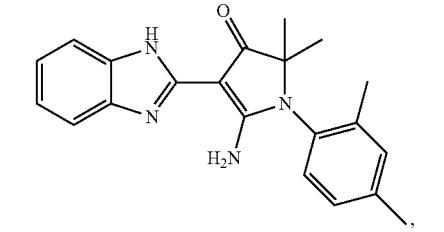
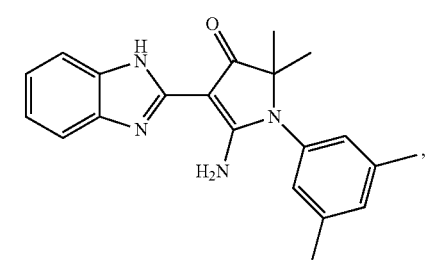
-continued
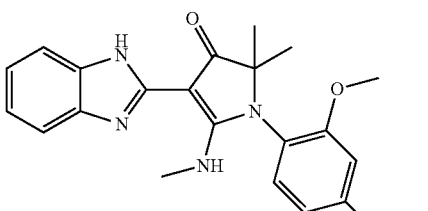
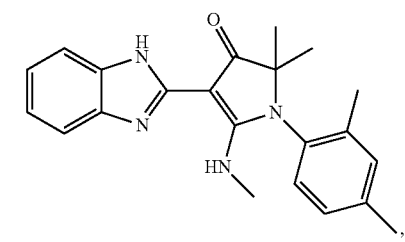
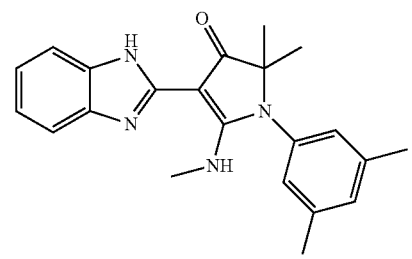
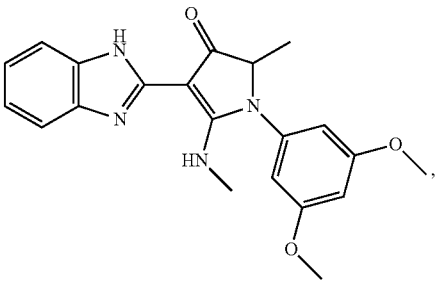
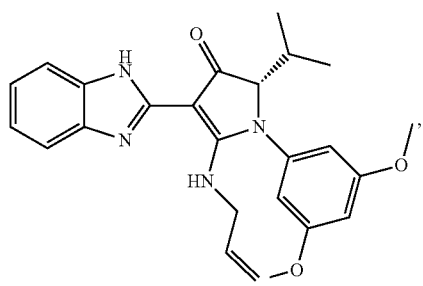
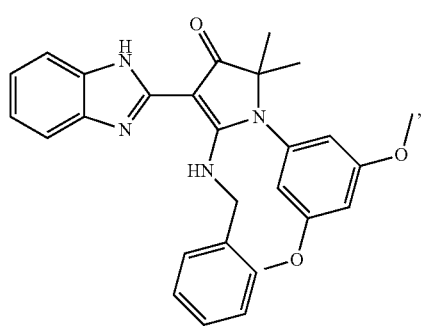

-continued
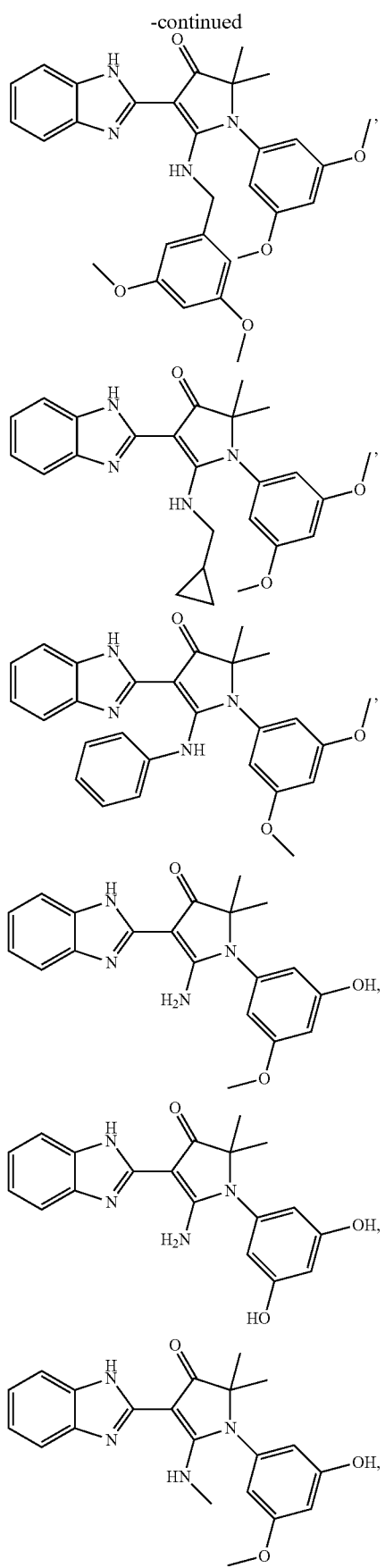
-continued
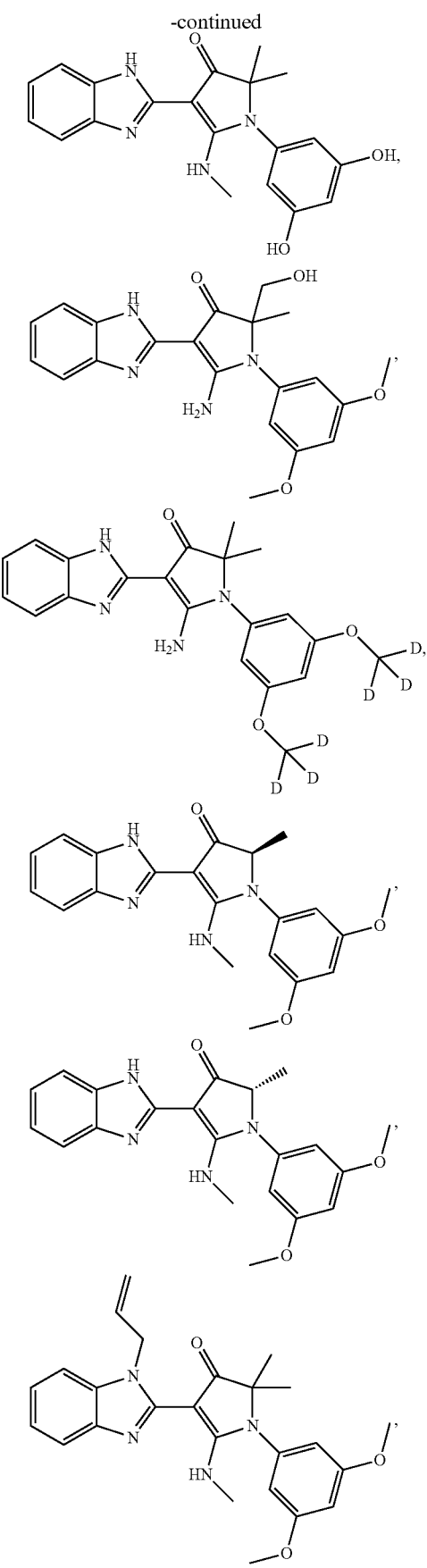

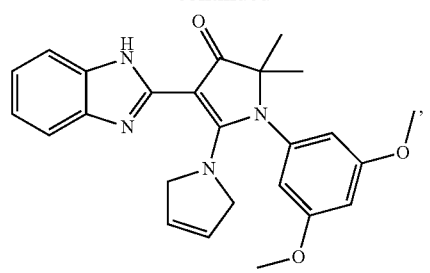
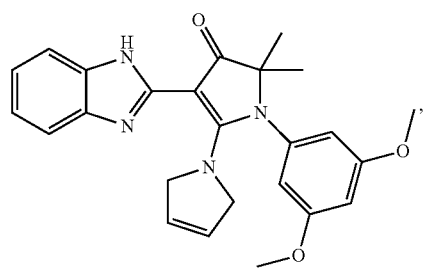
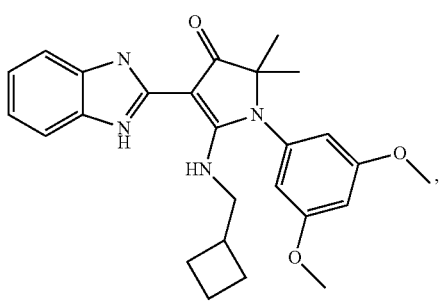
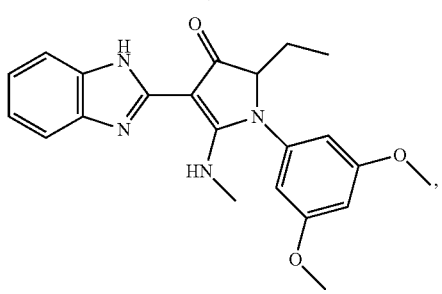
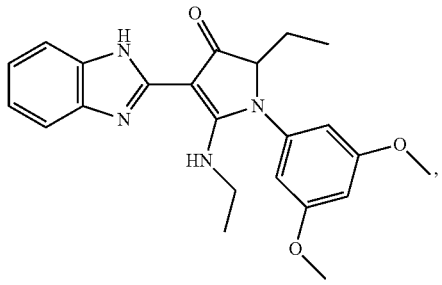
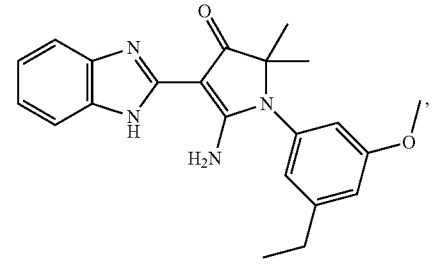
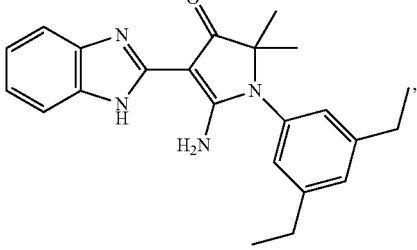
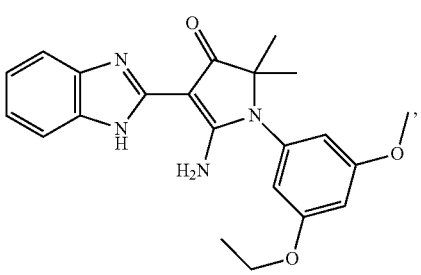
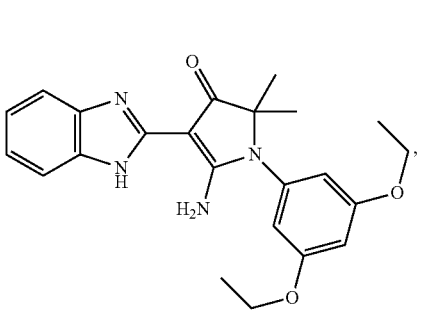
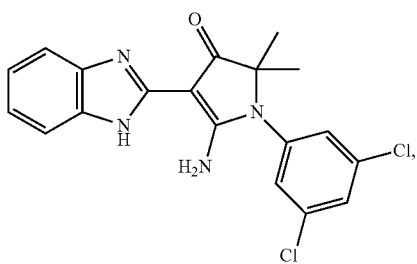
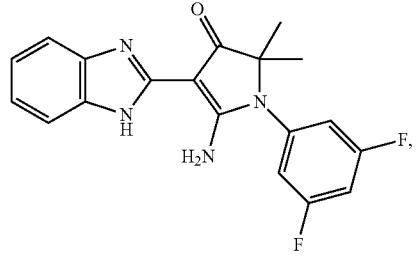
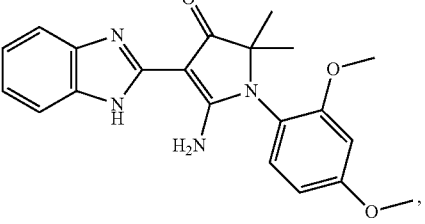

49
-continued
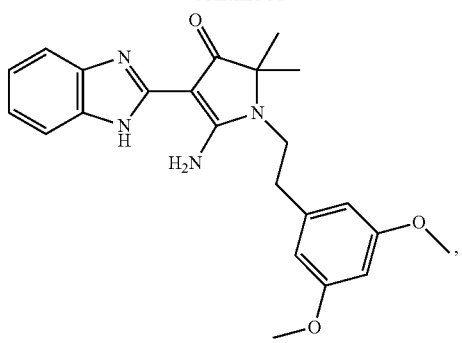
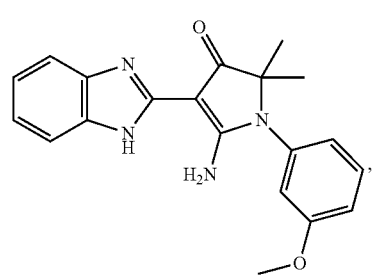
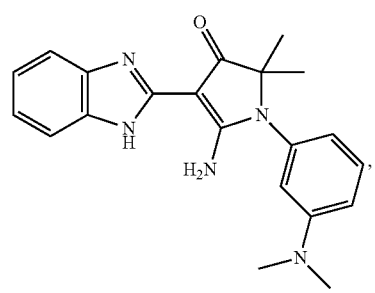
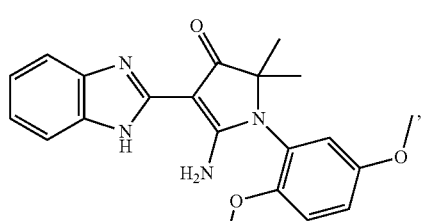
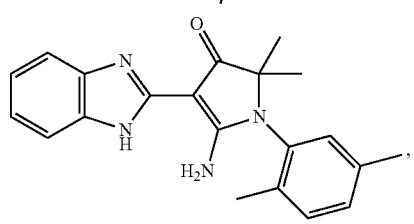
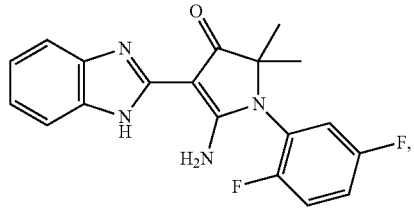
50
-continued
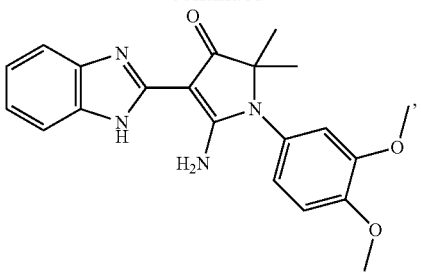
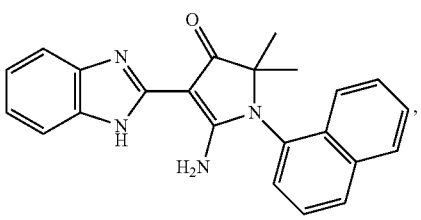
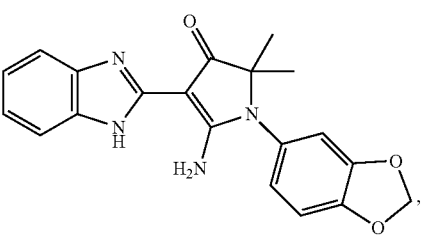
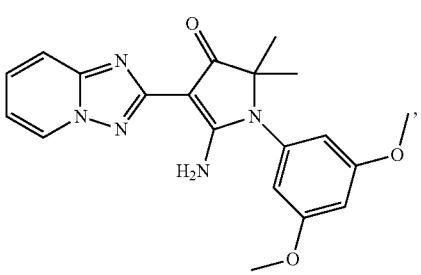
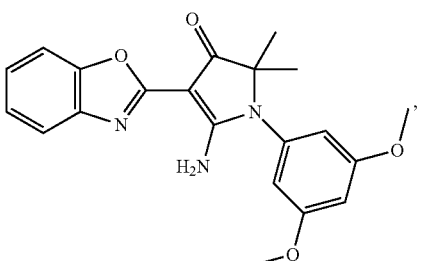
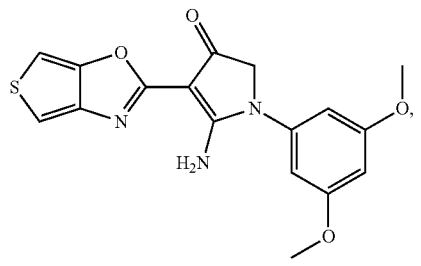

-continued
51
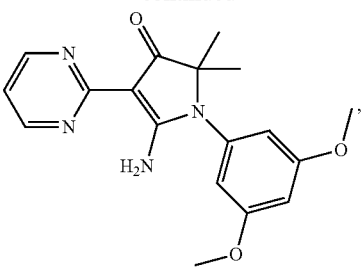
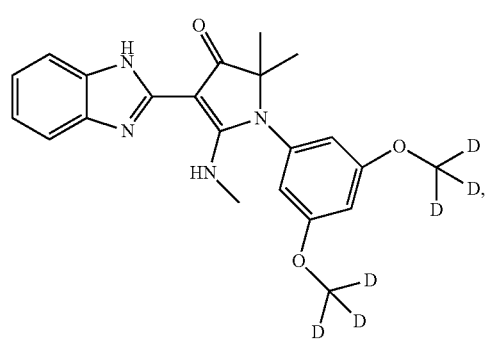
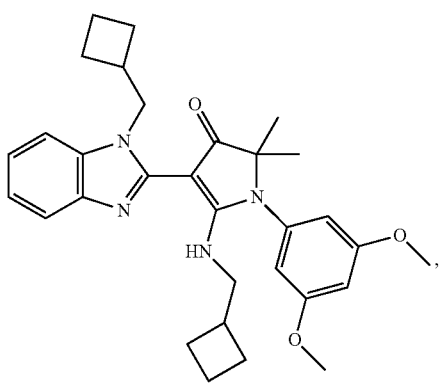
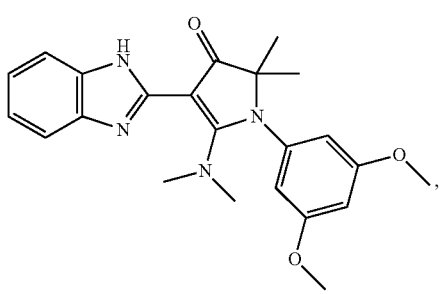
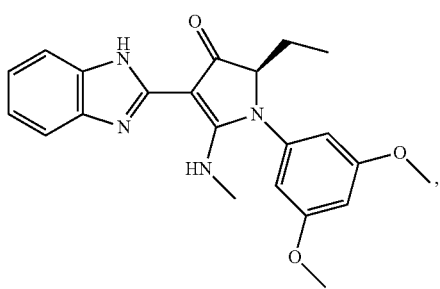
-continued
52
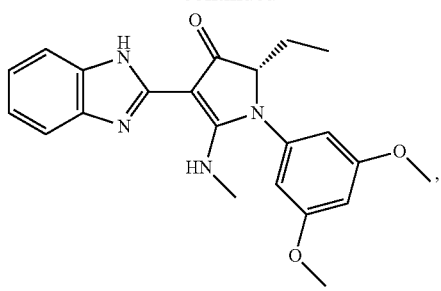
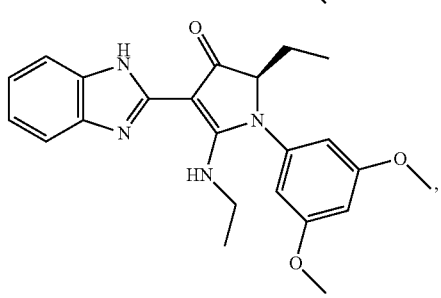
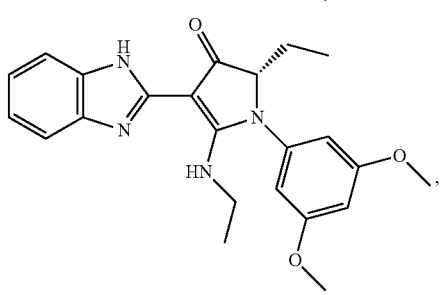
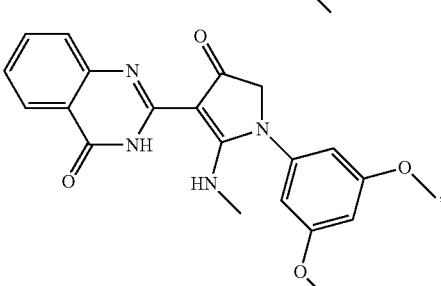
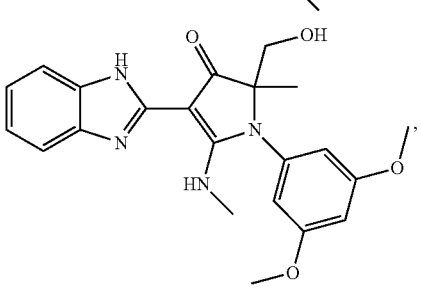

53
-continued
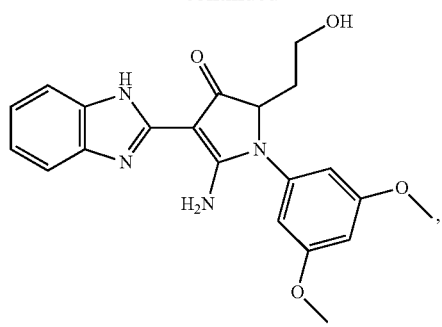
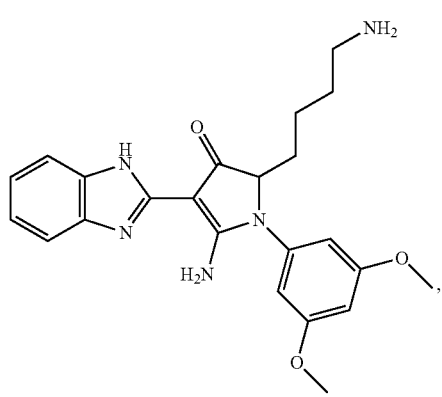
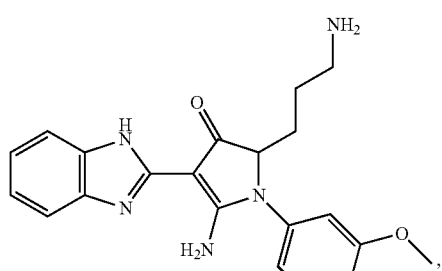
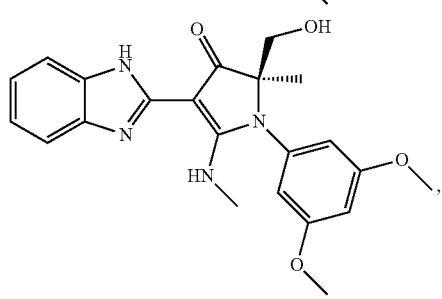
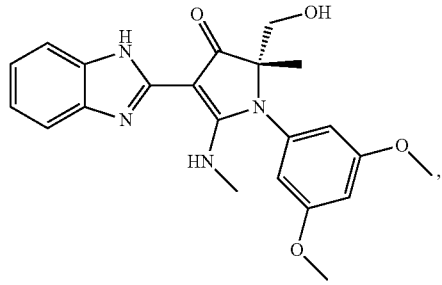
54
-continued
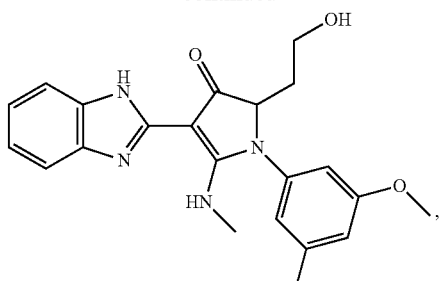
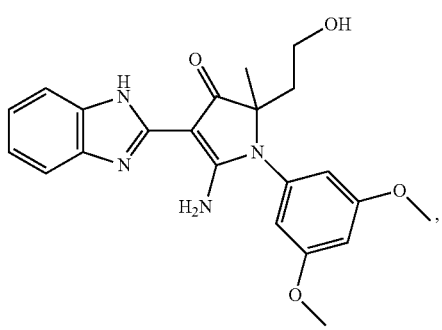
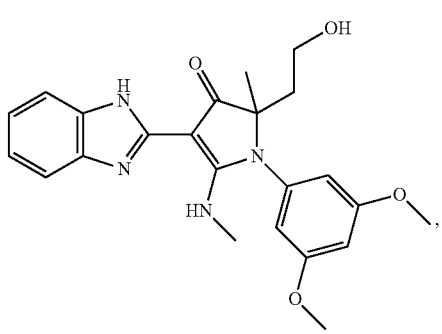
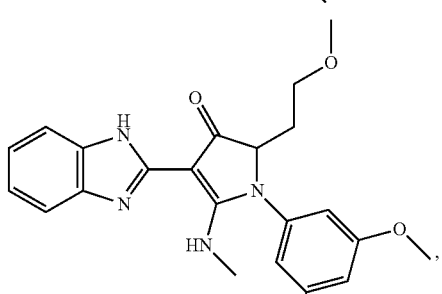
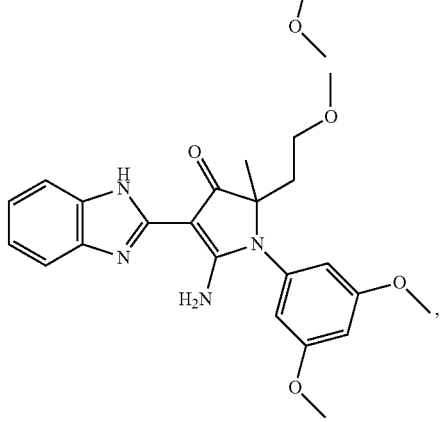

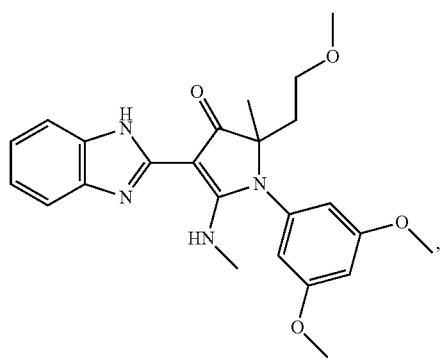
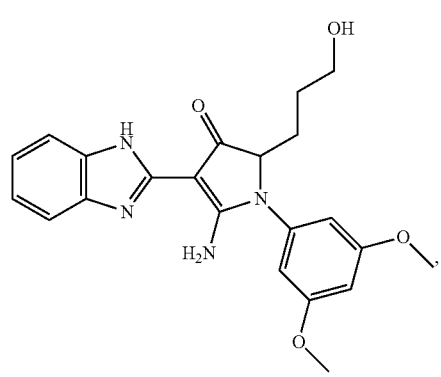
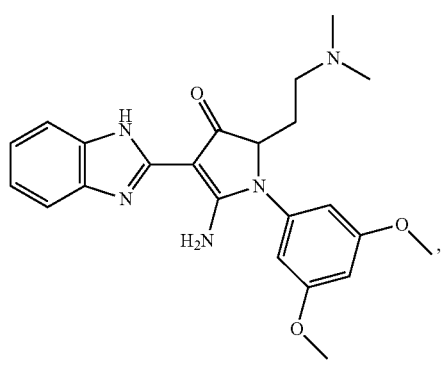
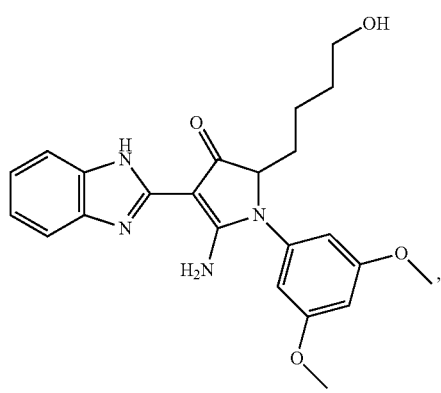
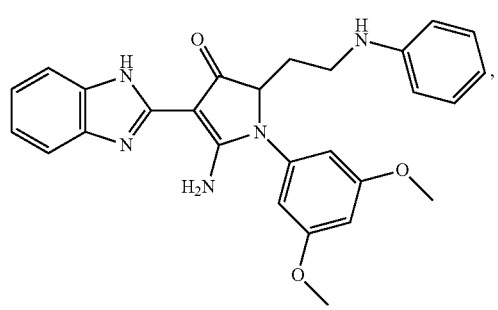
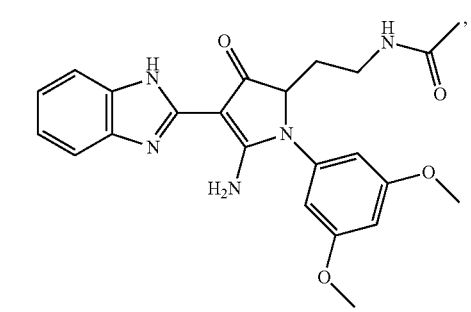
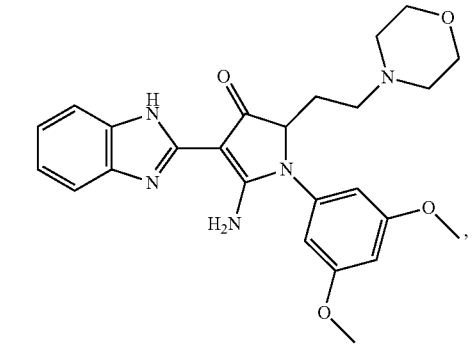
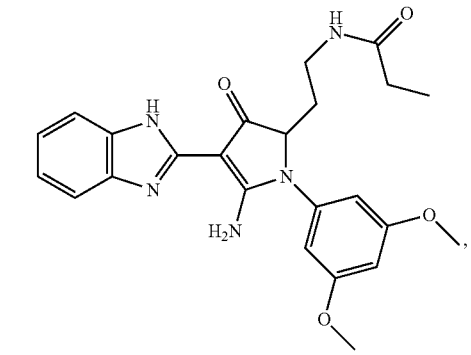

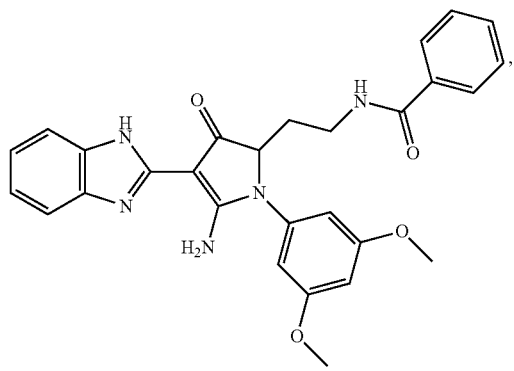
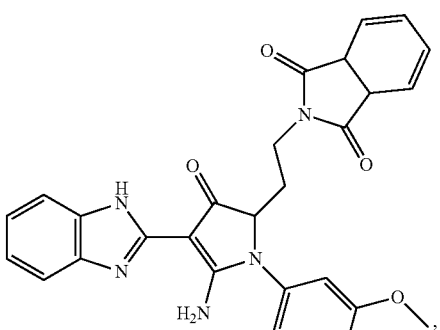
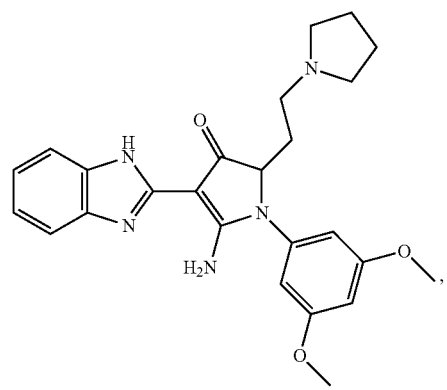
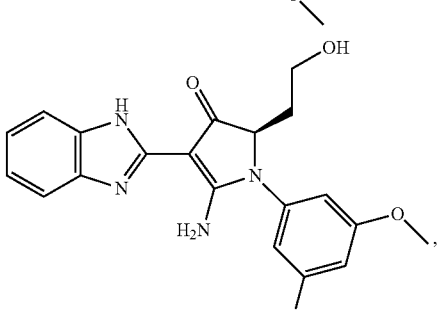
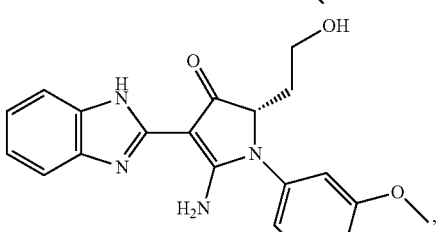
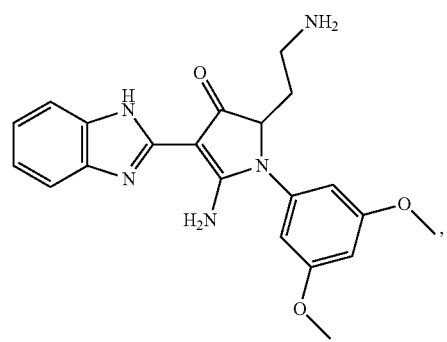
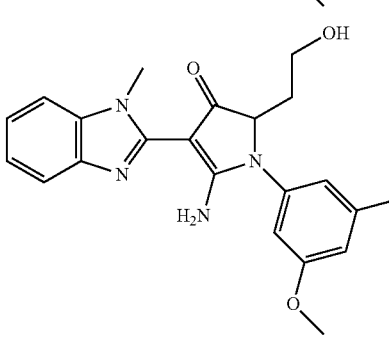
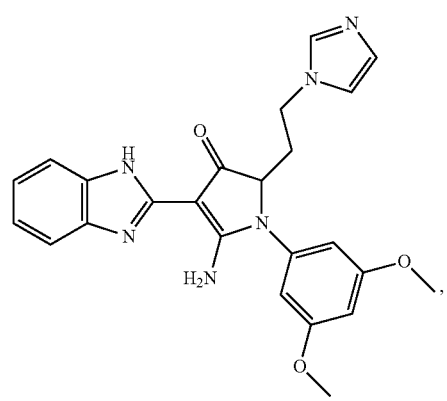
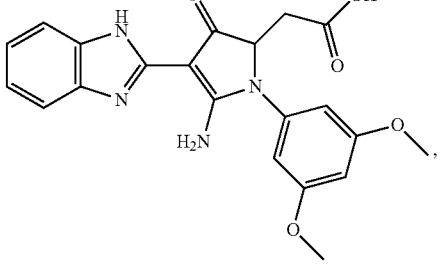

59
-continued
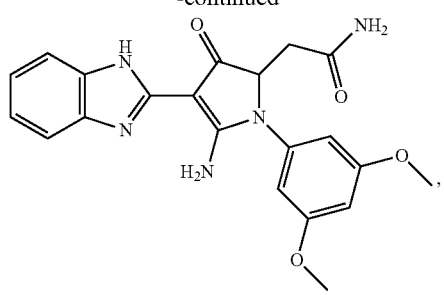
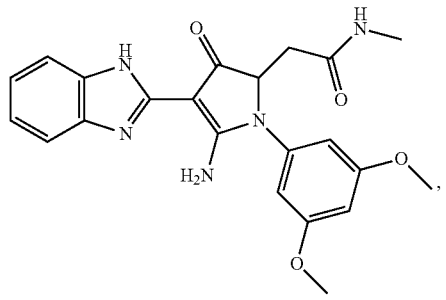
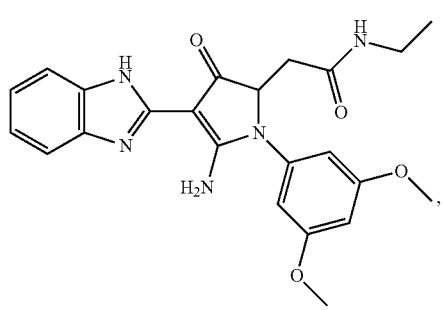
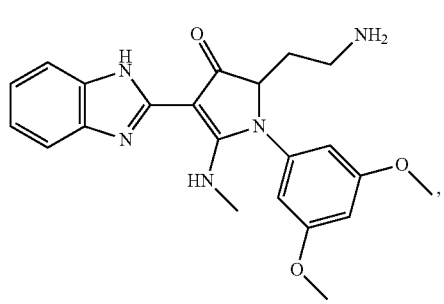
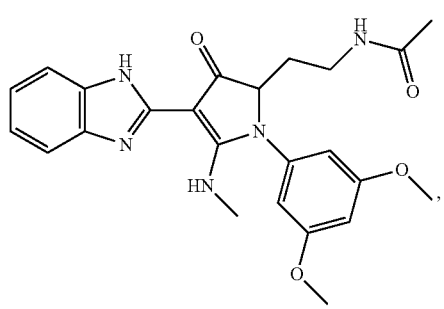
60
-continued
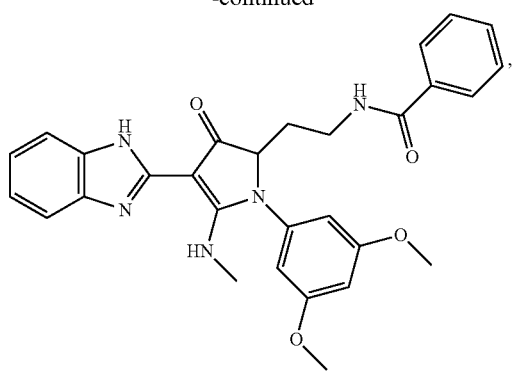
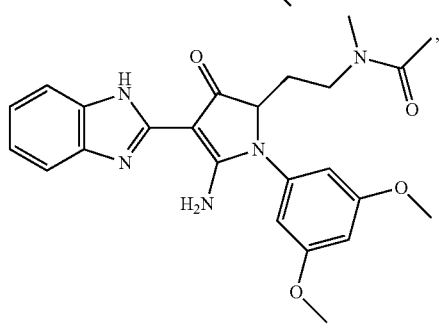
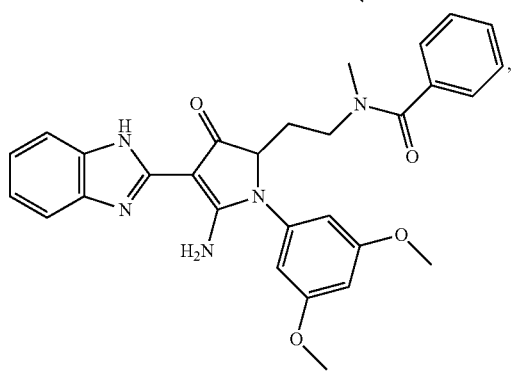
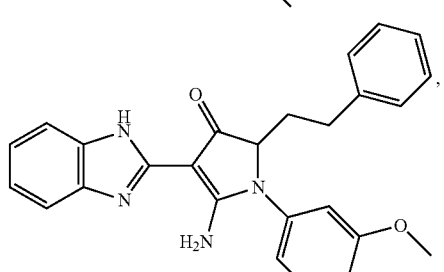
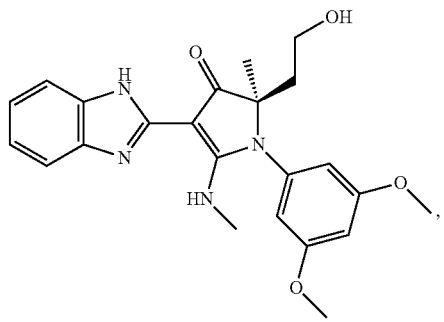

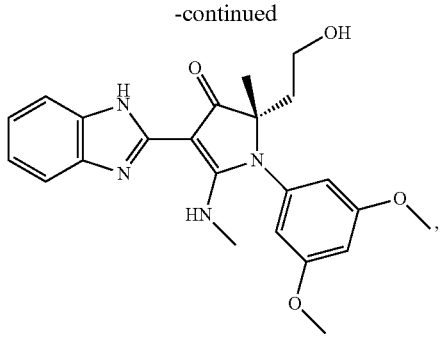
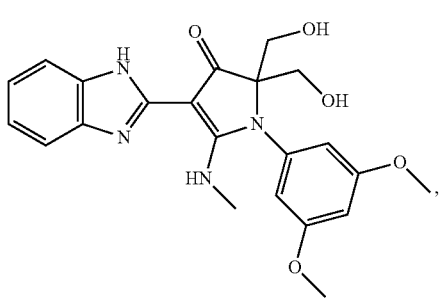
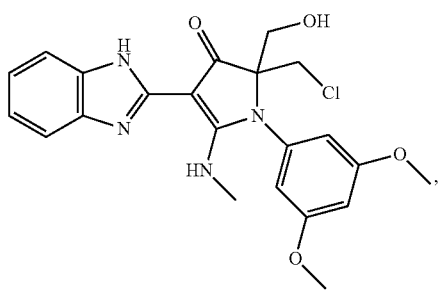
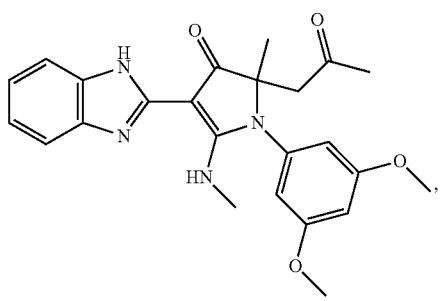

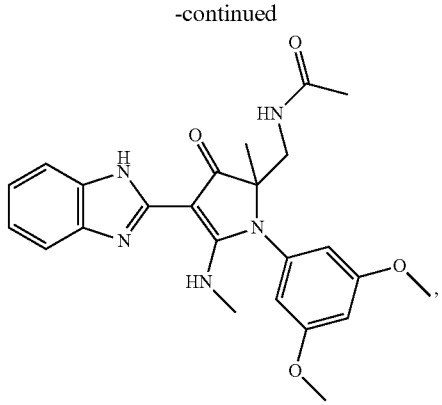
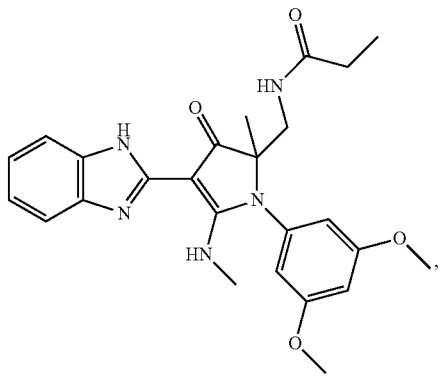
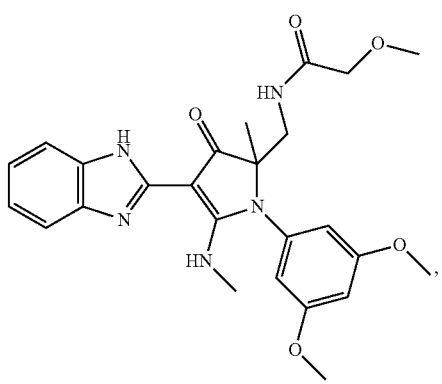
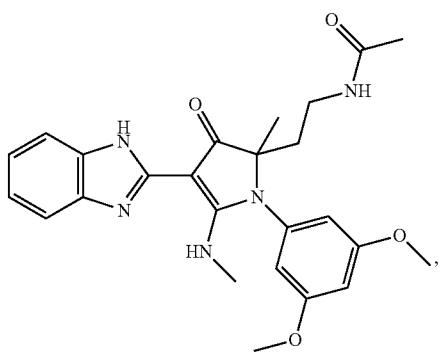

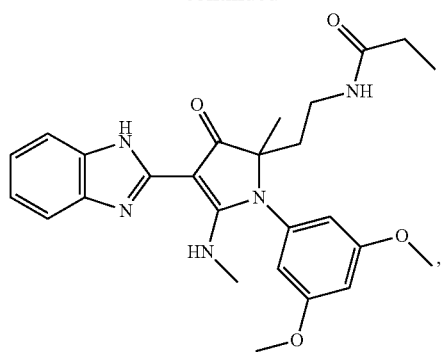
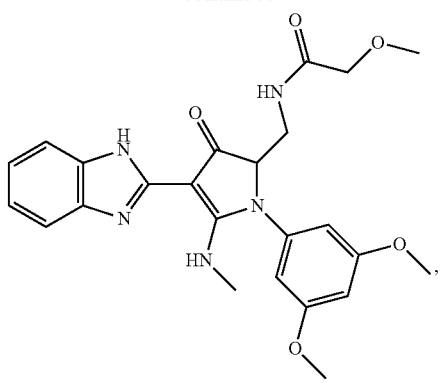
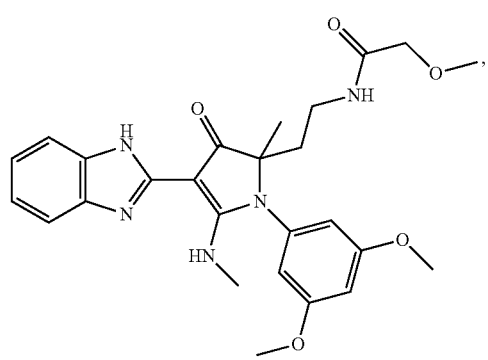
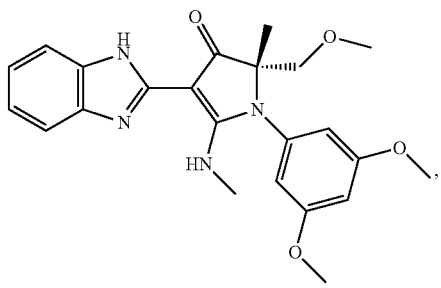
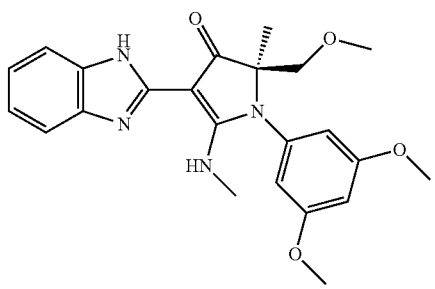
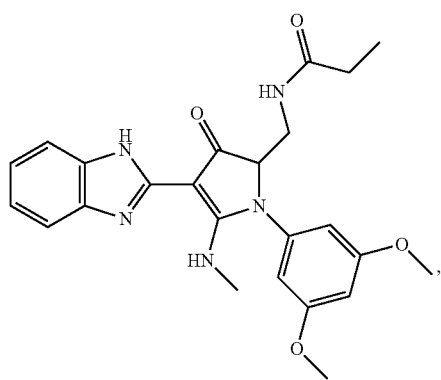
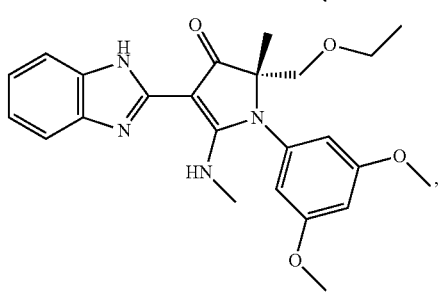

-continued
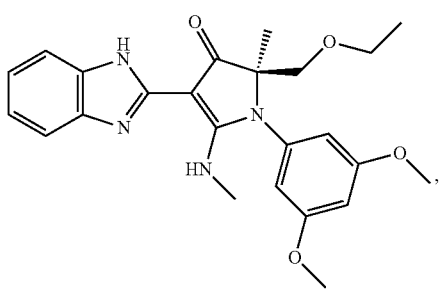
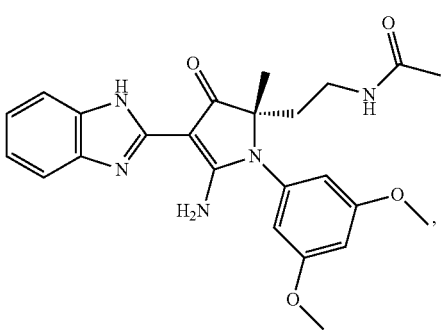
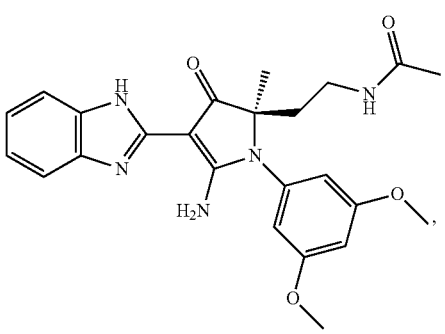
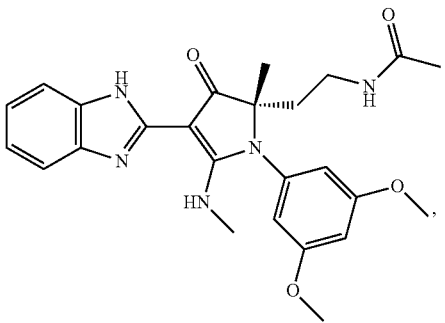
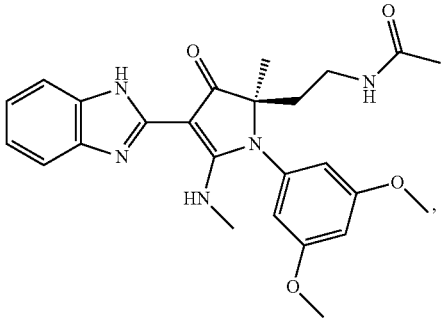
-continued
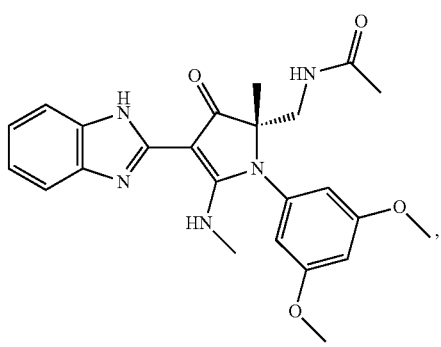
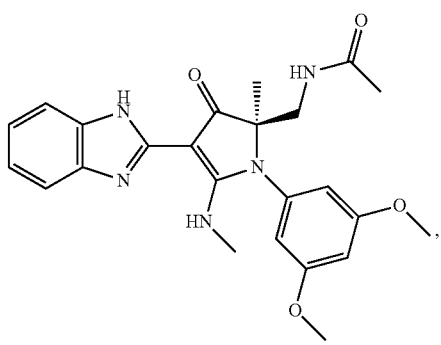
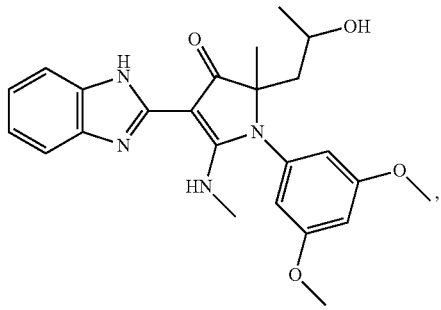
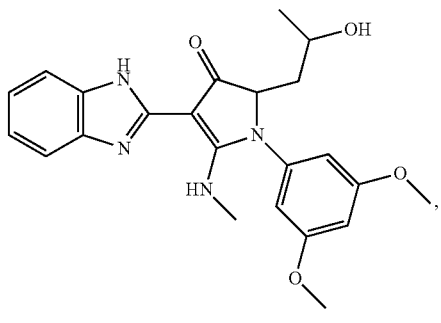
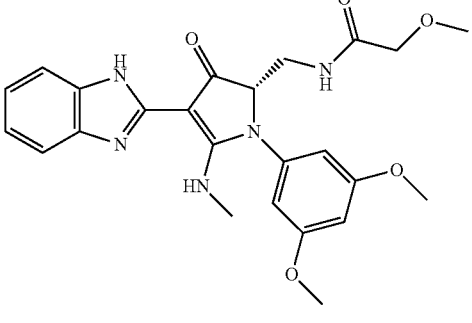

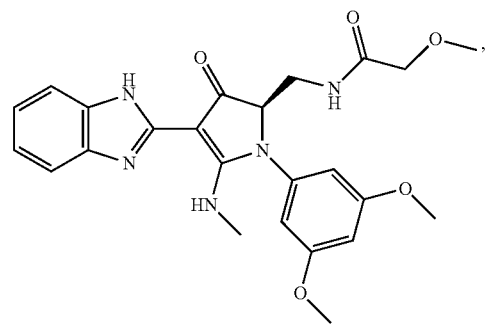

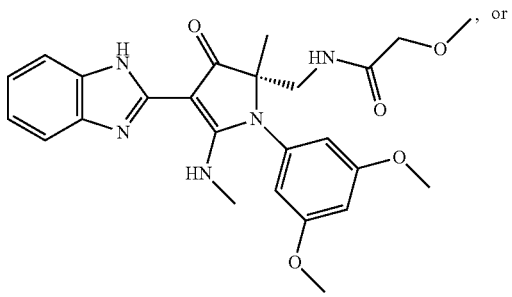

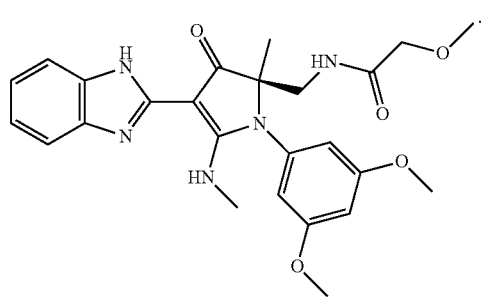

In one embodiment, X is CR⁷R⁸, wherein one of R⁷ and R⁸ is OR³, and the other is H or optionally substituted alkyl. Specific examples include, but are not limited to:

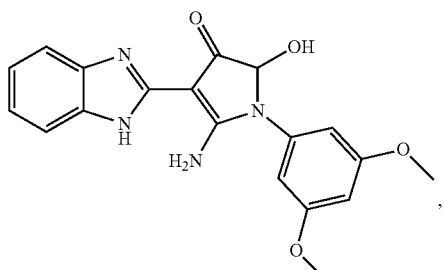

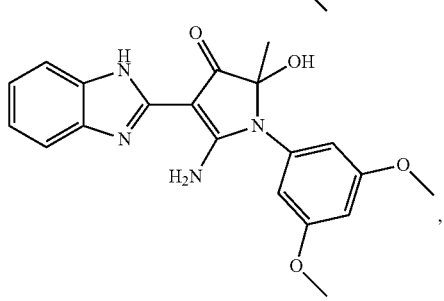

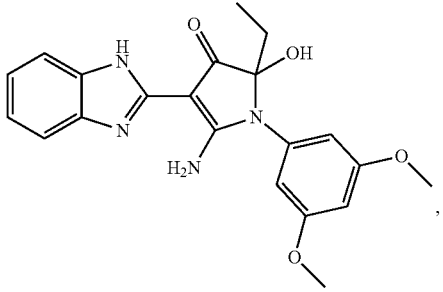

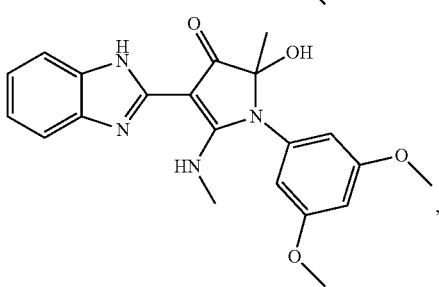

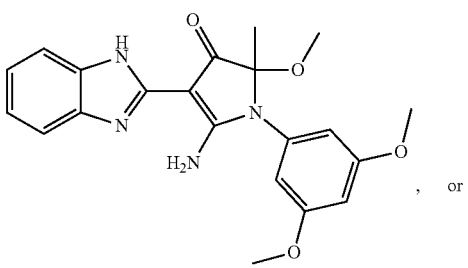

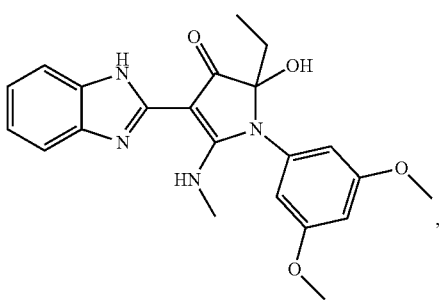

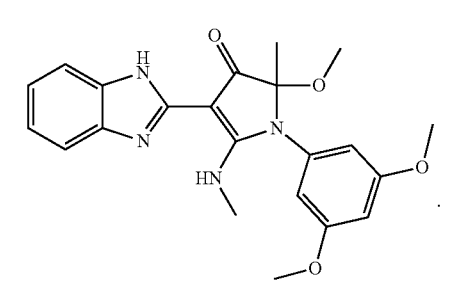 [SMILES: CNC1=C(c2nc3ccccc3[nH]2)C(=O)C(C)(OC)N1c1cc(OC)cc(OC)c1]

In one embodiment, X is CR⁷R⁸, wherein one of R⁷ and R⁸ is optionally substituted aryl or optionally substituted heteroaryl, and the other is H or optionally substituted alkyl. Specific examples include, but are not limited to:

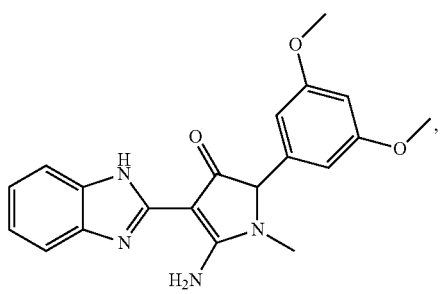
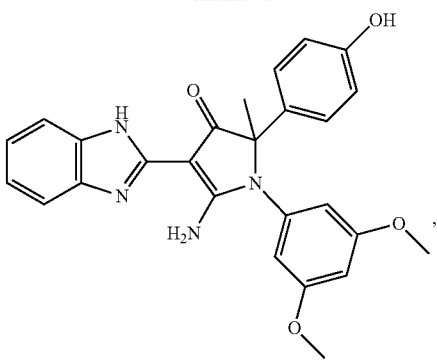
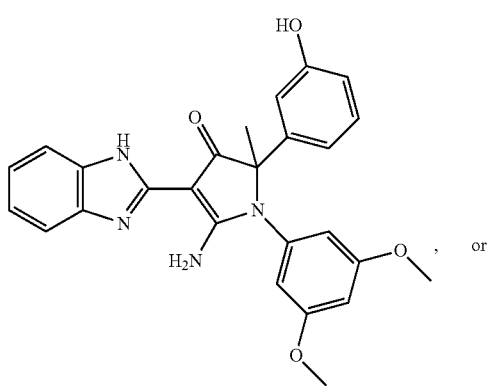
In one embodiment, X is CR$^7$R$^8$, wherein one of R$^7$ and R$^8$ is —C(O)OR$^3$ or —C(O)R$^3$, and the other is H, —OR$^3$, or optionally substituted alkyl; wherein R$^3$ can be the same or different. Specific examples include, but are not limited to:

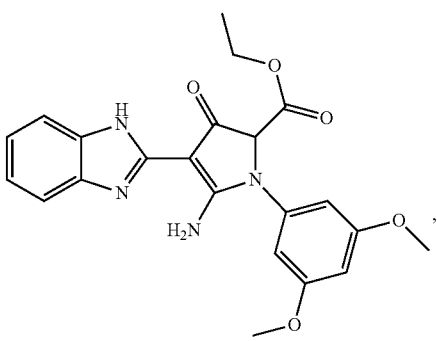

71
-continued
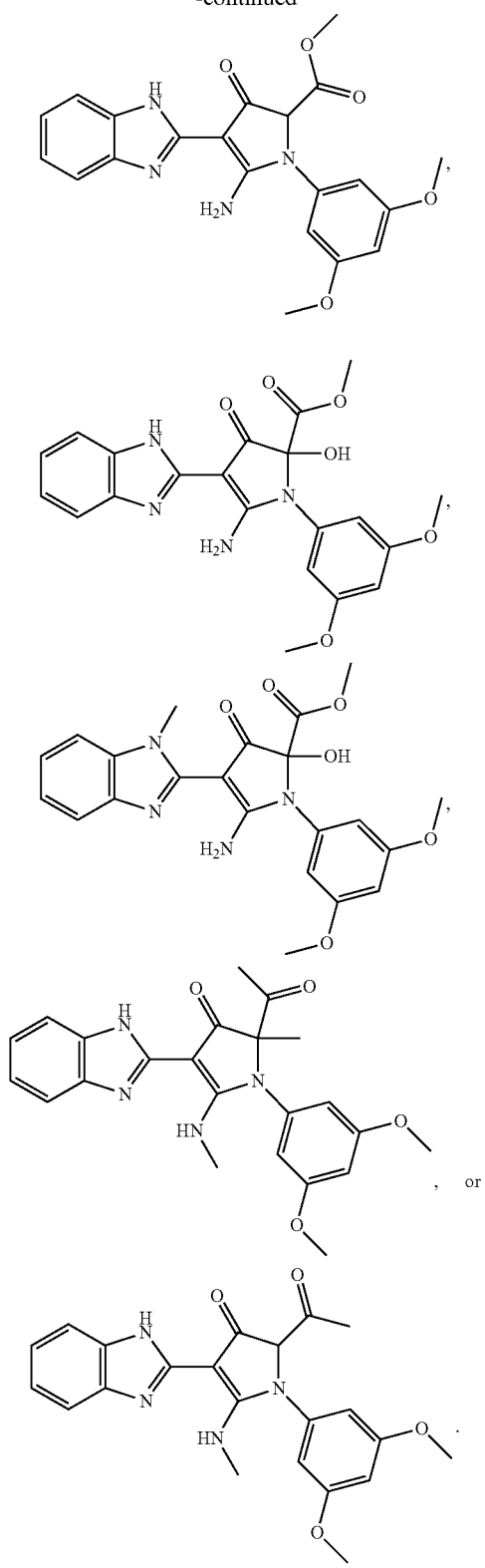
, or
72
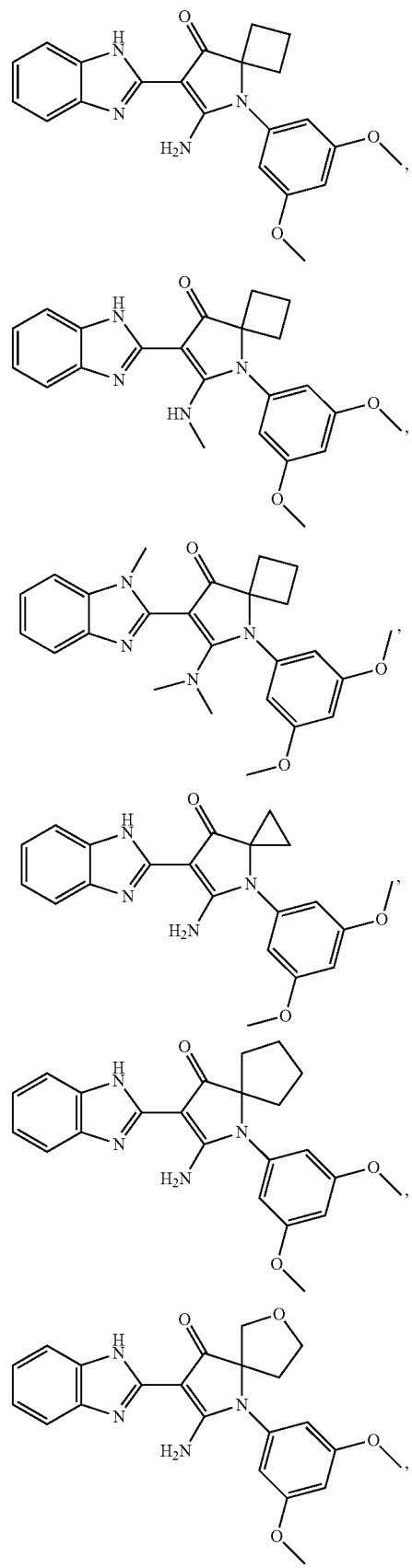
In one embodiment, X is $CR^7R^8$, wherein $R^7$ and $R^8$ together with the carbon atom to which they are attached form an optionally substituted 3- to 8-membered cycloalkyl or heterocyclyl ring. Specific examples include, but are not limited to:

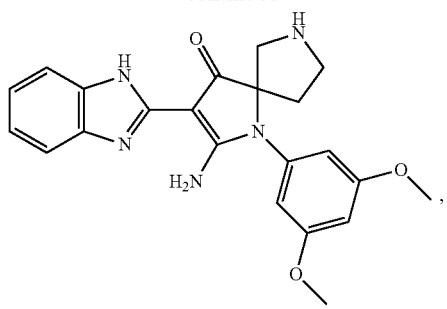
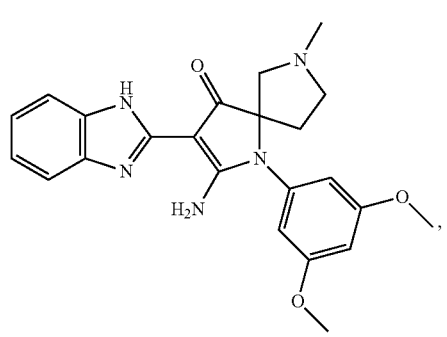
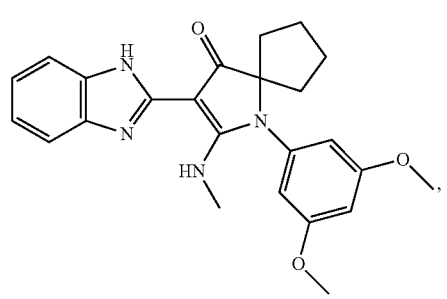
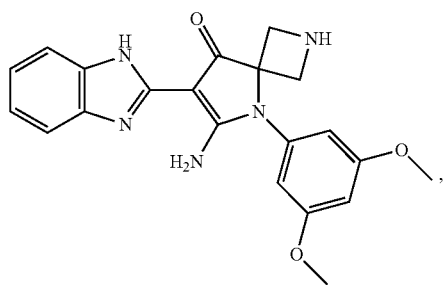
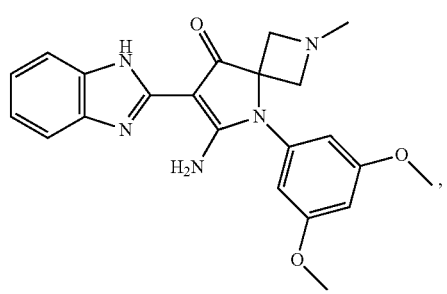
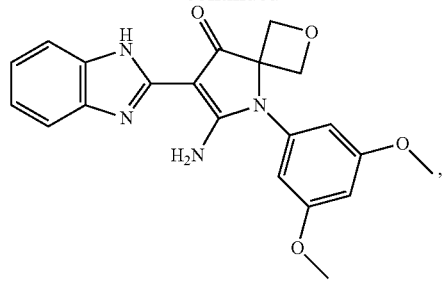
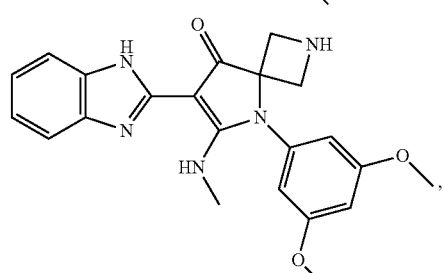
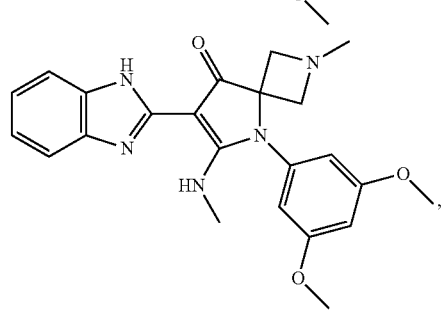
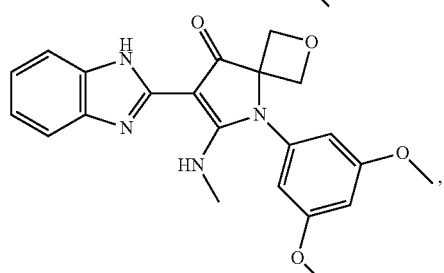
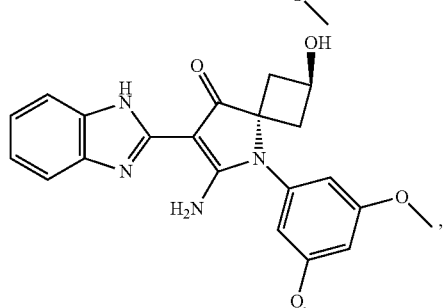
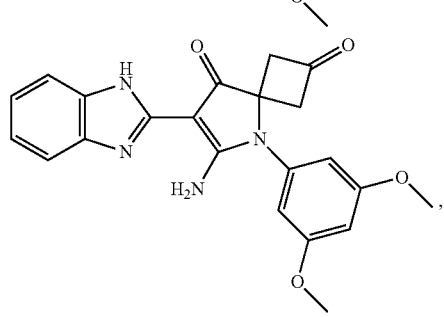

75
-continued
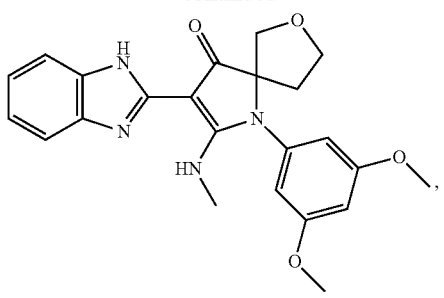
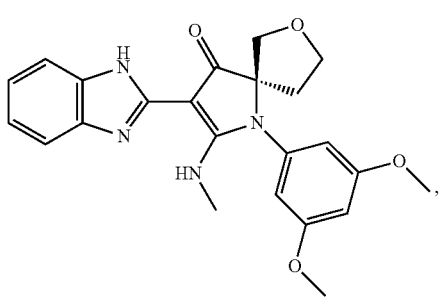
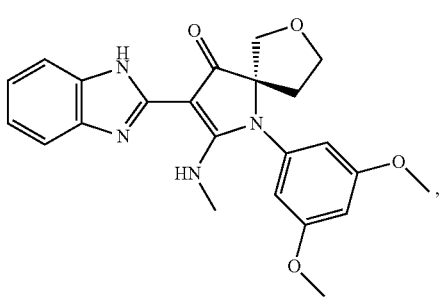
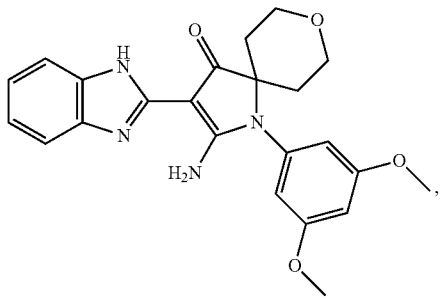
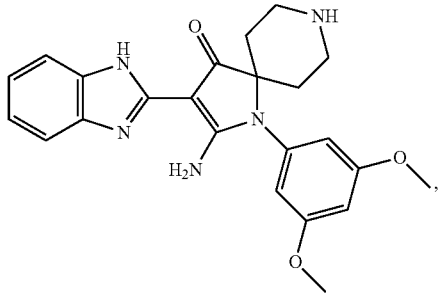
76
-continued
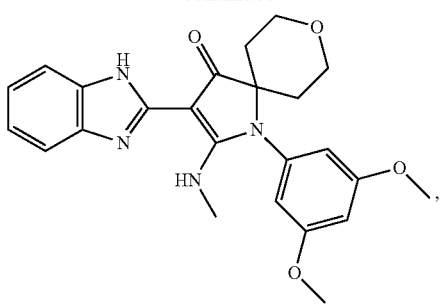
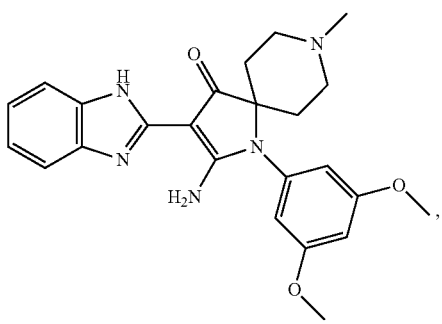
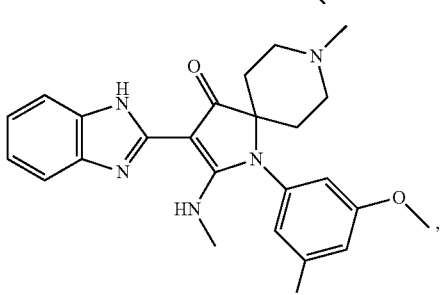
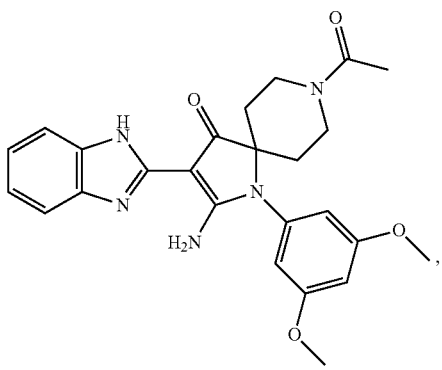
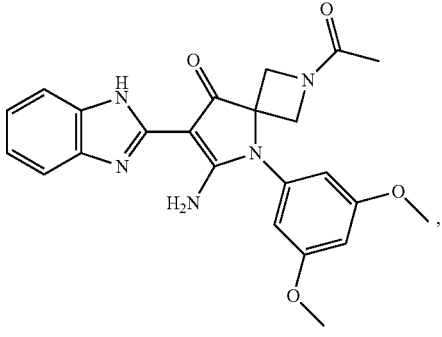

77
-continued
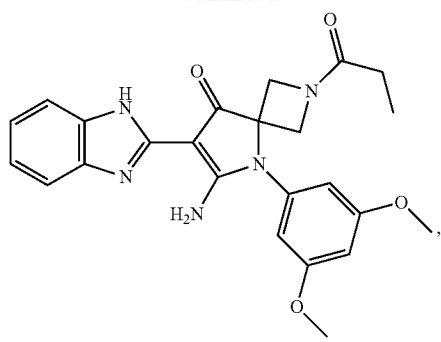
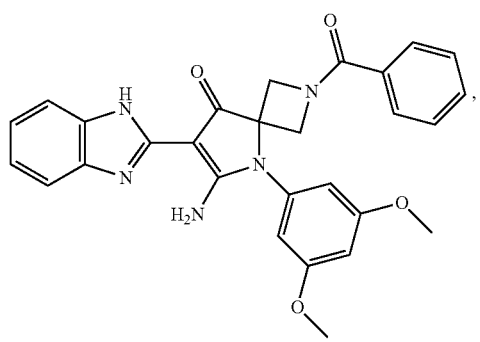
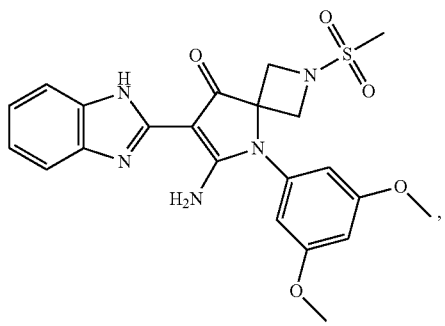
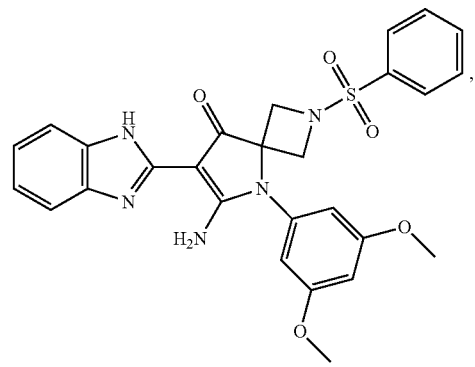
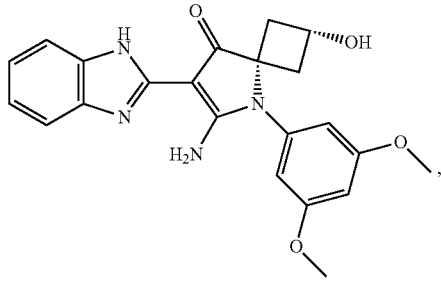
78
-continued
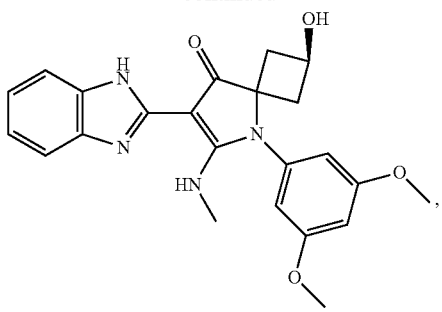
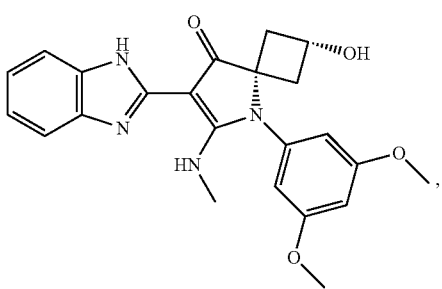
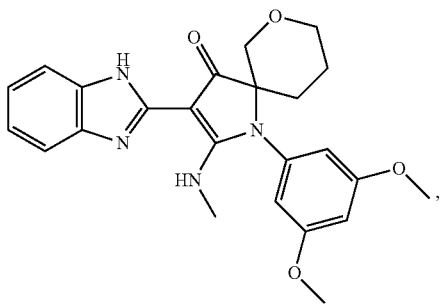
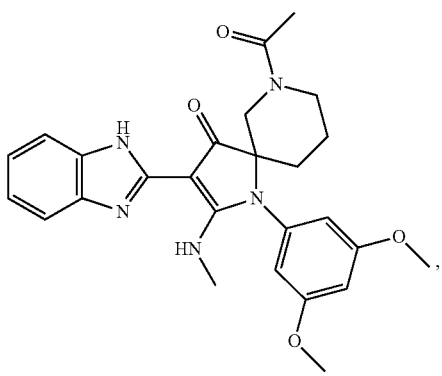
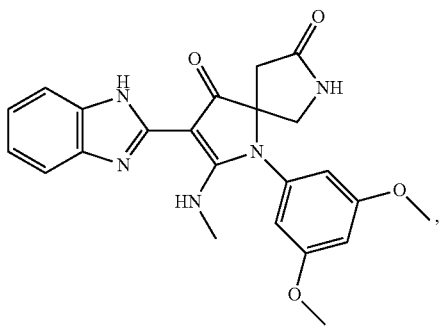

-continued
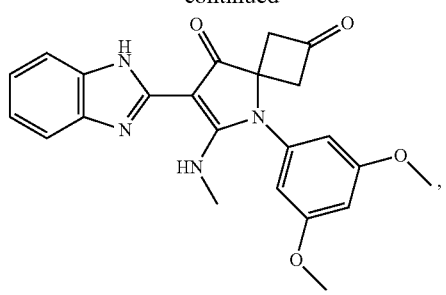
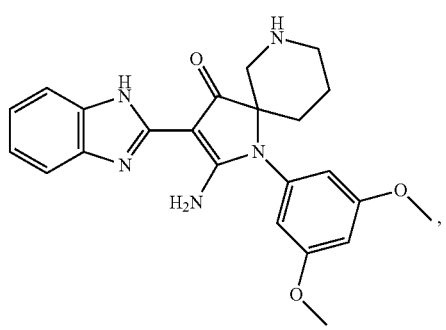
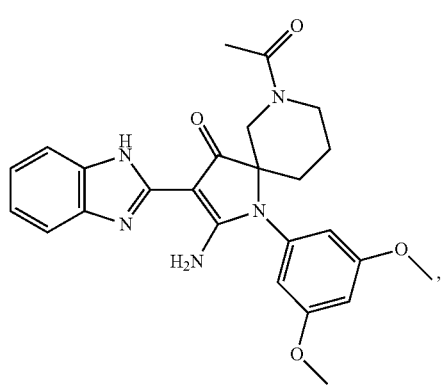
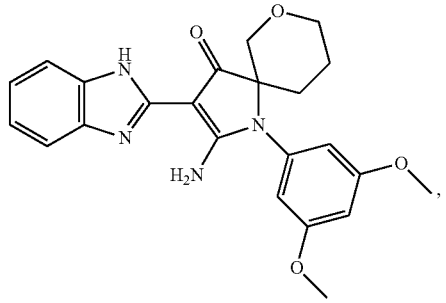
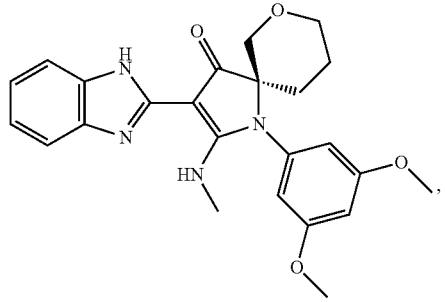
-continued
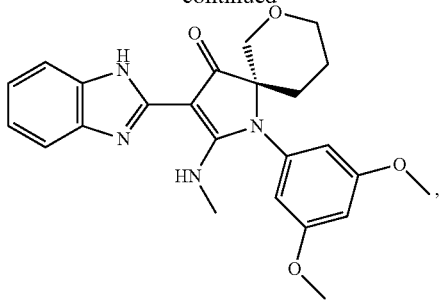
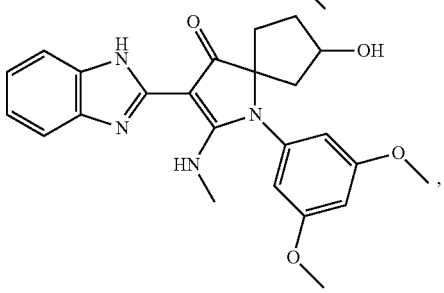
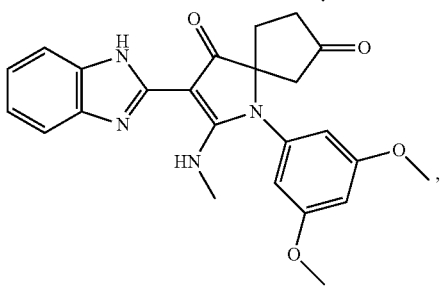
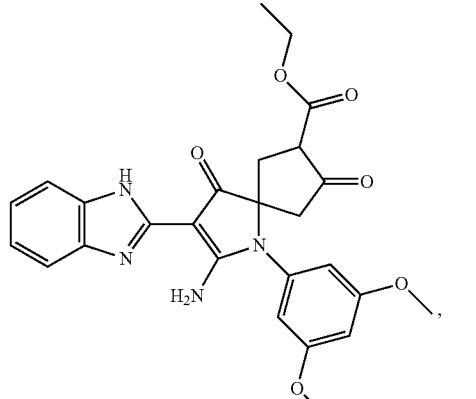, or
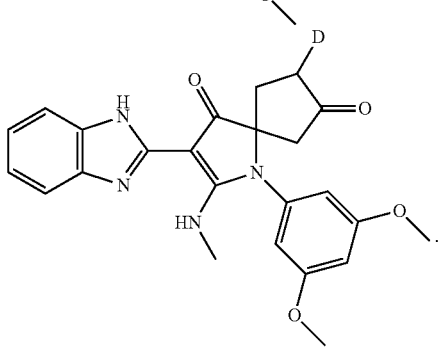.
In one embodiment, X is C=CR⁷R⁸. In specific embodiments, at least one of $R^7$ and $R^8$ is H, and the other is defined herein elsewhere. In specific embodiments, both $R^7$ and $R^8$ are H. Specific examples include, but are not limited to:

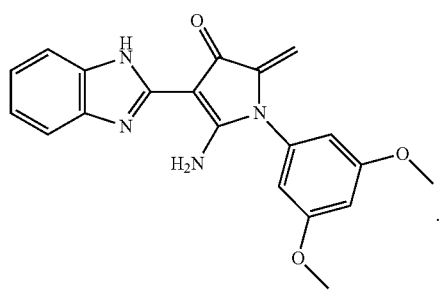 [SMILES: C=C1C(=O)C(c2nc3ccccc3[nH]2)=C(N)N1c1cc(OC)cc(OC)c1]
In one embodiment, X is NR⁹. Specific examples include, but are not limited to:
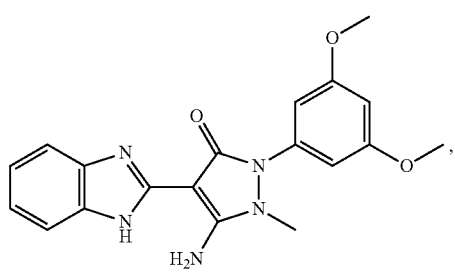
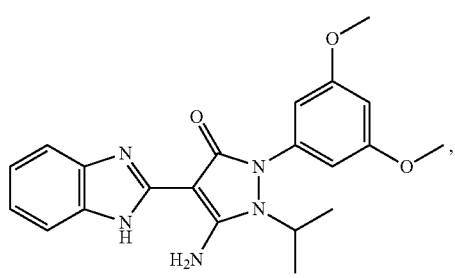
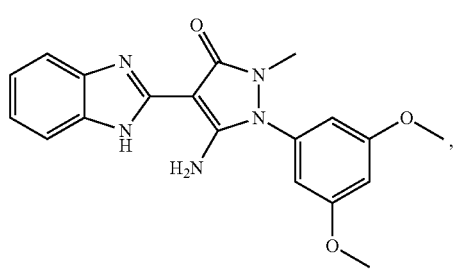
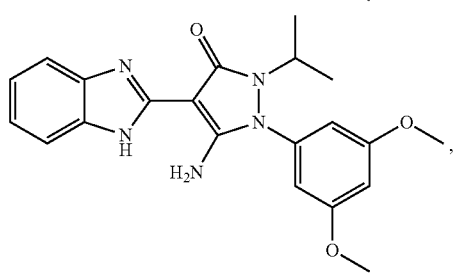
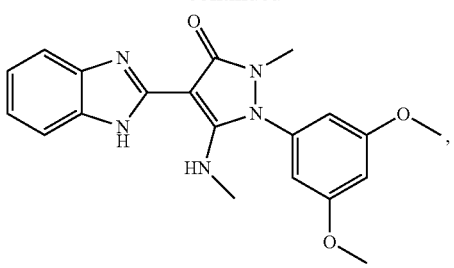
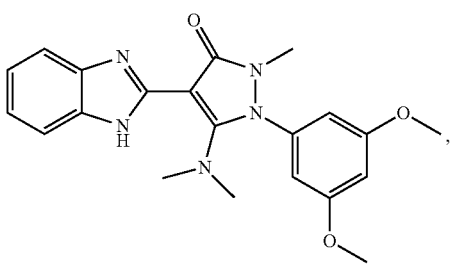
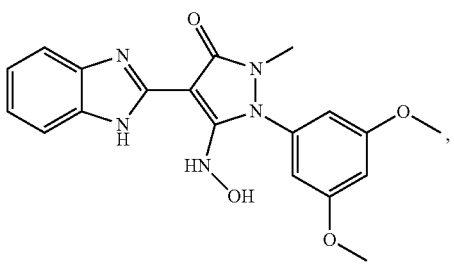
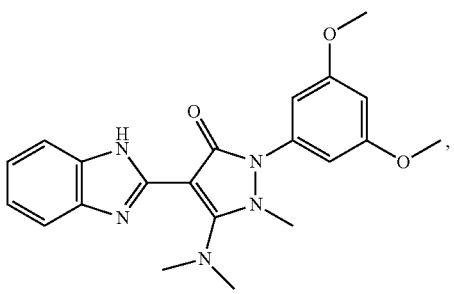
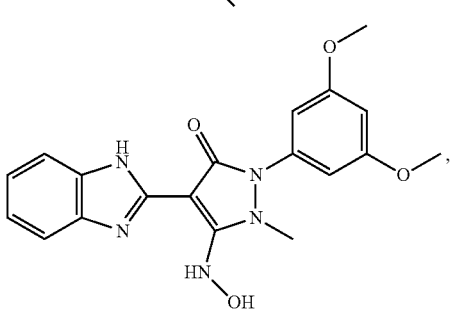
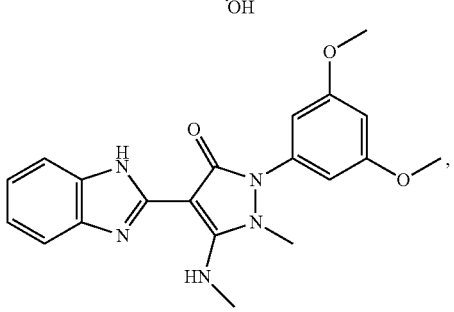

-continued
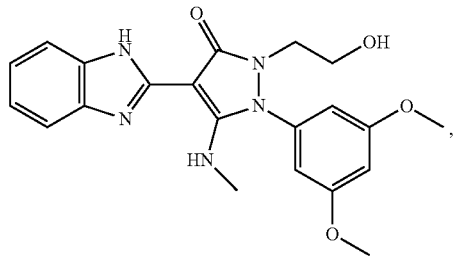
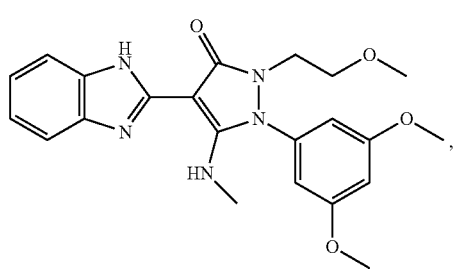
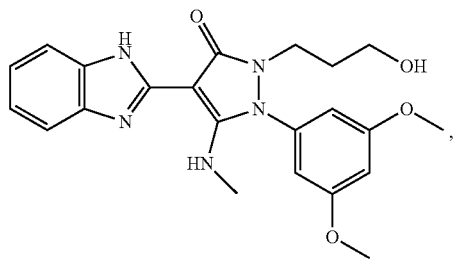
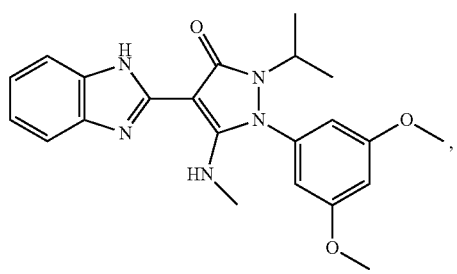
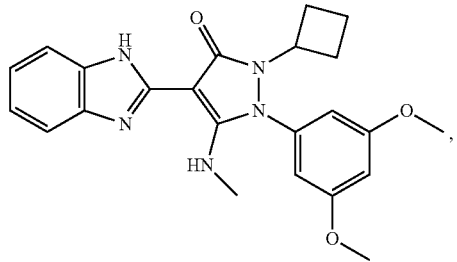
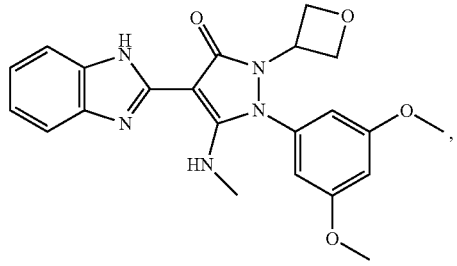
-continued
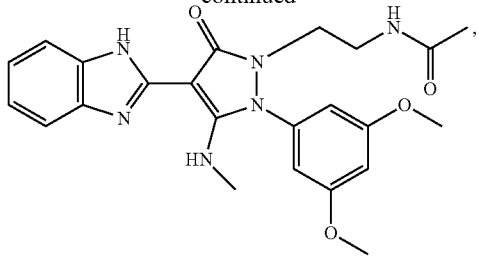
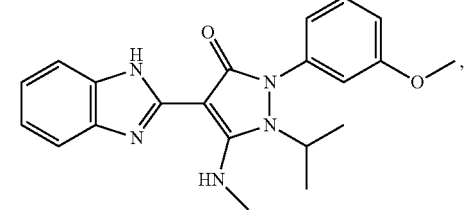
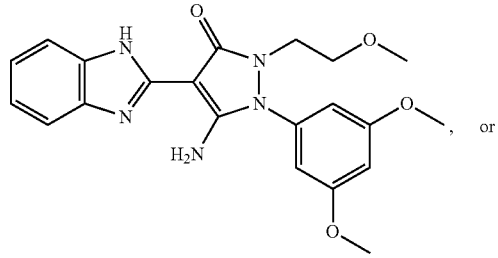
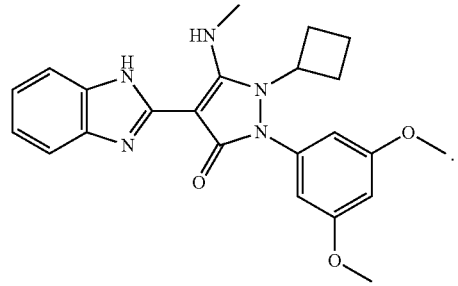
In one embodiment, X is NH in a compound of formula (Ib). The compound can have one or more tautomeric forms, for example, a compound of formula (Ib-1):
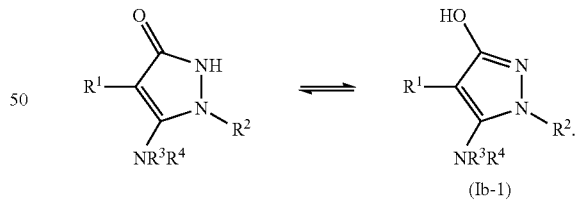
Specific examples include, but are not limited to:
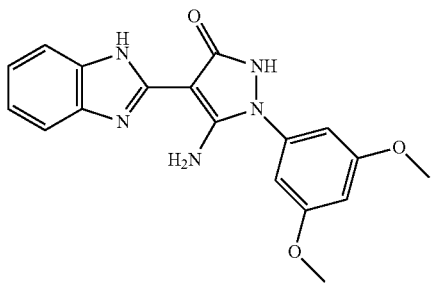

-continued
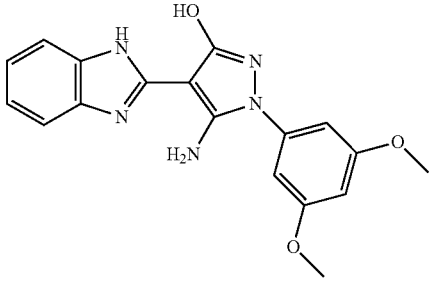
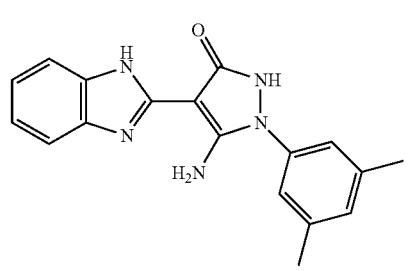
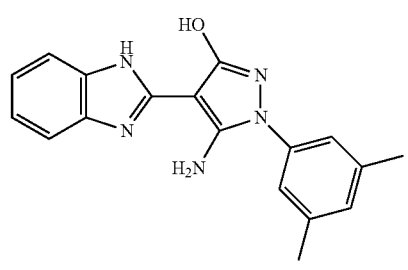
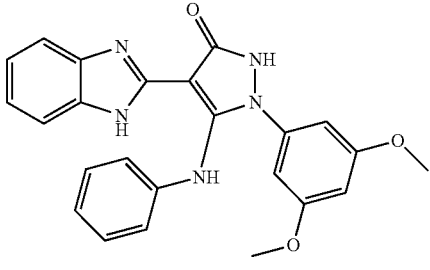
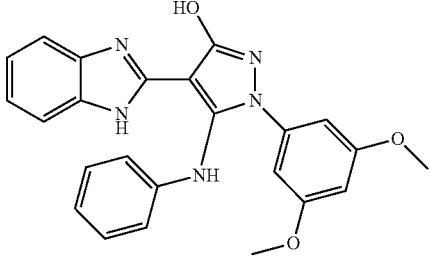
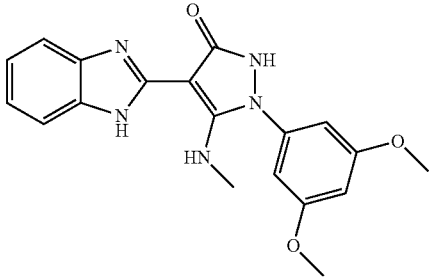
-continued
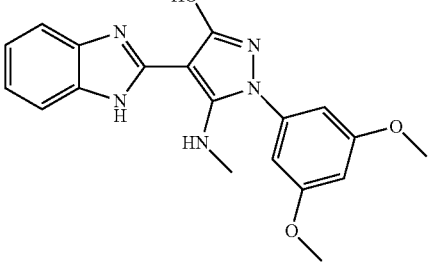
In one embodiment, $R^2$ is H in a compound of formula (Ib). The compound can have one or more tautomeric forms, for example, a compound of formula (Ib-2):
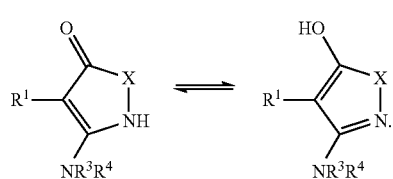
(Ib-2)
In one embodiment, X is $NR^9$. Specific examples include, but are not limited to:
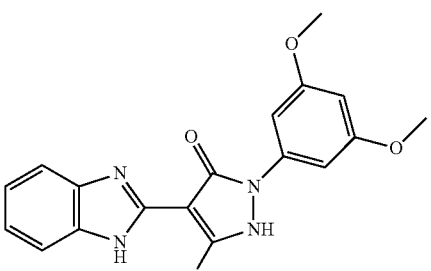
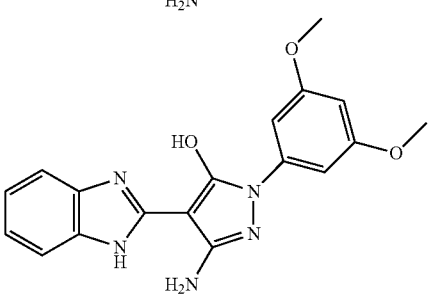
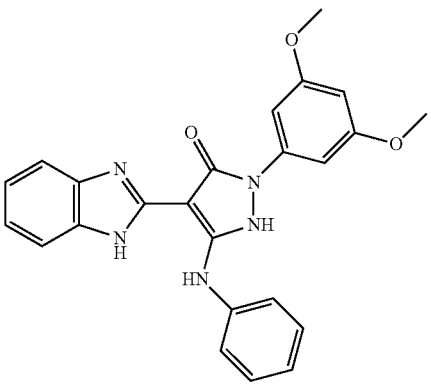

-continued

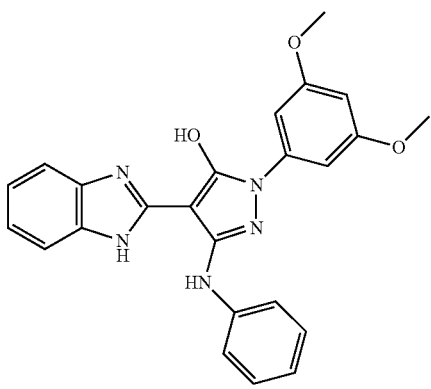

In one embodiment, provided herein is a compound of formula (Ic):

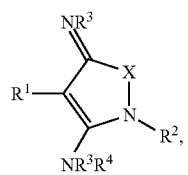

(Ic)

or a pharmaceutically acceptable salt thereof, wherein $R^1$, $R^2$, $R^3$, $R^4$, and X are defined herein elsewhere, and wherein each $R^3$ may be the same or different. Specific examples include, but are not limited to:

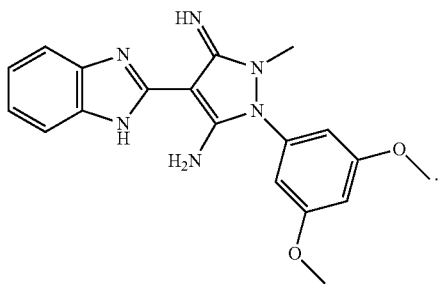 [SMILES: COc1cc(OC)cc(-n2c(N)c(-c3nc4ccccc4[nH]3)c(=N)n2C)c1]

In one embodiment, X is NH in a compound of formula (Ic). The compound can have one or more tautomeric forms, for example, a compound of formula (Ic-1):

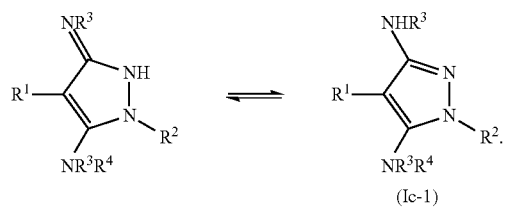

(Ic-1)

Specific examples include, but are not limited to:

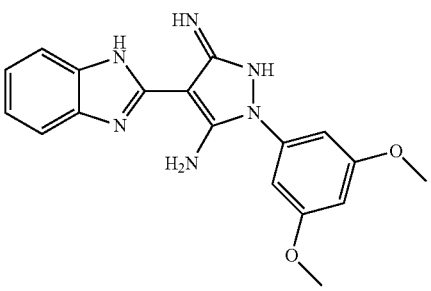

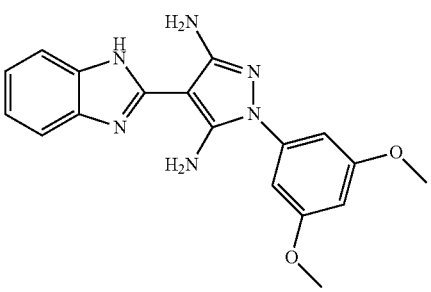

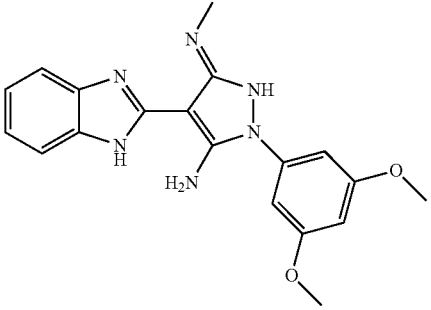

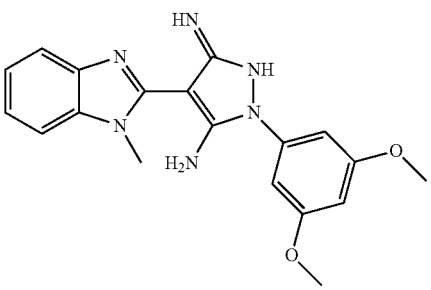

-continued

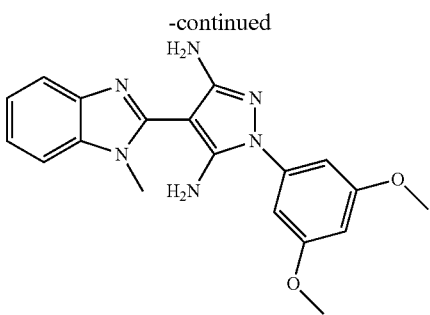

In one embodiment, provided herein is a compound of formula (Id):

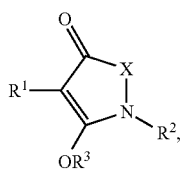
(Id)

or a pharmaceutically acceptable salt thereof, wherein $R^1$, $R^2$, $R^3$, $R^4$, and X are defined herein elsewhere. In one embodiment, $R^3$ is H in a compound of formula (Id). The compound can have in one or more tautomeric forms, for example, a compound of formula (Id-1) or (Id-2):

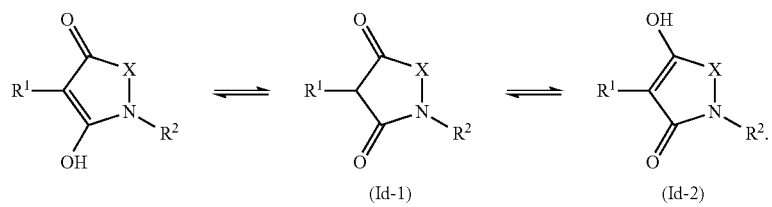

Specific examples include, but are not limited to:

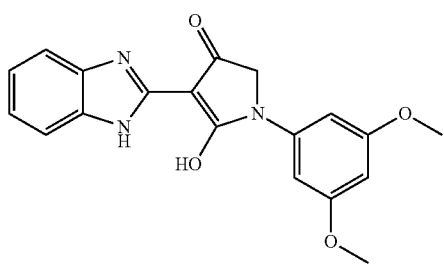

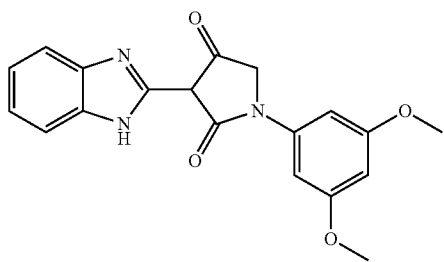

-continued

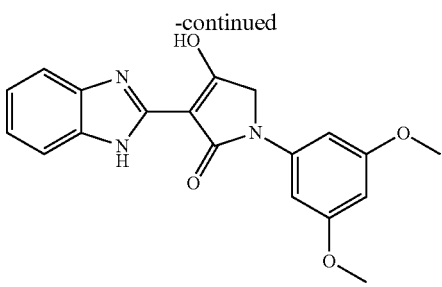

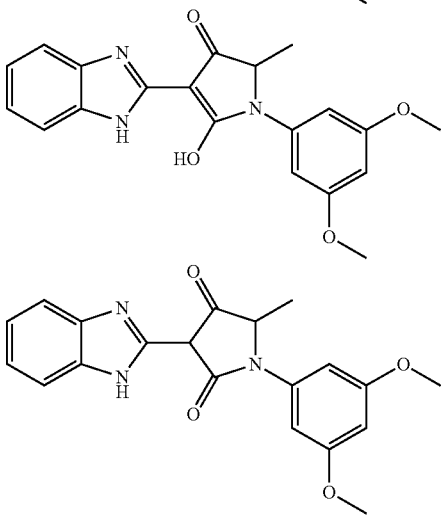

-continued

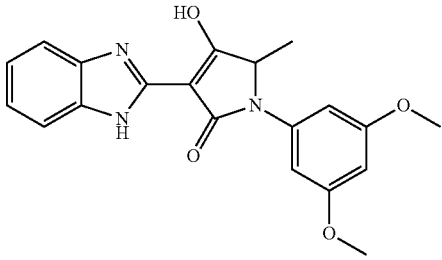

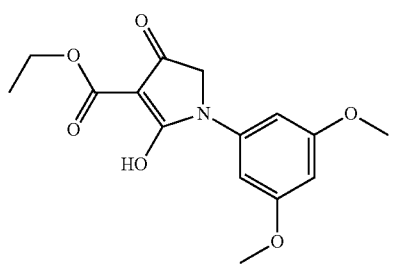

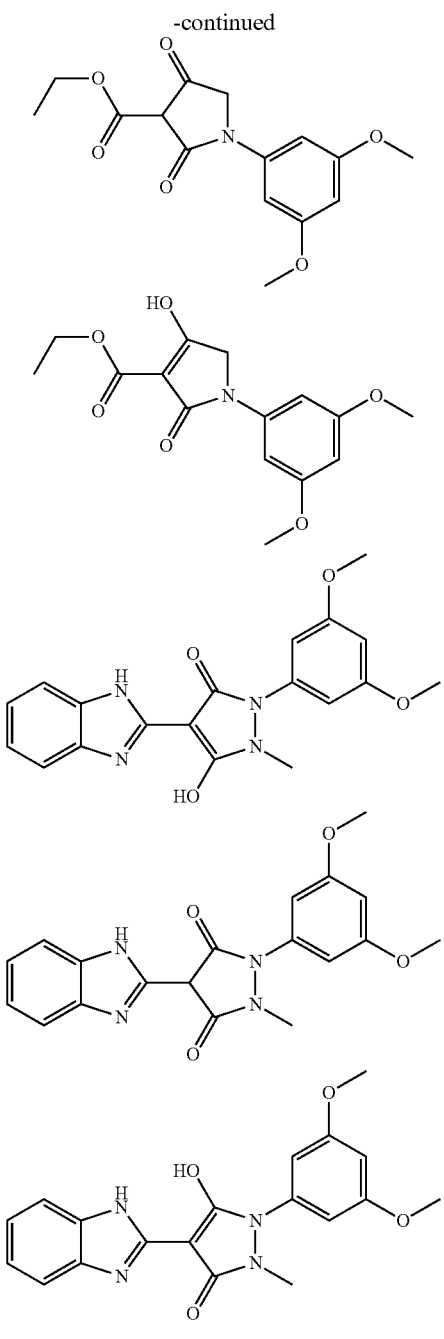

or a pharmaceutically acceptable salt thereof, wherein $R^3$, $R^4$, and X are defined herein elsewhere;

m is 0, 1, 2, or 3;

k is 0, 1, 2, or 3;

each occurrence of $R^{10}$ and each occurrence of $R^{12}$ are independently selected from: (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—$NO_2$), oxo (=O), —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$;

$R^{11}$ is selected from: (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) hydrogen, halo, cyano (—CN), nitro (—$NO_2$), oxo (=O), —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$;

wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^b$ and $R^c$ together with the N atom to which they are attached form heteroaryl or heterocyclyl, optionally substituted with one or more, in one embodiment, one, two, three, or four, substituents $Q^1$;

wherein each $Q^1$ is independently selected from the group consisting of (a) cyano, halo, oxo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; and wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heteroaryl or heterocyclyl.

In specific embodiments, m is 0. In specific embodiments, m is 1. In specific embodiments, m is 2. In specific embodiments, m is 3. In specific embodiments, k is 0. In specific embodiments, k is 1. In specific embodiments, k is 2. In specific embodiments, k is 3. In specific embodiments, $R^{11}$ is H. In specific embodiments, $R^{11}$ is H or optionally substituted alkyl. In specific embodiments, $R^{12}$ is OMe and k is 2. In other embodiments, $R^{12}$ is OMe and k is 1. In other embodiments, $R^{12}$ is OMe and k is 3. In specific embodiments, k is 2 or 3, at least one occurrence of $R^{12}$ is OMe.

In one embodiment, provided herein is a compound of formula (Ie):

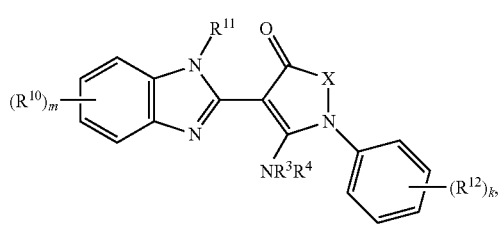

In one embodiment, provided herein is a compound of formula (If):

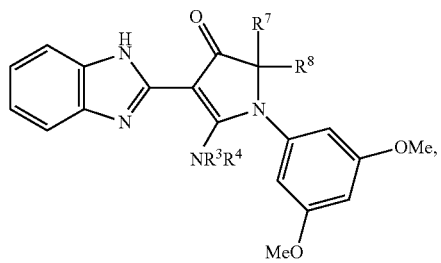

(If)

or a pharmaceutically acceptable salt thereof, wherein $R^3$, $R^4$, $R^7$, and $R^8$ are defined herein elsewhere.

In one embodiment, provided herein is a compound of formula (IIb):

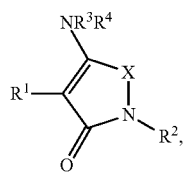

(IIb)

or a pharmaceutically acceptable salt thereof, wherein $R^1$, $R^2$, $R^3$, $R^4$, and X are defined herein elsewhere. Specific examples include, but are not limited to:

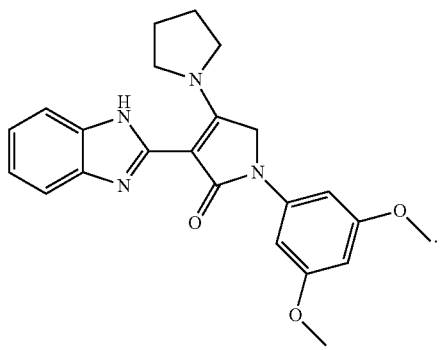 [SMILES: COc1cc(OC)cc(N2CC(N3CCCC3)=C(c3nc4ccccc4[nH]3)C2=O)c1]

In one embodiment, provided herein is a compound of formula (IIc):

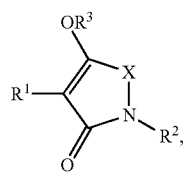

(IIc)

or a pharmaceutically acceptable salt thereof, wherein $R^1$, $R^2$, $R^3$, and X are defined herein elsewhere. Specific examples include, but are not limited to:

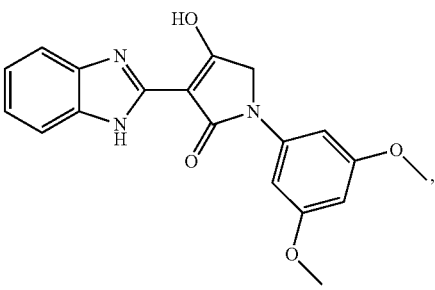

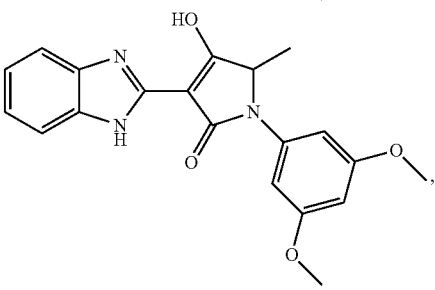

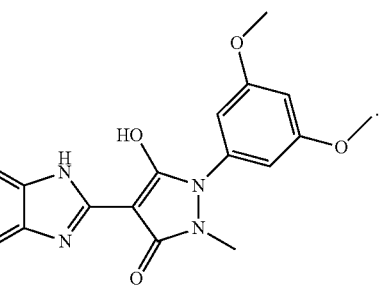

In one embodiment, provided herein is a compound of formula (III):

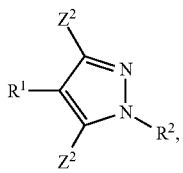

(III)

or a pharmaceutically acceptable salt thereof, wherein $R^1$, $R^2$, and $Z^2$ are defined herein elsewhere, and each $Z^2$ may be the same or different. Specific examples include, but are not limited to:

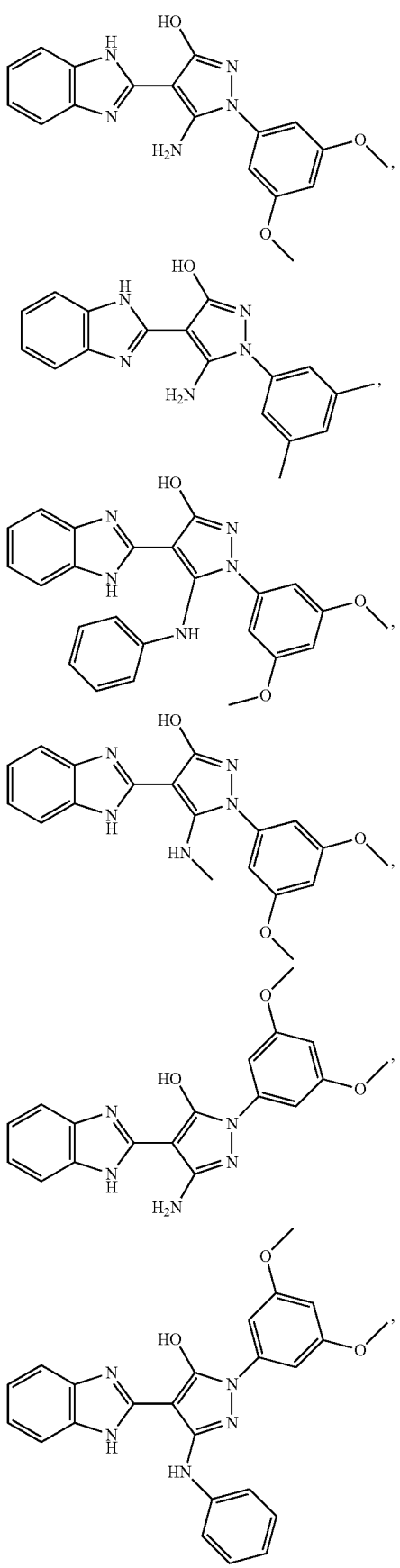

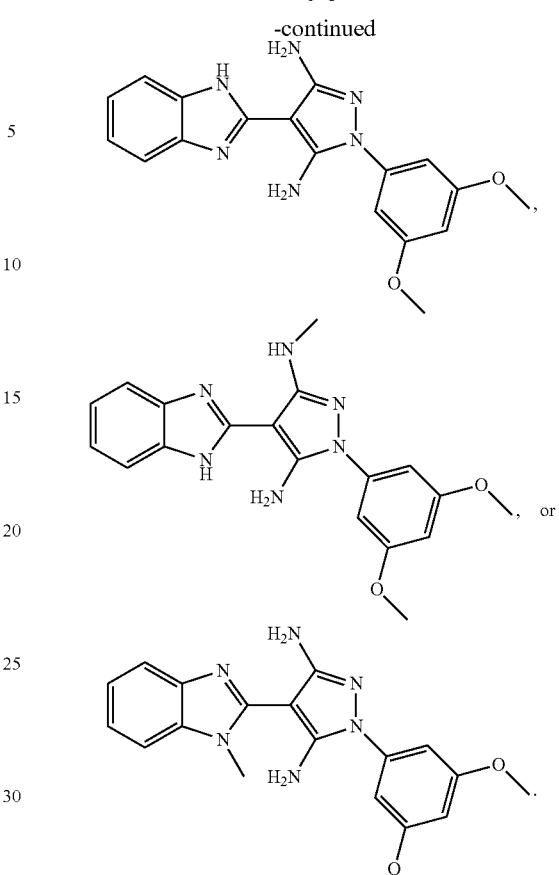

In one embodiment, X is not NH. In one embodiment, $R^2$ is not H. In one embodiment, $Z^2$ is not OH.

Any of the combinations of X, $Z^1$, $Z^2$, $R^1$, $R^2$, $R^3$, $R^4$, $R^5$, $R^6$, $R^7$, $R^8$, $R^9$, $R^{10}$, $R^{11}$, $R^{12}$, m, k, and n are encompassed by this disclosure and specifically provided herein.

It should be noted that if there is a discrepancy between a depicted structure and a chemical name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers. Where the compound provided herein contains an alkenyl or alkenylene group, the compound may exist as one geometric (i.e., cis/trans or E/Z) isomer or a mixture of geometric (i.e., cis/trans or E/Z) isomers. Unless otherwise specified, a compound provided herein is intended to encompass all geometric isomers.

Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contain, for example, an aromatic moiety. It follows that a single compound may exhibit more than one type of isomerism. It will be understood that unless otherwise specified, a compound provided herein is intended to encompass all possible tautomers. Similarly, unless otherwise specified, a compound provided herein is intended to encompass all possible stereoisomers.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. Conventional techniques for the preparation/isolation of individual enantiomers include synthesis from a suitable optically pure precursor, asymmetric synthesis from achiral starting materials, or resolution of an enantiomeric mixture, for example, by chiral chromatography, recrystallization, resolution, diastereomeric salt formation, or derivatization into diastereomeric adducts followed by separation. In some instances, for compounds that undergo epimerization in vivo, one of skill in the art will recognize that administration of a compound in its (R) form is equivalent to administration of the compound in its (S) form, and vice versa.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

In one embodiment, also provided herein are an isotopically enriched compound of formula (I), (II), (Ia), (Ib), (Ib-1), (Ib-2), (Ic), (Ic-1), (Id), (Id-1), (Id-2), (Ie), (If), (IIa), (IIb), (IIc), or (III), or a tautomer thereof.

Isotopic enrichment (for example, deuteration) of pharmaceuticals to improve pharmacokinetics ("PK"), pharmacodynamics ("PD"), and toxicity profiles, has been demonstrated previously with some classes of drugs. See, e.g., Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction.

This phenomenon is known as the Kinetic Isotope Effect ("KIE"). For example, if a C—H bond is broken during a rate-determining step in a chemical reaction (i.e., the step with the highest transition state energy), substitution of a deuterium for that hydrogen will cause a decrease in the reaction rate and the process will slow down. This phenomenon is known as the Deuterium Kinetic Isotope Effect ("DKIE"). See, e.g., Foster et al., Adv. Drug Res., vol. 14, pp. 1-36 (1985); Kushner et al., Can. J. Physiol. Pharmacol., vol. 77, pp. 79-88 (1999).

C. METHODS OF TREATMENT, PREVENTION, AND/OR MANAGEMENT

1. Binding to Opioid Receptor

In various embodiments, provided herein is a method of binding a compound provided herein to an opioid receptor, such as μ-opioid receptor. The method comprises contacting an opioid receptor with a compound provided herein.

In one embodiments, provided herein is a method of modulating the activity of an opioid receptor (e.g., μ-opioid receptor) via the binding of a ligand to an opioid receptor. In one embodiment, the method comprises contacting an opioid receptor with a compound provided herein. In another embodiment, the ligand is a drug molecule or another small molecule known to have binding affinity to an opioid receptor. In another embodiment, the ligand is a radioactively labeled compound, known to bind to an opioid receptor. In other embodiments, binding to an opioid receptor may be assessed using PET imaging known in the art, e.g. utilizing appropriate PET ligands. In some embodiments, the ligand is an allosteric modulator, agonist, antagonist, or inverse agonist of an opioid receptor. In some embodiments, the ligand is an agonist of an opioid receptor (e.g., μ-opioid receptor).

2. Modulation of Opioid Receptor Activity

In various embodiments, provided herein is a method of modulating (e.g., reducing or increasing) the activity of an opioid receptor, such as μ-opioid receptor. The method comprises contacting the receptor, such as μ-opioid receptor, with a compound provided herein, in vitro or in vivo. In one embodiment, an opioid receptor, such as, μ-opioid receptor, is contacted with a compound provided herein by administering to a subject a therapeutically effective amount of the compound provided herein, including a pharmaceutically acceptable salt thereof. The subject may be a human.

In one embodiment, the compound provided herein increases the activity of an opioid receptor, such as μ-opioid receptor. Increase of opioid receptor activity may be measured using assays known in the art. In some embodiments, the activity of μ-opioid receptor is increased by about 1%, about 5%, about 10%, about 20%, about 30%, about 40%, about 50%, about 60%, about 70%, about 80%, about 90%, about 95%, about 99%, or more, as compared with the activity obtained without contacting with the compounds provided herein. In one embodiment, the increase of receptor activity is dose-dependent. Exemplary assay methods include, but are not limited to, in vitro functional assays as described herein elsewhere. In one embodiment, the functional assay utilizes an appropriate cell-line expressing the desired opioid receptor, such as μ-opioid receptor. In other embodiments, the functional assay utilizes synaptosomes isolated from brain tissue of an appropriate organism. In other embodiments, increase of opioid receptor activity may be assessed using receptor binding experiments known in the art, e.g. utilizing appropriate membrane preparations. In one embodiment, the assay involves treatment of a test subject (e.g. a mouse or a rat) with a compound provided herein as well as a reference compound, followed by isolation of brain tissue and ex vivo analysis of receptor occupancy.

In certain embodiments, provided herein are methods of increasing the activity of an opioid receptor, such as μ-opioid receptor, in a subject (e.g., human) comprising administering to the subject an effective amount of a compound provided herein. In some embodiments, the activity of opioid receptor, such as, μ-opioid receptor, is increased by about 1%, about 5%, about 10%, about 20%, about 30%, about 40%, about 50%, about 60%, about 70%, about 80%, about 90%, about 95%, about 99%, or more, when measured using an assay known in the art.

In one embodiment, provided herein is a method of increasing the activity of an opioid receptor, such as μ-opioid receptor, by an opioid receptor ligand. In one embodiment, the method comprises contacting an opioid receptor with an agonist or an allosteric modulator of the opioid receptor.

In another embodiment, an agonist or an allosteric modulator of the opioid receptor is a compound provided herein.

In one embodiment, the compound provided herein reduces the activity of an opioid receptor, such as μ-opioid receptor. Reduction of opioid receptor activity may be measured using assays known in the art. In some embodiments, the activity of μ-opioid receptor is reduced by about 1%, about 5%, about 10%, about 20%, about 30%, about 40%, about 50%, about 60%, about 70%, about 80%, about 90%, about 95%, about 99%, or more, as compared with the activity obtained without contacting with the compounds provided herein. In one embodiment, the reduction of receptor activity is dose-dependent. Exemplary assay methods include, but are not limited to, in vitro functional assays as described herein elsewhere. In one embodiment, the functional assay utilizes an appropriate cell-line expressing the desired opioid receptor, such as μ-opioid receptor. In other embodiments, the functional assay utilizes synaptosomes isolated from brain tissue of an appropriate organism. In other embodiments, reduction of opioid receptor activity may be assessed using receptor binding experiments known in the art, e.g. utilizing appropriate membrane preparations. In one embodiment, the assay involves treatment of a test subject (e.g. a mouse or a rat) with a compound provided herein as well as a reference compound, followed by isolation of brain tissue and ex vivo analysis of receptor occupancy.

In certain embodiments, provided herein are methods of reducing the activity of an opioid receptor, such as μ-opioid receptor, in a subject (e.g., human) comprising administering to the subject an effective amount of a compound provided herein. In some embodiments, the activity of opioid receptor, such as, μ-opioid receptor, is reduced by about 1%, about 5%, about 10%, about 20%, about 30%, about 40%, about 50%, about 60%, about 70%, about 80%, about 90%, about 95%, about 99%, or more, when measured using an assay known in the art.

In one embodiment, provided herein is a method of reducing the activity of an opioid receptor, such as μ-opioid receptor, by an opioid receptor ligand. In one embodiment, the method comprises contacting an opioid receptor with an antagonist, an inverse agonist, or an allosteric modulator of the opioid receptor. In another embodiment, an antagonist, an inverse agonist, or an allosteric modulator of the opioid receptor is a compound provided herein.

3. Treatment, Prevention, and/or Management of Opioid Receptor Related Disorders In some embodiments, provided herein is a method of treating, preventing, and/or managing a disorder related to an opioid receptor, such as a neurological disorder. Without being limited by a particular theory, the treatment, prevention, and/or management is done by modulating the activity of opioid receptor using a composition or a compound provided herein. In one embodiment, provided herein is the use of a compound or a composition provided herein in the manufacture of a medicament for the treatment, prevention, and/or management of a disorder related to an opioid receptor, such as a neurological disorder provided herein. In one embodiment, provided herein is a compound or a composition for use in the treatment, prevention, and/or management of a disorder related to an opioid receptor, such as a neurological disorder provided herein.

In one embodiment, the method comprises administering to a subject (e.g., human) a therapeutically or prophylactically effective amount of a composition or a compound provided herein. In one embodiment, the subject is a human. In another embodiment, the compound provided herein modulates the activity of an opioid receptor (e.g., μ-opioid receptor). In certain embodiment, a compound provided herein is an agonist of μ-opioid receptor. In certain embodiment, a compound provided herein is an antagonist of μ-opioid receptor. In certain embodiments, the compounds provided herein are allosteric modulators of an opioid receptor. In certain embodiments, the compounds provided herein are selective for μ-opioid receptor over other CNS-related targets. In one embodiment, the compounds provided herein are highly brain penetrable in animals, such as rodents, and human. In some embodiments, modulation of opioid receptor activity may be assessed by functional assays as described herein elsewhere. In certain embodiments, the efficacious concentration of the compounds provided herein is less than 10 nM, less than 100 nM, less than 1 μM, less than 10 μM, less than 100 μM, or less than 1 mM. In other embodiments, compound's activity may be assessed in various art-recognized animal models.

In some embodiments, provided herein is a method of treating, preventing, and/or managing a disorder related to an opioid receptor, as described herein or known in the art, comprising administering to a subject an effective amount of a compound provided herein.

In some embodiments, provided herein is a method of treating, preventing, and/or managing pain, including but not limited to, migraine, inflammatory pain, neuropathic pain, postoperative pain, acute thermal hyperalgesia, mechanical allodynia, visceral pain, pathophysiological nociceptor pain, severe pain, and chronic pain, or any other painful disorder described herein, comprising administering to a subject an effective amount of a compound provided herein.

In some embodiments, provided herein is a method of treating, preventing, and/or managing diarrhea, comprising administering to a subject an effective amount of a compound provided herein.

In some embodiments, provided herein is a method of treating, preventing, and/or managing fibromyalgia, comprising administering to a subject an effective amount of a compound provided herein.

In some embodiments, the compounds provided herein are active in at least one model, which can be used to measure the activity of the compounds and estimate their efficacy in treating a disorder related to an opioid receptor. For example, when the model is for pain, the compounds are active when they inhibit reaction to pain stimuli by a test subject by about 5%, about 10%, about 20%, about 30%, about 40%, about 50%, about 60%, about 70%, about 80%, about 90%, about 95%, about 99%, or more, when compared to vehicle. In some embodiments, the compounds provided herein produce a similar disparity in measured endpoint between treated animals and animals administered vehicle.

In other embodiments, provided herein is a method of effecting a therapeutic effect as described herein elsewhere. The method comprises administering to a subject (e.g., a mammal) a therapeutically effective amount of a compound or a composition provided herein. The particular therapeutic effects may be measured using any model system known in the art or described herein, such as those involving an animal model of a disease.

In one embodiment, the compounds described herein treat, prevent, and/or manage a central nervous disorder, without causing addiction to said compounds.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. Generally, oral, intravenous, intracerebroventricular, and subcutaneous doses of the compounds provided herein for a patient will range from about 0.005 mg per kilogram to about 5 mg per kilogram of body weight per day. In one embodiment, the oral dose of a compound provided herein will range from about 10 mg to about 300 mg per day. In another embodiment, the oral dose of a compound provided herein will range from about 20 mg to about 250 mg per day. In another embodiment, the oral dose of a compound provided herein will range from about 100 mg to about 300 mg per day. In another embodiment, the oral dose of a compound provided herein will range from about 10 mg to about 100 mg per day. In another embodiment, the oral dose of a compound provided herein will range from about 25 mg to about 50 mg per day. In another embodiment, the oral dose of a compound provided herein will range from about 50 mg to about 200 mg per day. Each of the above-recited dosage ranges may be formulated as a single or multiple unit dosage formulations.

In some embodiments, the compound disclosed herein may be used in combination with one or more second active agent(s) to treat, prevent, and/or manage a disorder described herein. In one embodiment, the second active agent is known in the art, such as, e.g., those described in http://www.fda.gov/; The Merck Manual, 18th ed. 2006; and PDR: Physician Desk Reference 2010, 64th ed. 2009; the contents of each of which are hereby incorporated by reference in their entireties. In one embodiment, the second active agent is lurasidone, olanzapine, risperidone, aripiprazole, donepezil, rivastigmine, memantine, amphetamine, methylphenidate, atomoxetine, modafinil, sertraline, fluoxetine, or L-DOPA. In one embodiment, the second active agent includes, but is not limited to, lurasidone, olanzapine, risperidone, aripiprazole, donepezil, rivastigmine, memantine, amphetamine, methylphenidate, atomoxetine, modafinil, sertraline, fluoxetine, or L-DOPA. In one embodiment, the second active agent is an antipsychotic (e.g., haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, cyamemazine, chlorprothixene, clopenthixol, flupenthixol, thiothixene, zuclopenthixol, clozapine, olanzapine, risperidone, quetiapine, ziprasidone, amisulpride, asenapine, iloperidone, sertindole, aripiprazole, or lurasidone), antidepressant (e.g., doxepin, clomipramine, amoxapine, nortriptyline, citalopram, duloxetine, trazodone, venlafaxine, amitriptyline, escitalopram, amitriptyline/chlordiazepoxide, desipramine, nortriptyline, tranylcypromine, paroxetine, fluoxetine, mirtazapine, trimipramine, imipramine, protriptyline, bupropion, sertraline), NSAID (e.g., aspirin, diflunisal, salsalate, acetaminophen, ibuprofen, naproxen, fenoprofen, ketoprofen, flurbiprofen, oxaprozin, loxoprofen, indomethacin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, nimesulide, or licofelone), COX-2 inhibitor (e.g., celecoxib, parecoxib, lumiracoxib, etoricoxib, firocoxib), anticonvulsants (e.g., gabapentin, pregabalin, lamotrigine, carbamazepine, lacosamide, and topiramate), peripherally acting (non-CNS penetrant) μ-antagonists (e.g., alvimopan), muscle relaxant, or a laxative.

4. Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt thereof. Pharmaceutical compositions and dosage forms can further comprise one or more excipients.

In some embodiments, compounds disclosed herein may be formulated as an anti-abuse formulation such that it would be difficult for a subject to extract the compound from the formulation. Examples are known to persons of skill in the art.

Pharmaceutical compositions and dosage forms provided herein can also comprise one or more additional active ingredients. Examples of optional second, or additional, active ingredients are also disclosed herein.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intra-arterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., *Remington's Pharmaceutical Sciences,* 18th Ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising, active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

In other embodiments, dosage forms comprise the second active ingredient. The specific amount of the second active agent will depend on the specific agent used, the diseases or disorders being treated or managed, and the amount(s) of a compound provided herein, and any optional additional active agents concurrently administered to the patient.

(a) Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's The Science and Practice of Pharmacy*, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, and optional excipients, such as anhydrous lactose, microcrystalline cellulose, polyvinylpyrrolidone, stearic acid, colloidal anhydrous silica, and gelatin.

(b) Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

(c) Parenteral Dosage Forms

Parenteral dosage forms can be administered to patients by various routes including, but not limited to, subcutaneous, intravenous (including bolus injection), intramuscular, and intra-arterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

(d) Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences,* 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, prodrugs, or clathrates of the active ingredients can be used to further adjust the properties of the resulting composition.

5. Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

V. EXAMPLES

Certain embodiments are illustrated by the following non-limiting examples.

A. Synthesis of Compounds

In the examples below, unless otherwise indicated, all temperatures are set forth in degrees Celsius and all parts and percentages are by weight. Reagents may be purchased from commercial suppliers, such as Sigma-Aldrich Chemical Company, and may be used without further purification unless otherwise indicated. Reagents may also be prepared following standard literature procedures known to those skilled in the art. Solvents may be purchased from Aldrich in Sure-Seal bottles and used as received. All solvents may be purified using standard methods known to those skilled in the art, unless otherwise indicated.

The reactions set forth below were done generally at ambient temperature, unless otherwise indicated. The reaction flasks were fitted with rubber septa for introduction of substrates and reagents via syringe. Analytical thin layer chromatography (TLC) was performed using glass-backed silica gel pre-coated plates (Merck Art 5719) and eluted with appropriate solvent ratios (v/v). Reactions were assayed by TLC or LCMS, and terminated as judged by the consumption of starting material. Visualization of the TLC plates was done with UV light (254 wavelength) or with an appropriate TLC visualizing solvent, such as basic aqueous $KMnO_4$ solution activated with heat. Flash column chromatography (See, e.g., Still et al., J. Org. Chem., 43: 2923 (1978)) was performed using silica gel 60 (Merck Art 9385) or various MPLC systems.

The compound structures in the examples below were confirmed by one or more of the following methods: proton magnetic resonance spectroscopy, mass spectroscopy, and melting point. Proton magnetic resonance ($^1$H NMR) spectra were determined using an NMR spectrometer operating at 400 MHz field strength. Chemical shifts are reported in the form of delta ($\delta$) values given in parts per million (ppm) relative to an internal standard, such as tetramethylsilane (TMS). Alternatively, $^1$H NMR spectra were referenced to signals from residual protons in deuterated solvents as follows: $CDCl_3$=7.25 ppm; DMSO-$d_6$=2.49 ppm; $C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

B. Synthetic Schemes

Schemes below provide exemplary synthetic methods for the preparation of the compounds provided herein. One of ordinary skills in the art will understand that similar methods may be employed to prepare the compounds provided herein. In other words, one of ordinary skills in the art will recognize that suitable adjustments to reagents, protecting groups, reaction conditions, and reaction sequences may be employed to prepare a desired embodiment. The reactions may be scaled upwards or downwards to suit the amount of material to be prepared.

In one embodiment, the compound of formula (I), (II), or (III) may be prepared following the schemes provided below, using suitable starting materials known in the art and/or available from a commercial source. In one embodiment, the starting materials of the schemes provided herein may be prepared from commercially available compounds using procedures and conditions known in the art. One of ordinary skills in the art will understand that the substituents in the schemes provided below, such as A, B, R, $R_{aa}$, $R_{ab}$, and X; and integers, such as q; may be varied in order to prepare particular embodiments of a compound provided herein. When a scheme below employs a certain substituent, e.g., R, at more than one position of a particular molecule, the occurrences of such substituent may be the same or different. Exemplary procedures and conditions are provided herein.

General Procedure A:

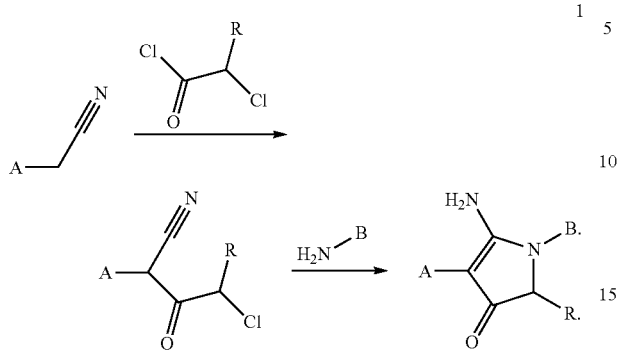

A substituted nitrile was condensed with an activated carbonyl compound (i.e., the acid chloride) using added base and heating when appropriate to complete the acylation. In a second step, an amine compound was added along with a base when appropriate. The intermediate cyclized under the reaction conditions or with added heating to give the target compound.

General Procedure B

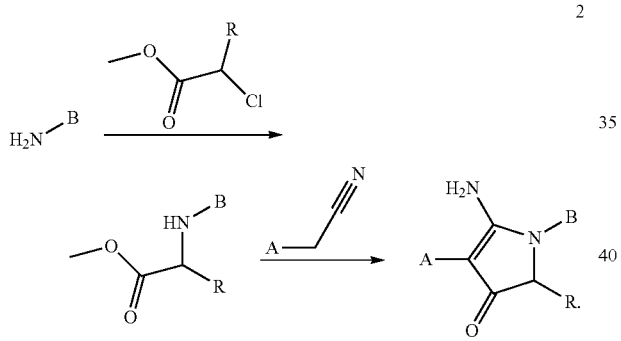

The steps of procedure A could be reversed such that the amino-ester was synthesized in the first step using added base and heating when appropriate. The activated nitrile was added in the second step with base and heating when appropriate to give the target molecule.

General Procedure C

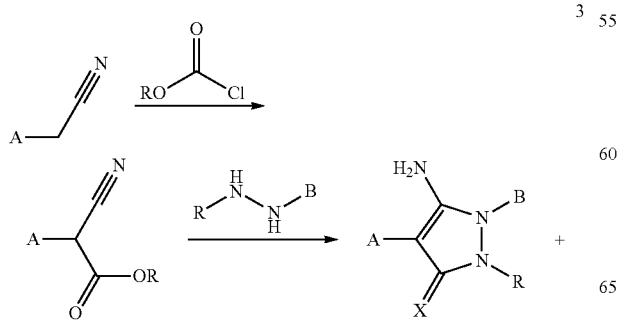

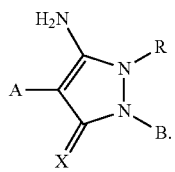

A functionalized acetonitrile (i.e., from condensation of a chloroformate with a nitrile) was condensed with a hydrazine to give mixtures of regioisomeric pyrazolones. These mixtures were separated by chromatography.

General Procedure D

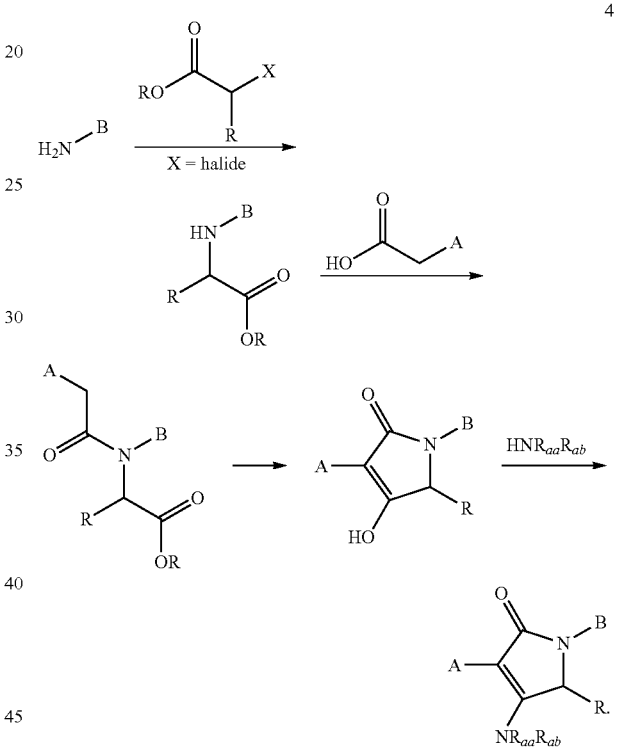

In another embodiment, compounds were generated by a multi-step procedure starting from a condensation of an amine with functionalized haloester followed by acylation of the product to form an amide bond. The dicarbonyl compound was cyclized with a base to form a cyclic vinylogous acid, which was treated with another amine to form a pyrrolone compound.

General Procedure E

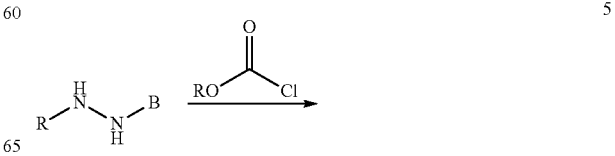

113

-continued

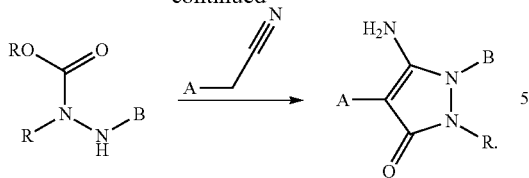

In another embodiment, a hydrazine was reacted with a chloroformate to make a hydrazine carboxylate. The intermediate was condensed with an acetonitrile compound to give the target molecule.

General Procedure F

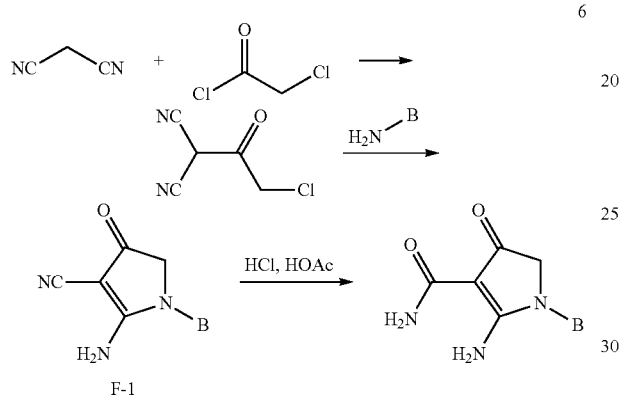

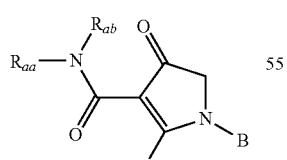

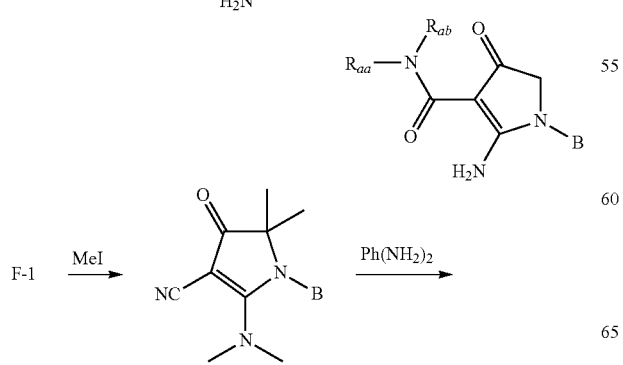

114

-continued

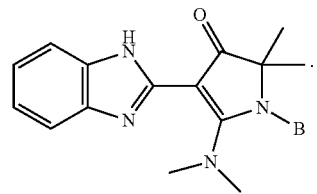

The product of the coupling reaction of malononitrile and 2-chloroacetyl chloride was condensed with an amine to give a pyrrolinone intermediate F-1. This intermediate was elaborated into several compounds including a primary amide, a hydroxy amide, an amidine, an acid, a secondary or tertiary amide, or a heterocycle by standard methods. In one embodiment, F-1 was methylated on carbon and nitrogen prior to heterocycle formation.

7. General Procedure G

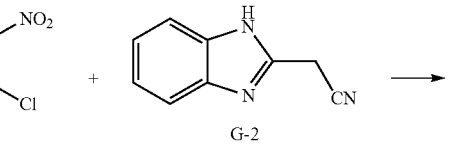

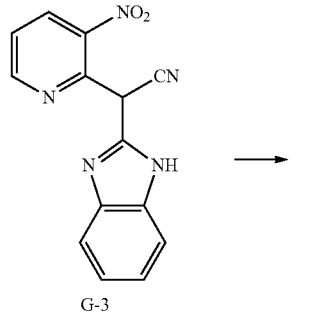

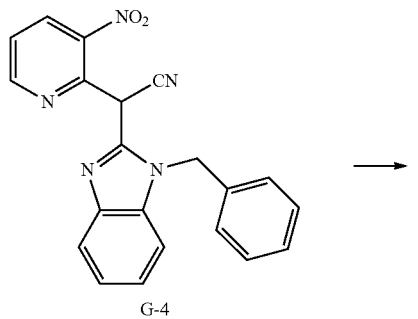

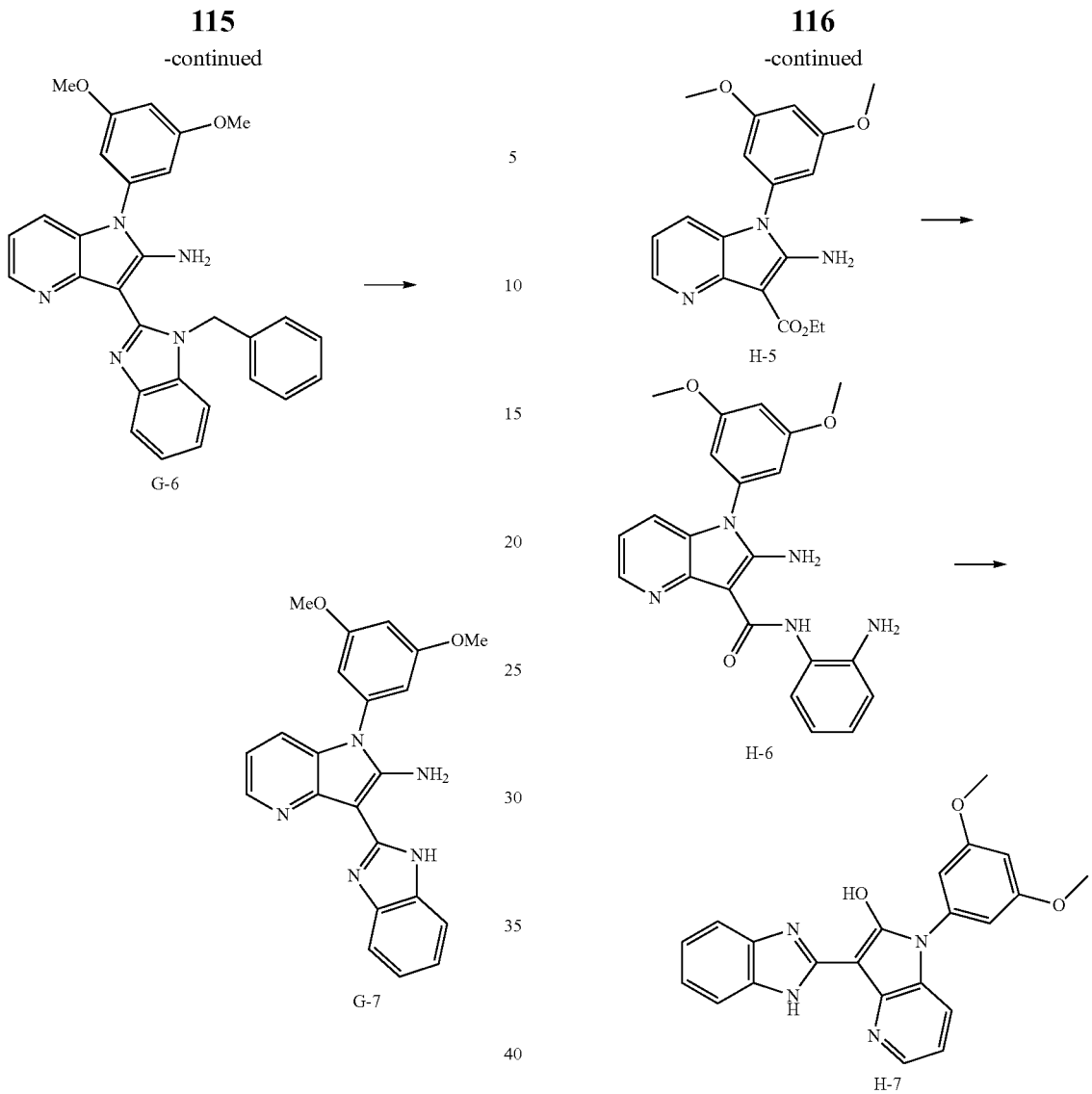

In one embodiment, 2-chloro-3-nitropyridine was alkylated with benzoacetonitrile under basic conditions and the benzimidazole nitrogen was protected with a benzyl group to give G-4. The nitro group was reduced and the resultant aniline reacted with the nitrile to give G-5. The ring nitrogen was alkylated under standard conditions and the benzyl group was removed to give G-7.

8. General Procedure H

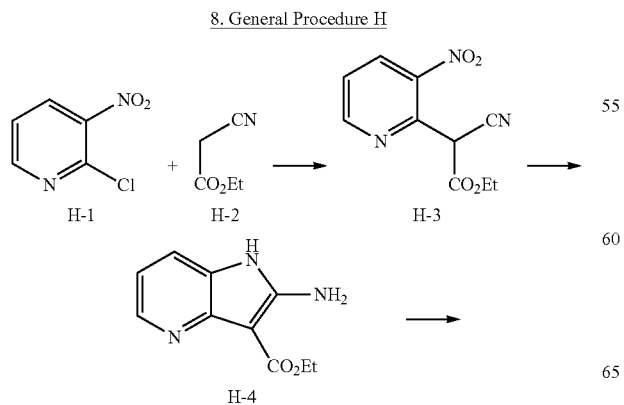

In another embodiment, 2-chloro-3-nitropyridine was alkylated with ethyl cyanoacetate under basic conditions to give H-3. The nitro group was reduced and the resultant aniline reacted with the nitrile to give H-4. The ring nitrogen was alkylated under standard conditions. The ester was reacted with O-phenylenediamine to give an amide which was cyclized to form a benzimidazole with concomitant transformation of the exocyclic amino group to a hydroxyl.

General Procedure I

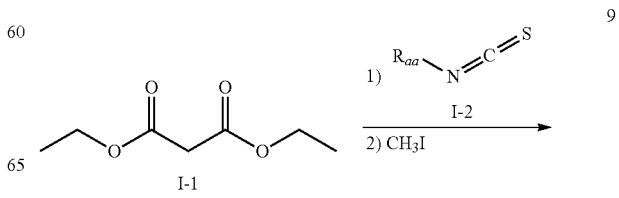

117

-continued

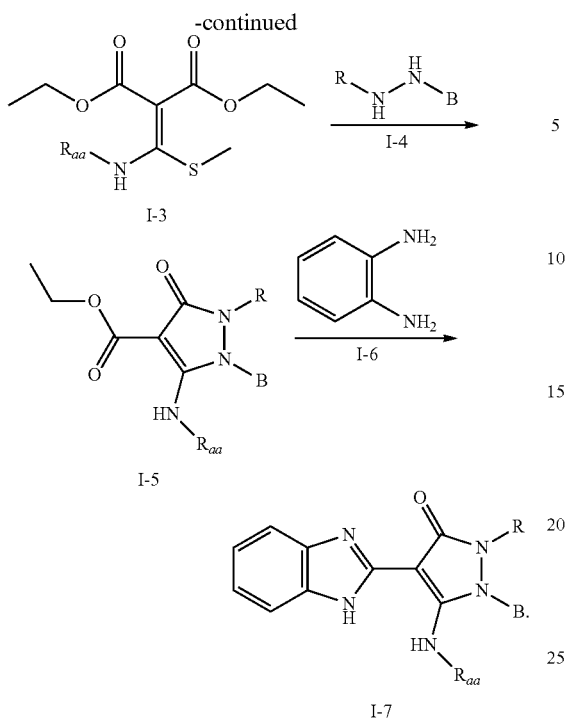

I-3

I-5

I-7

Diethylmalonate was reacted with an isothiocyanate and the resultant thiol was alkylated with methyl iodide to give Compound I-3. Compound I-3 was then condensed with a hydrazine to give a mixture of regioisomeric pyrazolones, which were separated by chromatography. In some cases, the ester was further elaborated under standard conditions to give heterocycles (e.g., benzimidazole).

General Procedure J

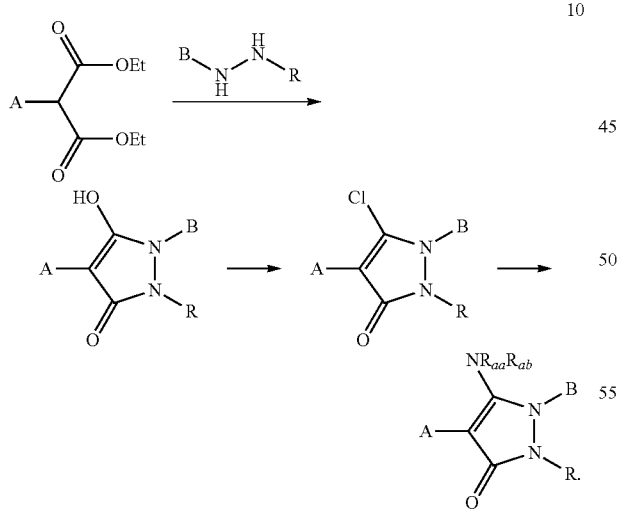

In some instances, a substituted malonate was reacted with a hydrazine to give a mixture of regioisomeric hydroxypyrazolones which were separated by chromatography. The hydroxy group was converted to a chloride using standard practice and reacted with various amines to give aminopyrazolones.

118

General Procedure K

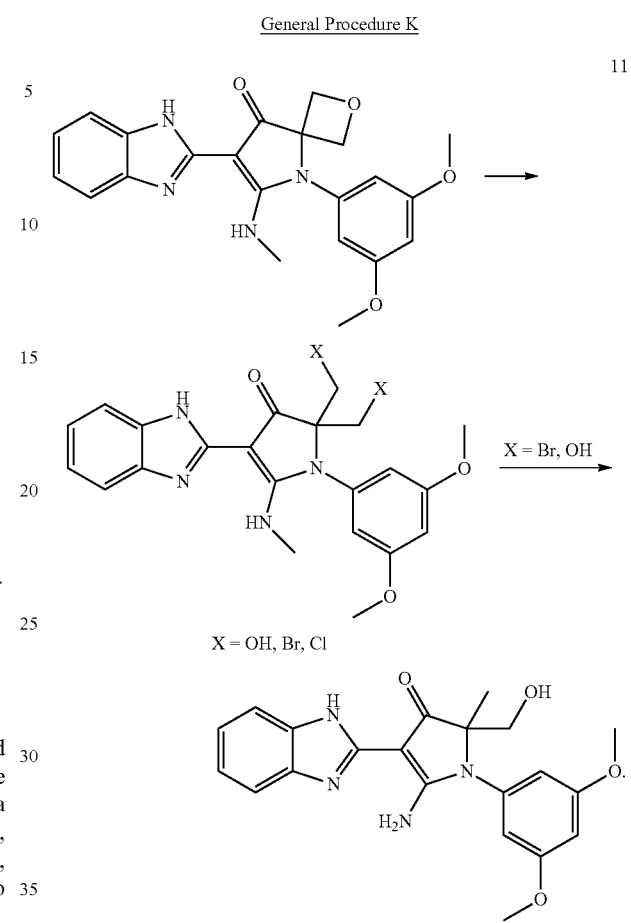

X = Br, OH

X = OH, Br, Cl

The oxetane ring of a compound was reacted with concentrated mineral acids to give mixtures of diols, dihalides, and halo-alcohols which were separated by chromatography. Bromides were removed by standard procedures.

12. General Procedure L

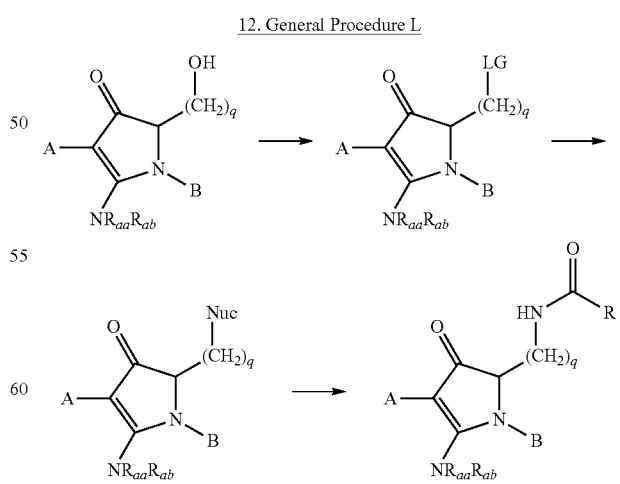

The hydroxy substituent of certain compounds was activated by standard protocols (e.g., conversion to a compound having a leaving group (LG) at the position occupied by hydroxy) and reacted with nucleophiles (Nuc) to give elaborated analogs. In some cases where the nucleophile was an amine, the nitrogen is reacted with an acyl group to give an amide.

13. General Procedure for Alpha Oxidation

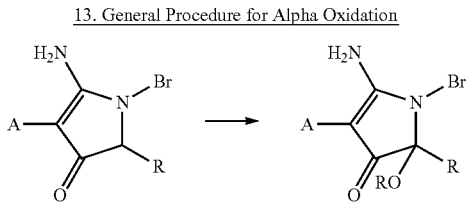

R = alkyl or H

Certain compounds were reactive towards oxidating agents including molecular oxygen under basic conditions. In certain instances where alcoholic solvents were used, the alcohol was sometimes found to be incorporated into the target compound.

14. General Procedure for N-Alkylation (N-alk)

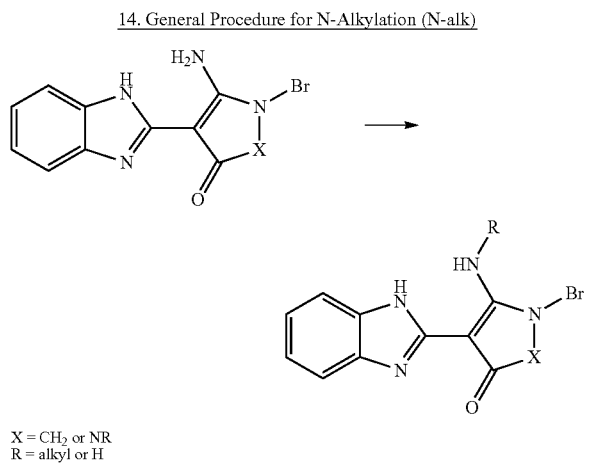

X = CH$_2$ or NR
R = alkyl or H

The exocyclic nitrogen and/or the benzimidazole nitrogen in certain compounds were alkylated using standard conditions. In the case where both nitrogens were alkylated, the resultant mixture of regioisomers were separated by chromatography.

General Procedure for O-Dealkylation (O-dealk)

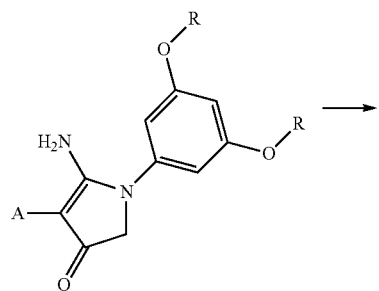

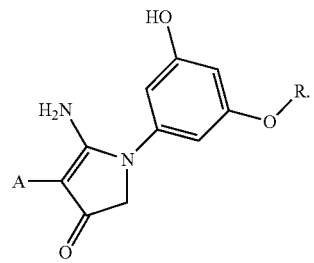

R = alkyl or H

Certain compounds contained one or two methyl aromatic ethers which were removed under standard conditions to give either one or two phenols.

C. Assays

1. In Vitro Assays

GTPγS Binding Assay: The GTPγS binding assay is a method for functional assessment of the effect of a ligand on a specific G-protein coupled receptor. Application of the assay for assessing potency and efficacy of G-protein mediated signal transduction relating to the mu-opioid receptor has been described. See, e.g., Rogers et al. 2003, Assay and Drug Development Technologies, 1(5).

Recombinant mu-opioid receptor was provided within isolated cell membrane preparations. GTP binding to the Gα G protein subunit associated with the mu-opioid receptor is an indication of agonist induced receptor activation. For the assay, GTP was substituted by [$^{35}$S] labeled GTPγS, which binds irreversibly to receptor localized activated G protein. After exposure to agonist, membranes were sedimented by centrifugation in the presence of scintillation beads. Sedimented [$^{35}$S] labeled GTPγS membrane complexes associated with scintillation beads were placed in a scintillation counter for quantitation of radioactivity as an indication of receptor activation. Dose response experiments provided both efficacy and potency values for the compounds tested.

Enzyme Fragment Complementation (EFC) Assay (BArr activity):

Enzyme fragment complementation can provide both efficacy and potency measurements for the ability of a ligand to recruit Beta-arrestin 2 to the receptor, in this case to the mu-opioid receptor. Cultured cells contain two recombinant constructs, the first contain DNA encoding the mu-opioid receptor with a C-terminal fusion to a portion of the Beta galactosidase enzyme. The second construct contain DNA encoding the Beta-arrestin 2 gene fused to a different portion of the beta-galactosidase gene. Neither portion of the beta-galactosidase gene, by itself is active, but if the two different portion are brought into proximity, enzyme activity is achieved. Recruitment of the Beta arrestin fusion protein to the mu-opioid receptor fusion protein provided enzyme fragment complementation for the beta-galactosidase enzyme resulting in active enzyme. Luminescent substrate was supplied to indicate activity.

In one embodiment, β-Arrestin was fused to an N-terminal deletion mutant of β-gal (termed the enzyme acceptor of EA) and the GPCR of interest was fused to a smaller (42 amino acids), weakly complementing fragment termed Pro-Link™. In cells that stably expressed these fusion proteins, ligand stimulation resulted in the interaction of β-Arrestin and the Prolink-tagged GPCR, forcing the complementation of the two β-gal fragments and resulting in the formation of a functional enzyme that converted substrate to detectable signal. See, e.g., PathHunter™ β-Arrestin Assay by DiscoverX Corporation.

2. In Vivo Assays

Tail-Flick Test in Mice:

Animals: Experimentally-naive, male, 7-8 week old B6 mice from Taconic Farms Inc. arrived at the laboratory at least 1 week prior to behavioral testing. Mice were housed in groups of n=4 per cage containing Alpha-dri cellulose bedding Animals had ad libitum access to standard rodent chow and water Animal housing and testing rooms were maintained under controlled environmental conditions and were within close proximity of each other Animal housing rooms were on a 12-hour light-dark cycle with lights on at 6:00 AM and maintained at 70° F. (range: 68-72° F.) with a humidity range of 20-40%. Testing rooms were maintained at 60-70° F. with a humidity range of 20-40%.

Procedures: Each treatment group included 8-12 animals. All treatment groups were randomized across time of day and study days. On the day of the test, the animals were transported in their home cages to the behavioral testing area at least one hour prior to the initiation of testing to acclimate to the experimental environment Animals were briefly removed from their home cages to place an identifying mark on their tails and to record their body weights. Baseline tail-flick latencies were determined for all mice 60 minutes prior to dosing (Tail-Flick Analgesia Meter, IITC Life Science, Woodland Hills, Calif., USA). Individual animals were held gently but firmly by the experimenter and the tails of the mice were exposed to a high-intensity, noxious, radiant heat stimulus. The stimulus was applied 1-2 cm from the tip of the tail for all animals. The stimulus intensity was set by adjusting the source to a level that yields baseline tail-flick latencies between 2-4 seconds. When a withdrawal tail-flick response occurred, the thermal stimulus was terminated automatically and the response latency was measured electronically. In the absence of a tail-flick response, the stimulus was terminated automatically after 10 seconds (cut-off time) to prevent tissue damage. After determination of baseline tail-flick latencies, animals were returned to their home cages. Mice were briefly removed from their home cages to administer test articles on a mg/kg (free base) basis by oral gavage (PO), intraperitoneal injection (IP), or subcutaneous injection (SC) at 10 mL/kg. In one embodiment, the experimenter was blinded to the treatments received by the animals. Tail-flick latencies again were measured at 30 and 120 minutes after dosing. The times of latency measurements after dosing were based on the route of administration and the exposure and pharmacokinetic profile of the test article, but a 90-minute separation between latency measurements in the same animals was recommended to prevent learning/conditioning of the response. At the end of the behavioral test, brain and plasma samples were collected from each animal and stored at −20 or −80° C. until analyzed for compound concentrations. The tail-flick instrument was cleaned with water and a 70% alcohol solution between animals. Tail-flick response latencies (in seconds) were recorded for each animal at each time point and converted to percent maximum possible effect (% MPE) using the following equation: % MPE=[(post-treatment latency-baseline latency)/(cut-off latency-baseline latency)]*100. Tail-flick latencies and % MPE values were analyzed by two-way analyses of variance with treatment condition and time as the between- and within-groups factors, respectively, and, if appropriate, post-hoc tests comparing test compound-treated groups to the vehicle-treated group (ANOVA, GraphPad Prism, GraphPad Software Inc., La Jolla, Calif., USA).

Fecal Boli Accumulation Assay in Mice:

Animals: Experimentally-naive, male, 7-8 week old C57BL/6 mice from Charles River Laboratories arrived at the laboratory at least 1 week prior to testing. Mice were housed in groups of n=2 per cage containing Alpha-dri cellulose bedding Animals had ad libitum access to standard rodent chow and water Animal housing and testing rooms were maintained under controlled environmental conditions and were within close proximity of each other Animal housing rooms were on a 12-hour light-dark cycle with lights on at 6:00 AM and maintained at 70° F. (range: 68-72° F.) with a humidity range of 20-40%. Testing rooms were maintained at 60-70° F. with a humidity range of 20-40%.

Procedures: Each treatment group included 8 animals. The day before each test day, food was removed from the home cages of test animals and immediately replaced with a known quantity of food, in order to allow determination of food consumption over the 24-hour period prior to the test. All treatment groups were randomized across test chambers and study days, with the caveat that each cage of animals (n=2) would be dosed and tested under identical treatment conditions, permitting their pre-test 24-hour food intake to be associated with a single dosing condition. On the test day, n=8 animals (4 cages of n=2/cage) were transported in their home cages to the testing room for a brief acclimation period (15-30 minutes) Animals were briefly removed from their home cages to place an identifying mark on their tails and to record their body weights. Mice were then treated with test articles on a mg/kg (free base) basis by oral gavage (PO), intraperitoneal injection (IP), or subcutaneous injection (SC) at 10 mL/kg Immediately following test article administration, mice were placed in individual test chambers, in which fecal boli could fall through the elevated grid floors and collect in the underlying pans. In one embodiment, the experimenter was blinded to the treatments received by the animals. At 1-hour intervals for 6 hours following treatment, and with minimal disturbances to the animals, each test chamber collection pan was removed briefly to transfer the fecal boli to a clean weigh boat, and the empty collection pan was returned to the test chamber. Fecal boli were counted and weighed (in g) immediately after collection, and both parameters were recorded for each animal at each time point. In addition, the food remaining in each home cage was weighed (in g) and the value recorded, in order to determine food consumption over the previous 24 hours. No food or water was available to the animals during testing. At the end of the test, brain and plasma samples were collected from each animal and stored at −20 or −80° C. until analyzed for compound concentrations. All test chambers were cleaned with water and a 70% alcohol solution at the end of each test. The following parameters were analyzed by two-way analyses of variance with treatment condition and time as the between- and within-groups factors, respectively, and, if appropriate, post-hoc tests comparing test compound-treated groups to the vehicle-treated group (ANOVA, GraphPad Prism, GraphPad Software Inc., La Jolla, Calif., USA): 24-hour food consumption (in g) and total accumulated fecal boli at each time point (i.e., the total weight in g and number of fecal pellets accumulated in 1, 2, 3, 4, 5 and 6 hours post dosing). See, e.g., Raehal et al., 2005, J. Pharmacol. Exp. Ther., 314(3), 1195-1201.

Rat Formalin Test:

Adult male Sprague-Dawley rats, weighing 250-300 g at the time of testing, were acclimated to the facility for at least 5 days before testing. On the test day, each animal was weighed, and a light-weight, 'C'-shaped, metal band was placed around one of the animal's hind paws and secured with a drop of adhesive Immediately after application of the paw band, each rat was placed individually in a Plexiglas cylinder on clean, absorbent bench paper to acclimate to the test-like environment for 60 minutes prior to formalin administration. Each animal was briefly removed from its acclimation cylinder to administer the test article. Typically, compounds were administered by the intraperitoneal route of administration 30 minutes prior to formalin injection. Rats were randomly divided into the following treatment groups: vehicle (45% (w/v) 2-hydroxypropyl-β-cyclodextrin, negative control), morphine (3 mg/kg, positive control) and 3 dose levels of the test compound. Each treatment group included 6 to 8 rats. Following acclimation, a dilute formalin solution (5%, 50 mL) was administered into the subcutaneous space of the dorsal surface of the metal-banded hind paw, and the animal immediately was placed in a test cylinder to begin the test session. The Automated Nociception Analyzer device (UCSD, San Diego, Calif.; see Yaksh et al. (2001) for reference) recorded the number of flinches of the formalin-injected, metal-banded hind paw for 60 minutes. The number of flinches was summed for each animal over two time intervals (i.e., phase I=0-9 minutes post formalin administration and phase II=10-60 minutes post formalin administration). Phase I and II flinch sum values were averaged for each treatment group. For each phase, data were compared statistically using one-way analyses of variance (ANOVA, GraphPad Prism Version 4.03, GraphPad Software, Inc., La Jolla, Calif.) with the level of significance set a priori at $p<0.05$. A significant overall ANOVA was followed by multiple comparisons versus the vehicle control group. See, e.g., Yaksh et al., (2001), J. Appl. Physiol., 90, 2386-2402.

In one embodiment, $EC_{50}$ values were obtained for selected examples. The tables below summarize $EC_{50}$ values obtained in duplicate for selected examples. The following abbreviations are used:

| GTP Activity | | | |
|---|---|---|---|
| $EC_{50}$ (μM) | | TOP relative to DAMGO | Abbreviation |
| <0.1 | and | >50 | ++++ |
| 0.1-1 | and | >50 | +++ |
| 1.0-10 | and | >50 | ++ |
| >10 | or | <50 | + |

| BArr Activity | | | |
|---|---|---|---|
| $EC_{50}$ (μM) | | TOP relative to Morphine | Abbreviation |
| <10 | and | >50 | +++ |
| <10 | and | 10-50 | ++ |
| >10 | or | <10 | + |

D. Compounds, Preparation Methods, and Biological Activity

Using procedures provided herein, the following compounds were prepared. The biological activities were measured.

| Cmpd No. | Structure | GTP Activity | BArr Activity | General Procedure | Exact Mass | MS M/Z Found (M + 1) |
|---|---|---|---|---|---|---|
| 1 | 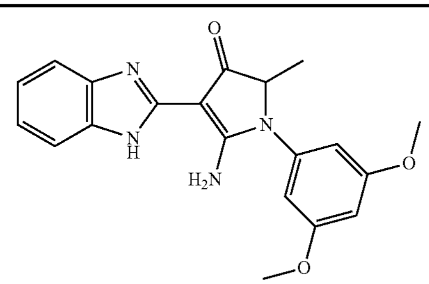 | +++ | ++ | B | 364 | 365 |
| 2 | 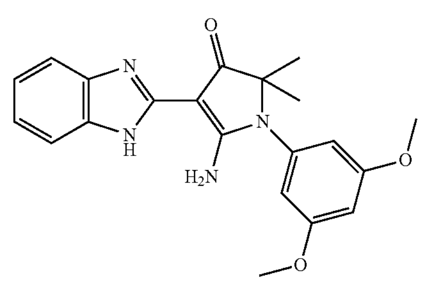 [SMILES: COc1cc(OC)cc(N2C(N)=C(c3nc4ccccc4[nH]3)C(=O)C2(C)C)c1] | +++ | ++ | B | 378 | 379 |
| 3 | 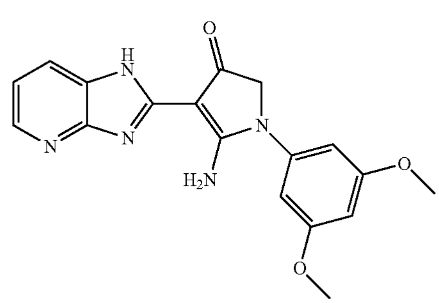 [SMILES: COc1cc(OC)cc(N2CC(=O)C(c3nc4ncccc4[nH]3)=C2N)c1] | + | | A | 351 | 352 |

-continued

| Cmpd No. | Structure | GTP Activity | BArr Activity | General Procedure | Exact Mass | MS M/Z Found (M + 1) |
|---|---|---|---|---|---|---|
| 4 | 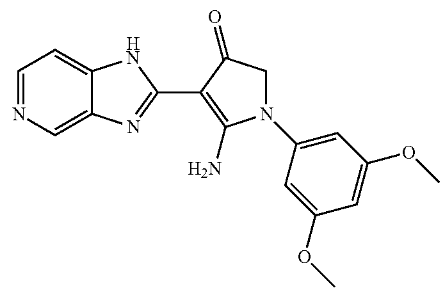 [SMILES: COc1cc(OC)cc(N2CC(=O)C(c3nc4cnccc4[nH]3)=C2N)c1] | + | | A | 351 | 352 |
| 5 | 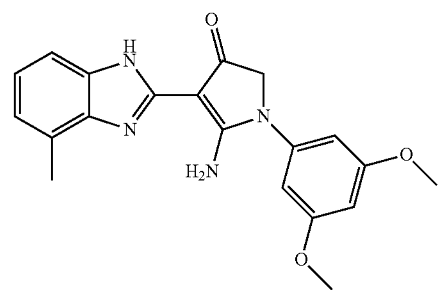 [SMILES: COc1cc(OC)cc(N2CC(=O)C(c3nc4c(C)cccc4[nH]3)=C2N)c1] | ++ | + | A | 364 | 365 |
| 6 | 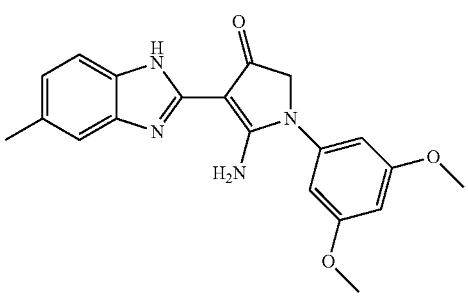 | ++ | + | A | 364 | 365 |
| 7 | 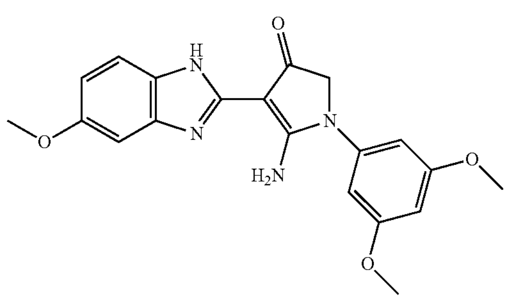 | ++ | + | A | 380 | 381 |
| 8 | 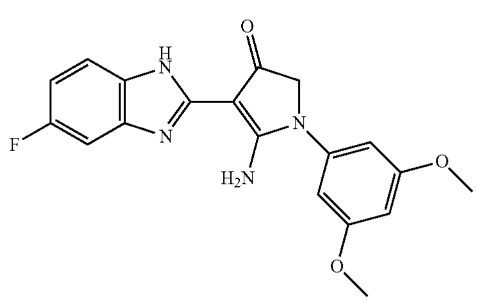 [SMILES: COc1cc(OC)cc(N2CC(=O)C(c3nc4cc(F)ccc4[nH]3)=C2N)c1] | + | | A | 368 | 369 |

-continued

| Cmpd No. | Structure | GTP Activity | BArr Activity | General Procedure | Exact Mass | MS M/Z Found (M + 1) |
|---|---|---|---|---|---|---|
| 9 | 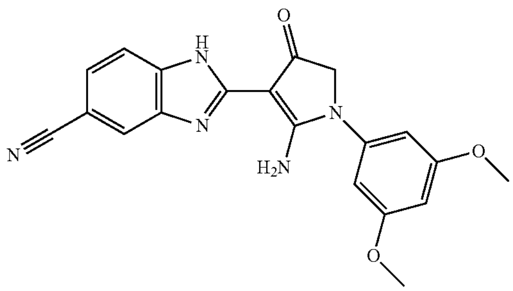 [SMILES: COc1cc(OC)cc(N2CC(=O)C(c3nc4cc(C#N)ccc4[nH]3)=C2N)c1] | + | | A | 375 | 376 |
| 10 | 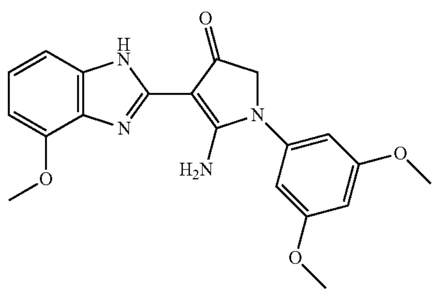 [SMILES: COc1cc(OC)cc(N2CC(=O)C(c3nc4c(OC)cccc4[nH]3)=C2N)c1] | + | + | A | 380 | 381 |
| 11 | 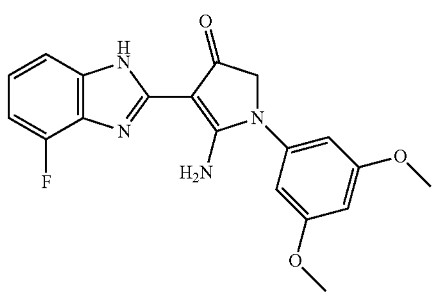 [SMILES: COc1cc(OC)cc(N2CC(=O)C(c3nc4c(F)cccc4[nH]3)=C2N)c1] | ++ | + | A | 368 | 369 |
| 12 | 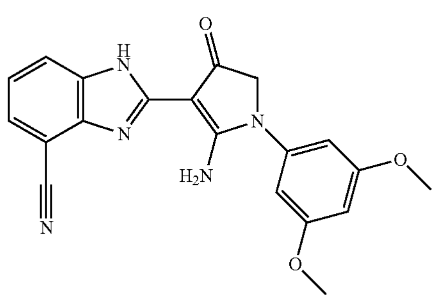 [SMILES: COc1cc(OC)cc(N2CC(=O)C(c3nc4c(C#N)cccc4[nH]3)=C2N)c1] | + | | A | 375 | 376 |
| 13 | 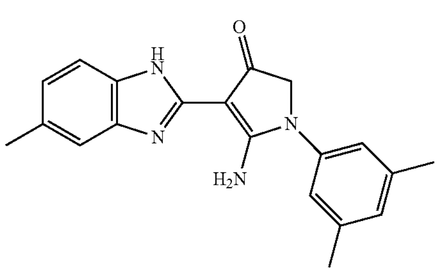 | + | | A | 332 | 333 |

-continued

| Cmpd No. | Structure | GTP Activity | BArr Activity | General Procedure | Exact Mass | MS M/Z Found (M + 1) |
|---|---|---|---|---|---|---|
| 14 | 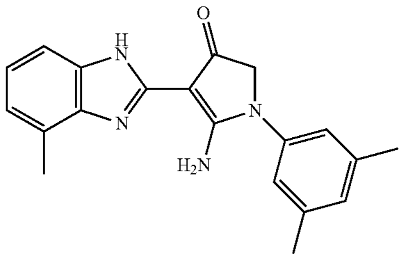 [SMILES: Cc1cc(C)cc(N2CC(=O)C(c3nc4c(C)cccc4[nH]3)=C2N)c1] | ++ | | A | 332 | 333 |
| 15 | 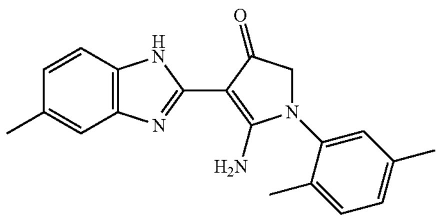 | ++ | | A | 332 | 333 |
| 16 | 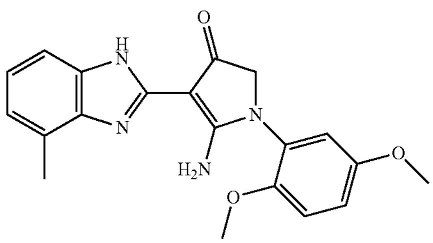 [SMILES: COc1ccc(OC)c(N2CC(=O)C(c3nc4c(C)cccc4[nH]3)=C2N)c1] | ++ | | A | 364 | 365 |
| 17 | 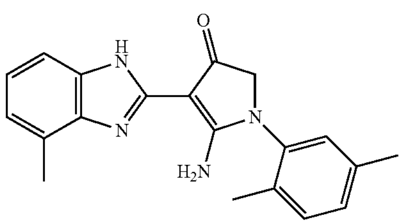 [SMILES: Cc1ccc(C)c(N2CC(=O)C(c3nc4c(C)cccc4[nH]3)=C2N)c1] | ++ | | A | 332 | 333 |
| 18 | 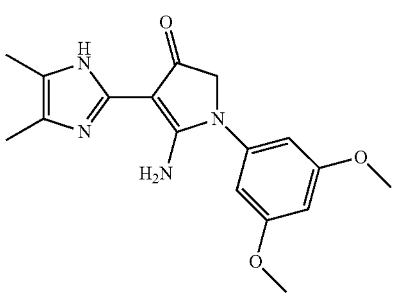 | + | | A | 328 | 329 |
| 19 | 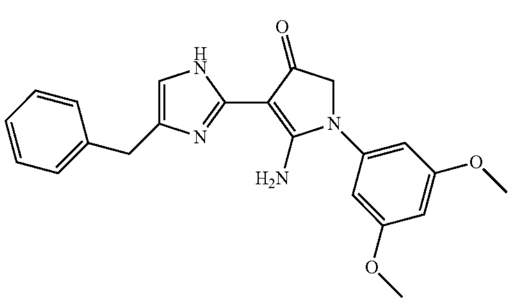 [SMILES: COc1cc(OC)cc(N2CC(=O)C(c3nc(Cc4ccccc4)c[nH]3)=C2N)c1] | + | + | A | 390 | 391 |

-continued

| Cmpd No. | Structure | GTP Activity | BArr Activity | General Procedure | Exact Mass | MS M/Z Found (M + 1) |
|---|---|---|---|---|---|---|
| 20 | 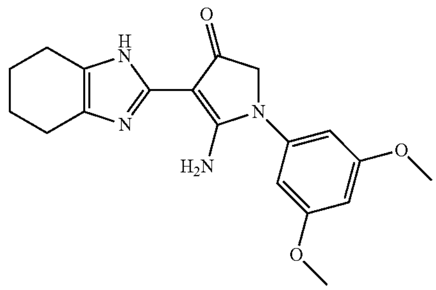 [SMILES: COc1cc(OC)cc(N2CC(=O)C(c3nc4c([nH]3)CCCC4)=C2N)c1] | + | | A | 354 | 355 |
| 21 | 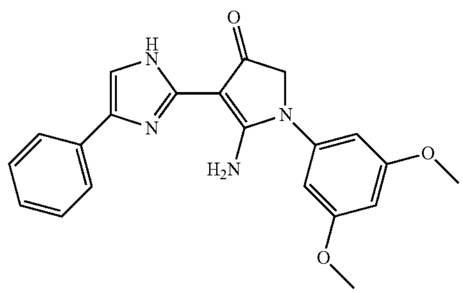 [SMILES: COc1cc(OC)cc(N2CC(=O)C(c3nc(-c4ccccc4)c[nH]3)=C2N)c1] | + | | A | 376 | 377 |
| 22 | 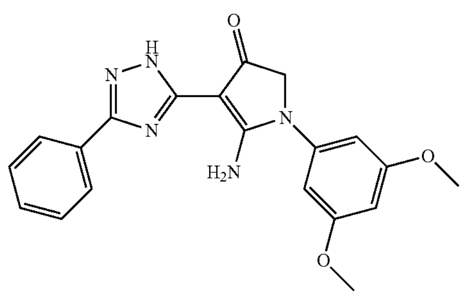 [SMILES: COc1cc(OC)cc(N2CC(=O)C(c3nc(-c4ccccc4)n[nH]3)=C2N)c1] | + | | A | 377 | 378 |
| 23 | 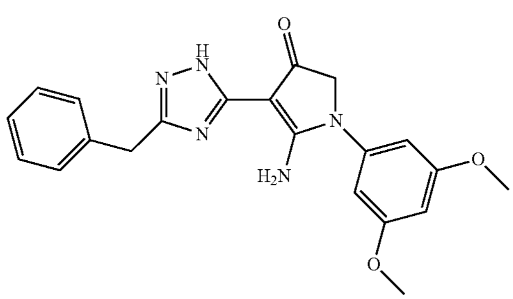 [SMILES: COc1cc(OC)cc(N2CC(=O)C(c3nc(Cc4ccccc4)n[nH]3)=C2N)c1] | + | | A | 391 | 392 |
| 24 | 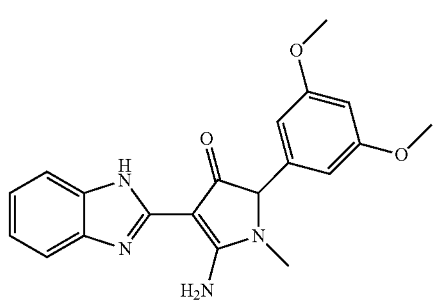 [SMILES: COc1cc(OC)cc(C2C(=O)C(c3nc4ccccc4[nH]3)=C(N)N2C)c1] | + | | A | 364 | 365 |

-continued

| Cmpd No. | Structure | GTP Activity | BArr Activity | General Procedure | Exact Mass | MS M/Z Found (M + 1) |
| --- | --- | --- | --- | --- | --- | --- |
| 25 | 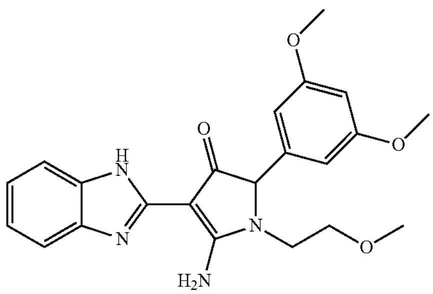 [SMILES: COCCN1C(N)=C(c2nc3ccccc3[nH]2)C(=O)C1c1cc(OC)cc(OC)c1] | + | + | A | 408 | 409 |
| 26 | 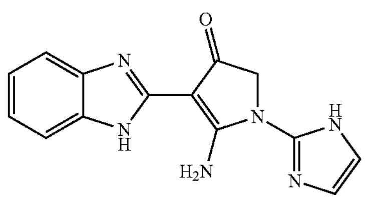 [SMILES: NC1=C(c2nc3ccccc3[nH]2)C(=O)CN1c1ncc[nH]1] | + | | A | 280 | 281 |
| 27 | 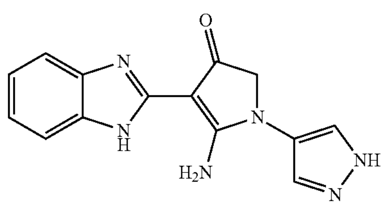 [SMILES: NC1=C(c2nc3ccccc3[nH]2)C(=O)CN1c1cn[nH]c1] | + | + | A | 280 | 281 |
| 28 | 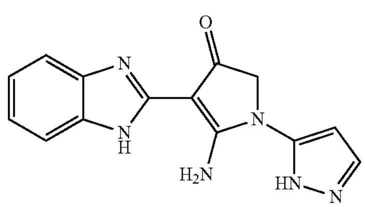 [SMILES: NC1=C(c2nc3ccccc3[nH]2)C(=O)CN1c1ccn[nH]1] | + | | A | 280 | 281 |
| 29 | 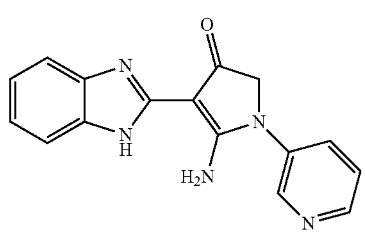 [SMILES: NC1=C(c2nc3ccccc3[nH]2)C(=O)CN1c1cccnc1] | + | | A | 291 | 292 |
| 30 | 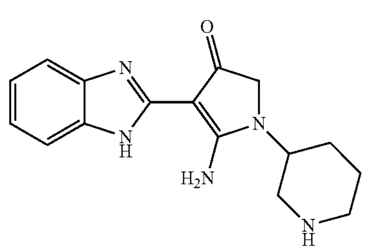 [SMILES: NC1=C(c2nc3ccccc3[nH]2)C(=O)CN1C1CCCNC1] | + | | A | 297 | 298 |

-continued

| Cmpd No. | Structure | GTP Activity | BArr Activity | General Procedure | Exact Mass | MS M/Z Found (M + 1) |
|---|---|---|---|---|---|---|
| 31 | 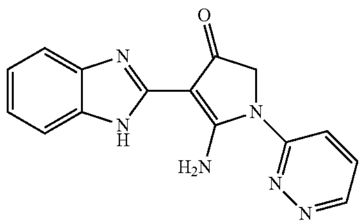 [SMILES: NC1=C(c2nc3ccccc3[nH]2)C(=O)CN1c1cccnn1] | + | | A | 292 | 293 |
| 32 | 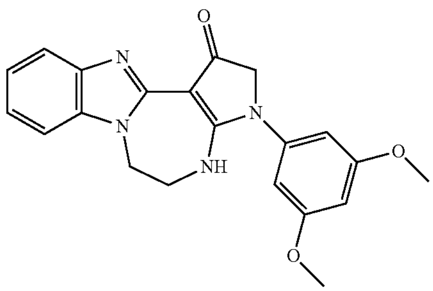 [SMILES: COc1cc(OC)cc(N2CC(=O)C3=C2NCCn2c3nc3ccccc32)c1] | + | + | N-alk | 376 | 377 |
| 33 | 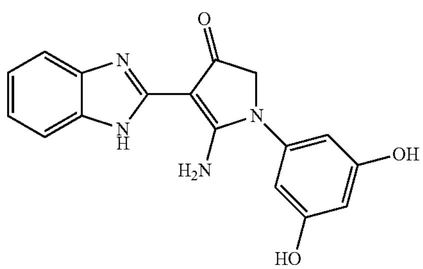 [SMILES: NC1=C(c2nc3ccccc3[nH]2)C(=O)CN1c1cc(O)cc(O)c1] | + | + | O-dealk | 322 | 323 |
| 34 | 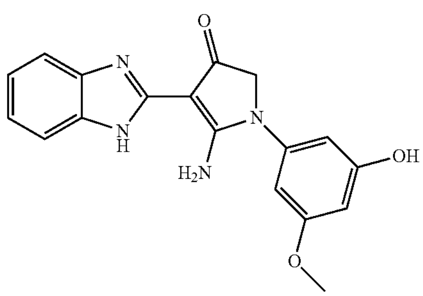 [SMILES: COc1cc(O)cc(N2CC(=O)C(c3nc4ccccc4[nH]3)=C2N)c1] | + | + | O-dealk | 336 | 337 |
| 35 | 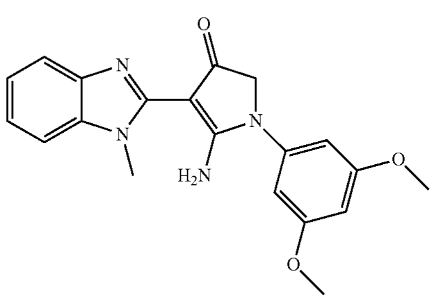 [SMILES: COc1cc(OC)cc(N2CC(=O)C(c3nc4ccccc4n3C)=C2N)c1] | + | + | A | 364 | 365 |

| Cmpd No. | Structure | GTP Activity | BArr Activity | General Procedure | Exact Mass | MS M/Z Found (M + 1) |
|---|---|---|---|---|---|---|
| 36 | 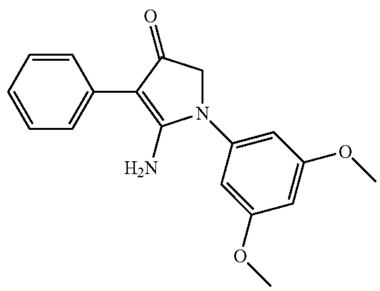 [SMILES: COc1cc(OC)cc(N2CC(=O)C(c3ccccc3)=C2N)c1] | + | | B | 310 | 311 |
| 37 | 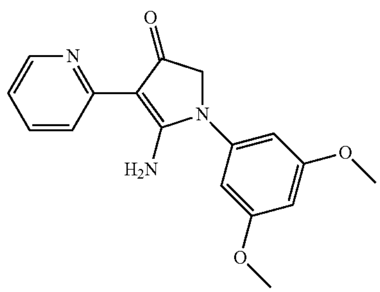 [SMILES: COc1cc(OC)cc(N2CC(=O)C(c3ccccn3)=C2N)c1] | + | + | A | 311 | 312 |
| 38 | 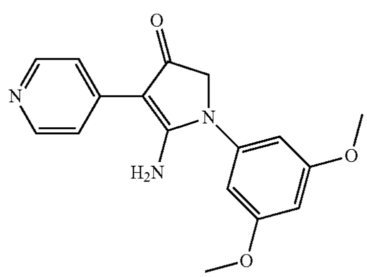 [SMILES: COc1cc(OC)cc(N2CC(=O)C(c3ccncc3)=C2N)c1] | + | | A | 311 | 312 |
| 39 | 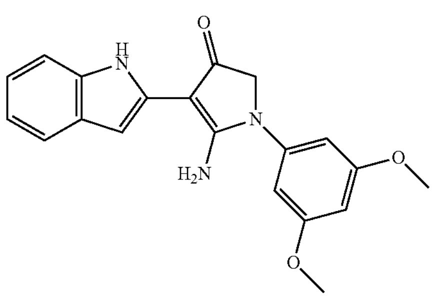 [SMILES: COc1cc(OC)cc(N2CC(=O)C(c3cc4ccccc4[nH]3)=C2N)c1] | + | | B | 349 | 350 |
| 40 | 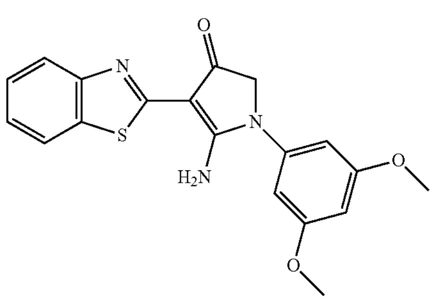 [SMILES: COc1cc(OC)cc(N2CC(=O)C(c3nc4ccccc4s3)=C2N)c1] | + | | A | 367 | 368 |

-continued

| Cmpd No. | Structure | GTP Activity | BArr Activity | General Procedure | Exact Mass | MS M/Z Found (M + 1) |
|---|---|---|---|---|---|---|
| 41 | 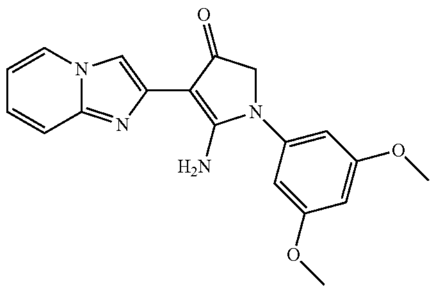 [SMILES: COc1cc(OC)cc(N2CC(=O)C(c3cn4ccccc4n3)=C2N)c1] | ++ | | B | 350 | 351 |
| 42 | 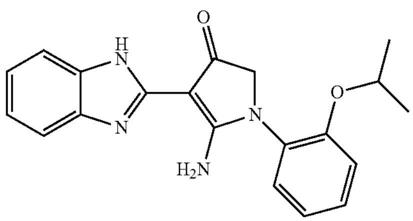 [SMILES: CC(C)Oc1ccccc1N1CC(=O)C(c2nc3ccccc3[nH]2)=C1N] | + | | A | 348 | 349 |
| 43 | 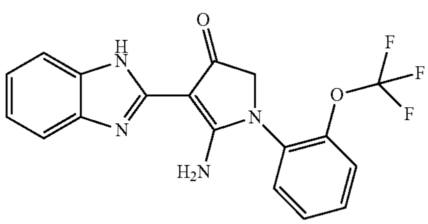 [SMILES: NC1=C(c2nc3ccccc3[nH]2)C(=O)CN1c1ccccc1OC(F)(F)F] | + | | A | 374 | 375 |
| 44 | 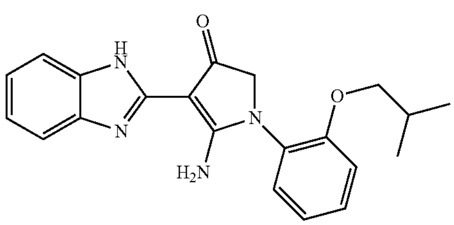 [SMILES: CC(C)COc1ccccc1N1CC(=O)C(c2nc3ccccc3[nH]2)=C1N] | + | | A | 362 | 363 |
| 45 | 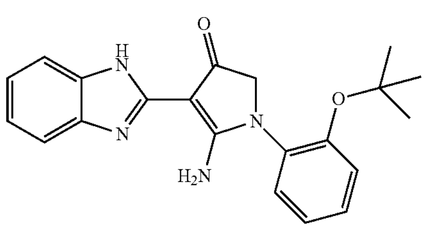 [SMILES: CC(C)(C)Oc1ccccc1N1CC(=O)C(c2nc3ccccc3[nH]2)=C1N] | ++ | + | A | 362 | 363 |
| 46 | 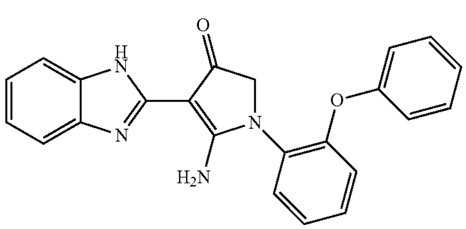 [SMILES: NC1=C(c2nc3ccccc3[nH]2)C(=O)CN1c1ccccc1Oc1ccccc1] | ++ | | A | 382 | 383 |

-continued

| Cmpd No. | Structure | GTP Activity | BArr Activity | General Procedure | Exact Mass | MS M/Z Found (M + 1) |
|---|---|---|---|---|---|---|
| 47 | 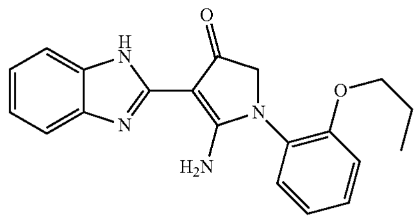 [SMILES: CCCOc1ccccc1N1CC(=O)C(c2nc3ccccc3[nH]2)=C1N] | + | | A | 348 | 349 |
| 48 | 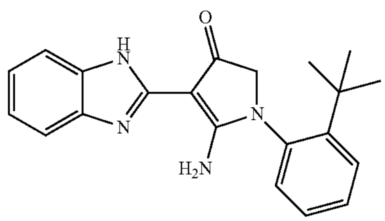 [SMILES: CC(C)(C)c1ccccc1N1CC(=O)C(c2nc3ccccc3[nH]2)=C1N] | ++ | + | A | 346 | 347 |
| 49 | 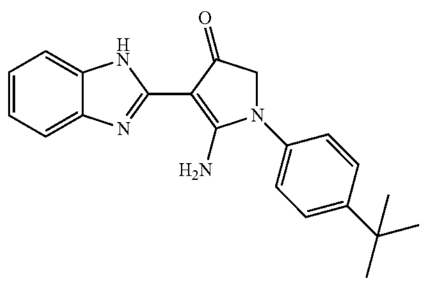 [SMILES: CC(C)(C)c1ccc(N2CC(=O)C(c3nc4ccccc4[nH]3)=C2N)cc1] | + | + | A | 346 | 347 |
| 50 | 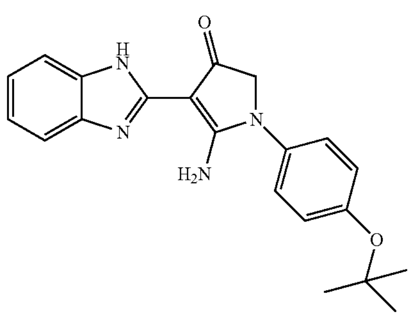 [SMILES: CC(C)(C)Oc1ccc(N2CC(=O)C(c3nc4ccccc4[nH]3)=C2N)cc1] | + | + | A | 362 | 363 |
| 51 | 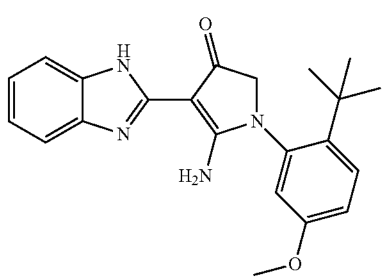 [SMILES: COc1ccc(C(C)(C)C)c(N2CC(=O)C(c3nc4ccccc4[nH]3)=C2N)c1] | + | | A | 376 | 377 |
| 52 | 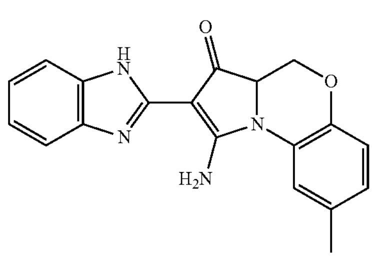 [SMILES: Cc1ccc2c(c1)N1C(N)=C(c3nc4ccccc4[nH]3)C(=O)C1CO2] | + | | B | 332 | 333 |

-continued

| Cmpd No. | Structure | GTP Activity | BArr Activity | General Procedure | Exact Mass | MS M/Z Found (M + 1) |
|---|---|---|---|---|---|---|
| 53 | 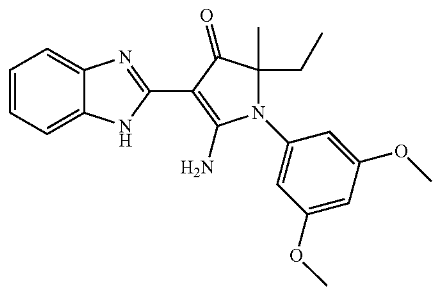 [SMILES: CCC1(C)C(=O)C(c2nc3ccccc3[nH]2)=C(N)N1c1cc(OC)cc(OC)c1] | +++ | + | A | 392 | 393 |
| 54 | 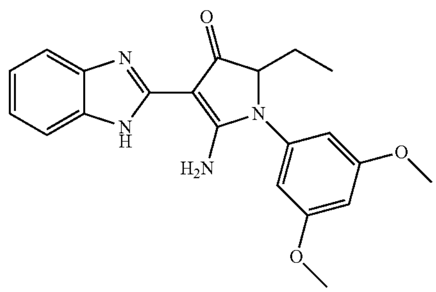 [SMILES: CCC1C(=O)C(c2nc3ccccc3[nH]2)=C(N)N1c1cc(OC)cc(OC)c1] | +++ | ++ | B | 378 | 379 |
| 55 | 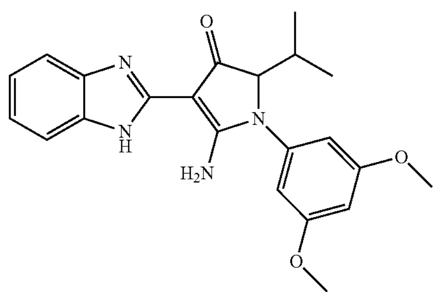 [SMILES: COc1cc(OC)cc(N2C(N)=C(c3nc4ccccc4[nH]3)C(=O)C2C(C)C)c1] | +++ | ++ | A | 392 | 393 |
| 56 | 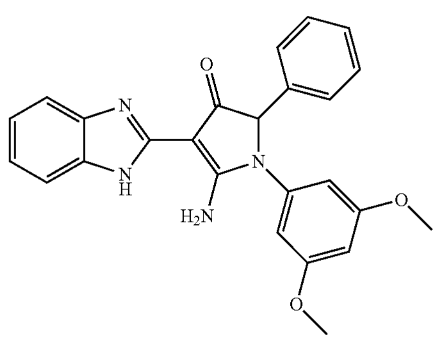 [SMILES: COc1cc(OC)cc(N2C(N)=C(c3nc4ccccc4[nH]3)C(=O)C2c2ccccc2)c1] | + | + | A | 426 | 427 |
| 57 | 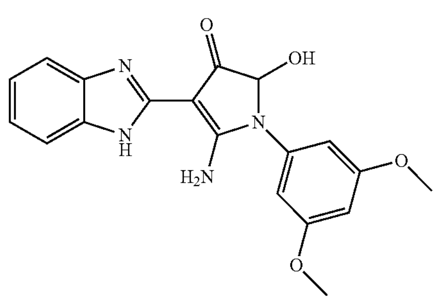 [SMILES: COc1cc(OC)cc(N2C(N)=C(c3nc4ccccc4[nH]3)C(=O)C2O)c1] | +++ | + | Alpha oxidation | 366 | 367 |

-continued

| Cmpd No. | Structure | GTP Activity | BArr Activity | General Procedure | Exact Mass | MS M/Z Found (M + 1) |
|---|---|---|---|---|---|---|
| 58 | 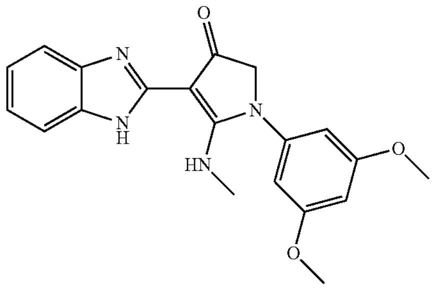 [SMILES: CNC1=C(c2nc3ccccc3[nH]2)C(=O)CN1c1cc(OC)cc(OC)c1] | +++ | ++ | N-alk | 364 | 365 |
| 59 | 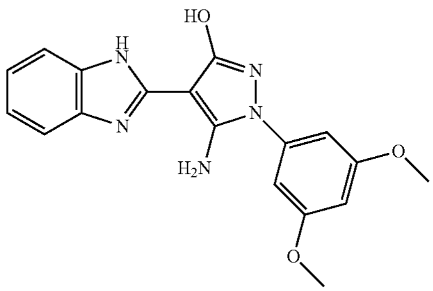 [SMILES: COc1cc(OC)cc(-n2nc(O)c(-c3nc4ccccc4[nH]3)c2N)c1] | + | | C | 351 | 352 |
| 60 | 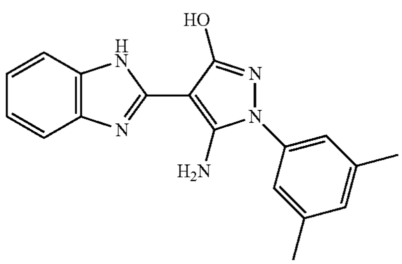 [SMILES: Cc1cc(C)cc(-n2nc(O)c(-c3nc4ccccc4[nH]3)c2N)c1] | + | | C | 319 | 320 |
| 61 | 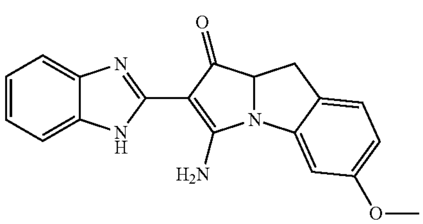 [SMILES: COc1ccc2c(c1)N1C(N)=C(c3nc4ccccc4[nH]3)C(=O)C1C2] | + | | B | 332 | 333 |
| 62 | 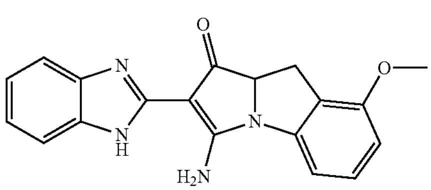 [SMILES: COc1cccc2c1CC1C(=O)C(c3nc4ccccc4[nH]3)=C(N)N21] | + | | B | 332 | 333 |
| 63 | 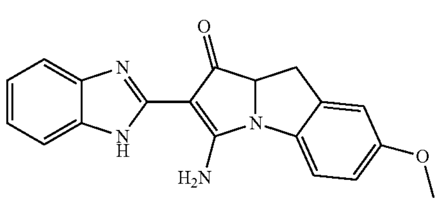 [SMILES: COc1ccc2c(c1)CC1C(=O)C(c3nc4ccccc4[nH]3)=C(N)N21] | + | | B | 332 | 333 |

| Cmpd No. | Structure | GTP Activity | BArr Activity | General Procedure | Exact Mass | MS M/Z Found (M + 1) |
|---|---|---|---|---|---|---|
| 64 | 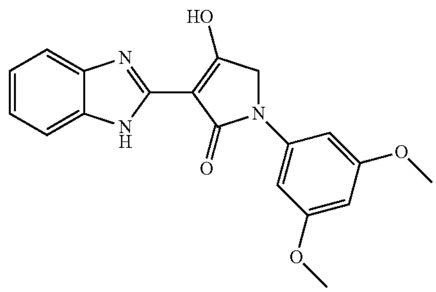 [SMILES: COc1cc(OC)cc(N2CC(O)=C(c3nc4ccccc4[nH]3)C2=O)c1] | + | | D | 351 | 352 |
| 65 | 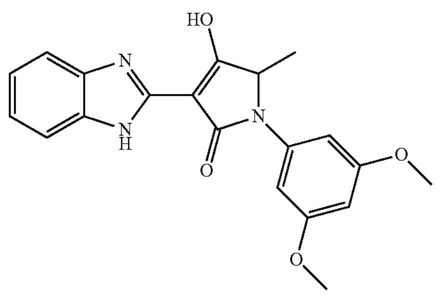 [SMILES: COc1cc(OC)cc(N2C(=O)C(c3nc4ccccc4[nH]3)=C(O)C2C)c1] | + | | D | 365 | 366 |
| 66 | 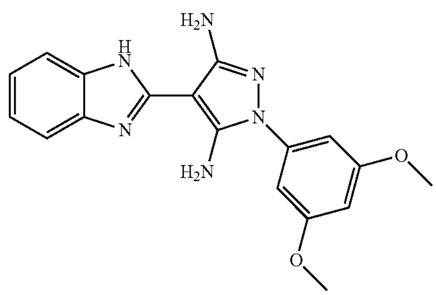 [SMILES: COc1cc(OC)cc(-n2nc(N)c(-c3nc4ccccc4[nH]3)c2N)c1] | +++ | + | C | 350 | 351 |
| 67 | 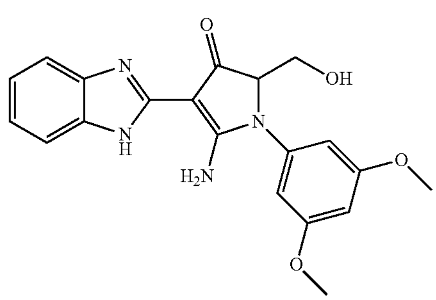 [SMILES: COc1cc(OC)cc(N2C(N)=C(c3nc4ccccc4[nH]3)C(=O)C2CO)c1] | ++ | + | A | 380 | 381 |
| 68 | 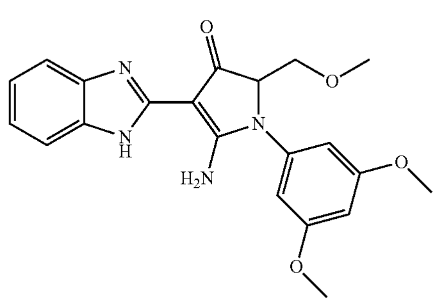 [SMILES: COCC1C(=O)C(c2nc3ccccc3[nH]2)=C(N)N1c1cc(OC)cc(OC)c1] | +++ | + | A | 394 | 395 |

-continued

| Cmpd No. | Structure | GTP Activity | BArr Activity | General Procedure | Exact Mass | MS M/Z Found (M + 1) |
|---|---|---|---|---|---|---|
| 69 | 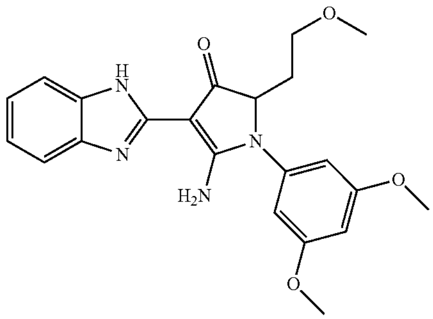 [SMILES: COCCC1C(=O)C(c2nc3ccccc3[nH]2)=C(N)N1c1cc(OC)cc(OC)c1] | +++ | + | A | 408 | 409 |
| 70 | 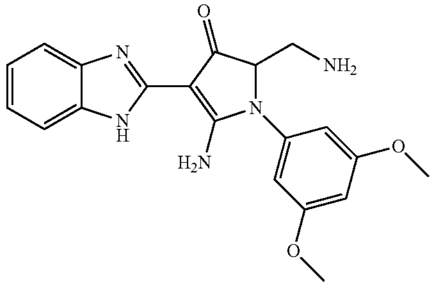 | +++ | + | A | 379 | 380 |
| 71 | 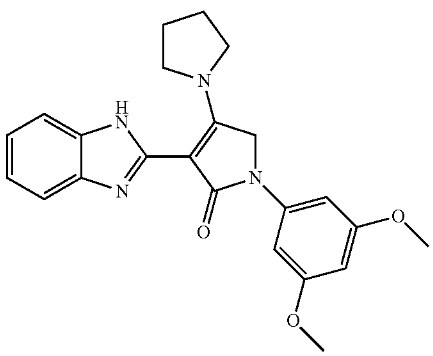 [SMILES: COc1cc(OC)cc(N2CC(N3CCCC3)=C(c3nc4ccccc4[nH]3)C2=O)c1] | + | | D | 404 | 405 |
| 72 | 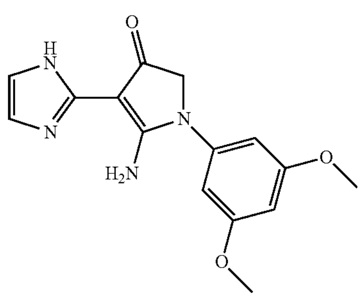 [SMILES: COc1cc(OC)cc(N2CC(=O)C(c3ncc[nH]3)=C2N)c1] | + | | A | 300 | 301 |
| 73 | 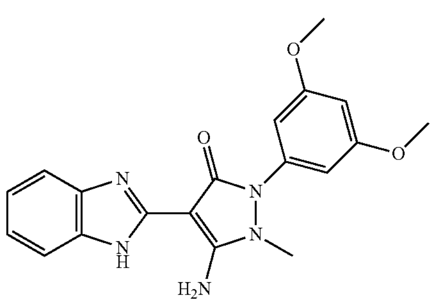 [SMILES: COc1cc(OC)cc(-n2c(=O)c(-c3nc4ccccc4[nH]3)c(N)n2C)c1] | + | | C | 365 | 366 |

-continued

| Cmpd No. | Structure | GTP Activity | BArr Activity | General Procedure | Exact Mass | MS M/Z Found (M + 1) |
|---|---|---|---|---|---|---|
| 74 | 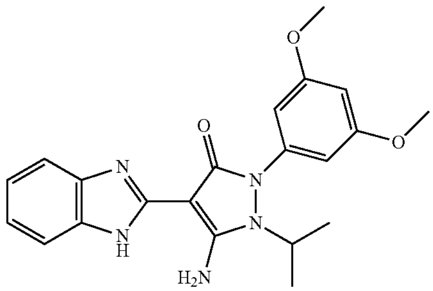 [SMILES: COc1cc(OC)cc(-n2c(=O)c(-c3nc4ccccc4[nH]3)c(N)n2C(C)C)c1] | ++ | | C | 393 | 394 |
| 75 | 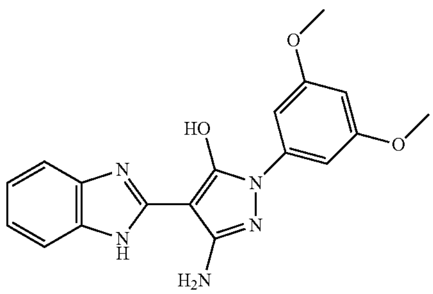 [SMILES: COc1cc(OC)cc(-n2nc(N)c(-c3nc4ccccc4[nH]3)c2O)c1] | + | | C | 351 | 352 |
| 76 | 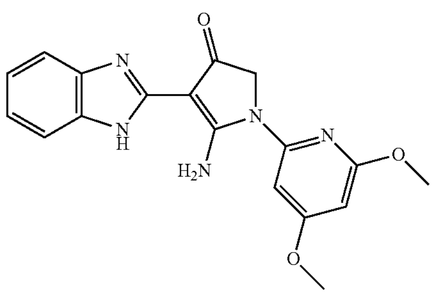 [SMILES: COc1cc(OC)nc(N2CC(=O)C(c3nc4ccccc4[nH]3)=C2N)c1] | + | | A | 351 | 352 |
| 77 | 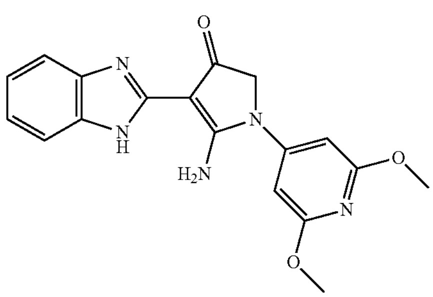 [SMILES: COc1cc(N2CC(=O)C(c3nc4ccccc4[nH]3)=C2N)cc(OC)n1] | + | | A | 351 | 352 |
| 78 | 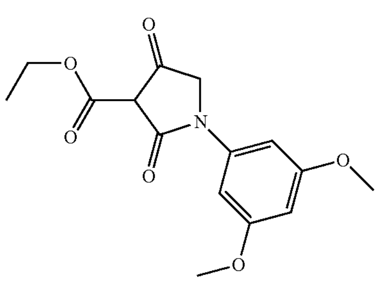 [SMILES: CCOC(=O)C1C(=O)CN(c2cc(OC)cc(OC)c2)C1=O] | + | | D | 307 | 308 |

-continued

| Cmpd No. | Structure | GTP Activity | BArr Activity | General Procedure | Exact Mass | MS M/Z Found (M + 1) |
|---|---|---|---|---|---|---|
| 79 | 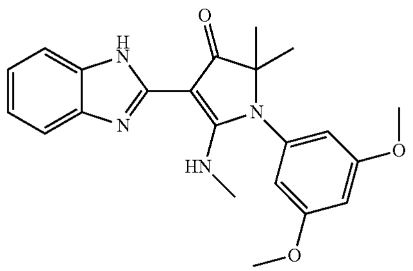 [SMILES: CNC1=C(c2nc3ccccc3[nH]2)C(=O)C(C)(C)N1c1cc(OC)cc(OC)c1] | ++++ | ++ | B | 392 | 393 |
| 80 | 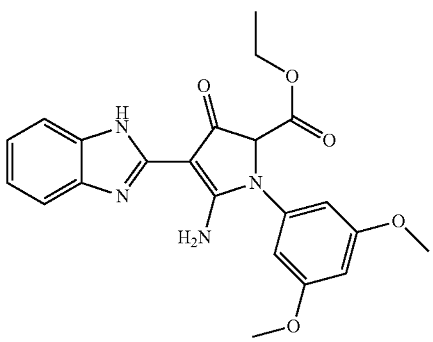 [SMILES: CCOC(=O)C1C(=O)C(c2nc3ccccc3[nH]2)=C(N)N1c1cc(OC)cc(OC)c1] | + | | A | 422 | 423 |
| 81 | 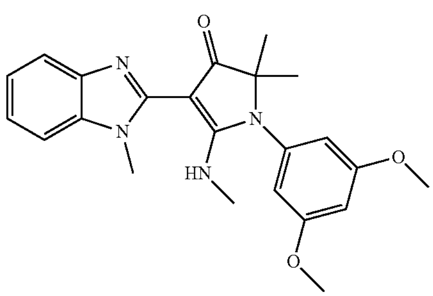 [SMILES: CNC1=C(c2nc3ccccc3n2C)C(=O)C(C)(C)N1c1cc(OC)cc(OC)c1] | +++ | + | N-alk | 406 | 407 |
| 82 | 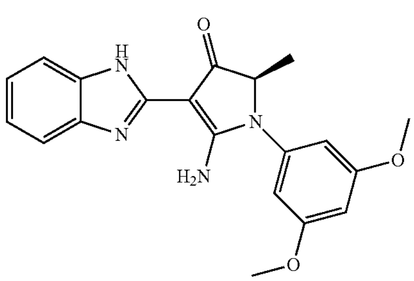 [SMILES: COc1cc(OC)cc(N2C(N)=C(c3nc4ccccc4[nH]3)C(=O)[C@H]2C)c1] | ++++ | ++ | B | 364 | 365 |
| 83 | 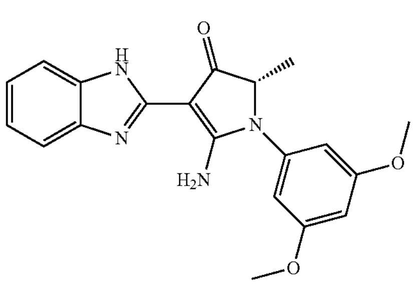 [SMILES: COc1cc(OC)cc(N2C(N)=C(c3nc4ccccc4[nH]3)C(=O)[C@@H]2C)c1] | ++ | + | B | 364 | 365 |

-continued

| Cmpd No. | Structure | GTP Activity | BArr Activity | General Procedure | Exact Mass | MS M/Z Found (M + 1) |
|---|---|---|---|---|---|---|
| 84 | 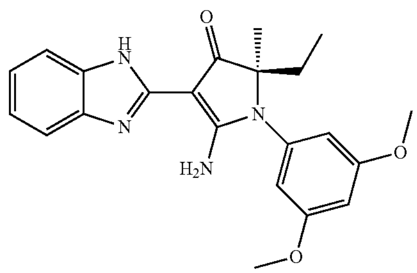 [SMILES: CC[C@]1(C)C(=O)C(c2nc3ccccc3[nH]2)=C(N)N1c1cc(OC)cc(OC)c1] | +++ | | A | 392 | 393 |
| 85 | 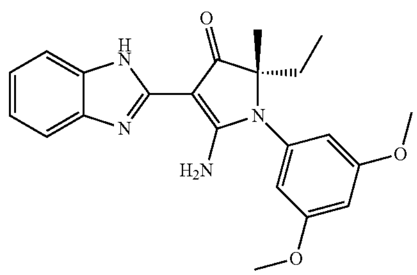 [SMILES: CC[C@@]1(C)C(=O)C(c2nc3ccccc3[nH]2)=C(N)N1c1cc(OC)cc(OC)c1] | +++ | + | A | 392 | 393 |
| 86 | 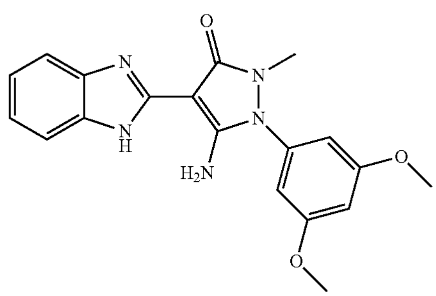 [SMILES: COc1cc(OC)cc(-n2c(N)c(-c3nc4ccccc4[nH]3)c(=O)n2C)c1] | +++ | | C | 365 | 366 |
| 87 | 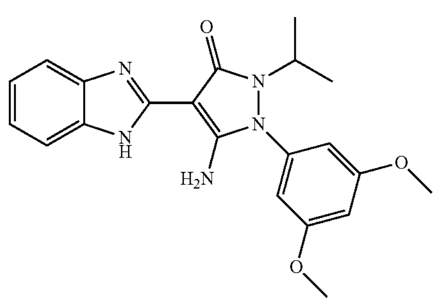 [SMILES: COc1cc(OC)cc(-n2c(N)c(-c3nc4ccccc4[nH]3)c(=O)n2C(C)C)c1] | + | | C | 393 | 394 |
| 88 | 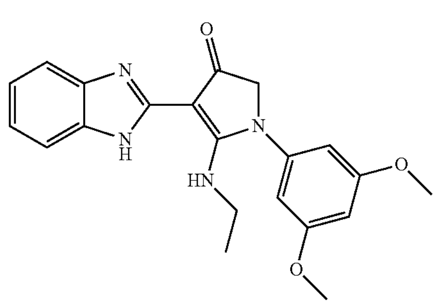 [SMILES: CCNC1=C(c2nc3ccccc3[nH]2)C(=O)CN1c1cc(OC)cc(OC)c1] | +++ | ++ | N-alk | 378 | 379 |

-continued
| Cmpd No. | Structure | GTP Activity | BArr Activity | General Procedure | Exact Mass | MS M/Z Found (M + 1) |
|---|---|---|---|---|---|---|
| 89 | 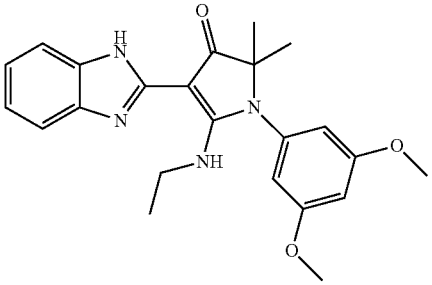 [SMILES: CCNC1=C(c2nc3ccccc3[nH]2)C(=O)C(C)(C)N1c1cc(OC)cc(OC)c1] | ++++ | ++ | N-alk | 406 | 407 |
| 90 | 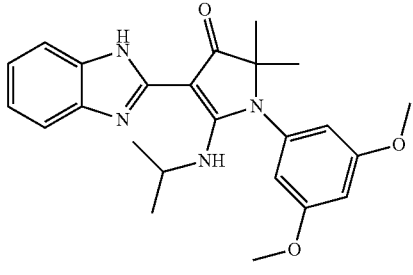 [SMILES: COc1cc(OC)cc(N2C(NC(C)C)=C(c3nc4ccccc4[nH]3)C(=O)C2(C)C)c1] | +++ | ++ | N-alk | 420 | 421 |
| 91 | 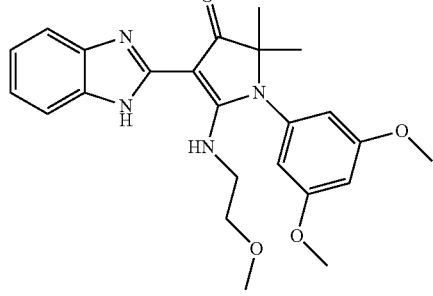 | ++ | + | N-alk | 436 | 437 |
| 92 | 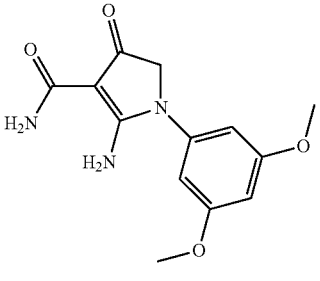 [SMILES: COc1cc(OC)cc(N2CC(=O)C(C(N)=O)=C2N)c1] | + | | F | 277 | 278 |
| 93 | 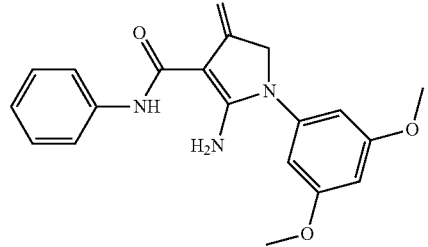 | + | | F | 353 | 354 |

| Cmpd No. | Structure | GTP Activity | BArr Activity | General Procedure | Exact Mass | MS M/Z Found (M + 1) |
|---|---|---|---|---|---|---|
| 94 | 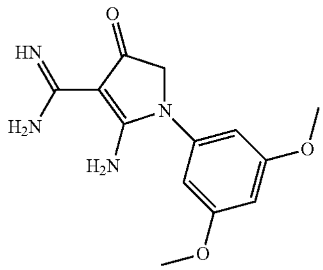 [SMILES: COc1cc(OC)cc(N2CC(=O)C(C(=N)N)=C2N)c1] | + | | F | 276 | 277 |
| 95 | 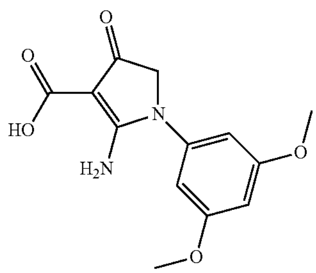 [SMILES: COc1cc(OC)cc(N2CC(=O)C(C(=O)O)=C2N)c1] | + | | F | 278 | 279 |
| 96 | 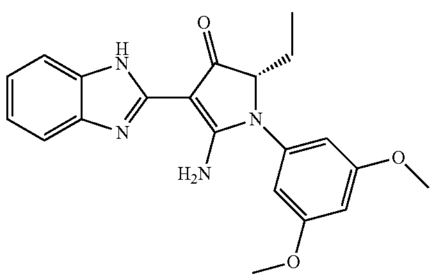 [SMILES: CC[C@H]1C(=O)C(c2nc3ccccc3[nH]2)=C(N)N1c1cc(OC)cc(OC)c1] | ++++ | ++ | B | 378 | 379 |
| 97 | 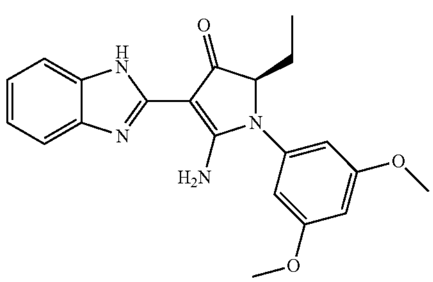 [SMILES: CC[C@@H]1C(=O)C(c2nc3ccccc3[nH]2)=C(N)N1c1cc(OC)cc(OC)c1] | ++ | + | B | 378 | 379 |
| 98 | 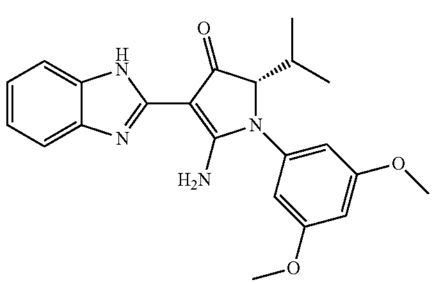 [SMILES: COc1cc(OC)cc(N2C(N)=C(c3nc4ccccc4[nH]3)C(=O)[C@@H]2C(C)C)c1] | ++++ | ++ | A | 392 | 393 |

-continued

| Cmpd No. | Structure | GTP Activity | BArr Activity | General Procedure | Exact Mass | MS M/Z Found (M + 1) |
|---|---|---|---|---|---|---|
| 99 | 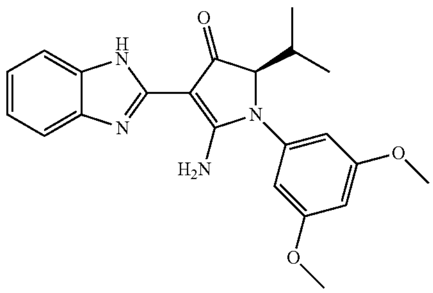 [SMILES: COc1cc(OC)cc(N2C(N)=C(c3nc4ccccc4[nH]3)C(=O)[C@H]2C(C)C)c1] | + | + | A | 392 | 393 |
| 100 | 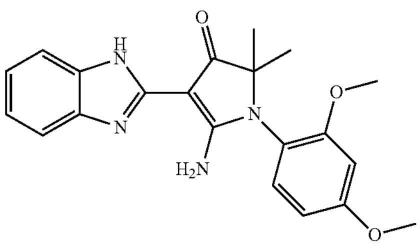 [SMILES: COc1ccc(N2C(N)=C(c3nc4ccccc4[nH]3)C(=O)C2(C)C)c(OC)c1] | + | | B | 378 | 379 |
| 101 | 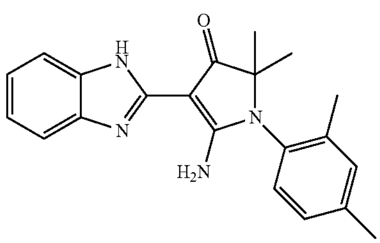 [SMILES: Cc1ccc(N2C(N)=C(c3nc4ccccc4[nH]3)C(=O)C2(C)C)c(C)c1] | +++ | | B | 346 | 347 |
| 102 | 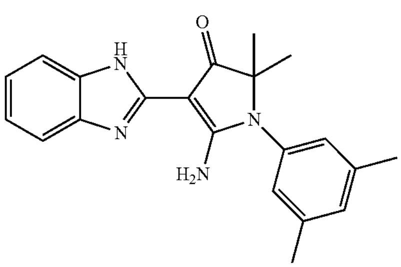 [SMILES: Cc1cc(C)cc(N2C(N)=C(c3nc4ccccc4[nH]3)C(=O)C2(C)C)c1] | +++ | | B | 346 | 347 |
| 103 | 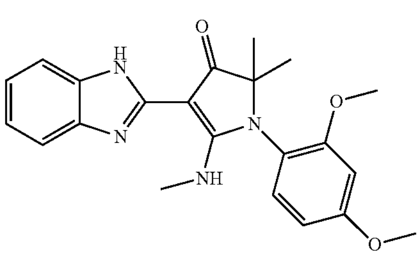 [SMILES: CNC1=C(c2nc3ccccc3[nH]2)C(=O)C(C)(C)N1c1ccc(OC)cc1OC] | + | | N-alk | 392 | 393 |
| 104 | 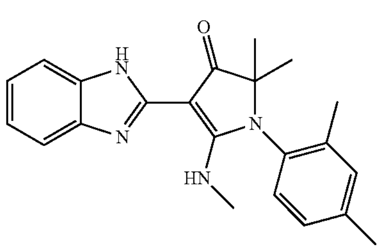 [SMILES: CNC1=C(c2nc3ccccc3[nH]2)C(=O)C(C)(C)N1c1ccc(C)cc1C] | ++ | | N-alk | 360 | 361 |

-continued

| Cmpd No. | Structure | GTP Activity | BArr Activity | General Procedure | Exact Mass | MS M/Z Found (M + 1) |
|---|---|---|---|---|---|---|
| 105 | 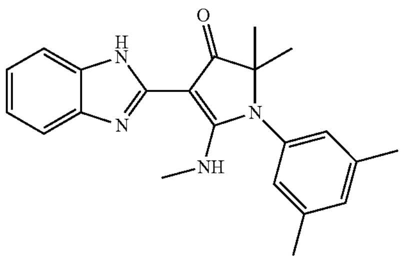 [SMILES: CNC1=C(c2nc3ccccc3[nH]2)C(=O)C(C)(C)N1c1cc(C)cc(C)c1] | +++ | + | N-alk | 360 | 361 |
| 106 | 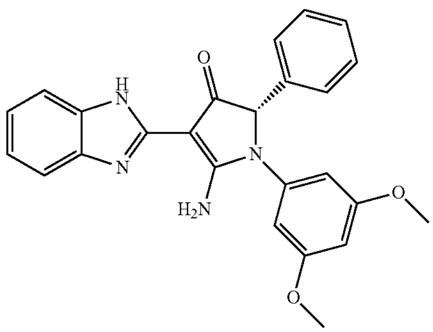 [SMILES: COc1cc(OC)cc(N2C(N)=C(c3nc4ccccc4[nH]3)C(=O)[C@@H]2c2ccccc2)c1] | ++ | | A | 426 | 427 |
| 107 | 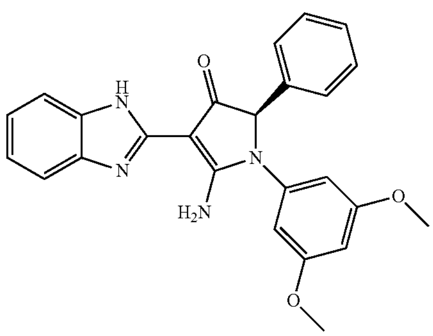 [SMILES: COc1cc(OC)cc(N2C(N)=C(c3nc4ccccc4[nH]3)C(=O)[C@H]2c2ccccc2)c1] | + | | A | 426 | 427 |
| 108 | 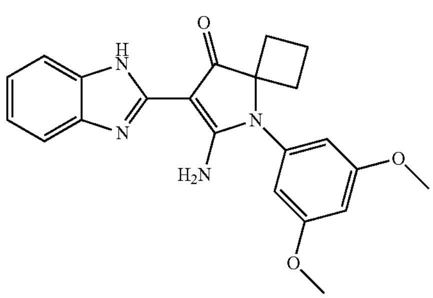 [SMILES: COc1cc(OC)cc(N2C(N)=C(c3nc4ccccc4[nH]3)C(=O)C23CCC3)c1] | ++++ | + | A | 390 | 391 |
| 109 | 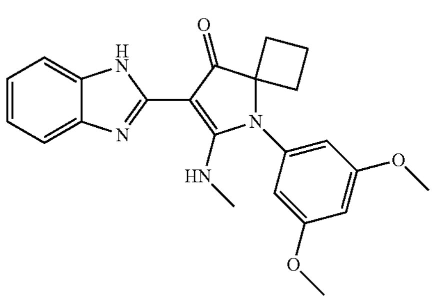 [SMILES: CNC1=C(c2nc3ccccc3[nH]2)C(=O)C2(CCC2)N1c1cc(OC)cc(OC)c1] | ++++ | ++ | N-alk | 404 | 405 |

-continued

| Cmpd No. | Structure | GTP Activity | BArr Activity | General Procedure | Exact Mass | MS M/Z Found (M + 1) |
|---|---|---|---|---|---|---|
| 110 | 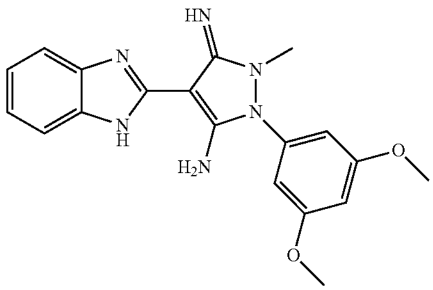 [SMILES: COc1cc(OC)cc(-n2c(N)c(-c3nc4ccccc4[nH]3)c(=N)n2C)c1] | +++ | + | C | 364 | 365 |
| 111 | 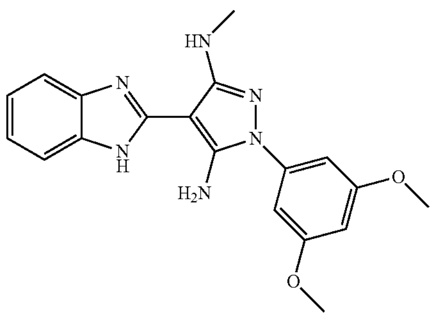 [SMILES: CNc1nn(-c2cc(OC)cc(OC)c2)c(N)c1-c1nc2ccccc2[nH]1] | + | | N-alk | 364 | 365 |
| 112 | 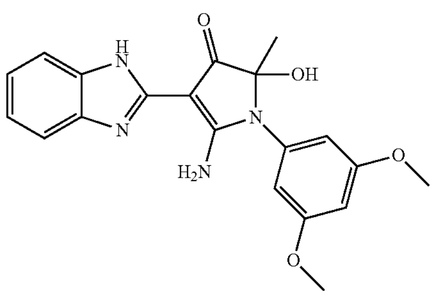 [SMILES: COc1cc(OC)cc(N2C(N)=C(c3nc4ccccc4[nH]3)C(=O)C2(C)O)c1] | +++ | + | Alpha oxidation | 380 | 381 |
| 113 | 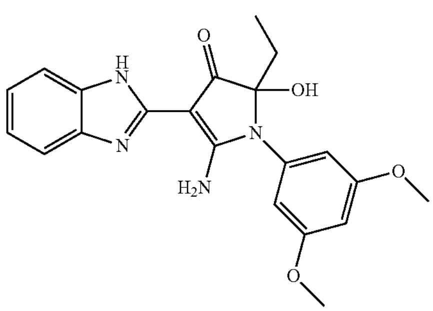 [SMILES: CCC1(O)C(=O)C(c2nc3ccccc3[nH]2)=C(N)N1c1cc(OC)cc(OC)c1] | +++ | + | Alpha oxidation | 394 | 395 |
| 114 | 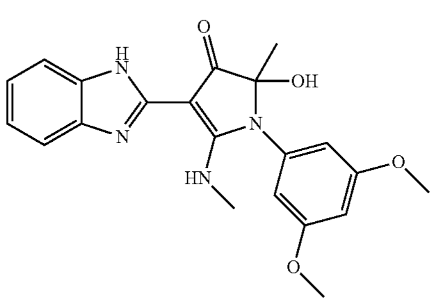 [SMILES: CNC1=C(c2nc3ccccc3[nH]2)C(=O)C(C)(O)N1c1cc(OC)cc(OC)c1] | +++ | + | Alpha oxidation | 394 | 395 |

-continued

| Cmpd No. | Structure | GTP Activity | BArr Activity | General Procedure | Exact Mass | MS M/Z Found (M + 1) |
|---|---|---|---|---|---|---|
| 115 | 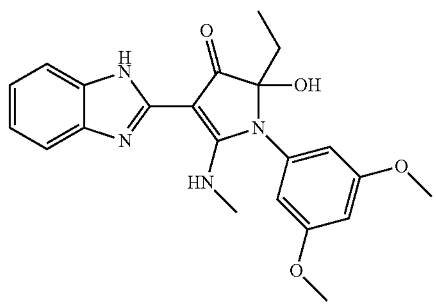 [SMILES: CCC1(O)C(=O)C(c2nc3ccccc3[nH]2)=C(NC)N1c1cc(OC)cc(OC)c1] | +++ | + | Alpha oxidation | 408 | 409 |
| 116 | 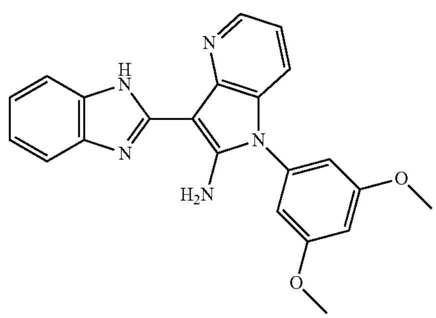 [SMILES: COc1cc(OC)cc(-n2c(N)c(-c3nc4ccccc4[nH]3)c3ncccc32)c1] | | + | G | 385 | 386 |
| 117 | 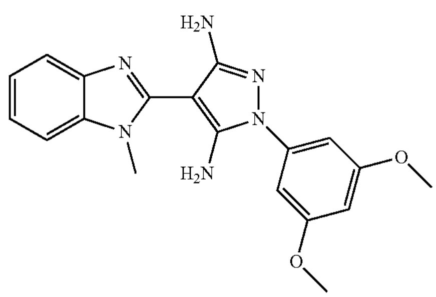 [SMILES: COc1cc(OC)cc(-n2nc(N)c(-c3nc4ccccc4n3C)c2N)c1] | | + | N-alk | 364 | 365 |
| 118 | 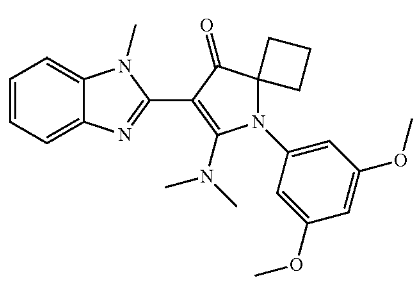 [SMILES: COc1cc(OC)cc(N2C(N(C)C)=C(c3nc4ccccc4n3C)C(=O)C23CCC3)c1] | | + | N-alk | 432 | 433 |
| 119 | 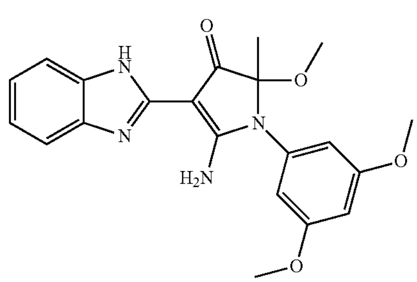 [SMILES: COc1cc(OC)cc(N2C(N)=C(c3nc4ccccc4[nH]3)C(=O)C2(C)OC)c1] | ++ | + | Alpha oxidation | 394 | 395 |

-continued

| Cmpd No. | Structure | GTP Activity | BArr Activity | General Procedure | Exact Mass | MS M/Z Found (M + 1) |
|---|---|---|---|---|---|---|
| 120 | 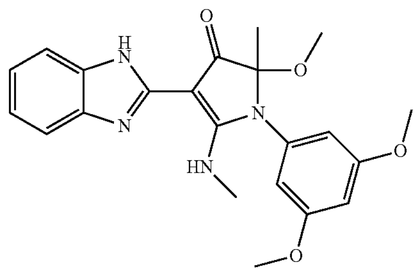 [SMILES: CNC1=C(c2nc3ccccc3[nH]2)C(=O)C(C)(OC)N1c1cc(OC)cc(OC)c1] | +++ | + | Alpha oxidation | 408 | 409 |
| 121 | 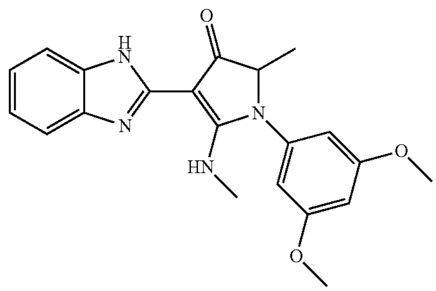 [SMILES: CNC1=C(c2nc3ccccc3[nH]2)C(=O)C(C)N1c1cc(OC)cc(OC)c1] | ++++ | ++ | N-alk | 378 | 379 |
| 122 | 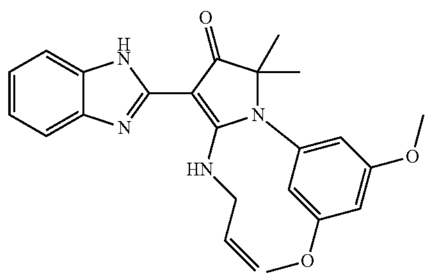 [SMILES: C=CCNC1=C(c2nc3ccccc3[nH]2)C(=O)C(C)(C)N1c1cc(OC)cc(OC)c1] | +++ | | N-alk | 418 | 419 |
| 123 | 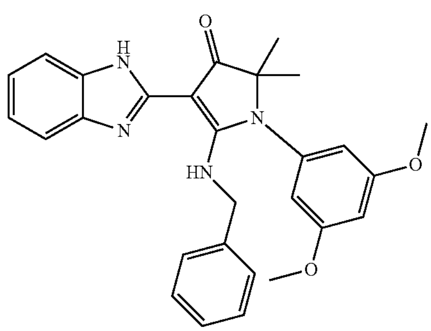 [SMILES: COc1cc(OC)cc(N2C(NCc3ccccc3)=C(c3nc4ccccc4[nH]3)C(=O)C2(C)C)c1] | + | | N-alk | 468 | 469 |
| 124 | 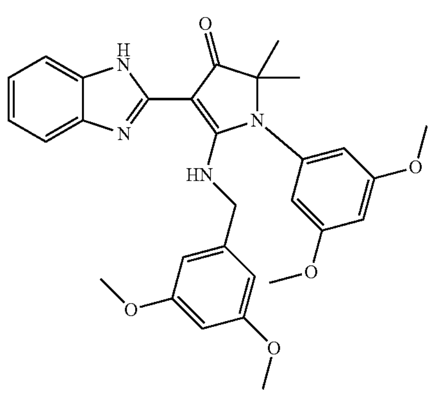 [SMILES: COc1cc(CNC2=C(c3nc4ccccc4[nH]3)C(=O)C(C)(C)N2c2cc(OC)cc(OC)c2)cc(OC)c1] | + | | N-alk | 528 | 529 |

-continued

| Cmpd No. | Structure | GTP Activity | BArr Activity | General Procedure | Exact Mass | MS M/Z Found (M + 1) |
|---|---|---|---|---|---|---|
| 125 | 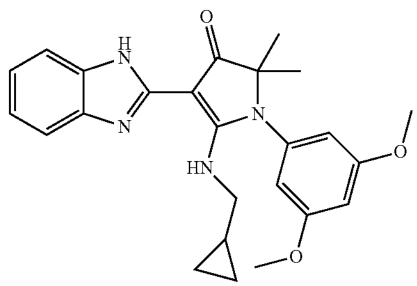 [SMILES: COc1cc(OC)cc(N2C(NCC3CC3)=C(c3nc4ccccc4[nH]3)C(=O)C2(C)C)c1] | ++ | | N-alk | 432 | 433 |
| 126 | 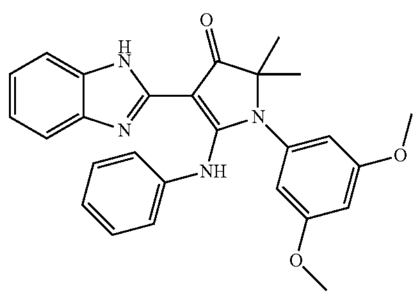 [SMILES: COc1cc(OC)cc(N2C(Nc3ccccc3)=C(c3nc4ccccc4[nH]3)C(=O)C2(C)C)c1] | ++ | | N-alk | 454 | 455 |
| 127 | 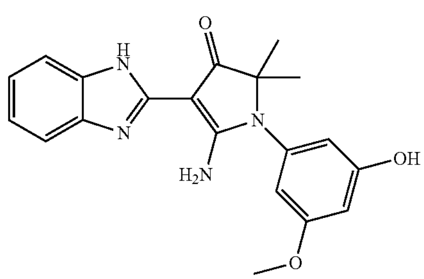 [SMILES: COc1cc(O)cc(N2C(N)=C(c3nc4ccccc4[nH]3)C(=O)C2(C)C)c1] | + | | O-dealk | 364 | 365 |
| 128 | 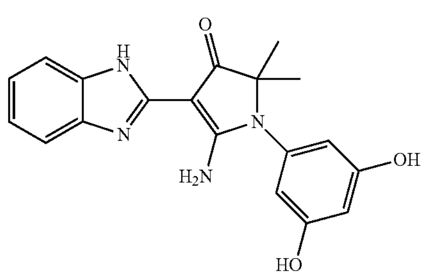 [SMILES: CC1(C)C(=O)C(c2nc3ccccc3[nH]2)=C(N)N1c1cc(O)cc(O)c1] | + | | O-dealk | 350 | 351 |
| 129 | 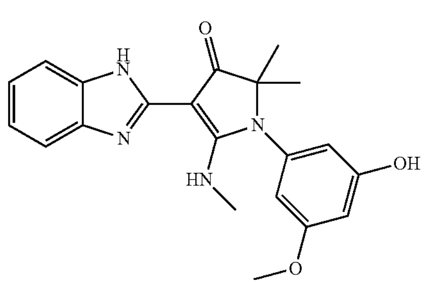 [SMILES: CNC1=C(c2nc3ccccc3[nH]2)C(=O)C(C)(C)N1c1cc(O)cc(OC)c1] | +++ | | O-dealk | 378 | 379 |

-continued

| Cmpd No. | Structure | GTP Activity | BArr Activity | General Procedure | Exact Mass | MS M/Z Found (M + 1) |
|---|---|---|---|---|---|---|
| 130 | 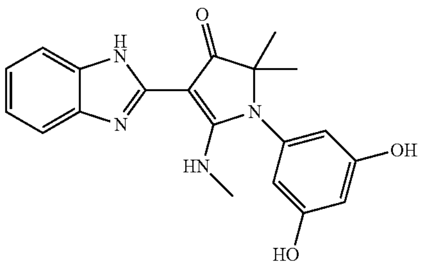 [SMILES: CNC1=C(c2nc3ccccc3[nH]2)C(=O)C(C)(C)N1c1cc(O)cc(O)c1] | + | | O-dealk | 364 | 365 |
| 131 | 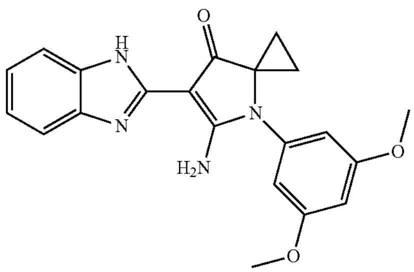 [SMILES: COc1cc(OC)cc(N2C(N)=C(c3nc4ccccc4[nH]3)C(=O)C23CC3)c1] | ++ | | A | 376 | 377 |
| 132 | 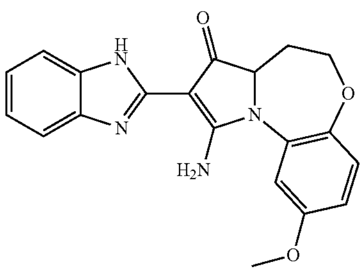 [SMILES: COc1ccc2c(c1)N1C(N)=C(c3nc4ccccc4[nH]3)C(=O)C1CCO2] | + | | B | 362 | 363 |
| 133 | 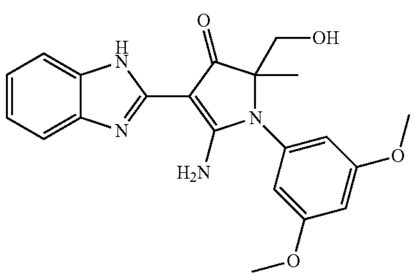 [SMILES: COc1cc(OC)cc(N2C(N)=C(c3nc4ccccc4[nH]3)C(=O)C2(C)CO)c1] | +++ | + | A | 394 | 395 |
| 134 | 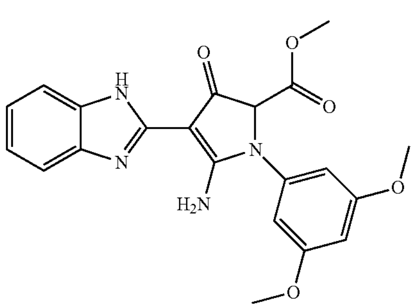 [SMILES: COC(=O)C1C(=O)C(c2nc3ccccc3[nH]2)=C(N)N1c1cc(OC)cc(OC)c1] | ++ | + | A | 408 | 409 |

-continued

| Cmpd No. | Structure | GTP Activity | BArr Activity | General Procedure | Exact Mass | MS M/Z Found (M + 1) |
|---|---|---|---|---|---|---|
| 135 | 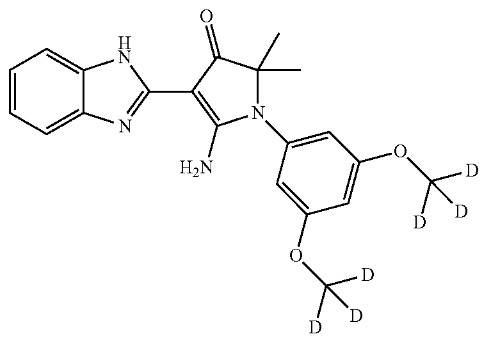 [SMILES: [2H]C([2H])([2H])Oc1cc(OC([2H])([2H])[2H])cc(N2C(N)=C(c3nc4ccccc4[nH]3)C(=O)C2(C)C)c1] | +++ | + | B | 384 | 385 |
| 136 | 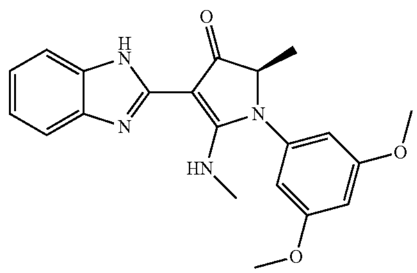 [SMILES: CNC1=C(c2nc3ccccc3[nH]2)C(=O)[C@@H](C)N1c1cc(OC)cc(OC)c1] | ++++ | ++ | N-alk | 378 | 379 |
| 137 | 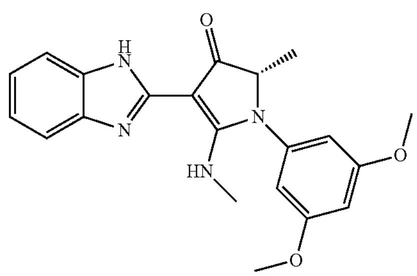 [SMILES: CNC1=C(c2nc3ccccc3[nH]2)C(=O)[C@H](C)N1c1cc(OC)cc(OC)c1] | +++ | ++ | N-alk | 378 | 379 |
| 138 | 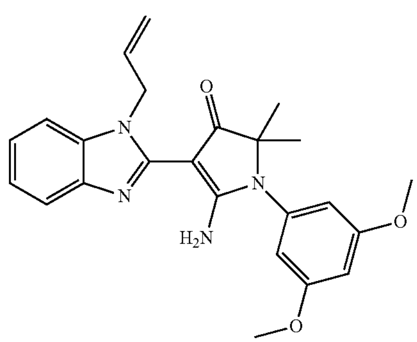 [SMILES: C=CCn1c(C2=C(N)N(c3cc(OC)cc(OC)c3)C(C)(C)C2=O)nc2ccccc21] | + | | N-alk | 418 | 419 |
| 139 | 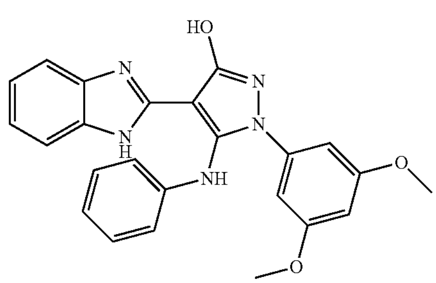 [SMILES: COc1cc(OC)cc(-n2nc(O)c(-c3nc4ccccc4[nH]3)c2Nc2ccccc2)c1] | + | | I | 427 | 428 |

-continued

| Cmpd No. | Structure | GTP Activity | BArr Activity | General Procedure | Exact Mass | MS M/Z Found (M + 1) |
|---|---|---|---|---|---|---|
| 140 | 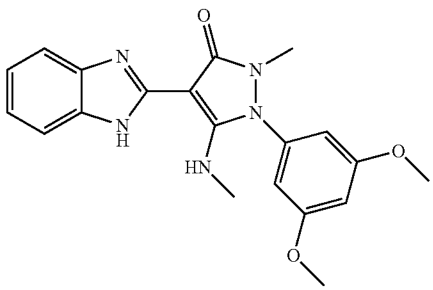 [SMILES: CNc1c(-c2nc3ccccc3[nH]2)c(=O)n(C)n1-c1cc(OC)cc(OC)c1] | ++++ | + | N-alk | 379 | 380 |
| 141 | 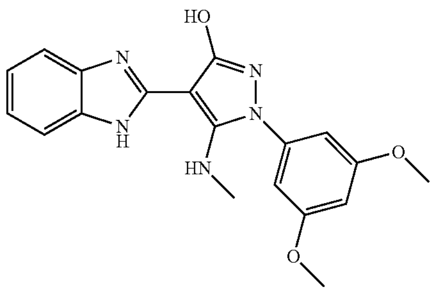 [SMILES: CNc1c(-c2nc3ccccc3[nH]2)c(O)nn1-c1cc(OC)cc(OC)c1] | + | | I | 365 | 366 |
| 142 | 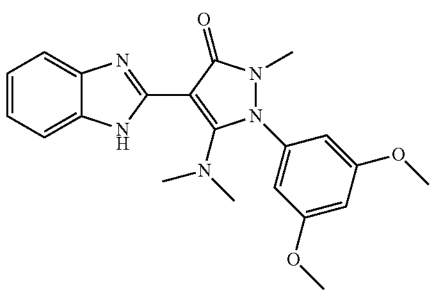 [SMILES: COc1cc(OC)cc(-n2c(N(C)C)c(-c3nc4ccccc4[nH]3)c(=O)n2C)c1] | + | | J | 393 | 394 |
| 143 | 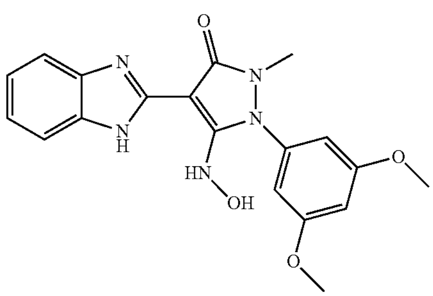 [SMILES: COc1cc(OC)cc(-n2c(NO)c(-c3nc4ccccc4[nH]3)c(=O)n2C)c1] | ++ | | F | 381 | 382 |
| 144 | 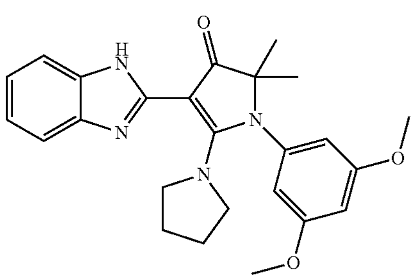 [SMILES: COc1cc(OC)cc(N2C(N3CCCC3)=C(c3nc4ccccc4[nH]3)C(=O)C2(C)C)c1] | ++ | | N-alk | 432 | 433 |

-continued

| Cmpd No. | Structure | GTP Activity | BArr Activity | General Procedure | Exact Mass | MS M/Z Found (M + 1) |
|---|---|---|---|---|---|---|
| 145 | 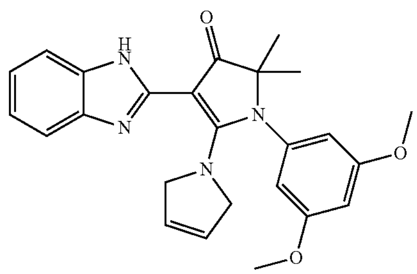 [SMILES: COc1cc(OC)cc(N2C(N3CC=CC3)=C(c3nc4ccccc4[nH]3)C(=O)C2(C)C)c1] | + | | N-alk | 430 | 431 |
| 146 | 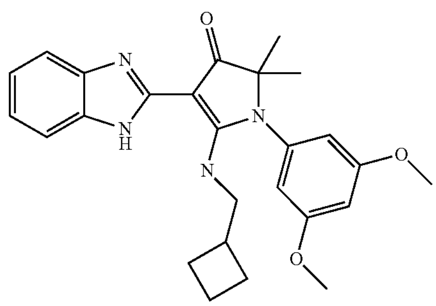 [SMILES: COc1cc(OC)cc(N2C(NCC3CCC3)=C(c3nc4ccccc4[nH]3)C(=O)C2(C)C)c1] | + | | N-alk | 446 | 447 |
| 147 | 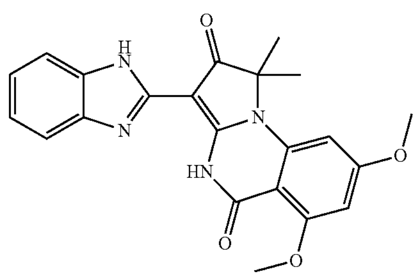 [SMILES: COc1cc(OC)c2c(c1)N1C(=C(c3nc4ccccc4[nH]3)C(=O)C1(C)C)NC2=O] | + | | A | 404 | 405 |
| 148 | 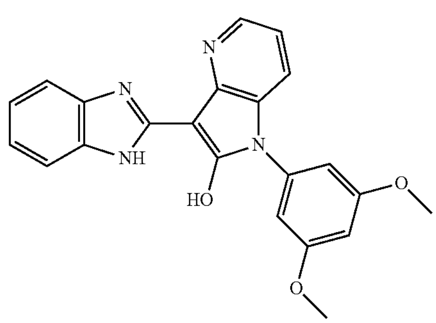 [SMILES: COc1cc(OC)cc(-n2c(O)c(-c3nc4ccccc4[nH]3)c3ncccc32)c1] | + | | H | 386 | 387 |
| 149 | 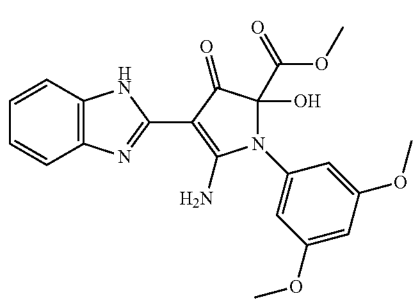 [SMILES: COC(=O)C1(O)C(=O)C(c2nc3ccccc3[nH]2)=C(N)N1c1cc(OC)cc(OC)c1] | + | | Alpha oxidation | 424 | 425 |

-continued

| Cmpd No. | Structure | GTP Activity | BArr Activity | General Procedure | Exact Mass | MS M/Z Found (M + 1) |
|---|---|---|---|---|---|---|
| 150 | 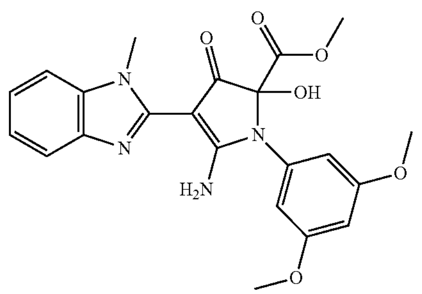 [SMILES: COC(=O)C1(O)C(=O)C(c2nc3ccccc3n2C)=C(N)N1c1cc(OC)cc(OC)c1] | + | | Alpha oxidation | 438 | 439 |
| 151 | 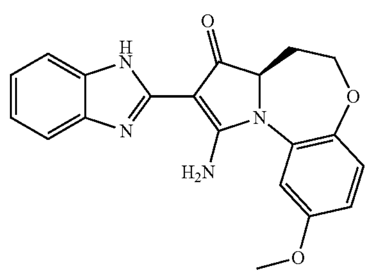 [SMILES: COc1ccc2c(c1)N1C(N)=C(c3nc4ccccc4[nH]3)C(=O)[C@H]1CCO2] | + | | B | 362 | 363 |
| 152 | 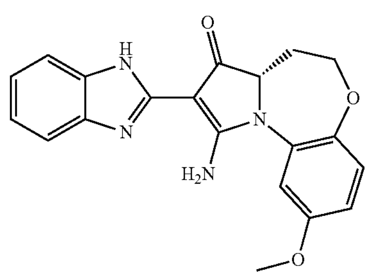 | + | | B | 362 | 363 |
| 153 | 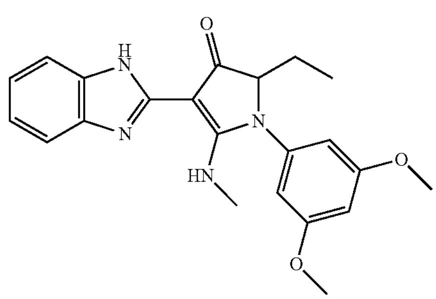 | ++++ | ++ | N-alk | 392 | 393 |
| 154 | 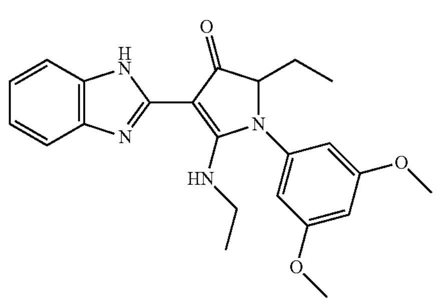 | +++ | ++ | N-alk | 406 | 407 |

-continued

| Cmpd No. | Structure | GTP Activity | BArr Activity | General Procedure | Exact Mass | MS M/Z Found (M + 1) |
|---|---|---|---|---|---|---|
| 155 | 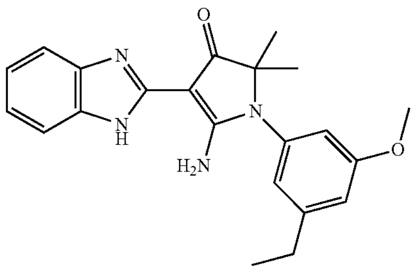 [SMILES: CCc1cc(OC)cc(N2C(N)=C(c3nc4ccccc4[nH]3)C(=O)C2(C)C)c1] | +++ | + | A | 376 | 377 |
| 156 | 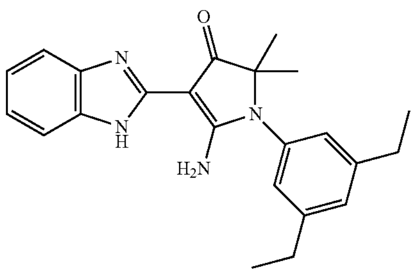 [SMILES: CCc1cc(CC)cc(N2C(N)=C(c3nc4ccccc4[nH]3)C(=O)C2(C)C)c1] | +++ | + | A | 374 | 375 |
| 157 | 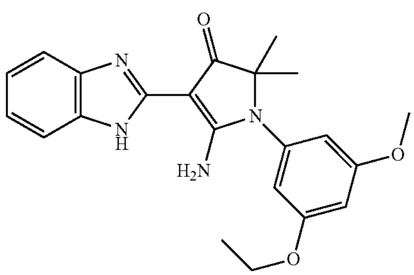 [SMILES: CCOc1cc(OC)cc(N2C(N)=C(c3nc4ccccc4[nH]3)C(=O)C2(C)C)c1] | +++ | + | A | 392 | 393 |
| 158 | 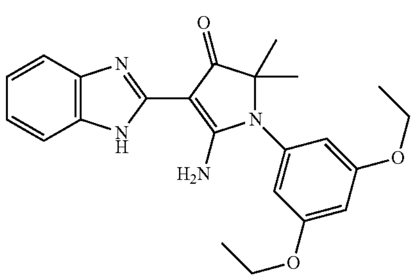 [SMILES: CCOc1cc(OCC)cc(N2C(N)=C(c3nc4ccccc4[nH]3)C(=O)C2(C)C)c1] | ++ | + | A | 406 | 407 |
| 159 | 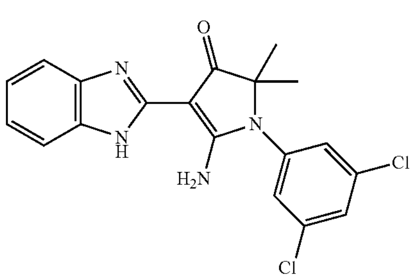 [SMILES: CC1(C)C(=O)C(c2nc3ccccc3[nH]2)=C(N)N1c1cc(Cl)cc(Cl)c1] | ++ | | A | 386 | 387 |

-continued

| Cmpd No. | Structure | GTP Activity | BArr Activity | General Procedure | Exact Mass | MS M/Z Found (M + 1) |
|---|---|---|---|---|---|---|
| 160 | 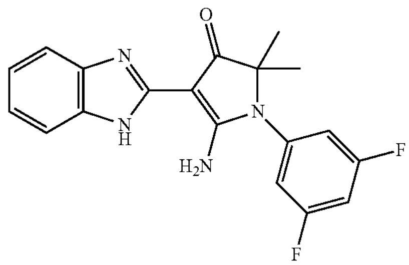 [SMILES: CC1(C)C(=O)C(c2nc3ccccc3[nH]2)=C(N)N1c1cc(F)cc(F)c1] | + | | A | 354 | 355 |
| 161 | 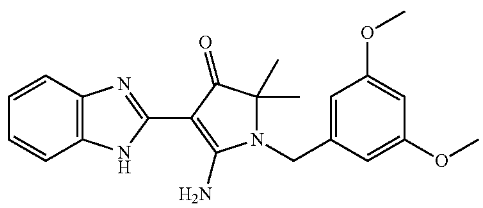 [SMILES: COc1cc(CN2C(N)=C(c3nc4ccccc4[nH]3)C(=O)C2(C)C)cc(OC)c1] | + | + | A | 392 | 393 |
| 162 | 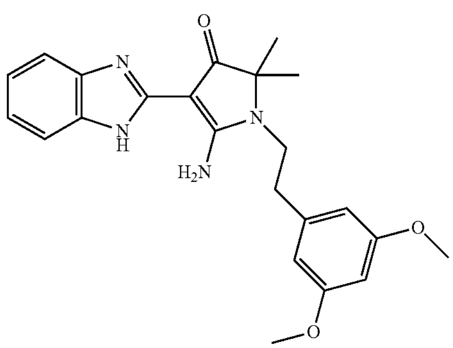 [SMILES: COc1cc(CCN2C(N)=C(c3nc4ccccc4[nH]3)C(=O)C2(C)C)cc(OC)c1] | + | | A | 406 | 407 |
| 163 | 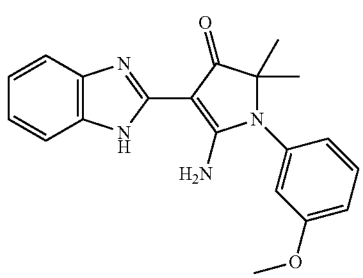 [SMILES: COc1cccc(N2C(N)=C(c3nc4ccccc4[nH]3)C(=O)C2(C)C)c1] | ++ | + | A | 348 | 349 |
| 164 | 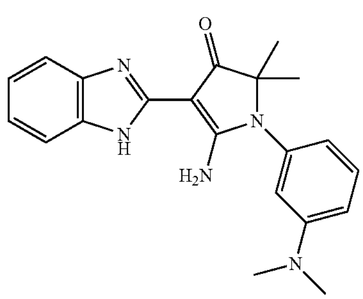 [SMILES: CN(C)c1cccc(N2C(N)=C(c3nc4ccccc4[nH]3)C(=O)C2(C)C)c1] | ++ | | A | 361 | 362 |

-continued

| Cmpd No. | Structure | GTP Activity | BArr Activity | General Procedure | Exact Mass | MS M/Z Found (M + 1) |
|---|---|---|---|---|---|---|
| 165 | 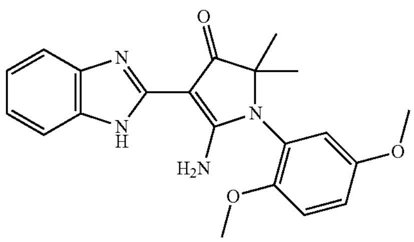 [SMILES: COc1ccc(OC)c(N2C(N)=C(c3nc4ccccc4[nH]3)C(=O)C2(C)C)c1] | ++ | | A | 378 | 379 |
| 166 | 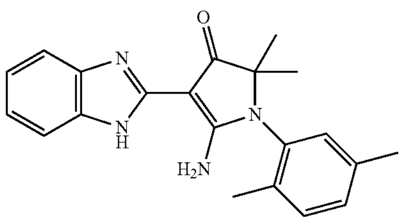 [SMILES: Cc1ccc(C)c(N2C(N)=C(c3nc4ccccc4[nH]3)C(=O)C2(C)C)c1] | + | | A | 346 | 347 |
| 167 | 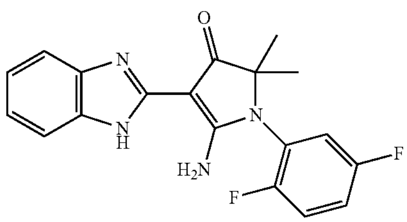 [SMILES: CC1(C)C(=O)C(c2nc3ccccc3[nH]2)=C(N)N1c1cc(F)ccc1F] | + | | A | 354 | 355 |
| 168 | 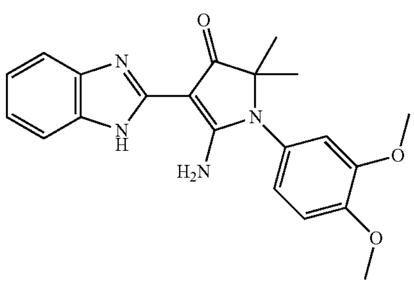 [SMILES: COc1ccc(N2C(N)=C(c3nc4ccccc4[nH]3)C(=O)C2(C)C)cc1OC] | + | + | A | 378 | 379 |
| 169 | 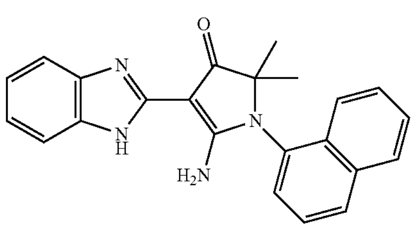 [SMILES: CC1(C)C(=O)C(c2nc3ccccc3[nH]2)=C(N)N1c1cccc2ccccc12] | + | | A | 368 | 369 |
| 170 | 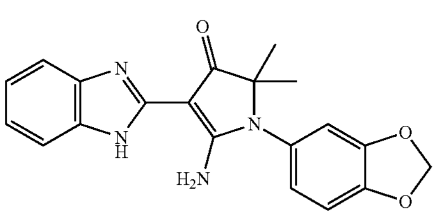 [SMILES: CC1(C)C(=O)C(c2nc3ccccc3[nH]2)=C(N)N1c1ccc2c(c1)OCO2] | + | | A | 362 | 363 |

-continued

| Cmpd No. | Structure | GTP Activity | BArr Activity | General Procedure | Exact Mass | MS M/Z Found (M + 1) |
|---|---|---|---|---|---|---|
| 171 | 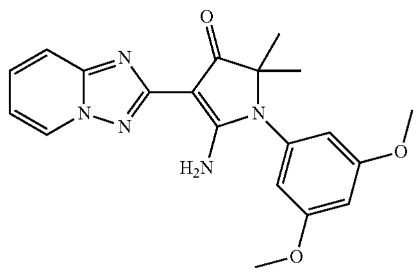 [SMILES: COc1cc(OC)cc(N2C(N)=C(c3nc4ccccn4n3)C(=O)C2(C)C)c1] | + | | A | 379 | 380 |
| 172 | 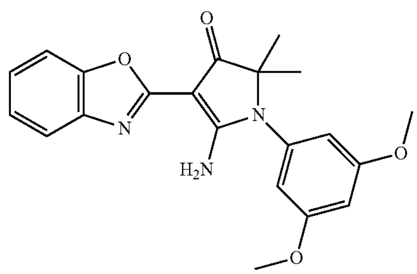 [SMILES: COc1cc(OC)cc(N2C(N)=C(c3nc4ccccc4o3)C(=O)C2(C)C)c1] | + | | A | 379 | 380 |
| 173 | 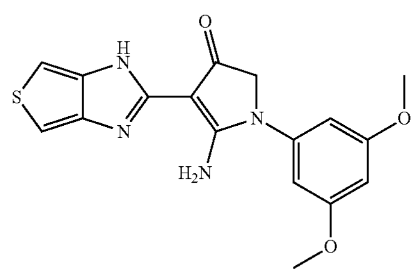 [SMILES: COc1cc(OC)cc(N2CC(=O)C(c3nc4cscc4[nH]3)=C2N)c1] | ++ | | A | 356 | 357 |
| 174 | 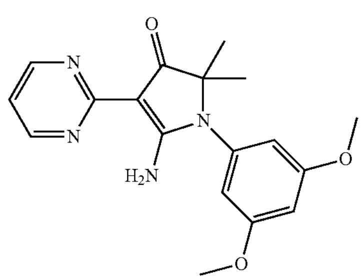 [SMILES: COc1cc(OC)cc(N2C(N)=C(c3ncccn3)C(=O)C2(C)C)c1] | + | | A | 340 | 341 |
| 175 | 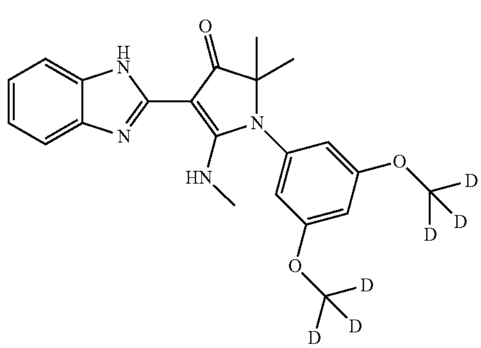 [SMILES: [2H]C([2H])([2H])Oc1cc(OC([2H])([2H])[2H])cc(N2C(NC)=C(c3nc4ccccc4[nH]3)C(=O)C2(C)C)c1] | ++++ | | B | 398 | 399 |

-continued

| Cmpd No. | Structure | GTP Activity | BArr Activity | General Procedure | Exact Mass | MS M/Z Found (M + 1) |
|---|---|---|---|---|---|---|
| 176 | 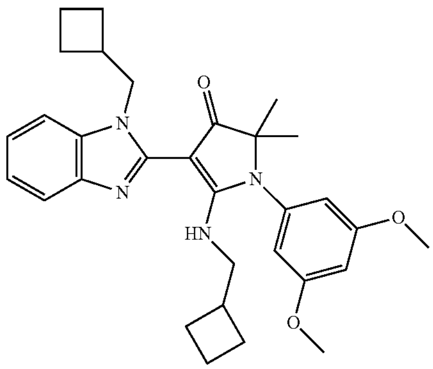 [SMILES: COc1cc(OC)cc(N2C(NCC3CCC3)=C(c3nc4ccccc4n3CC3CCC3)C(=O)C2(C)C)c1] | + | | N-alk | 514 | 515 |
| 177 | 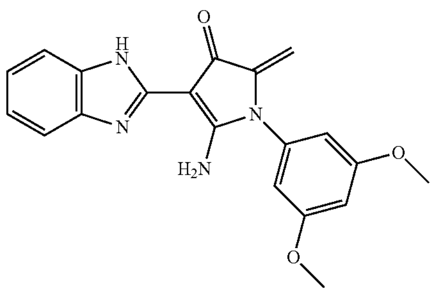 [SMILES: C=C1C(=O)C(c2nc3ccccc3[nH]2)=C(N)N1c1cc(OC)cc(OC)c1] | +++ | | Alpha oxidation | 362 | 363 |
| 178 | 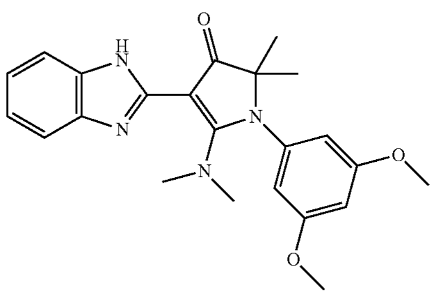 [SMILES: COc1cc(OC)cc(N2C(N(C)C)=C(c3nc4ccccc4[nH]3)C(=O)C2(C)C)c1] | + | | F | 406 | 407 |
| 179 | 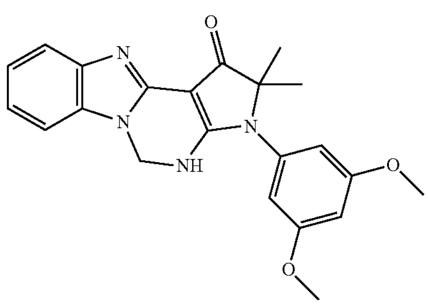 [SMILES: COc1cc(OC)cc(N2C3=C(C(=O)C2(C)C)c2nc4ccccc4n2CN3)c1] | + | | N-alk of Cmpd. No. 2 | 390 | 391 |
| 180 | 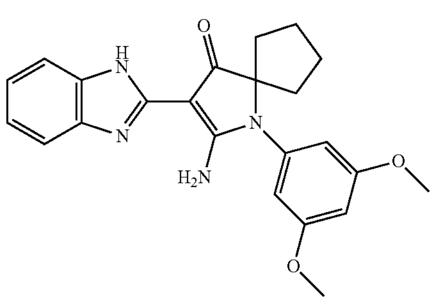 [SMILES: COc1cc(OC)cc(N2C(N)=C(c3nc4ccccc4[nH]3)C(=O)C23CCCC3)c1] | +++ | ++ | A | 404 | 405 |

-continued

| Cmpd No. | Structure | GTP Activity | BArr Activity | General Procedure | Exact Mass | MS M/Z Found (M + 1) |
|---|---|---|---|---|---|---|
| 181 | 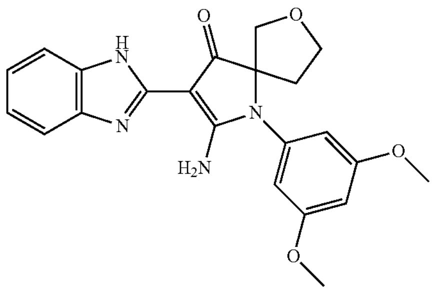 [SMILES: COc1cc(OC)cc(N2C(N)=C(c3nc4ccccc4[nH]3)C(=O)C23CCOC3)c1] | +++ | ++ | B | 406 | 407 |
| 182 | 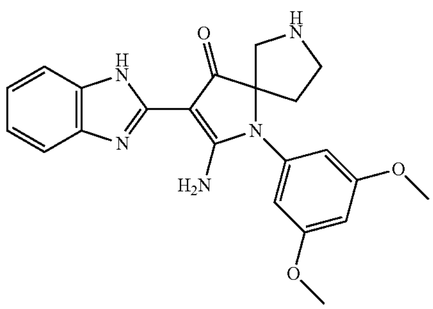 [SMILES: COc1cc(OC)cc(N2C(N)=C(c3nc4ccccc4[nH]3)C(=O)C23CCNC3)c1] | +++ | | B | 405 | 406 |
| 183 | 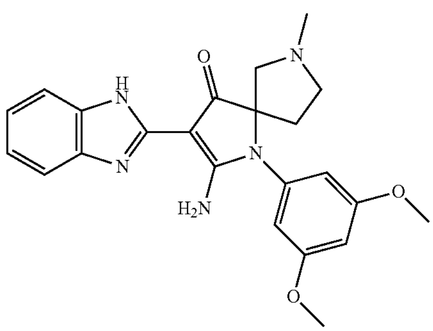 [SMILES: COc1cc(OC)cc(N2C(N)=C(c3nc4ccccc4[nH]3)C(=O)C23CCN(C)C3)c1] | ++ | | B | 419 | 420 |
| 184 | 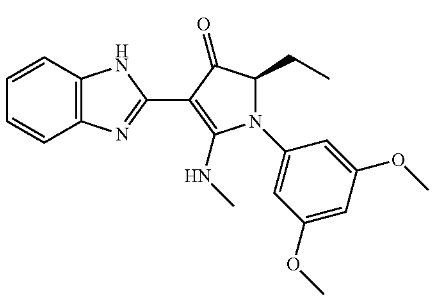 [SMILES: CC[C@@H]1C(=O)C(c2nc3ccccc3[nH]2)=C(NC)N1c1cc(OC)cc(OC)c1] | +++ | + | N-alk | 392 | 393 |
| 185 | 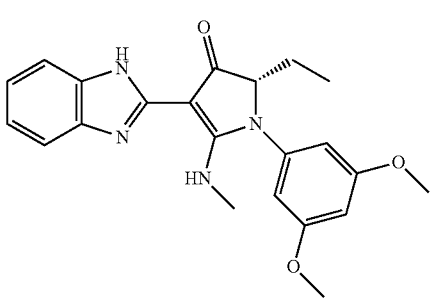 [SMILES: CC[C@H]1C(=O)C(c2nc3ccccc3[nH]2)=C(NC)N1c1cc(OC)cc(OC)c1] | ++++ | ++ | N-alk | 392 | 393 |

-continued

| Cmpd No. | Structure | GTP Activity | BArr Activity | General Procedure | Exact Mass | MS M/Z Found (M + 1) |
|---|---|---|---|---|---|---|
| 186 | 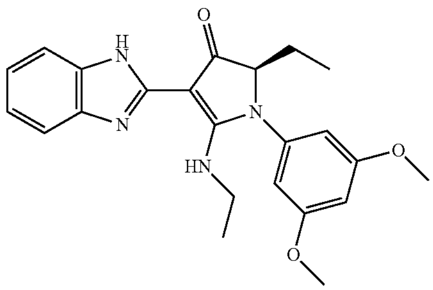 [SMILES: CCNC1=C(c2nc3ccccc3[nH]2)C(=O)[C@@H](CC)N1c1cc(OC)cc(OC)c1] | +++ | + | N-alk | 406 | 407 |
| 187 | 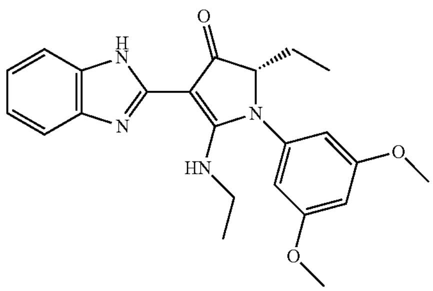 [SMILES: CCNC1=C(c2nc3ccccc3[nH]2)C(=O)[C@H](CC)N1c1cc(OC)cc(OC)c1] | ++++ | +++ | N-alk | 406 | 407 |
| 188 | 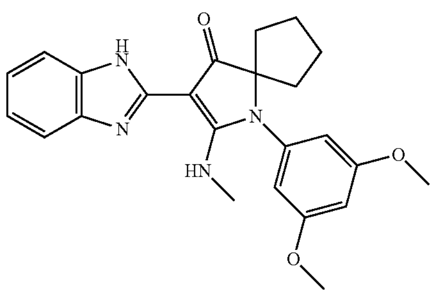 [SMILES: CNC1=C(c2nc3ccccc3[nH]2)C(=O)C2(CCCC2)N1c1cc(OC)cc(OC)c1] | ++++ | ++ | N-alk | 418 | 419 |
| 189 | 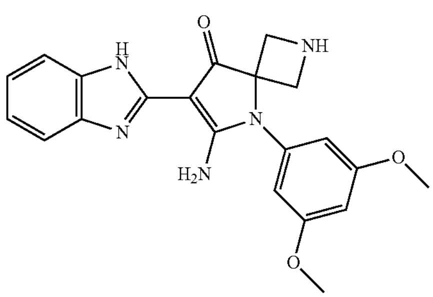 [SMILES: COc1cc(OC)cc(N2C(N)=C(c3nc4ccccc4[nH]3)C(=O)C23CNC3)c1] | ++ | | B | 391 | 392 |
| 190 | 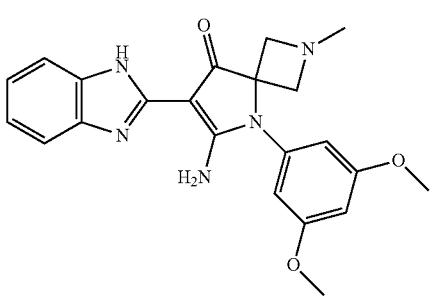 [SMILES: COc1cc(OC)cc(N2C(N)=C(c3nc4ccccc4[nH]3)C(=O)C23CN(C)C3)c1] | ++ | + | B | 405 | 406 |

-continued

| Cmpd No. | Structure | GTP Activity | BArr Activity | General Procedure | Exact Mass | MS M/Z Found (M + 1) |
|---|---|---|---|---|---|---|
| 191 | 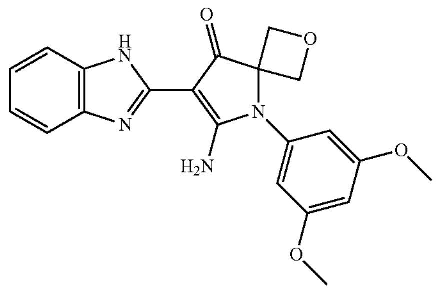 [SMILES: COc1cc(OC)cc(N2C(N)=C(c3nc4ccccc4[nH]3)C(=O)C23COC3)c1] | +++ | + | B | 392 | 393 |
| 192 | 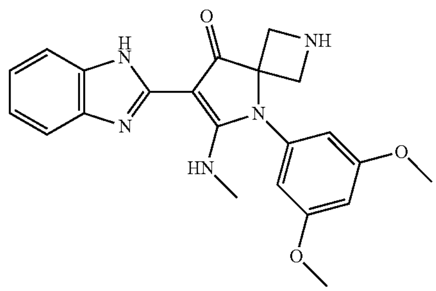 [SMILES: CNC1=C(c2nc3ccccc3[nH]2)C(=O)C2(CNC2)N1c1cc(OC)cc(OC)c1] | +++ | + | N-alk | 405 | 406 |
| 193 | 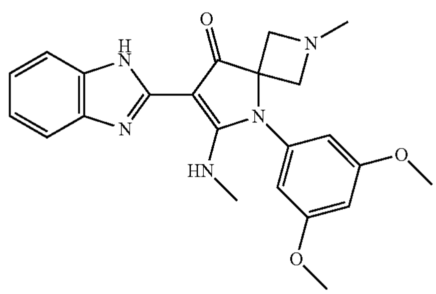 [SMILES: CNC1=C(c2nc3ccccc3[nH]2)C(=O)C2(CN(C)C2)N1c1cc(OC)cc(OC)c1] | +++ | + | N-alk | 419 | 420 |
| 194 | 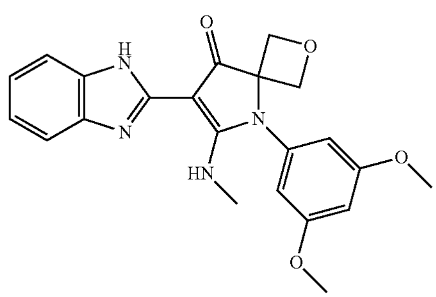 [SMILES: CNC1=C(c2nc3ccccc3[nH]2)C(=O)C2(COC2)N1c1cc(OC)cc(OC)c1] | ++++ | + | N-alk | 406 | 407 |
| 195 | 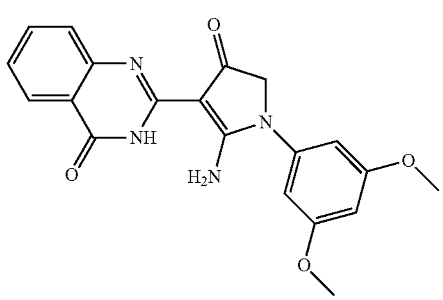 [SMILES: COc1cc(OC)cc(N2CC(=O)C(c3nc4ccccc4c(=O)[nH]3)=C2N)c1] | + | | A | 378 | 379 |

-continued

| Cmpd No. | Structure | GTP Activity | BArr Activity | General Procedure | Exact Mass | MS M/Z Found (M + 1) |
|---|---|---|---|---|---|---|
| 196 | 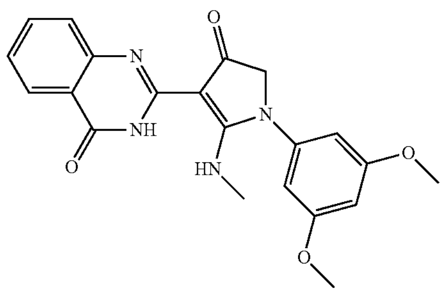 [SMILES: CNC1=C(c2nc3ccccc3c(=O)[nH]2)C(=O)CN1c1cc(OC)cc(OC)c1] | + | | N-alk | 392 | 393 |
| 197 | 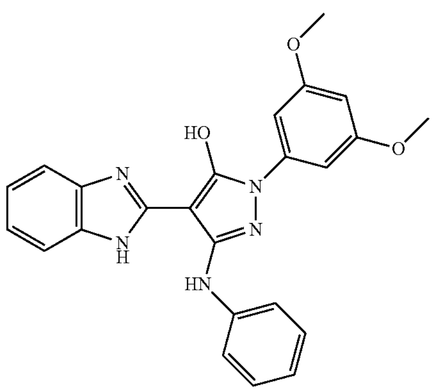 [SMILES: COc1cc(OC)cc(-n2nc(Nc3ccccc3)c(-c3nc4ccccc4[nH]3)c2O)c1] | ++ | | I | 427 | 428 |
| 198 | 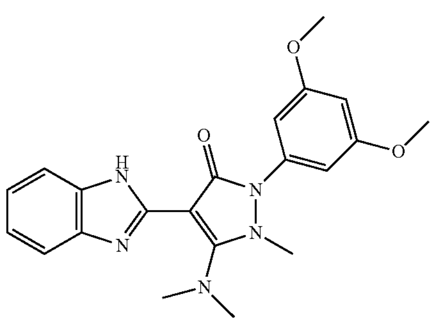 [SMILES: COc1cc(OC)cc(-n2c(=O)c(-c3nc4ccccc4[nH]3)c(N(C)C)n2C)c1] | + | | J | 393 | 394 |
| 199 | 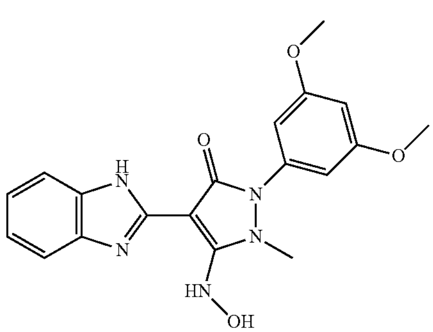 [SMILES: COc1cc(OC)cc(-n2c(=O)c(-c3nc4ccccc4[nH]3)c(NO)n2C)c1] | + | | J | 381 | 382 |

-continued

| Cmpd No. | Structure | GTP Activity | BArr Activity | General Procedure | Exact Mass | MS M/Z Found (M + 1) |
|---|---|---|---|---|---|---|
| 200 | 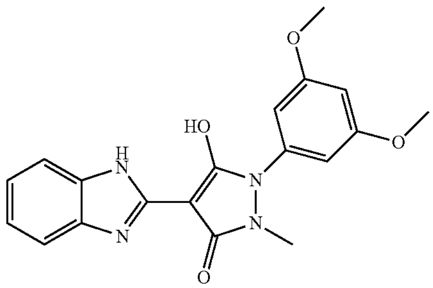 [SMILES: COc1cc(OC)cc(-n2c(O)c(-c3nc4ccccc4[nH]3)c(=O)n2C)c1] | + | + | J | 366 | 367 |
| 201 | 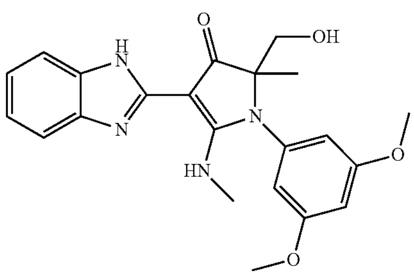 [SMILES: CNC1=C(c2nc3ccccc3[nH]2)C(=O)C(C)(CO)N1c1cc(OC)cc(OC)c1] | ++++ | + | K | 408 | 409 |
| 202 | 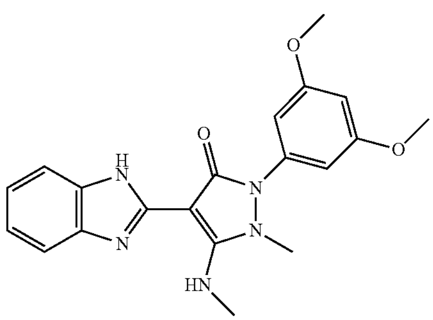 [SMILES: CNc1c(-c2nc3ccccc3[nH]2)c(=O)n(-c2cc(OC)cc(OC)c2)n1C] | + | | I | 379 | 380 |
| 203 | 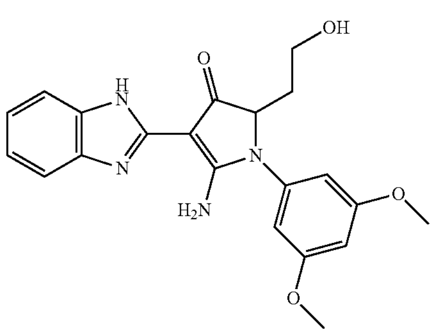 [SMILES: COc1cc(OC)cc(N2C(N)=C(c3nc4ccccc4[nH]3)C(=O)C2CCO)c1] | ++++ | ++ | B | 394 | 395 |

-continued

| Cmpd No. | Structure | GTP Activity | BArr Activity | General Procedure | Exact Mass | MS M/Z Found (M + 1) |
|---|---|---|---|---|---|---|
| 204 | 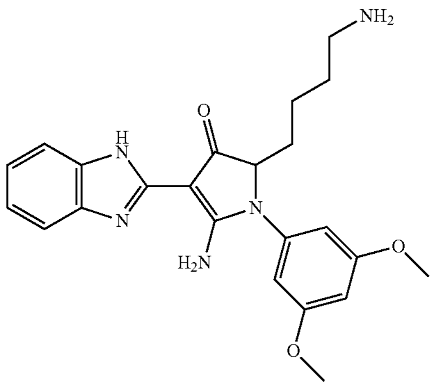 [SMILES: COc1cc(OC)cc(N2C(N)=C(c3nc4ccccc4[nH]3)C(=O)C2CCCCN)c1] | +++ | | A | 421 | 422 |
| 205 | 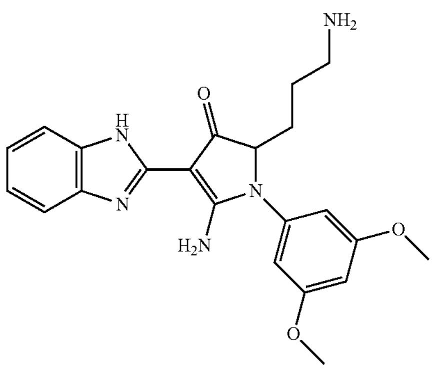 [SMILES: COc1cc(OC)cc(N2C(N)=C(c3nc4ccccc4[nH]3)C(=O)C2CCCN)c1] | + | | B | 407 | 408 |
| 206 | 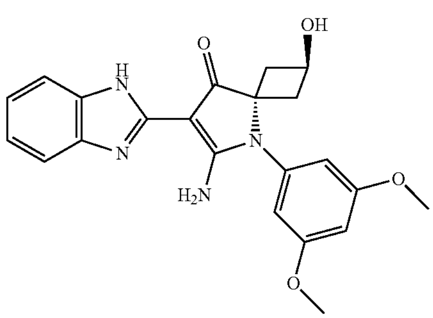 [SMILES: COc1cc(OC)cc(N2C(N)=C(c3nc4ccccc4[nH]3)C(=O)[C@]23C[C@@H](O)C3)c1] | +++ | + | B | 406 | 407 |
| 207 | 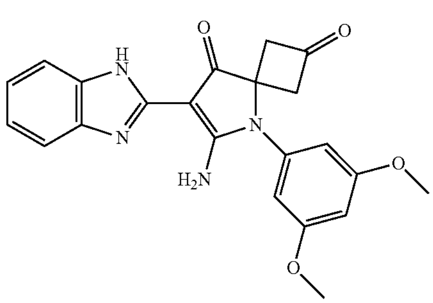 [SMILES: COc1cc(OC)cc(N2C(N)=C(c3nc4ccccc4[nH]3)C(=O)C23CC(=O)C3)c1] | +++ | + | Oxidation of Cmpd. No. 258 | 404 | 405 |

-continued

| Cmpd No. | Structure | GTP Activity | BArr Activity | General Procedure | Exact Mass | MS M/Z Found (M + 1) |
|---|---|---|---|---|---|---|
| 208 | 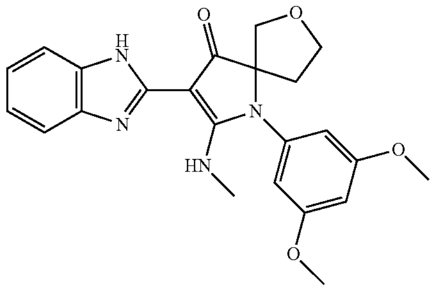 [SMILES: CNC1=C(c2nc3ccccc3[nH]2)C(=O)C2(CCOC2)N1c1cc(OC)cc(OC)c1] | ++++ | ++ | B, N-alk | 420 | 421 |
| 209 | 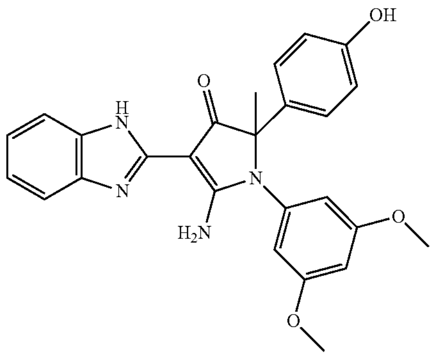 [SMILES: COc1cc(OC)cc(N2C(N)=C(c3nc4ccccc4[nH]3)C(=O)C2(C)c2ccc(O)cc2)c1] | ++ | | B | 456 | 457 |
| 210 | 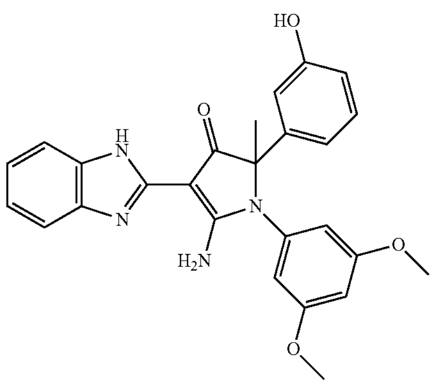 [SMILES: COc1cc(OC)cc(N2C(N)=C(c3nc4ccccc4[nH]3)C(=O)C2(C)c2cccc(O)c2)c1] | ++ | | B | 456 | 457 |
| 211 | 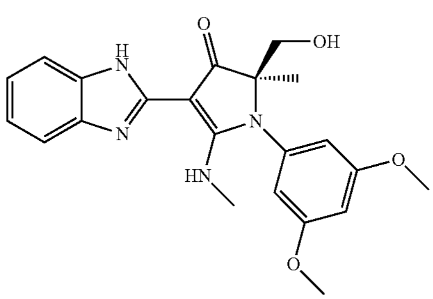 [SMILES: CNC1=C(c2nc3ccccc3[nH]2)C(=O)[C@@](C)(CO)N1c1cc(OC)cc(OC)c1] | +++ | + | B, N-alk | 408 | 409 |

-continued

| Cmpd No. | Structure | GTP Activity | BArr Activity | General Procedure | Exact Mass | MS M/Z Found (M + 1) |
|---|---|---|---|---|---|---|
| 212 | 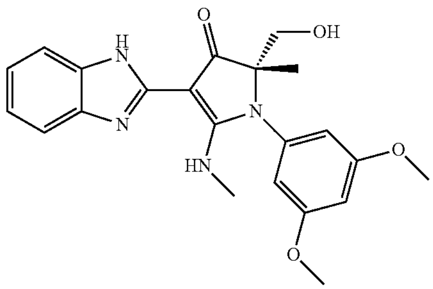 [SMILES: CNC1=C(c2nc3ccccc3[nH]2)C(=O)[C@](C)(CO)N1c1cc(OC)cc(OC)c1] | ++++ | + | B, N-alk | 408 | 409 |
| 213 | 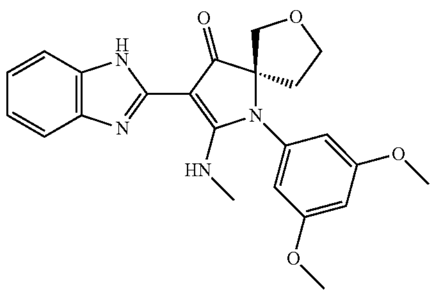 [SMILES: CNC1=C(c2nc3ccccc3[nH]2)C(=O)[C@]2(CCOC2)N1c1cc(OC)cc(OC)c1] | ++++ | ++ | B, N-alk | 420 | 421 |
| 214 | 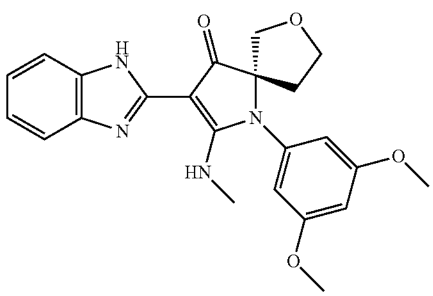 [SMILES: CNC1=C(c2nc3ccccc3[nH]2)C(=O)[C@@]2(CCOC2)N1c1cc(OC)cc(OC)c1] | ++++ | ++ | B, N-alk | 420 | 421 |
| 215 | 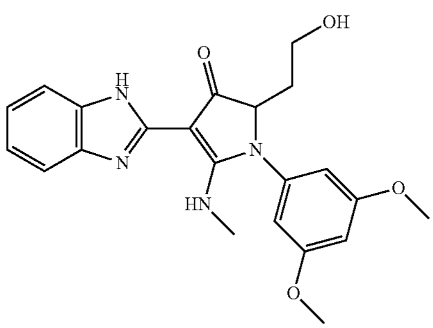 [SMILES: CNC1=C(c2nc3ccccc3[nH]2)C(=O)C(CCO)N1c1cc(OC)cc(OC)c1] | ++++ | ++ | B, N-alk | 408 | 409 |
| 216 | 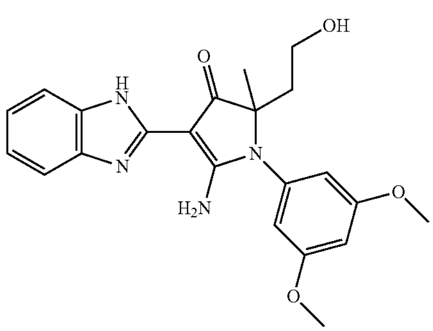 [SMILES: COc1cc(OC)cc(N2C(N)=C(c3nc4ccccc4[nH]3)C(=O)C2(C)CCO)c1] | +++ | + | B | 408 | 409 |

-continued
| Cmpd No. | Structure | GTP Activity | BArr Activity | General Procedure | Exact Mass | MS M/Z Found (M + 1) |
|---|---|---|---|---|---|---|
| 217 | 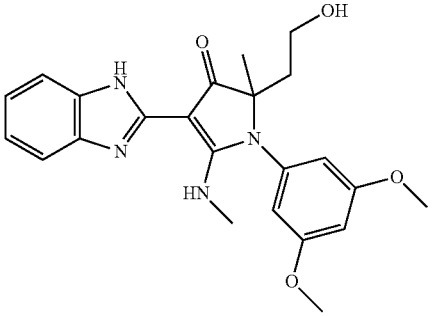 [SMILES: CNC1=C(c2nc3ccccc3[nH]2)C(=O)C(C)(CCO)N1c1cc(OC)cc(OC)c1] | ++++ | + | B, N-alk | 422 | 423 |
| 218 | 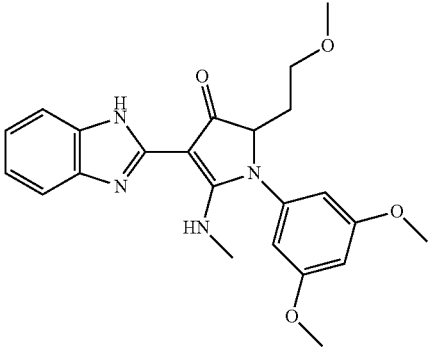 [SMILES: CNC1=C(c2nc3ccccc3[nH]2)C(=O)C(CCOC)N1c1cc(OC)cc(OC)c1] | ++++ | ++ | B, N-alk | 422 | 423 |
| 219 | 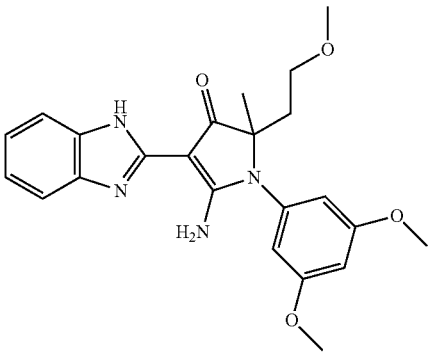 [SMILES: COCCC1(C)C(=O)C(c2nc3ccccc3[nH]2)=C(N)N1c1cc(OC)cc(OC)c1] | +++ | + | B | 422 | 423 |
| 220 | 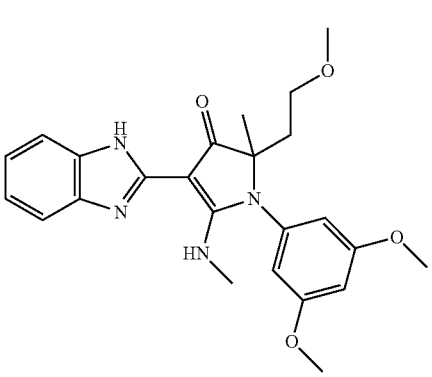 [SMILES: CNC1=C(c2nc3ccccc3[nH]2)C(=O)C(C)(CCOC)N1c1cc(OC)cc(OC)c1] | ++++ | + | B, N-alk | 436 | 437 |

-continued

| Cmpd No. | Structure | GTP Activity | BArr Activity | General Procedure | Exact Mass | MS M/Z Found (M + 1) |
|---|---|---|---|---|---|---|
| 221 | 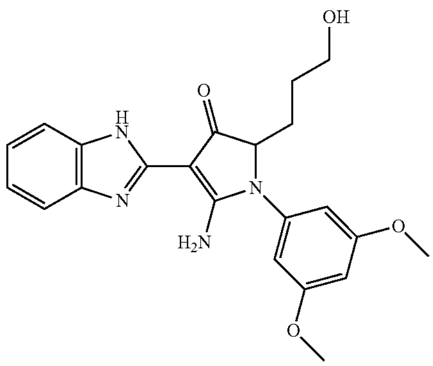 [SMILES: COc1cc(OC)cc(N2C(N)=C(c3nc4ccccc4[nH]3)C(=O)C2CCCO)c1] | +++ | | B | 408 | 409 |
| 222 | 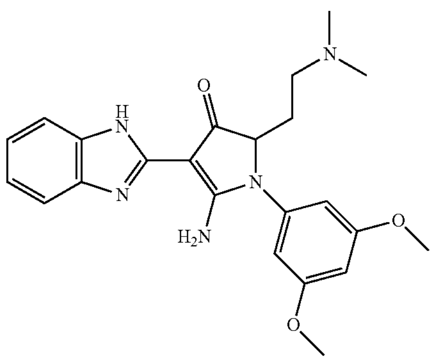 [SMILES: COc1cc(OC)cc(N2C(N)=C(c3nc4ccccc4[nH]3)C(=O)C2CCN(C)C)c1] | ++ | | L | 421 | 422 |
| 223 | 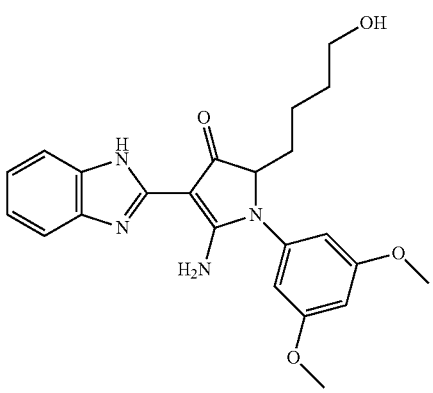 [SMILES: COc1cc(OC)cc(N2C(N)=C(c3nc4ccccc4[nH]3)C(=O)C2CCCCO)c1] | +++ | | B | 422 | 423 |
| 224 | 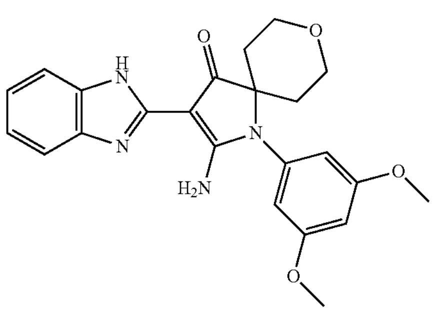 [SMILES: COc1cc(OC)cc(N2C(N)=C(c3nc4ccccc4[nH]3)C(=O)C23CCOCC3)c1] | +++ | + | B | 420 | 421 |

| Cmpd No. | Structure | GTP Activity | BArr Activity | General Procedure | Exact Mass | MS M/Z Found (M + 1) |
|---|---|---|---|---|---|---|
| 225 | 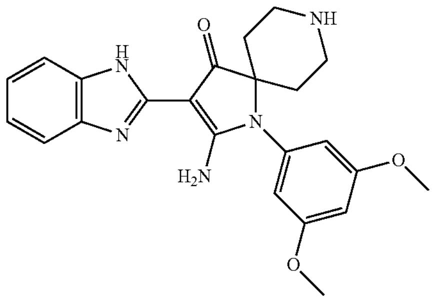 [SMILES: COc1cc(OC)cc(N2C(N)=C(c3nc4ccccc4[nH]3)C(=O)C23CCNCC3)c1] | + | | B | 419 | 420 |
| 226 | 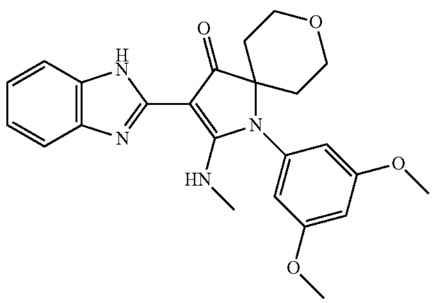 [SMILES: CNC1=C(c2nc3ccccc3[nH]2)C(=O)C2(CCOCC2)N1c1cc(OC)cc(OC)c1] | +++ | + | N-alk | 434 | 435 |
| 227 | 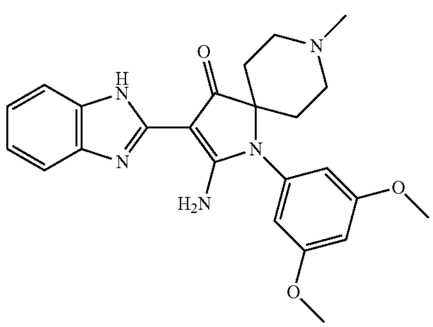 [SMILES: COc1cc(OC)cc(N2C(N)=C(c3nc4ccccc4[nH]3)C(=O)C23CCN(C)CC3)c1] | + | | B | 433 | 434 |
| 228 | 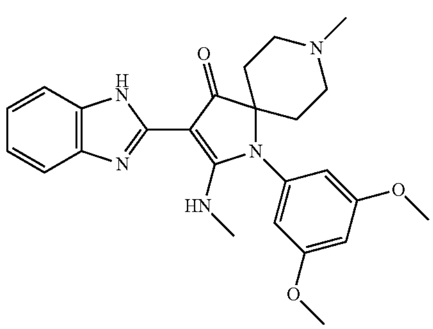 [SMILES: CNC1=C(c2nc3ccccc3[nH]2)C(=O)C2(CCN(C)CC2)N1c1cc(OC)cc(OC)c1] | + | | N-alk | 447 | 448 |

-continued

| Cmpd No. | Structure | GTP Activity | BArr Activity | General Procedure | Exact Mass | MS M/Z Found (M + 1) |
|---|---|---|---|---|---|---|
| 229 | 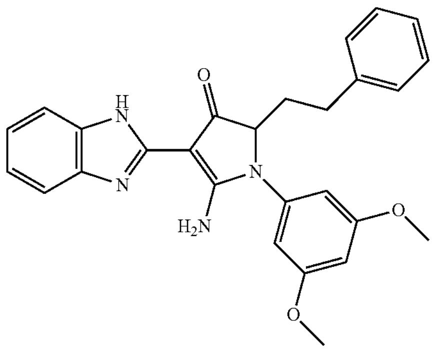 [SMILES: COc1cc(OC)cc(N2C(N)=C(c3nc4ccccc4[nH]3)C(=O)C2CCc2ccccc2)c1] | ++ | | B | 454 | 455 |
| 230 | 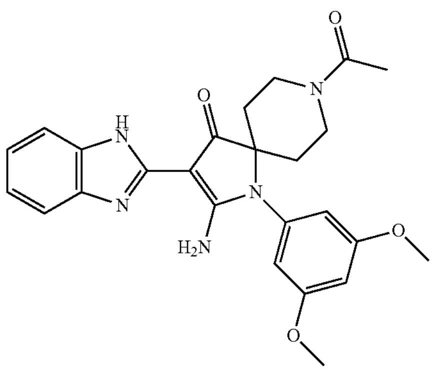 [SMILES: COc1cc(OC)cc(N2C(N)=C(c3nc4ccccc4[nH]3)C(=O)C23CCN(C(C)=O)CC3)c1] | + | | N-Acylation of Cmpd. No. 225 | 461 | 462 |
| 231 | 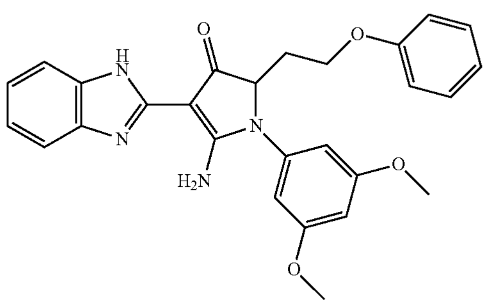 [SMILES: COc1cc(OC)cc(N2C(N)=C(c3nc4ccccc4[nH]3)C(=O)C2CCOc2ccccc2)c1] | ++ | | L | 470 | 471 |
| 232 | 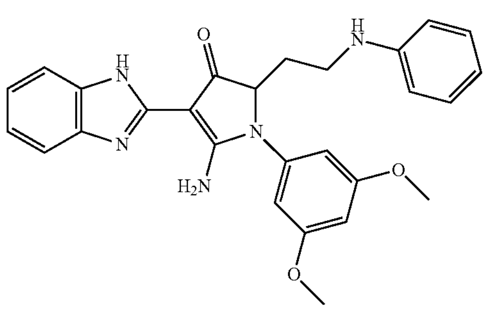 [SMILES: COc1cc(OC)cc(N2C(N)=C(c3nc4ccccc4[nH]3)C(=O)C2CCNc2ccccc2)c1] | +++ | | L | 469 | 470 |

| Cmpd No. | Structure | GTP Activity | BArr Activity | General Procedure | Exact Mass | MS M/Z Found (M + 1) |
|---|---|---|---|---|---|---|
| 233 | 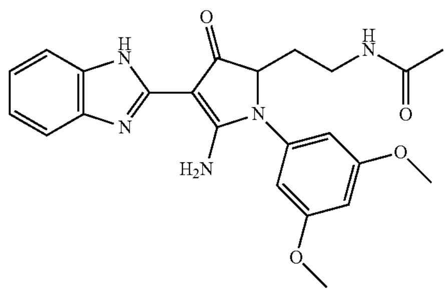 [SMILES: COc1cc(OC)cc(N2C(N)=C(c3nc4ccccc4[nH]3)C(=O)C2CCNC(C)=O)c1] | ++++ | +++ | N-Acylation of Cmpd. No. 238 | 435 | 436 |
| 234 | 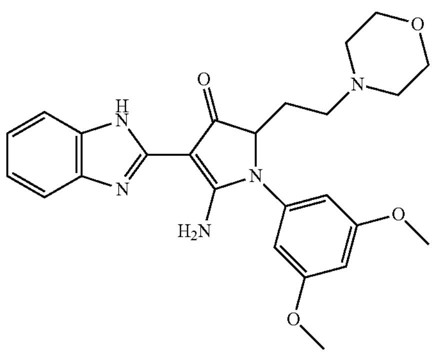 [SMILES: COc1cc(OC)cc(N2C(N)=C(c3nc4ccccc4[nH]3)C(=O)C2CCN2CCOCC2)c1] | +++ | | L | 463 | 464 |
| 235 | 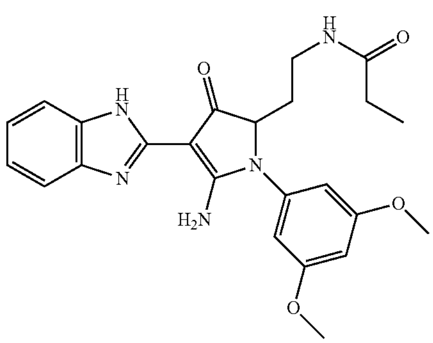 [SMILES: CCC(=O)NCCC1C(=O)C(c2nc3ccccc3[nH]2)=C(N)N1c1cc(OC)cc(OC)c1] | ++++ | +++ | N-Acylation of Cmpd. No. 238 | 449 | 450 |
| 236 | 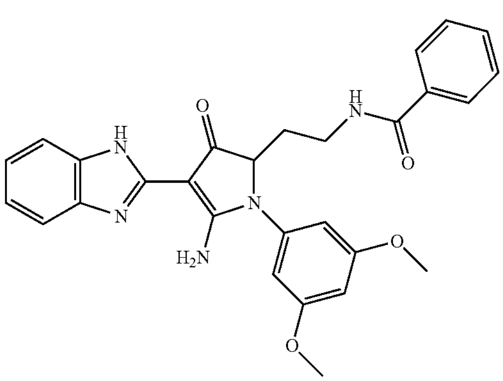 [SMILES: COc1cc(OC)cc(N2C(N)=C(c3nc4ccccc4[nH]3)C(=O)C2CCNC(=O)c2ccccc2)c1] | ++++ | ++ | N-Acylation of Cmpd. No. 238 | 497 | 498 |

-continued

| Cmpd No. | Structure | GTP Activity | BArr Activity | General Procedure | Exact Mass | MS M/Z Found (M + 1) |
|---|---|---|---|---|---|---|
| 237 | 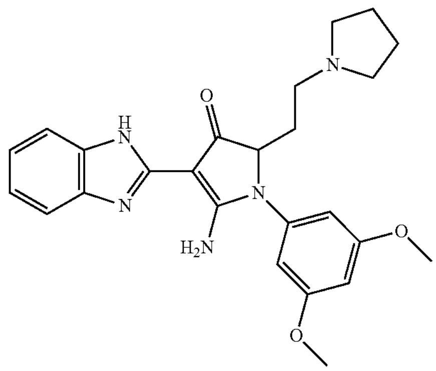 [SMILES: COc1cc(OC)cc(N2C(N)=C(c3nc4ccccc4[nH]3)C(=O)C2CCN2CCCC2)c1] | ++ | | L | 447 | 448 |
| 238 | 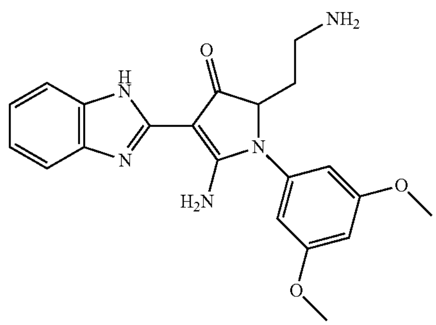 | ++ | | A | 393 | 394 |
| 239 | 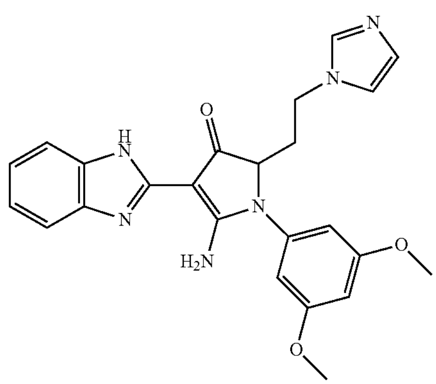 [SMILES: COc1cc(OC)cc(N2C(N)=C(c3nc4ccccc4[nH]3)C(=O)C2CCn2ccnc2)c1] | +++ | + | L | 444 | 445 |
| 240 | 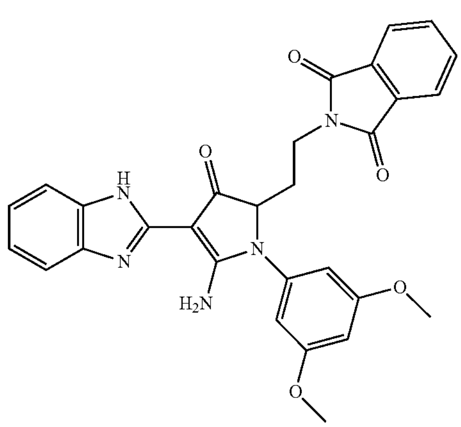 [SMILES: COc1cc(OC)cc(N2C(N)=C(c3nc4ccccc4[nH]3)C(=O)C2CCN2C(=O)c3ccccc3C2=O)c1] | + | | A | 523 | 524 |

-continued

| Cmpd No. | Structure | GTP Activity | BArr Activity | General Procedure | Exact Mass | MS M/Z Found (M + 1) |
|---|---|---|---|---|---|---|
| 241 | 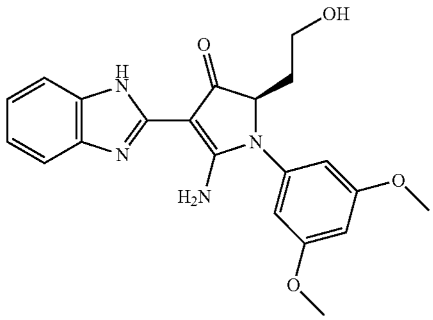 [SMILES: COc1cc(OC)cc(N2C(N)=C(c3nc4ccccc4[nH]3)C(=O)[C@H]2CCO)c1] | +++ | + | B | 394 | 395 |
| 242 | 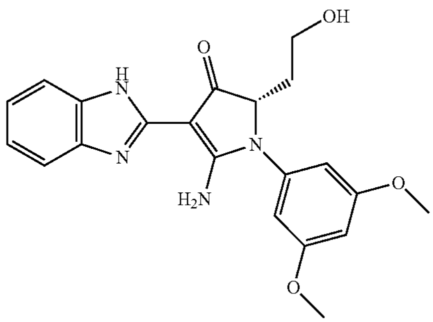 | ++++ | ++ | B | 394 | 395 |
| 243 | 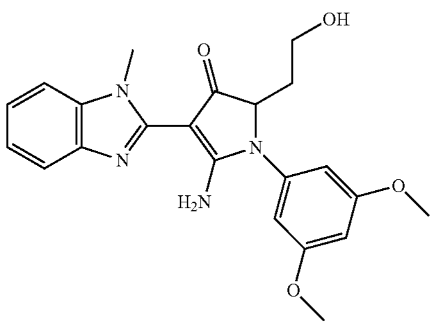 [SMILES: COc1cc(OC)cc(N2C(N)=C(c3nc4ccccc4n3C)C(=O)C2CCO)c1] | + | | N-alk | 408 | 409 |
| 244 | 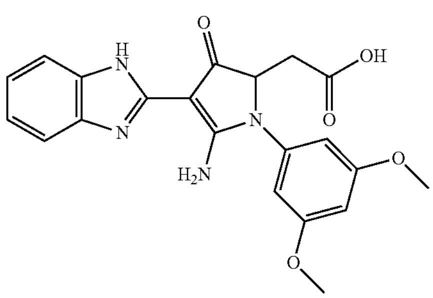 [SMILES: COc1cc(OC)cc(N2C(N)=C(c3nc4ccccc4[nH]3)C(=O)C2CC(=O)O)c1] | ++ | | B | 408 | 409 |
| 245 | 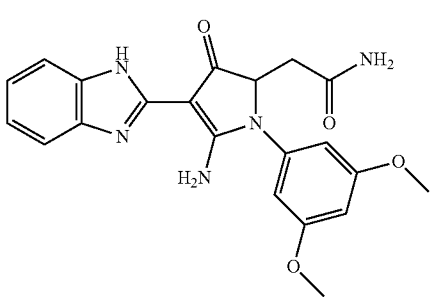 | + | | Amidation of Cmpd. No. 244 | 407 | 408 |

| Cmpd No. | Structure | GTP Activity | BArr Activity | General Procedure | Exact Mass | MS M/Z Found (M + 1) |
|---|---|---|---|---|---|---|
| 246 | 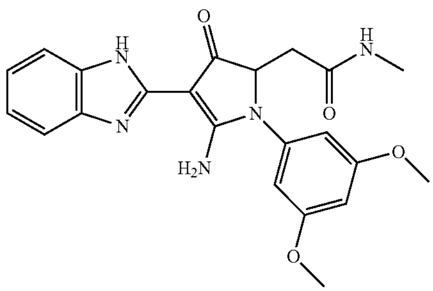 [SMILES: CNC(=O)CC1C(=O)C(c2nc3ccccc3[nH]2)=C(N)N1c1cc(OC)cc(OC)c1] | ++ | | Amidation of Cmpd. No. 244 | 421 | 422 |
| 247 | 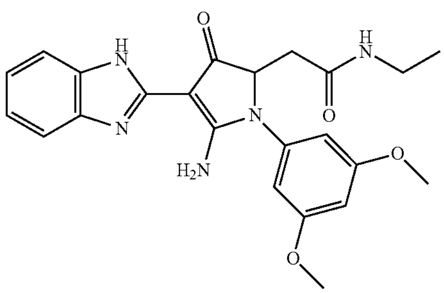 [SMILES: CCNC(=O)CC1C(=O)C(c2nc3ccccc3[nH]2)=C(N)N1c1cc(OC)cc(OC)c1] | + | | Amidation of Cmpd. No. 244 | 435 | 436 |
| 248 | 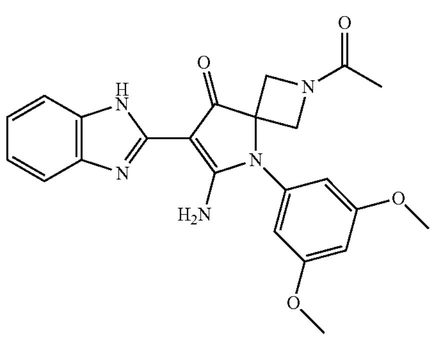 [SMILES: COc1cc(OC)cc(N2C(N)=C(c3nc4ccccc4[nH]3)C(=O)C23CN(C(C)=O)C3)c1] | +++ | | N-Acylation of Cmpd. No. 189 | 433 | 434 |
| 249 | 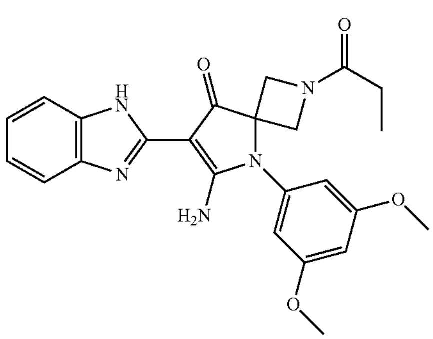 [SMILES: CCC(=O)N1CC2(C1)C(=O)C(c1nc3ccccc3[nH]1)=C(N)N2c1cc(OC)cc(OC)c1] | ++ | | N-Acylation of Cmpd. No. 189 | 447 | 448 |

-continued

| Cmpd No. | Structure | GTP Activity | BArr Activity | General Procedure | Exact Mass | MS M/Z Found (M + 1) |
|---|---|---|---|---|---|---|
| 250 | 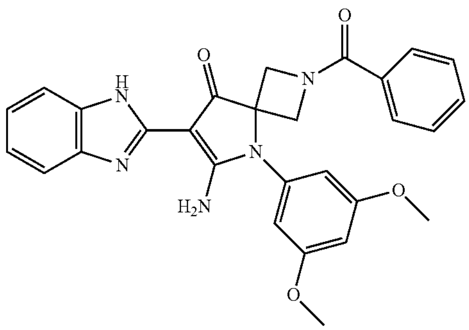 [SMILES: COc1cc(OC)cc(N2C(N)=C(c3nc4ccccc4[nH]3)C(=O)C23CN(C(=O)c2ccccc2)C3)c1] | | ++ | N-Acylation of Cmpd. No. 189 | 495 | 496 |
| 251 | 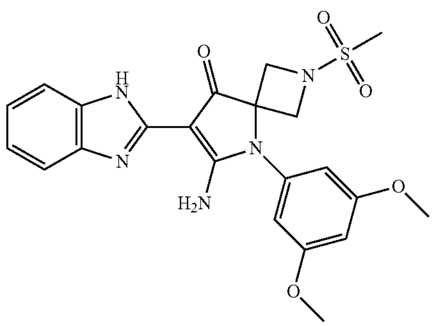 [SMILES: COc1cc(OC)cc(N2C(N)=C(c3nc4ccccc4[nH]3)C(=O)C23CN(S(C)(=O)=O)C3)c1] | | +++ | Sulfonylation of Cmpd. No. 189 | 469 | 470 |
| 252 | 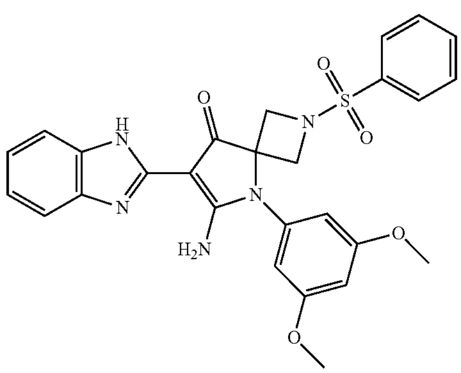 [SMILES: COc1cc(OC)cc(N2C(N)=C(c3nc4ccccc4[nH]3)C(=O)C23CN(S(=O)(=O)c2ccccc2)C3)c1] | | + | Sulfonylation of Cmpd. No. 189 | 531 | 532 |
| 253 | 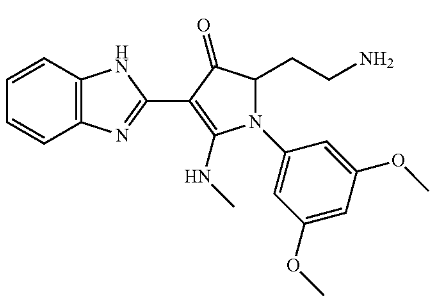 [SMILES: CNC1=C(c2nc3ccccc3[nH]2)C(=O)C(CCN)N1c1cc(OC)cc(OC)c1] | | +++ | N-Alk of Cmpd. No. 240 and treatment with hydrazine | 407 | 408 |

| Cmpd No. | Structure | GTP Activity | BArr Activity | General Procedure | Exact Mass | MS M/Z Found (M + 1) |
|---|---|---|---|---|---|---|
| 254 | 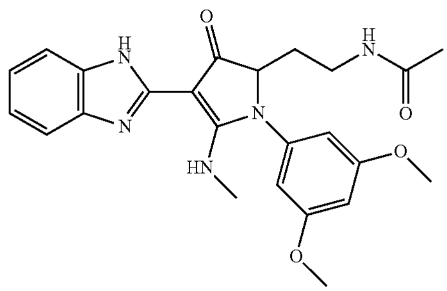 [SMILES: CNC1=C(c2nc3ccccc3[nH]2)C(=O)C(CCNC(C)=O)N1c1cc(OC)cc(OC)c1] | ++++ | +++ | N-acylation of Cmpd. No. 253 | 449 | 450 |
| 255 | 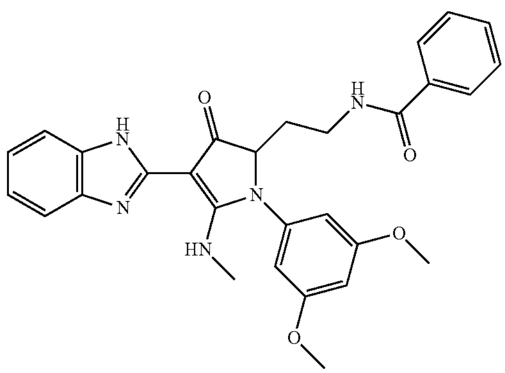 [SMILES: CNC1=C(c2nc3ccccc3[nH]2)C(=O)C(CCNC(=O)c2ccccc2)N1c1cc(OC)cc(OC)c1] | ++++ | ++ | N-acylation of Cmpd. No. 253 | 511 | 512 |
| 256 | 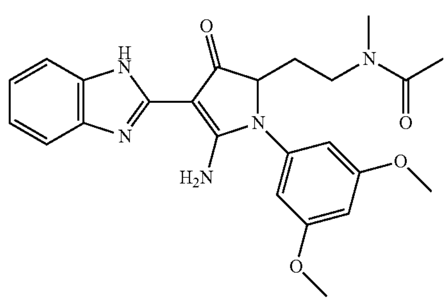 [SMILES: COc1cc(OC)cc(N2C(N)=C(c3nc4ccccc4[nH]3)C(=O)C2CCN(C)C(C)=O)c1] | +++ | + | L | 449 | 450 |
| 257 | 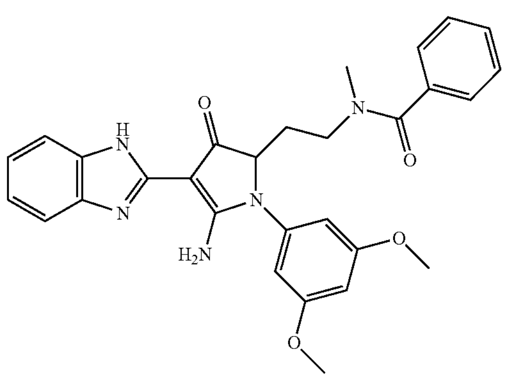 [SMILES: COc1cc(OC)cc(N2C(N)=C(c3nc4ccccc4[nH]3)C(=O)C2CCN(C)C(=O)c2ccccc2)c1] | +++ | | L | 511 | 512 |

-continued

| Cmpd No. | Structure | GTP Activity | BArr Activity | General Procedure | Exact Mass | MS M/Z Found (M + 1) |
|---|---|---|---|---|---|---|
| 258 | 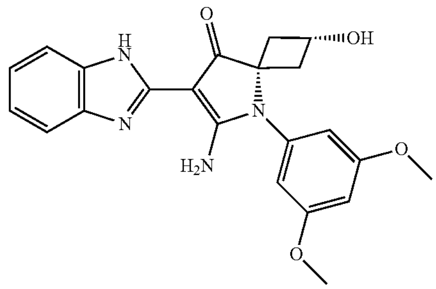 [SMILES: COc1cc(OC)cc(N2C(N)=C(c3nc4ccccc4[nH]3)C(=O)[C@]23C[C@H](O)C3)c1] | +++ | | B | 406 | 407 |
| 259 | 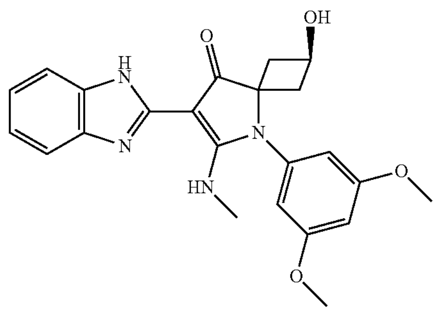 | ++++ | + | N-alk | 420 | 421 |
| 260 | 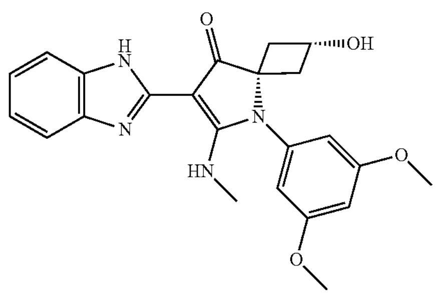 [SMILES: CNC1=C(c2nc3ccccc3[nH]2)C(=O)[C@]2(C[C@H](O)C2)N1c1cc(OC)cc(OC)c1] | +++ | + | N-alk | 420 | 421 |
| 261 | 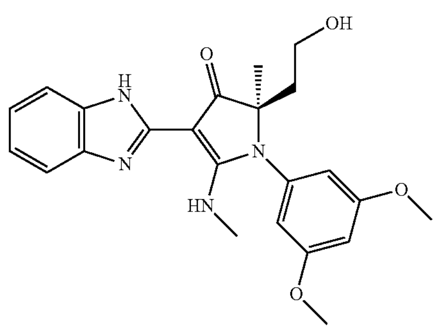 [SMILES: CNC1=C(c2nc3ccccc3[nH]2)C(=O)[C@@](C)(CCO)N1c1cc(OC)cc(OC)c1] | +++ | + | N-alk | 422 | 423 |
| 262 | 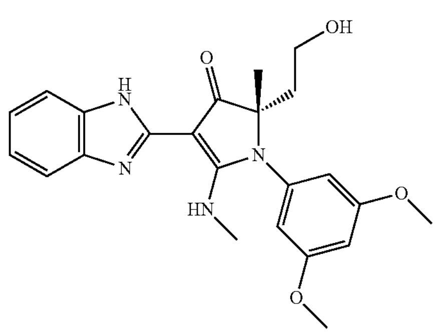 [SMILES: CNC1=C(c2nc3ccccc3[nH]2)C(=O)[C@](C)(CCO)N1c1cc(OC)cc(OC)c1] | ++++ | + | N-alk | 422 | 423 |

-continued

| Cmpd No. | Structure | GTP Activity | BArr Activity | General Procedure | Exact Mass | MS M/Z Found (M + 1) |
|---|---|---|---|---|---|---|
| 263 | 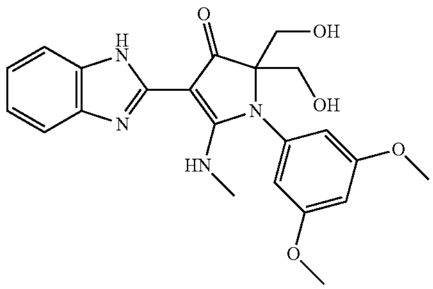 [SMILES: CNC1=C(c2nc3ccccc3[nH]2)C(=O)C(CO)(CO)N1c1cc(OC)cc(OC)c1] | +++ | + | Cmpd. No. 194 treated with aqueous HCl | 424 | 425 |
| 264 | 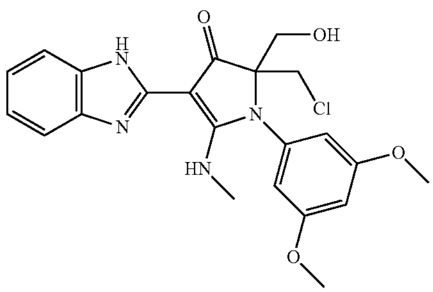 [SMILES: CNC1=C(c2nc3ccccc3[nH]2)C(=O)C(CO)(CCl)N1c1cc(OC)cc(OC)c1] | +++ | + | Cmpd. No. 194 treated with aqueous HCl | 442 | 443 |
| 265 | 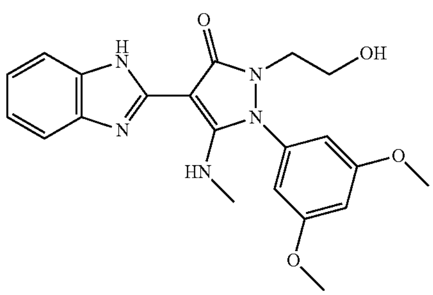 [SMILES: CNc1c(-c2nc3ccccc3[nH]2)c(=O)n(CCO)n1-c1cc(OC)cc(OC)c1] | +++ | + | C, N-alk | 409 | 410 |
| 266 | 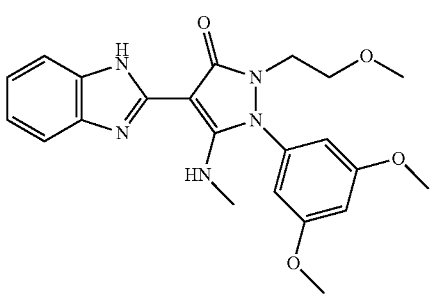 [SMILES: CNc1c(-c2nc3ccccc3[nH]2)c(=O)n(CCOC)n1-c1cc(OC)cc(OC)c1] | ++++ | + | C, N-alk | 423 | 424 |
| 267 | 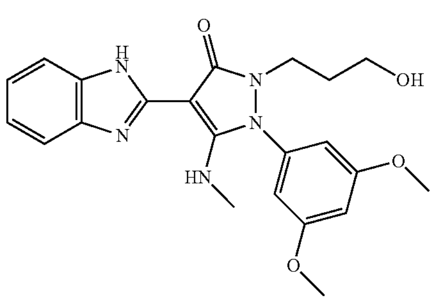 [SMILES: CNc1c(-c2nc3ccccc3[nH]2)c(=O)n(CCCO)n1-c1cc(OC)cc(OC)c1] | ++++ | + | C, N-alk | 423 | 424 |

-continued

| Cmpd No. | Structure | GTP Activity | BArr Activity | General Procedure | Exact Mass | MS M/Z Found (M + 1) |
|---|---|---|---|---|---|---|
| 268 | 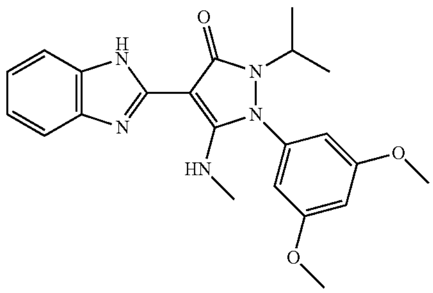 [SMILES: CNc1c(-c2nc3ccccc3[nH]2)c(=O)n(C(C)C)n1-c1cc(OC)cc(OC)c1] | + | | N-alk | 407 | 408 |
| 269 | 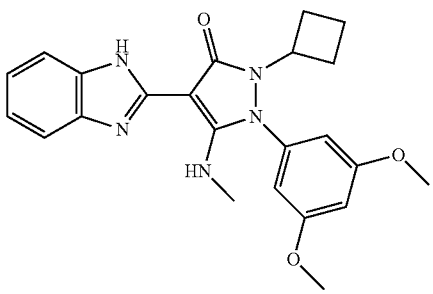 [SMILES: CNc1c(-c2nc3ccccc3[nH]2)c(=O)n(C2CCC2)n1-c1cc(OC)cc(OC)c1] | +++ | | C, N-alk | 419 | 420 |
| 270 | 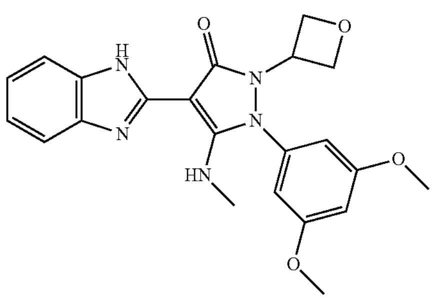 [SMILES: CNc1c(-c2nc3ccccc3[nH]2)c(=O)n(C2COC2)n1-c1cc(OC)cc(OC)c1] | ++++ | | C, N-alk | 421 | 422 |
| 271 | 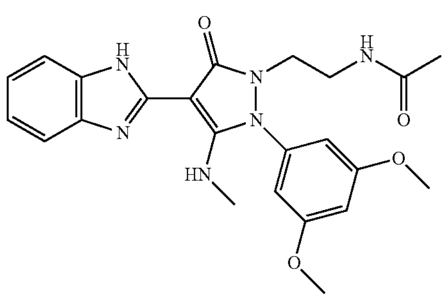 | +++ | | C, N-alk | 450 | 451 |
| 272 | 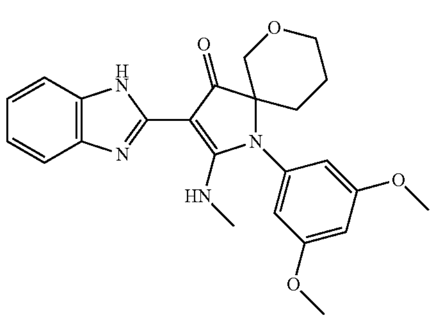 [SMILES: CNC1=C(c2nc3ccccc3[nH]2)C(=O)C2(CCCOC2)N1c1cc(OC)cc(OC)c1] | ++++ | ++ | B, N-alk | 434 | 435 |

-continued

| Cmpd No. | Structure | GTP Activity | BArr Activity | General Procedure | Exact Mass | MS M/Z Found (M + 1) |
|---|---|---|---|---|---|---|
| 273 | 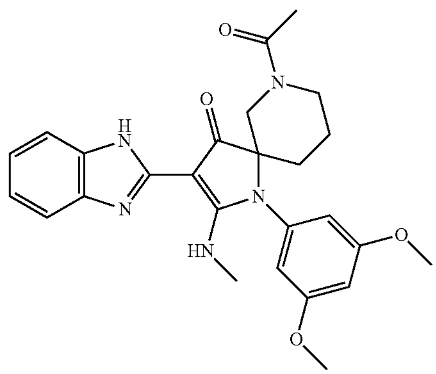 [SMILES: CNC1=C(c2nc3ccccc3[nH]2)C(=O)C2(CCCN(C(C)=O)C2)N1c1cc(OC)cc(OC)c1] | +++ | | B, N-alk | 475 | 476 |
| 274 | 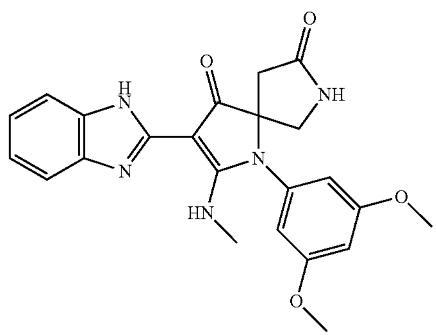 [SMILES: CNC1=C(c2nc3ccccc3[nH]2)C(=O)C2(CNC(=O)C2)N1c1cc(OC)cc(OC)c1] | +++ | | Ring expansion of Cmpd. No. 275 using 1) NH$_4$OH—HCl 2) SOCl$_2$ | 433 | 434 |
| 275 | 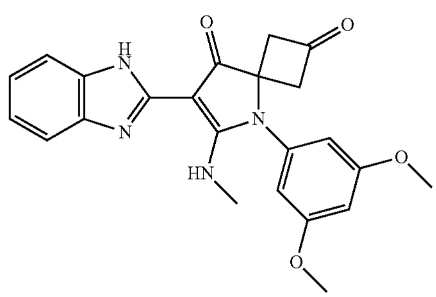 [SMILES: CNC1=C(c2nc3ccccc3[nH]2)C(=O)C2(CC(=O)C2)N1c1cc(OC)cc(OC)c1] | ++++ | + | B, N-alk | 418 | 419 |
| 276 | 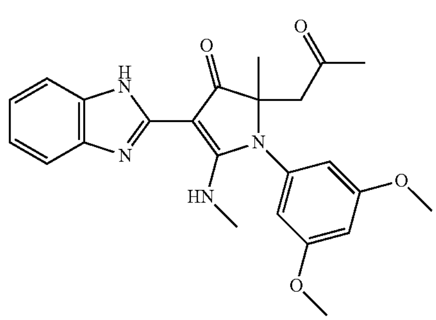 [SMILES: CNC1=C(c2nc3ccccc3[nH]2)C(=O)C(C)(CC(C)=O)N1c1cc(OC)cc(OC)c1] | +++ | | From Cmpd. No. 217: 1) oxidation 2) MeMgBr 3) oxidation | 434 | 435 |

| Cmpd No. | Structure | GTP Activity | BArr Activity | General Procedure | Exact Mass | MS M/Z Found (M + 1) |
|---|---|---|---|---|---|---|
| 277 | 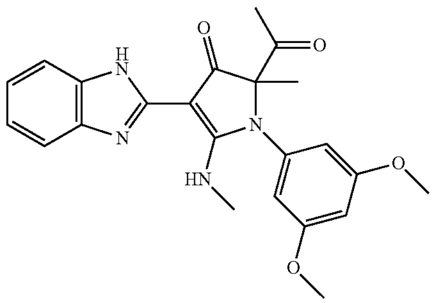 [SMILES: CNC1=C(c2nc3ccccc3[nH]2)C(=O)C(C)(C(C)=O)N1c1cc(OC)cc(OC)c1] | | +++ | From Cmpd. No. 201:<br>1) oxidation<br>2) MeMgBr<br>3) oxidation | 420 | 421 |
| 278 | 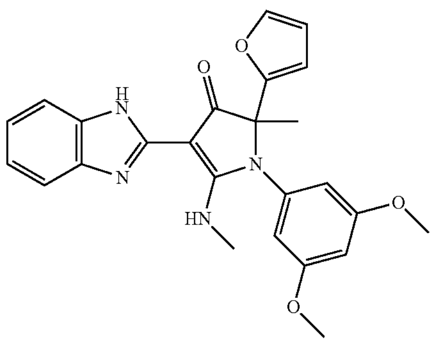 [SMILES: CNC1=C(c2nc3ccccc3[nH]2)C(=O)C(C)(c2ccco2)N1c1cc(OC)cc(OC)c1] | | +++ | B, N-alk | 444 | 445 |
| 279 | 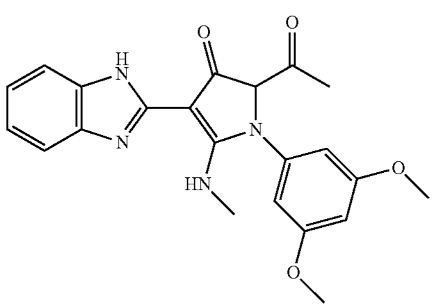 [SMILES: CNC1=C(c2nc3ccccc3[nH]2)C(=O)C(C(C)=O)N1c1cc(OC)cc(OC)c1] | | ++++ | B, deprotection | 406 | 407 |
| 280 | 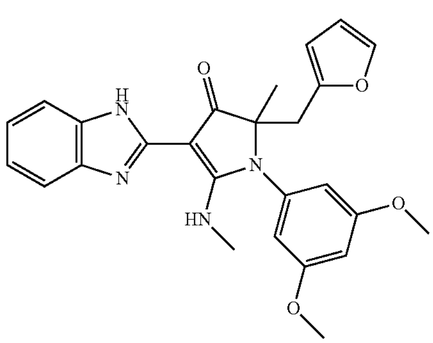 [SMILES: CNC1=C(c2nc3ccccc3[nH]2)C(=O)C(C)(Cc2ccco2)N1c1cc(OC)cc(OC)c1] | | +++ | B, N-alk | 458 | 459 |

| Cmpd No. | Structure | GTP Activity | BArr Activity | General Procedure | Exact Mass | MS M/Z Found (M + 1) |
|---|---|---|---|---|---|---|
| 281 | 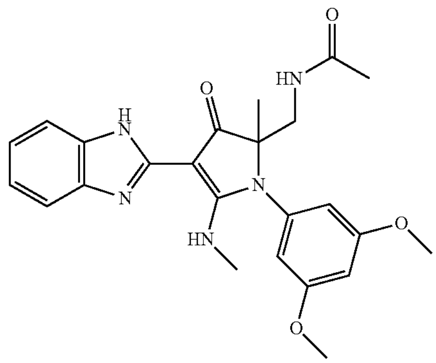 [SMILES: CNC1=C(c2nc3ccccc3[nH]2)C(=O)C(C)(CNC(C)=O)N1c1cc(OC)cc(OC)c1] | ++++ | ++ | L | 449 | 450 |
| 282 | 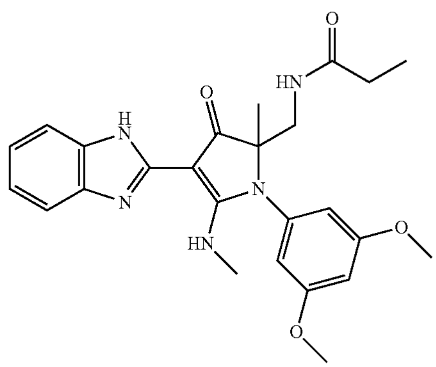 [SMILES: CCC(=O)NCC1(C)C(=O)C(c2nc3ccccc3[nH]2)=C(NC)N1c1cc(OC)cc(OC)c1] | ++++ | ++ | L | 463 | 464 |
| 283 | 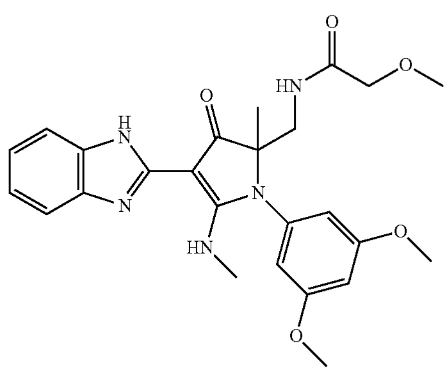 [SMILES: CNC1=C(c2nc3ccccc3[nH]2)C(=O)C(C)(CNC(=O)COC)N1c1cc(OC)cc(OC)c1] | ++++ | + | L | 479 | 480 |
| 284 | 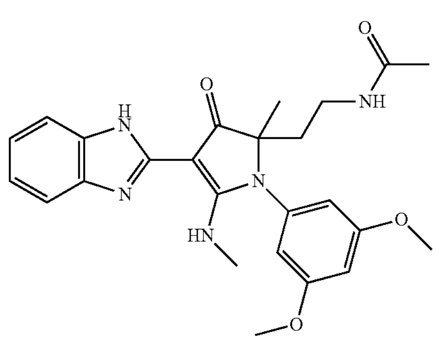 [SMILES: CNC1=C(c2nc3ccccc3[nH]2)C(=O)C(C)(CCNC(C)=O)N1c1cc(OC)cc(OC)c1] | ++++ | + | L | 463 | 464 |

-continued

| Cmpd No. | Structure | GTP Activity | BArr Activity | General Procedure | Exact Mass | MS M/Z Found (M + 1) |
|---|---|---|---|---|---|---|
| 285 | 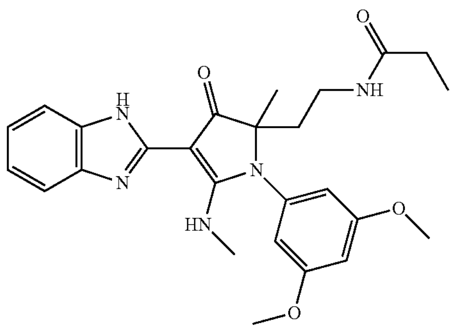 [SMILES: CCC(=O)NCCC1(C)C(=O)C(c2nc3ccccc3[nH]2)=C(NC)N1c1cc(OC)cc(OC)c1] | ++++ | ++ | L | 477 | 478 |
| 286 | 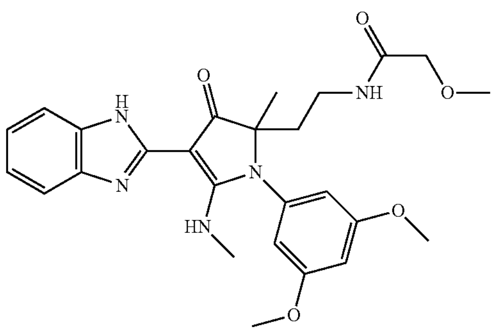 [SMILES: CNC1=C(c2nc3ccccc3[nH]2)C(=O)C(C)(CCNC(=O)COC)N1c1cc(OC)cc(OC)c1] | ++++ | + | L | 493 | 494 |
| 287 | 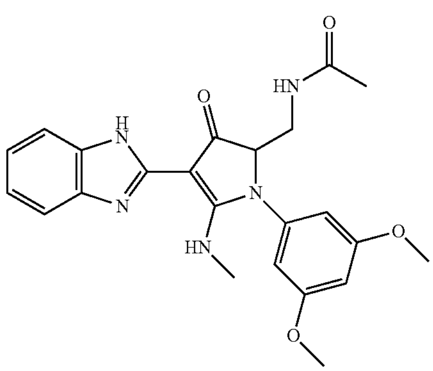 [SMILES: CNC1=C(c2nc3ccccc3[nH]2)C(=O)C(CNC(C)=O)N1c1cc(OC)cc(OC)c1] | ++++ | ++ | B | 435 | 436 |
| 288 | 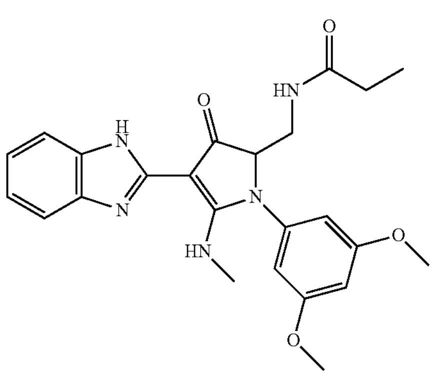 [SMILES: CCC(=O)NCC1C(=O)C(c2nc3ccccc3[nH]2)=C(NC)N1c1cc(OC)cc(OC)c1] | ++++ | ++ | B | 449 | 450 |

-continued

| Cmpd No. | Structure | GTP Activity | BArr Activity | General Procedure | Exact Mass | MS M/Z Found (M + 1) |
|---|---|---|---|---|---|---|
| 289 | 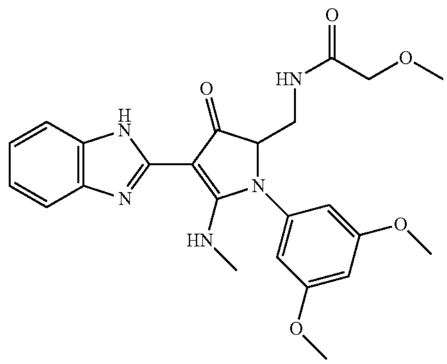 [SMILES: CNC1=C(c2nc3ccccc3[nH]2)C(=O)C(CNC(=O)COC)N1c1cc(OC)cc(OC)c1] | ++++ | + | B | 465 | 466 |
| 290 | 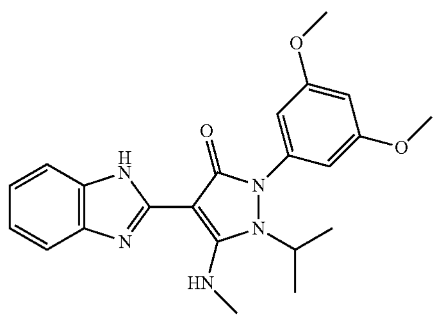 [SMILES: CNc1c(-c2nc3ccccc3[nH]2)c(=O)n(-c2cc(OC)cc(OC)c2)n1C(C)C] | | + | N-alk | 407 | 408 |
| 291 | 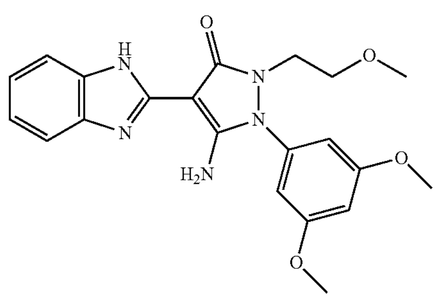 [SMILES: COCCn1c(=O)c(-c2nc3ccccc3[nH]2)c(N)n1-c1cc(OC)cc(OC)c1] | | + | B | 409 | 410 |
| 292 | 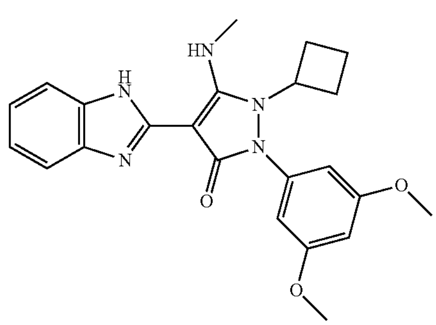 [SMILES: CNc1c(-c2nc3ccccc3[nH]2)c(=O)n(-c2cc(OC)cc(OC)c2)n1C1CCC1] | | + | N-alk | 419 | 420 |

-continued

| Cmpd No. | Structure | GTP Activity | BArr Activity | General Procedure | Exact Mass | MS M/Z Found (M + 1) |
|---|---|---|---|---|---|---|
| 293 | 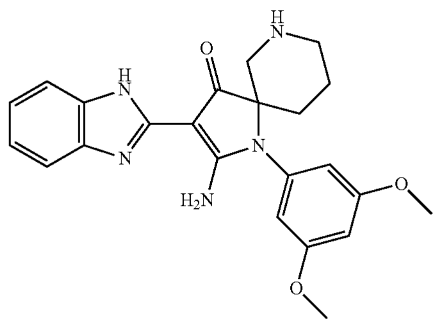 [SMILES: COc1cc(OC)cc(N2C(N)=C(c3nc4ccccc4[nH]3)C(=O)C23CCCNC3)c1] | ++ | | B | 419 | 420 |
| 294 | 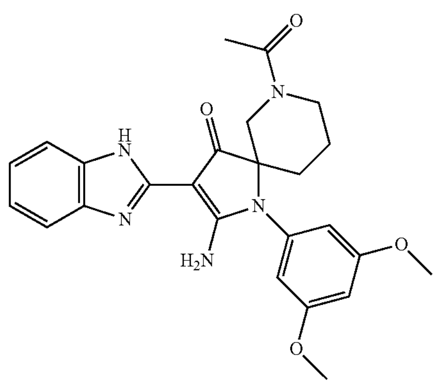 [SMILES: COc1cc(OC)cc(N2C(N)=C(c3nc4ccccc4[nH]3)C(=O)C23CCCN(C(C)=O)C3)c1] | ++ | | N-Acylation of Cmpd. No. 293 | 461 | 462 |
| 295 | 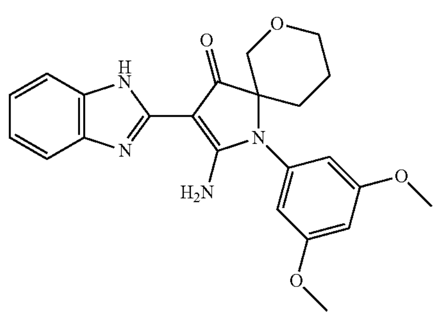 [SMILES: COc1cc(OC)cc(N2C(N)=C(c3nc4ccccc4[nH]3)C(=O)C23CCCOC3)c1] | +++ | | B | 420 | 421 |
| 296 | 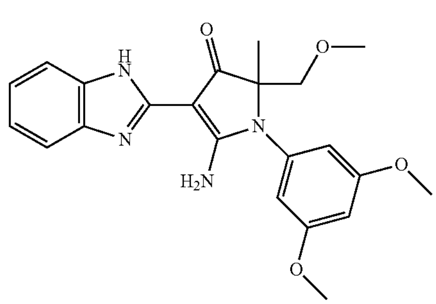 [SMILES: COCC1(C)C(=O)C(c2nc3ccccc3[nH]2)=C(N)N1c1cc(OC)cc(OC)c1] | +++ | | B | 408 | 409 |

-continued

| Cmpd No. | Structure | GTP Activity | BArr Activity | General Procedure | Exact Mass | MS M/Z Found (M + 1) |
|---|---|---|---|---|---|---|
| 297 | 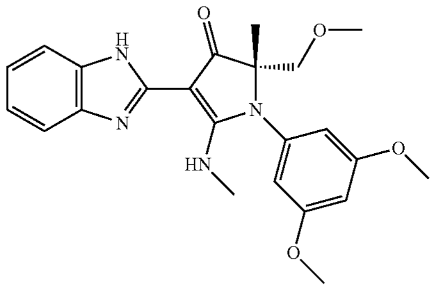 [SMILES: CNC1=C(c2nc3ccccc3[nH]2)C(=O)[C@](C)(COC)N1c1cc(OC)cc(OC)c1] | +++ | + | N-alk | 422 | 423 |
| 298 | 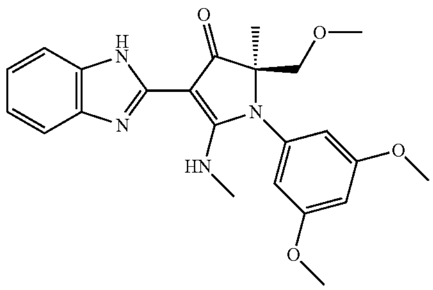 [SMILES: CNC1=C(c2nc3ccccc3[nH]2)C(=O)[C@@](C)(COC)N1c1cc(OC)cc(OC)c1] | ++++ | + | N-alk | 422 | 423 |
| 299 | 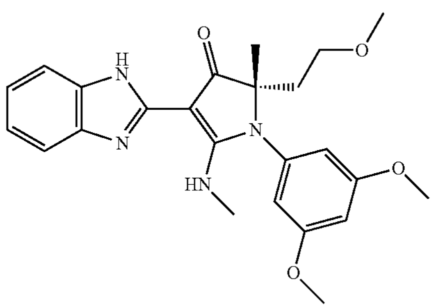 [SMILES: CNC1=C(c2nc3ccccc3[nH]2)C(=O)[C@](C)(CCOC)N1c1cc(OC)cc(OC)c1] | +++ | + | B, N-alk | 436 | 437 |
| 300 | 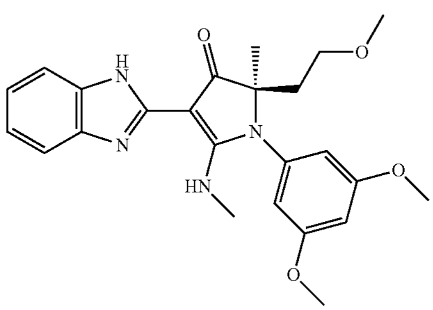 [SMILES: CNC1=C(c2nc3ccccc3[nH]2)C(=O)[C@@](C)(CCOC)N1c1cc(OC)cc(OC)c1] | ++++ | + | B, N-alk | 436 | 437 |
| 301 | 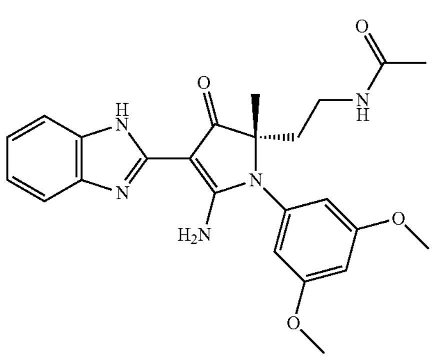 [SMILES: COc1cc(OC)cc(N2C(N)=C(c3nc4ccccc4[nH]3)C(=O)[C@]2(C)CCNC(C)=O)c1] | +++ | | L | 449 | 450 |

-continued

| Cmpd No. | Structure | GTP Activity | BArr Activity | General Procedure | Exact Mass | MS M/Z Found (M + 1) |
|---|---|---|---|---|---|---|
| 302 | 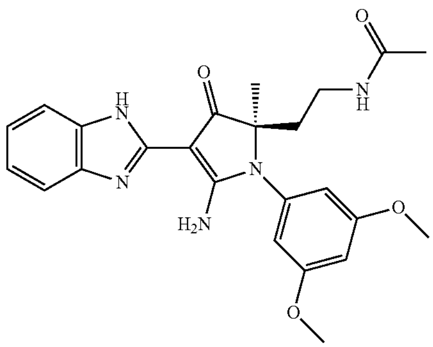 [SMILES: COc1cc(OC)cc(N2C(N)=C(c3nc4ccccc4[nH]3)C(=O)[C@@]2(C)CCNC(C)=O)c1] | +++ | | L | 449 | 450 |
| 303 | 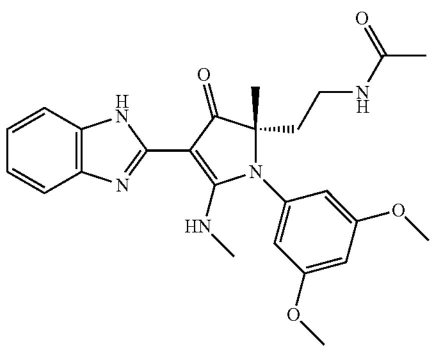 [SMILES: CNC1=C(c2nc3ccccc3[nH]2)C(=O)[C@](C)(CCNC(C)=O)N1c1cc(OC)cc(OC)c1] | ++++ | ++ | L | 463 | 464 |
| 304 | 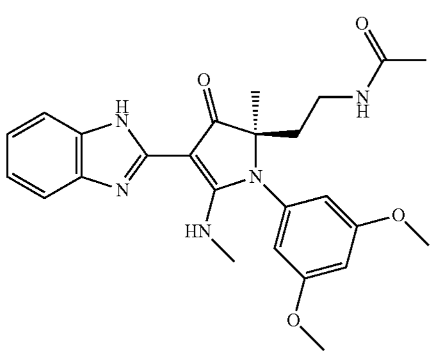 [SMILES: CNC1=C(c2nc3ccccc3[nH]2)C(=O)[C@@](C)(CCNC(C)=O)N1c1cc(OC)cc(OC)c1] | ++++ | + | L | 463 | 464 |
| 305 | 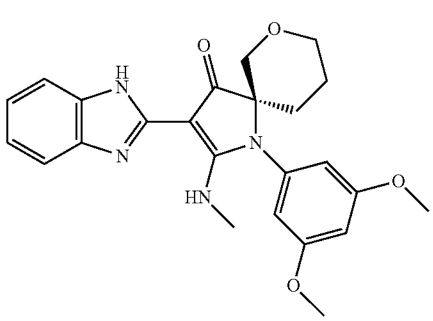 [SMILES: CNC1=C(c2nc3ccccc3[nH]2)C(=O)[C@]2(CCCOC2)N1c1cc(OC)cc(OC)c1] | ++++ | ++ | B, N-alk | 434 | 435 |

| Cmpd No. | Structure | GTP Activity | BArr Activity | General Procedure | Exact Mass | MS M/Z Found (M + 1) |
|---|---|---|---|---|---|---|
| 306 | 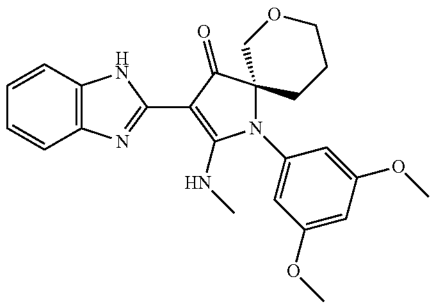 [SMILES: CNC1=C(c2nc3ccccc3[nH]2)C(=O)[C@@]2(CCCOC2)N1c1cc(OC)cc(OC)c1] | +++ | + | B, N-alk | 434 | 435 |
| 307 | 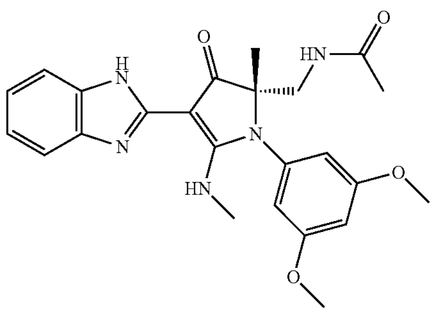 [SMILES: CNC1=C(c2nc3ccccc3[nH]2)C(=O)[C@](C)(CNC(C)=O)N1c1cc(OC)cc(OC)c1] | +++ | ++ | L | 449 | 450 |
| 308 | 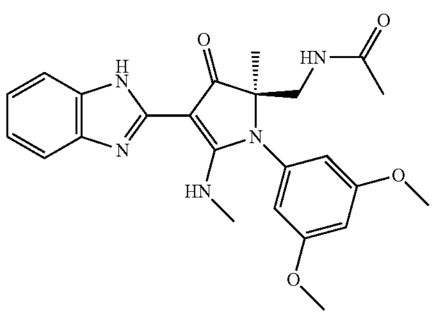 [SMILES: CNC1=C(c2nc3ccccc3[nH]2)C(=O)[C@@](C)(CNC(C)=O)N1c1cc(OC)cc(OC)c1] | ++++ | ++ | L | 449 | 450 |
| 309 | 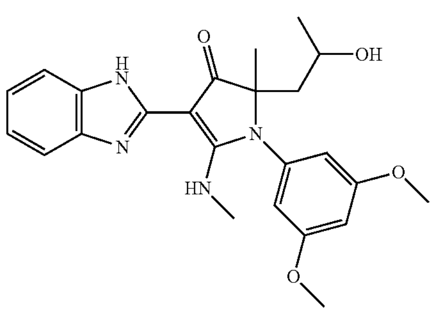 [SMILES: CNC1=C(c2nc3ccccc3[nH]2)C(=O)C(C)(CC(C)O)N1c1cc(OC)cc(OC)c1] | ++++ | + | 1) Oxidation of Cmpd. No. 217; 2) MeMgBr | 436 | 437 |
| 310 | 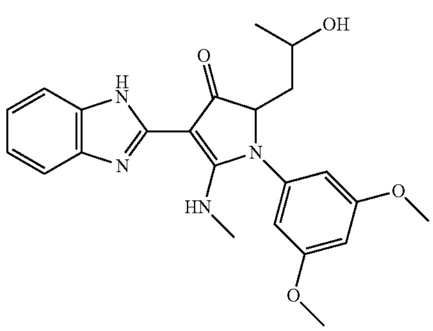 [SMILES: CNC1=C(c2nc3ccccc3[nH]2)C(=O)C(CC(C)O)N1c1cc(OC)cc(OC)c1] | ++++ | ++ | 1) Oxidation of Cmpd. No. 215; 2) MeMgBr | 422 | 423 |

| Cmpd No. | Structure | GTP Activity | BArr Activity | General Procedure | Exact Mass | MS M/Z Found (M + 1) |
|---|---|---|---|---|---|---|
| 311 | 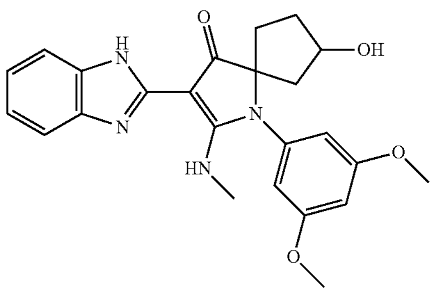 [SMILES: CNC1=C(c2nc3ccccc3[nH]2)C(=O)C2(CCC(O)C2)N1c1cc(OC)cc(OC)c1] | ++++ | | Reduction of Cmpd. No. 312 | 434 | 435 |
| 312 | 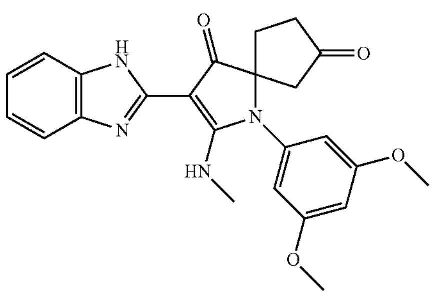 [SMILES: CNC1=C(c2nc3ccccc3[nH]2)C(=O)C2(CCC(=O)C2)N1c1cc(OC)cc(OC)c1] | ++++ | | Decarboxylation of Cmpd. No. 313 | 432 | 433 |
| 313 | 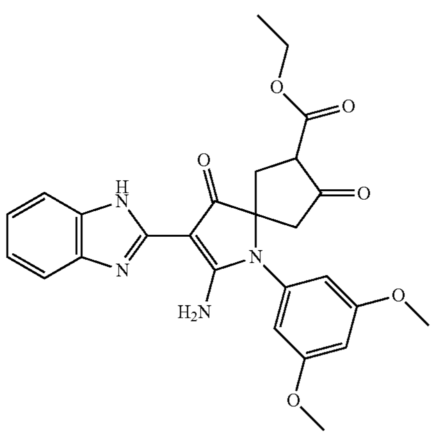 [SMILES: CCOC(=O)C1CC2(CC1=O)C(=O)C(c1nc3ccccc3[nH]1)=C(N)N2c1cc(OC)cc(OC)c1] | ++ | | Ring expansion of Cmpd. No. 207 with ethyl azidoacetate and BF₃ | 490 | 491 |
| 314 | 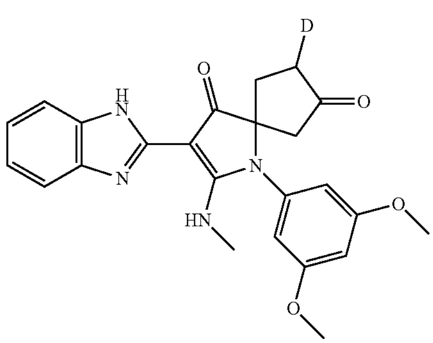 [SMILES: [2H]C1CC2(CC1=O)C(=O)C(c1nc3ccccc3[nH]1)=C(NC)N2c1cc(OC)cc(OC)c1] | ++++ | | Deuterium exchange of Cmpd. No. 312 using CD₃OD | 433 | 434 |

| Cmpd No. | Structure | GTP Activity | BArr Activity | General Procedure | Exact Mass | MS M/Z Found (M + 1) |
|---|---|---|---|---|---|---|
| 315 | 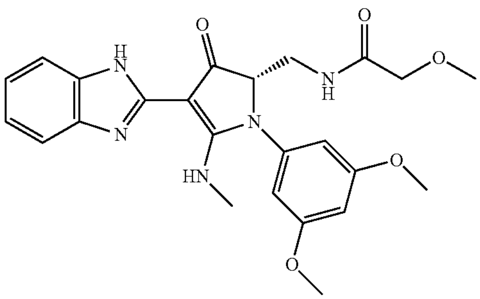 [SMILES: CNC1=C(c2nc3ccccc3[nH]2)C(=O)[C@H](CNC(=O)COC)N1c1cc(OC)cc(OC)c1] | ++++ | | A | 465 | 466 |
| 316 | 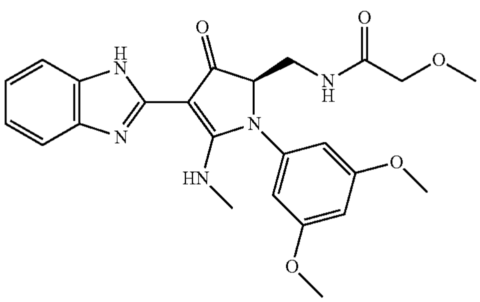 [SMILES: CNC1=C(c2nc3ccccc3[nH]2)C(=O)[C@@H](CNC(=O)COC)N1c1cc(OC)cc(OC)c1] | ++++ | | A | 465 | 466 |
| 317 | 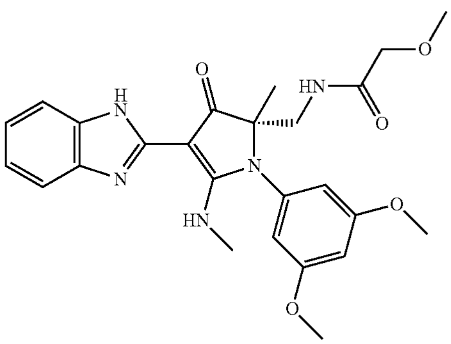 [SMILES: CNC1=C(c2nc3ccccc3[nH]2)C(=O)[C@](C)(CNC(=O)COC)N1c1cc(OC)cc(OC)c1] | +++ | | L | 479 | 480 |
| 318 | 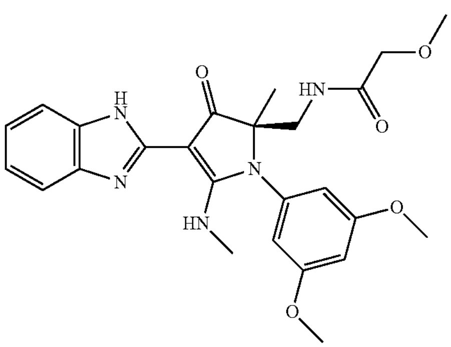 [SMILES: CNC1=C(c2nc3ccccc3[nH]2)C(=O)[C@@](C)(CNC(=O)COC)N1c1cc(OC)cc(OC)c1] | ++++ | | L | 479 | 480 |

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated herein by reference in their entireties. Citation or identification of any reference in this application is not an admission that such reference is available as prior art to this application. The full scope of the disclosure is better understood with reference to the appended claims.

What is claimed:

1. A compound of formula (I):

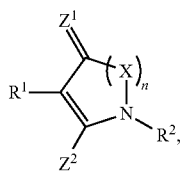

or a pharmaceutically acceptable salt thereof, wherein
$R^1$ is heteroaryl which is optionally substituted;
$R^2$ is aryl which is optionally substituted;
$Z^1$ is =O;
$Z^2$ is $NR^3R^4$;
X is $CR^7R^8$;
n is 1;
$R^3$ is (i) hydrogen; or (ii) alkyl, alkenyl, heteroalkyl, cycloalkyl, heterocyclyl, aryl, heteroaryl, aralkyl, or heteroaralkyl, each of which is optionally substituted; or (iii) $R^3$ and $R^4$ together with the nitrogen atom to which they are attached form an optionally substituted 3- to 8-membered heterocyclyl or heteroaryl ring; or (iv) $R^4$ is OH and $R^3$ is hydrogen;
$R^4$ is (i) alkyl, alkenyl, heteroalkyl, cycloalkyl, heterocyclyl, aryl, heteroaryl, aralkyl, or heteroaralkyl, each of which is optionally substituted; or (ii) $R^3$ and $R^4$ together with the nitrogen atom to which they are attached form an optionally substituted 3- to 8-membered heterocyclyl or heteroaryl ring; or (iii) $R^4$ is OH and $R^3$ is hydrogen;
$R^7$ and $R^8$ are independently (i) hydrogen, halo, or cyano; or (ii) alkyl, alkenyl, heteroalkyl, alkoxyl, aminoalkyl, cycloalkyl, heterocyclyl, aryl, heteroaryl, aralkyl, or heteroaralkyl, each of which is optionally substituted; or (iii) $OR^3$, $C(O)OR^3$, $—C(O)NH_2$, $—C(O)NR^3R^4$, or $C(O)R^3$; or (iv) $R^7$ and $R^8$ together with the carbon atom to which they are attached form an optionally substituted 3- to 8-membered heterocyclyl, heteroaryl, aryl, or cycloalkyl ring; and
optionally $R^2$ and $R^7$ or $R^8$ together with the atoms to which they are attached form an optionally substituted heterocyclyl or heteroaryl ring.

2. A compound selected from

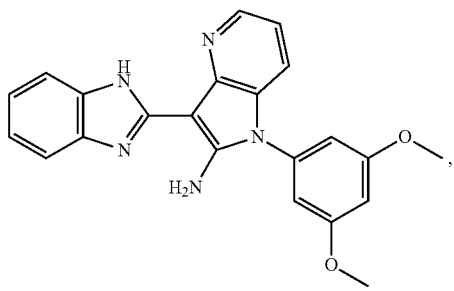

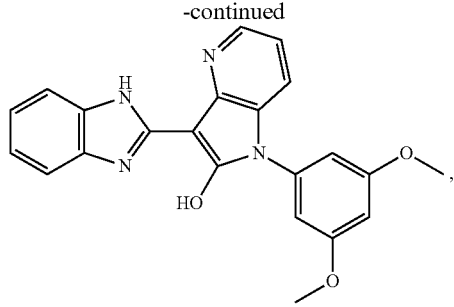

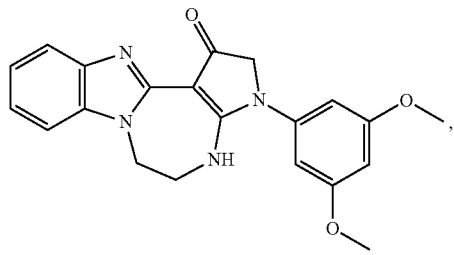

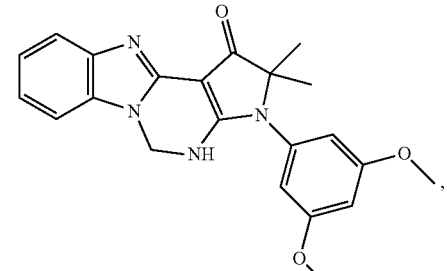

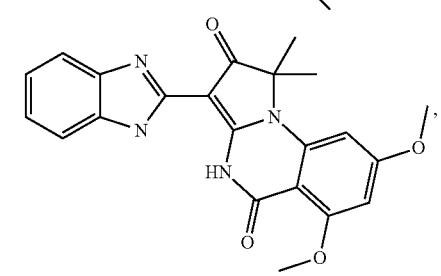

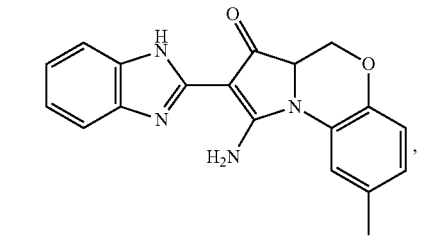

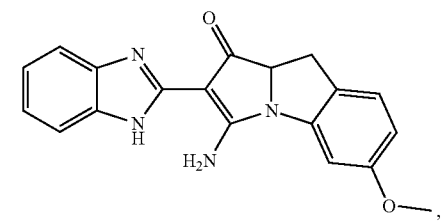

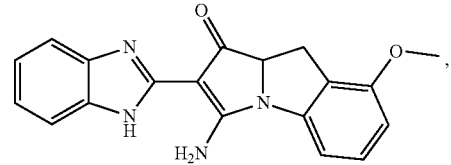

-continued
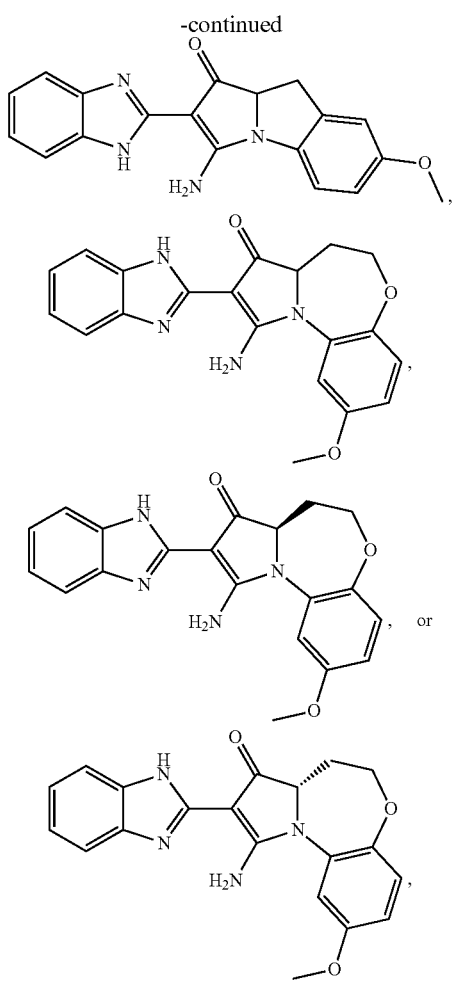
or a pharmaceutically acceptable salt thereof.
3. The compound of claim 1, or a pharmaceutically acceptable salt thereof, wherein $R^7$ and $R^8$ are each independently H or optionally substituted alkyl.
4. A compound selected from
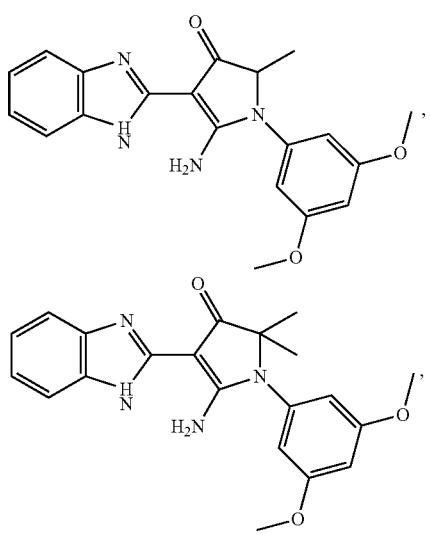
-continued
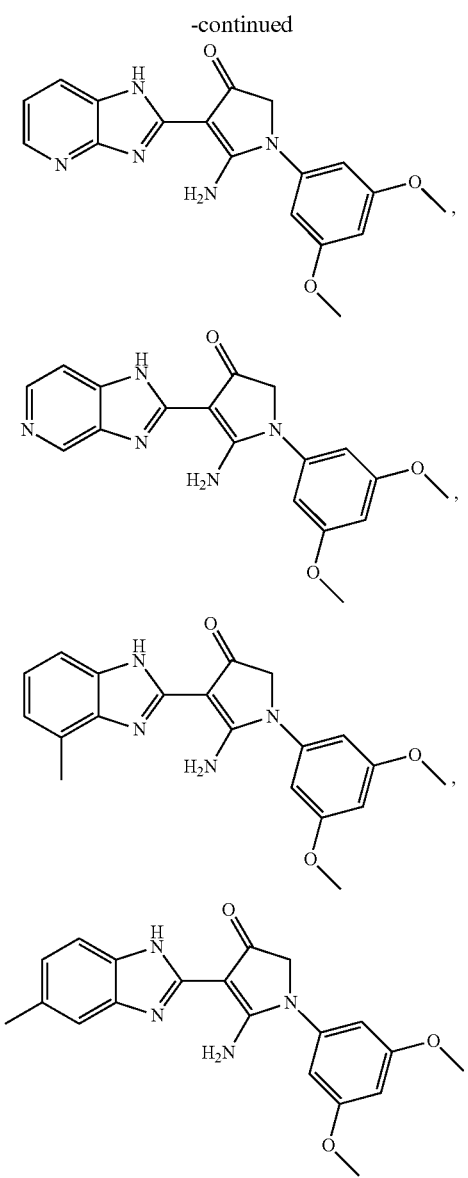
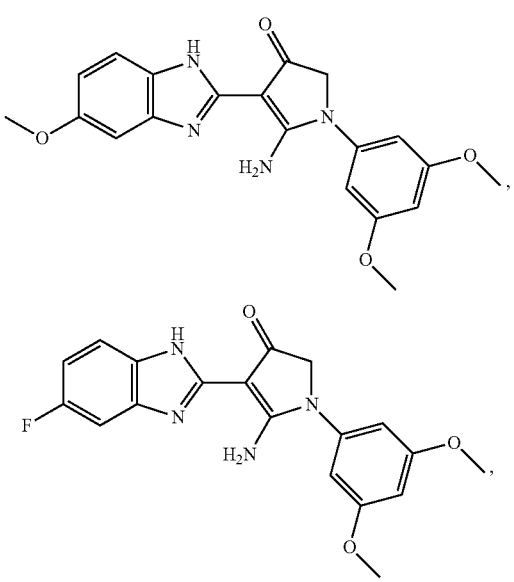

-continued
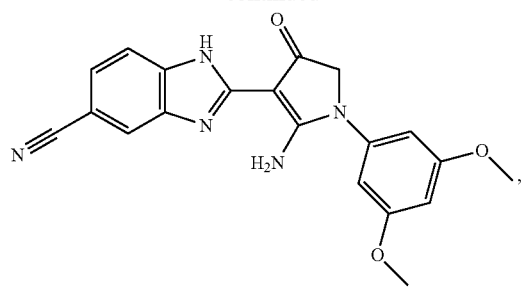
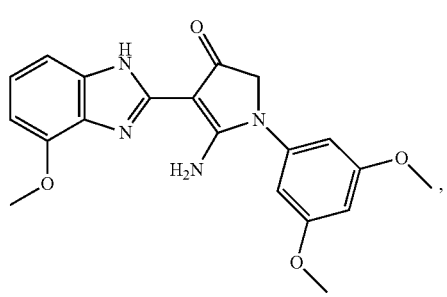
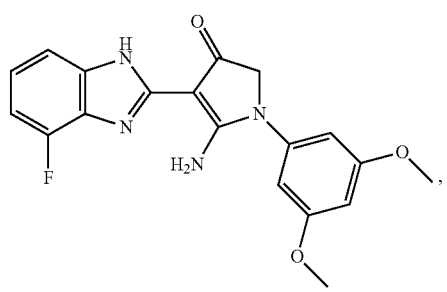
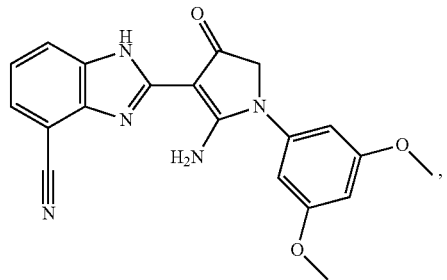
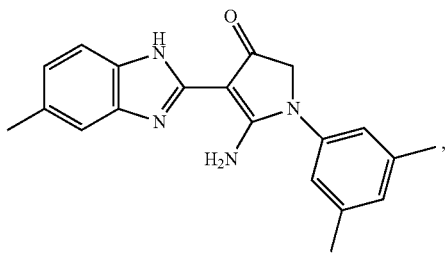
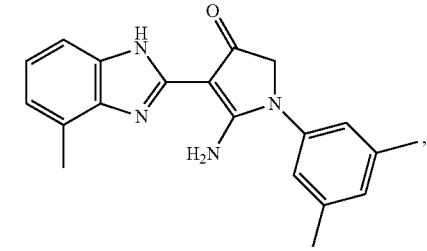
-continued
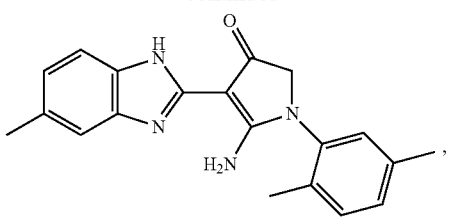
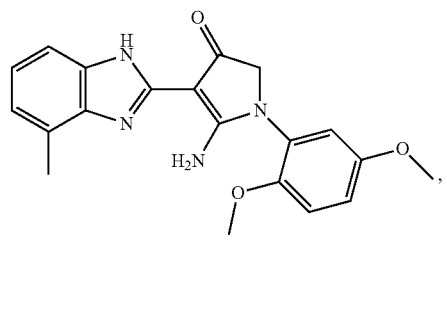
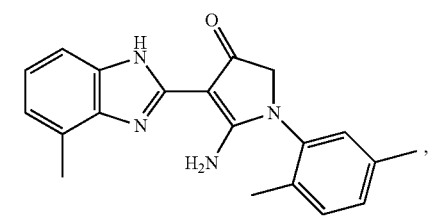
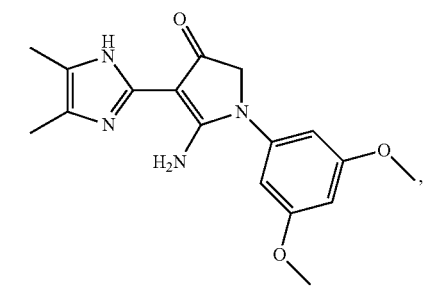
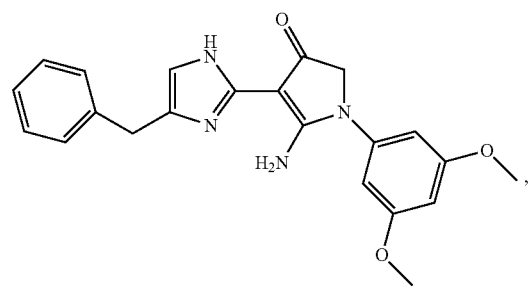
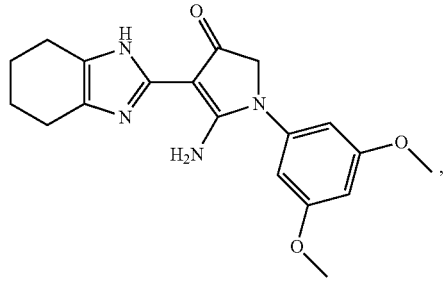

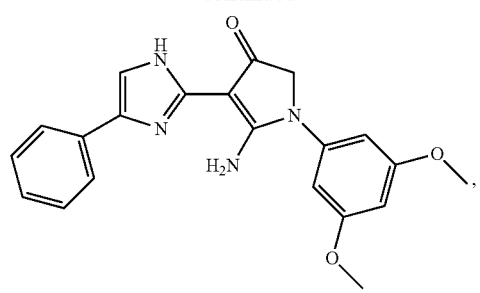,
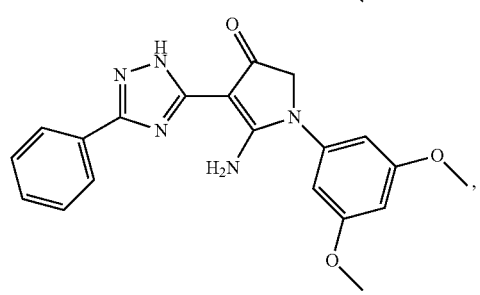,
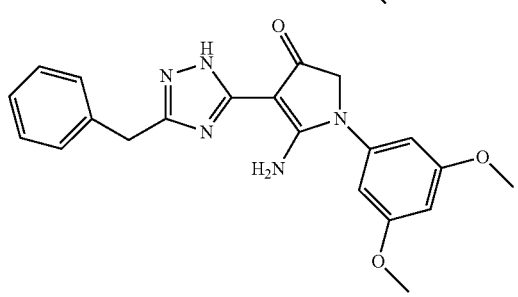,
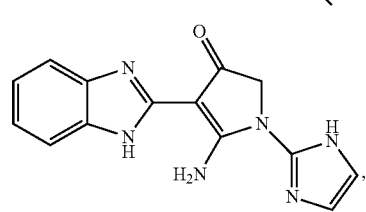,
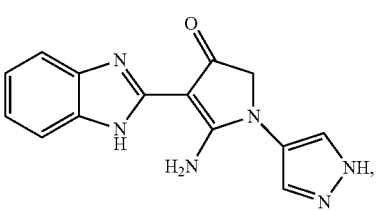,
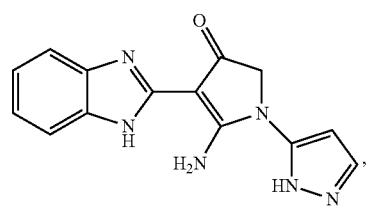,
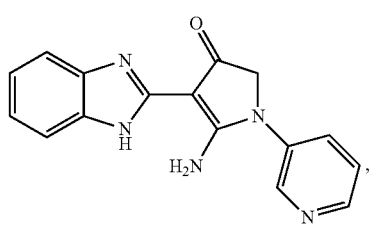,
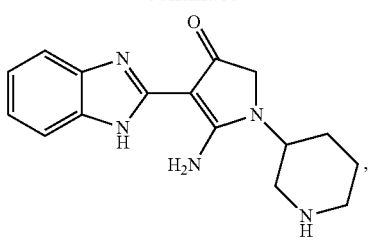,
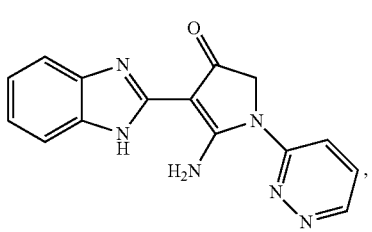,
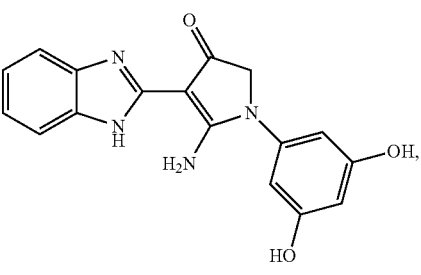,
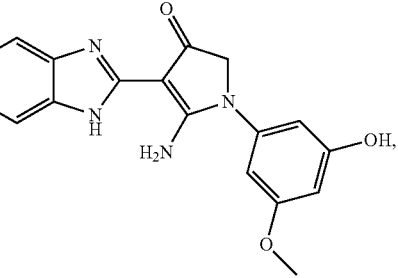,
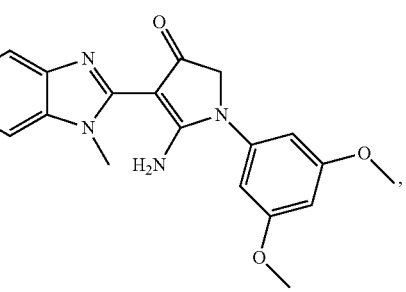,
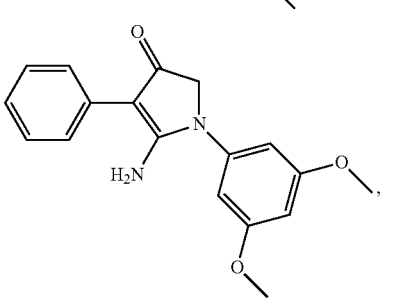, 265
-continued 266
-continued 267
-continued
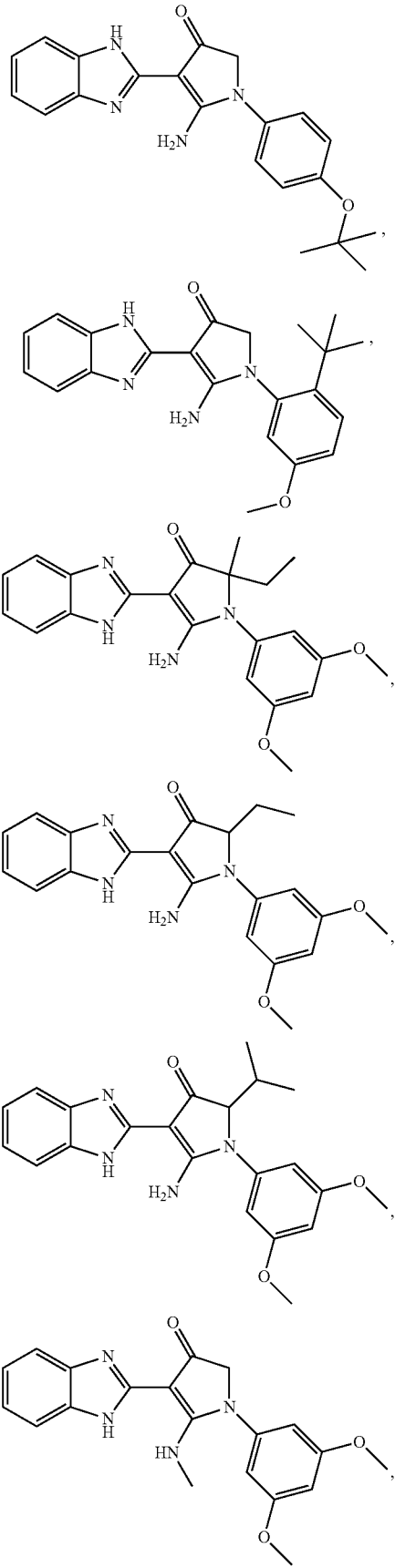
268
-continued
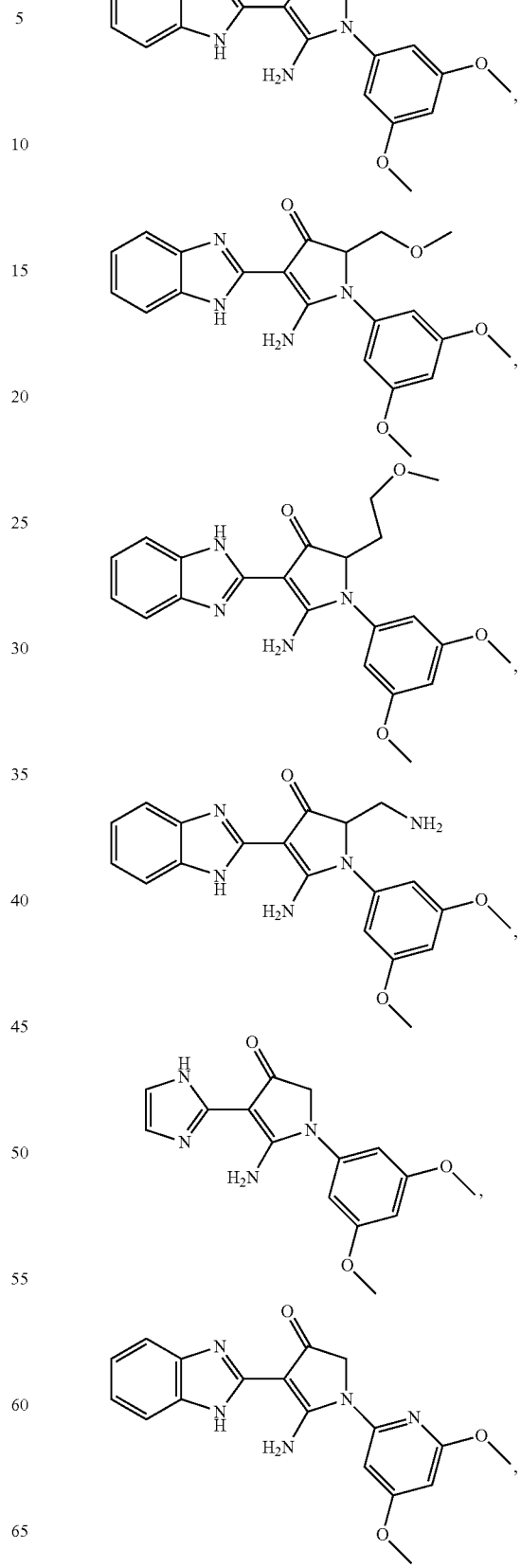

269
-continued
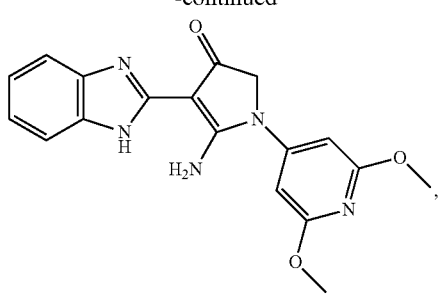
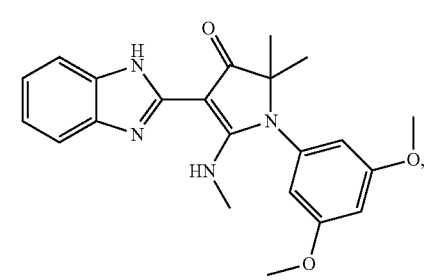
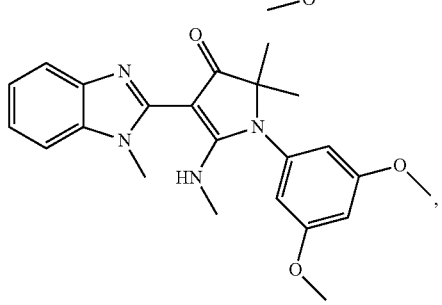
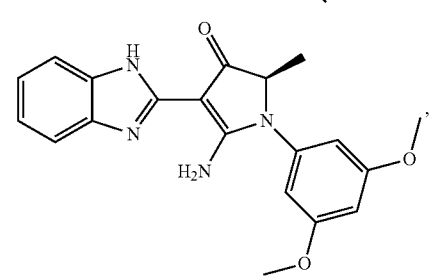
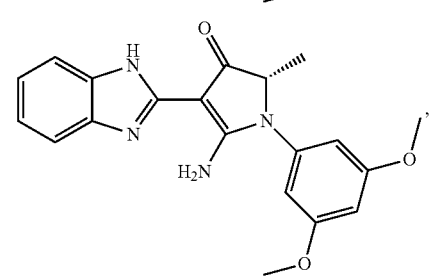
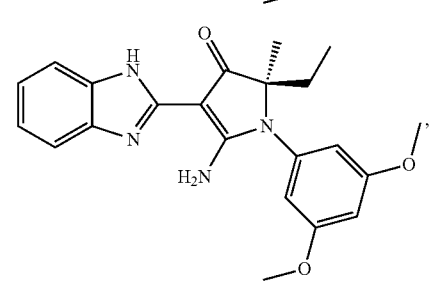
270
-continued
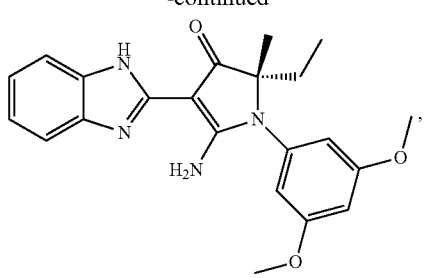
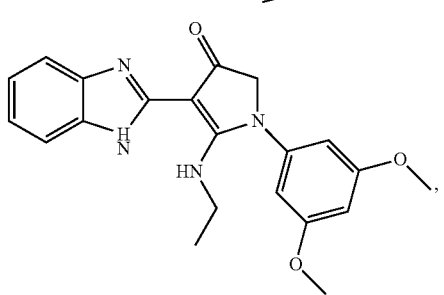
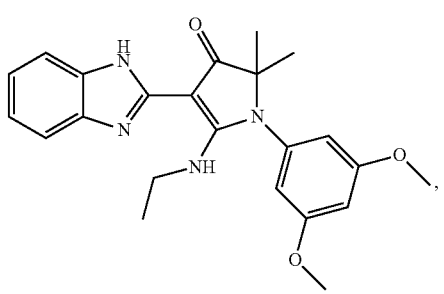
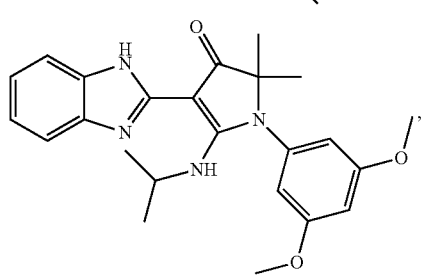
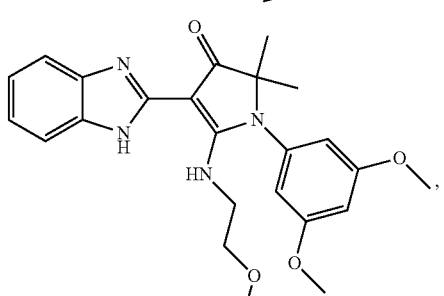
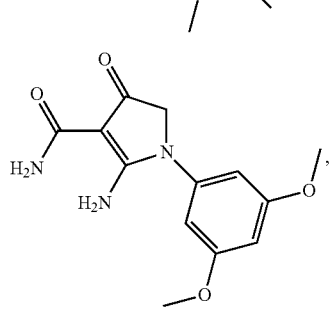

-continued
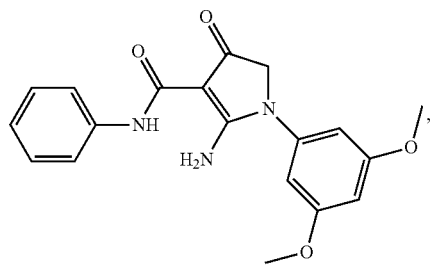
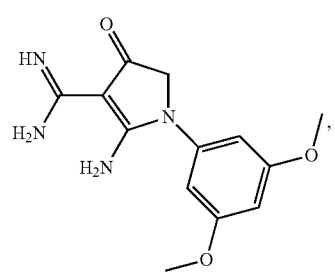
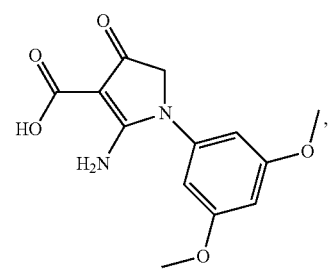
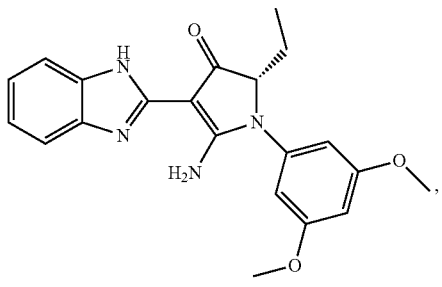
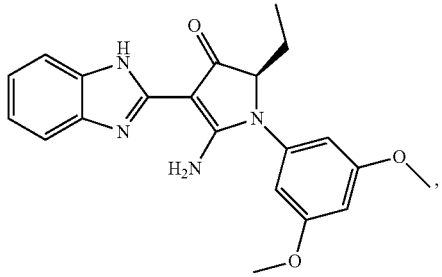
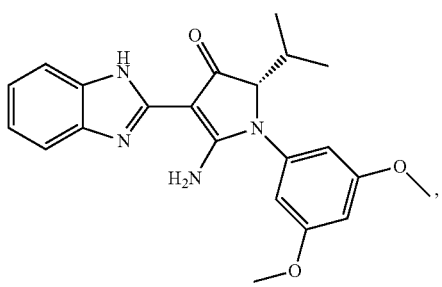
-continued
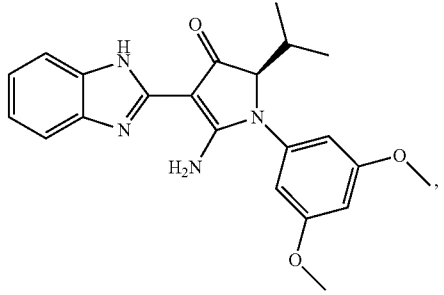
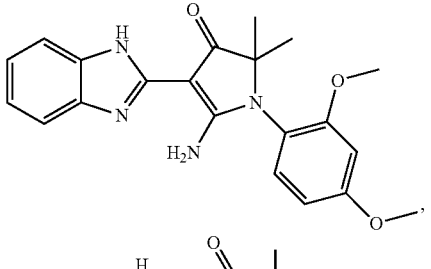
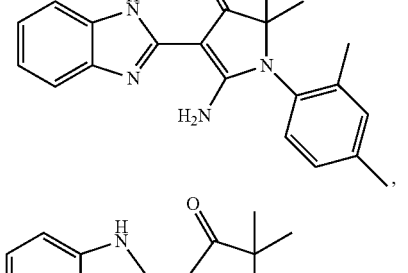
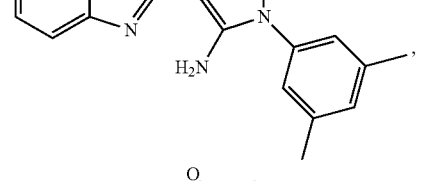
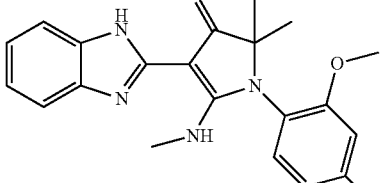
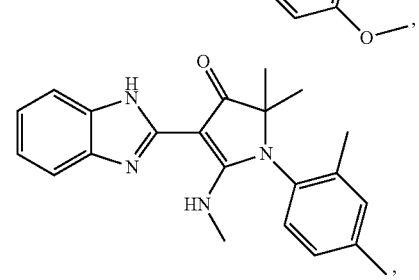
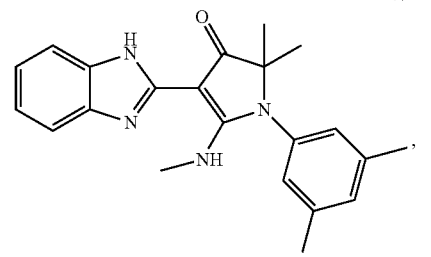

273
-continued
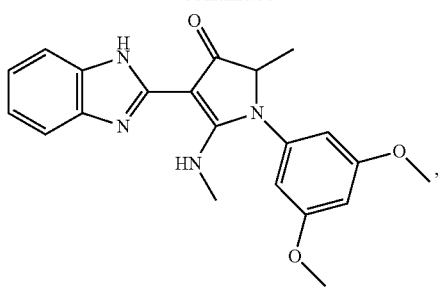
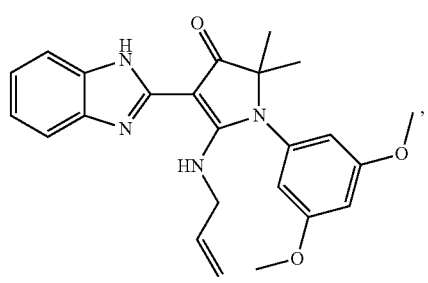
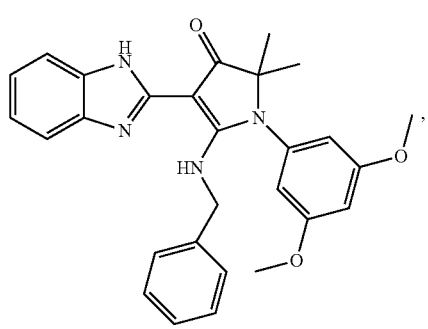
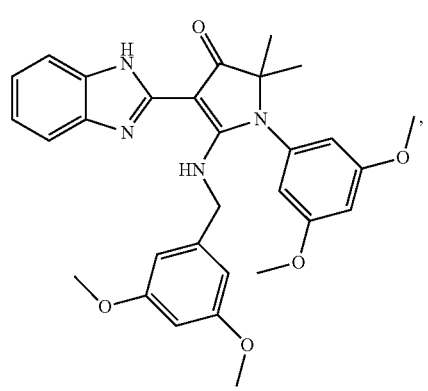
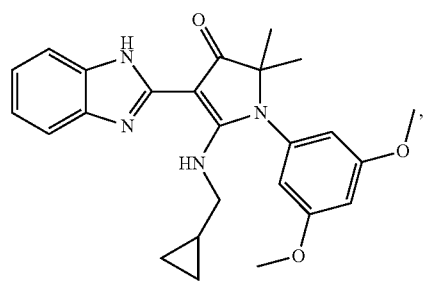
274
-continued
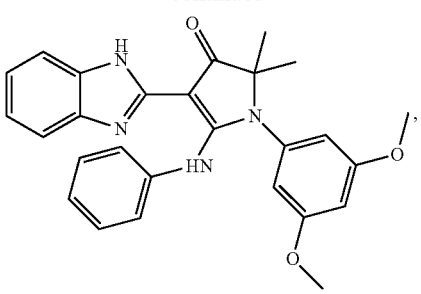
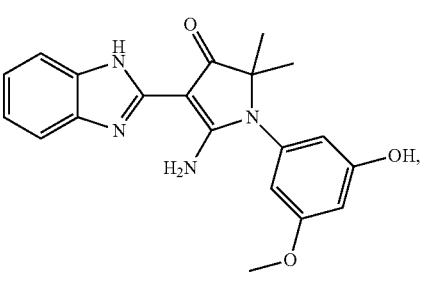
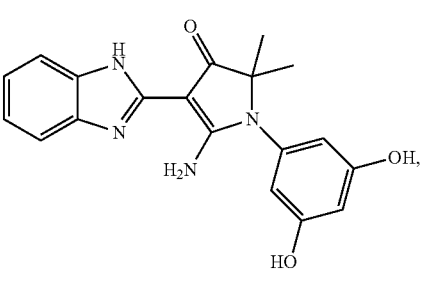
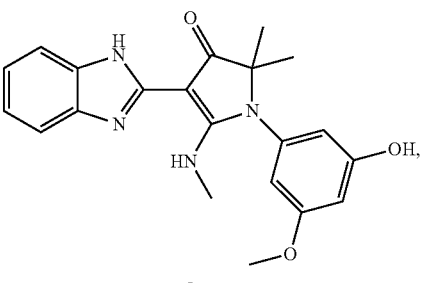
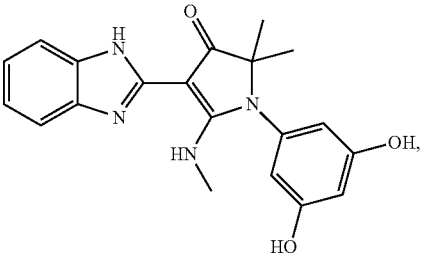
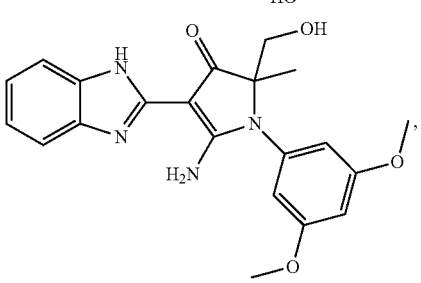

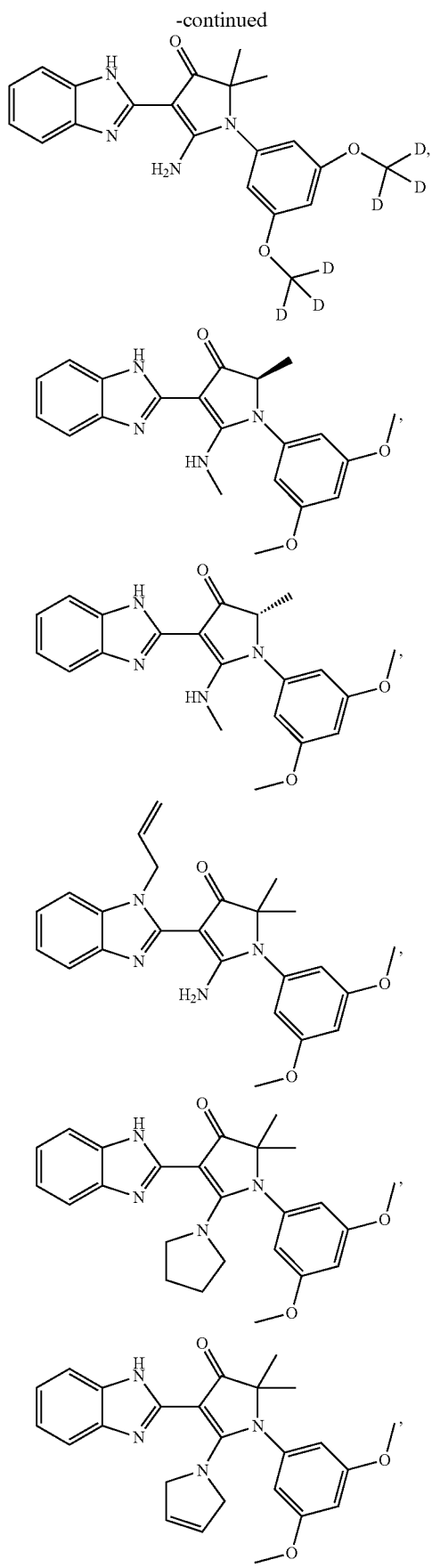
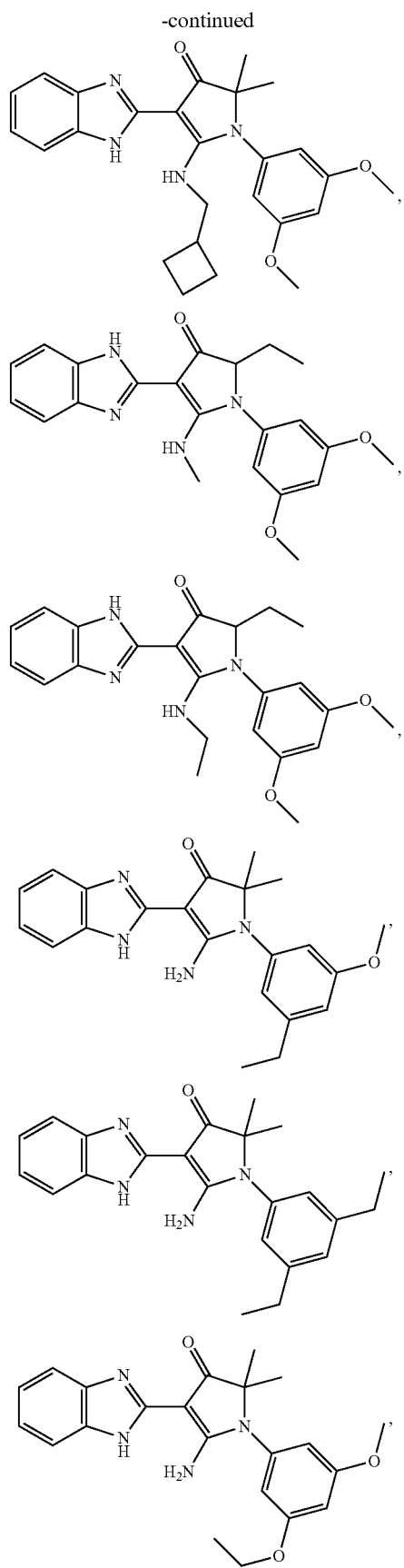

-continued
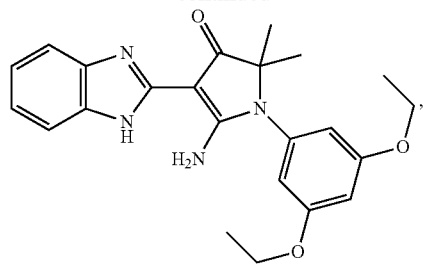
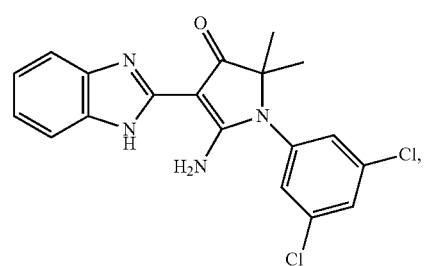
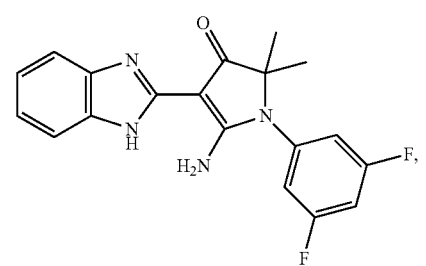
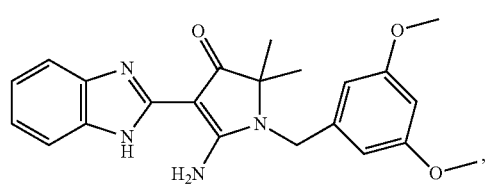
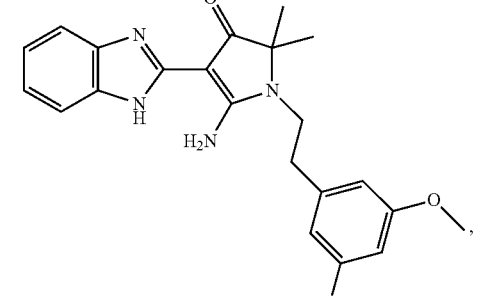
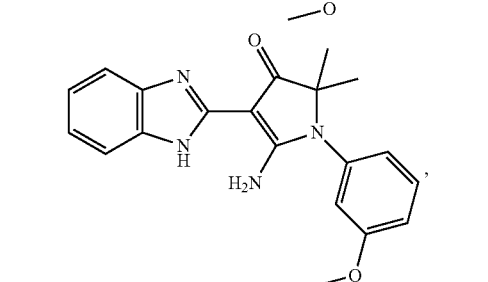
-continued
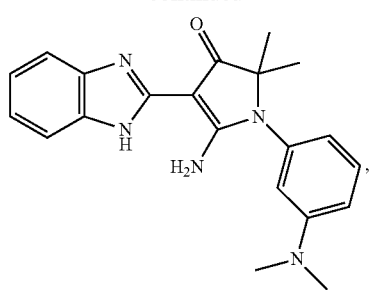
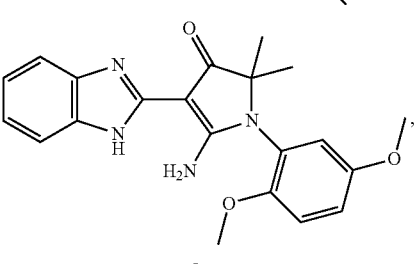
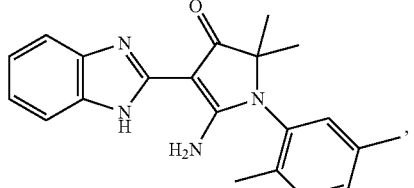
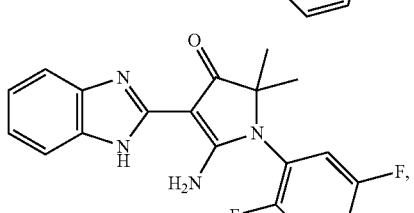
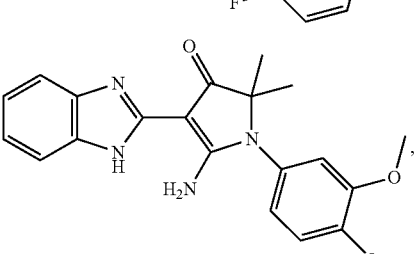
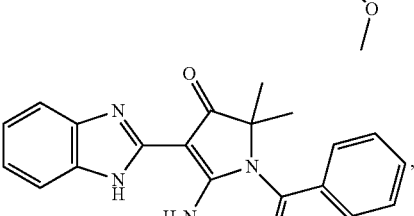
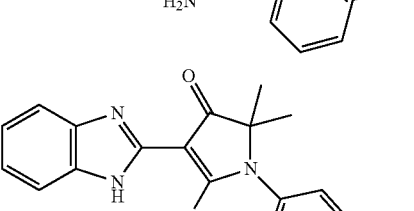
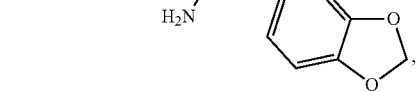

279
-continued
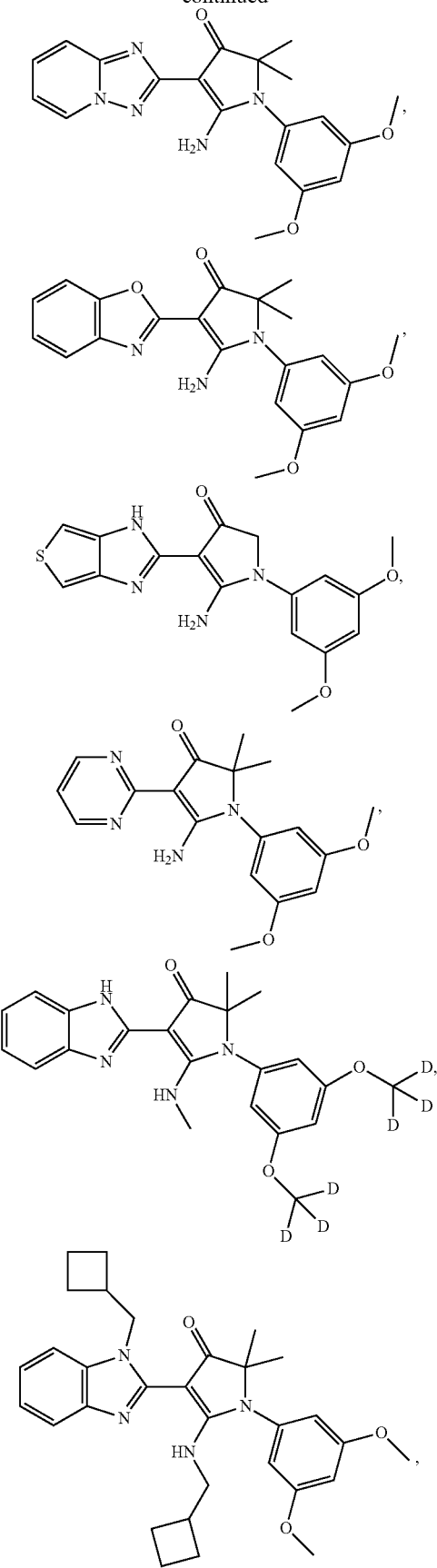
280
-continued
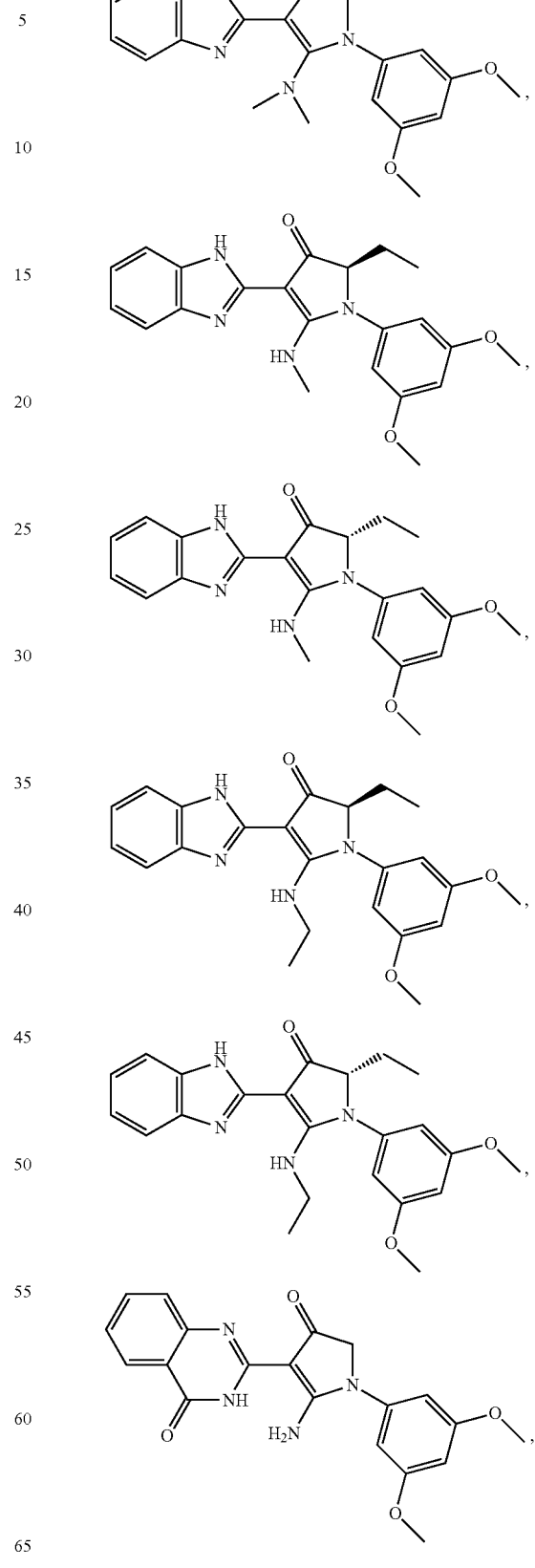

281
-continued
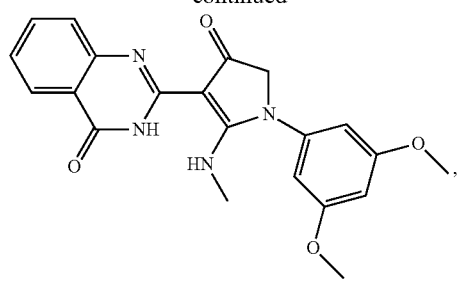
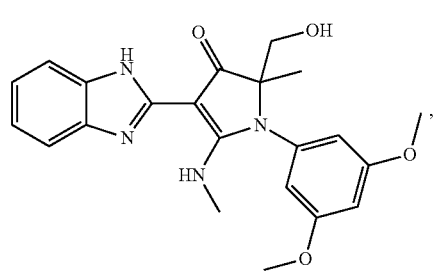
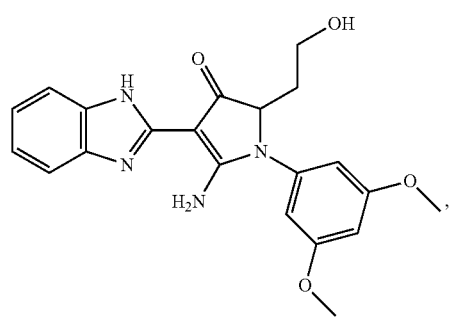
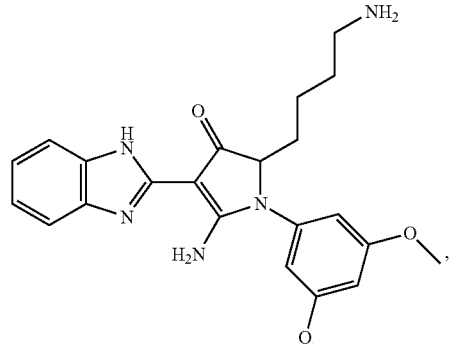
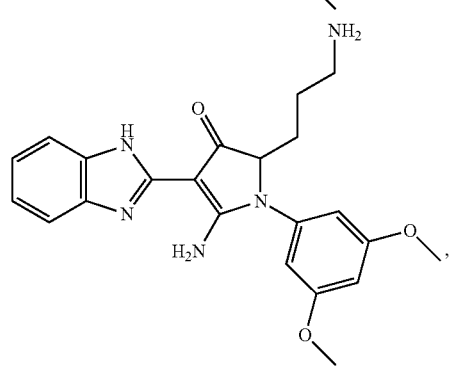
282
-continued
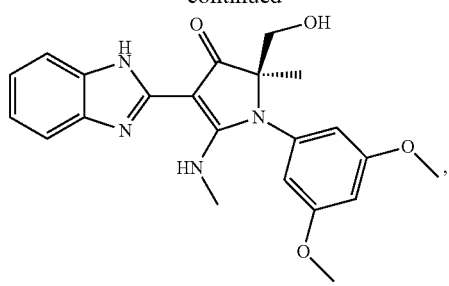
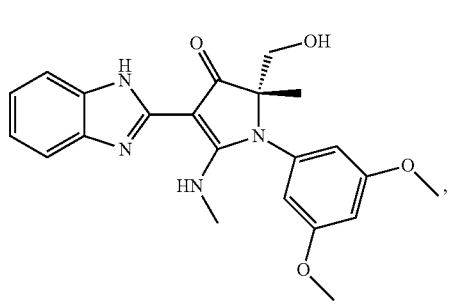
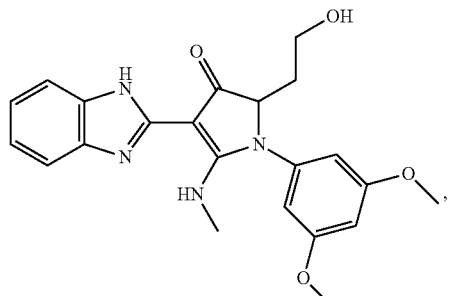
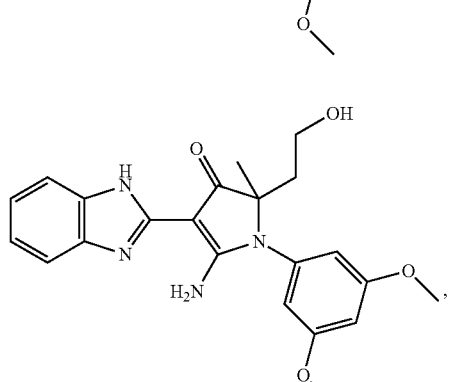
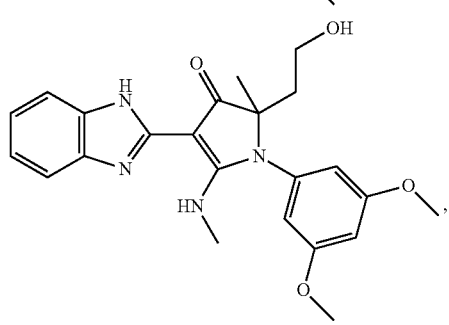

-continued
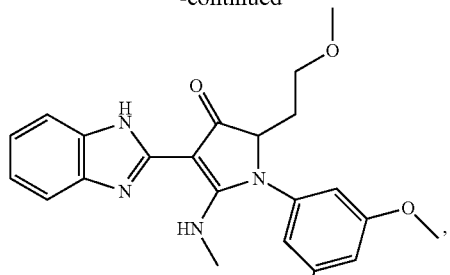
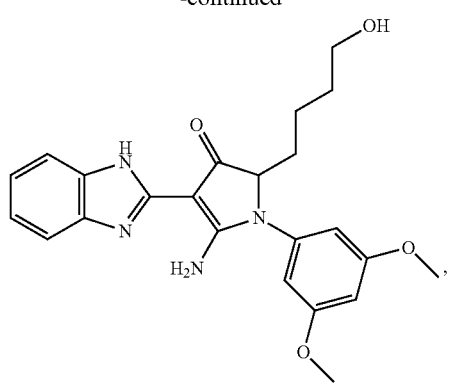
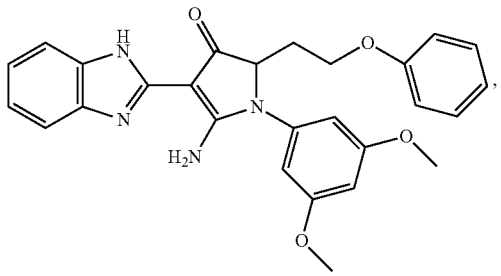
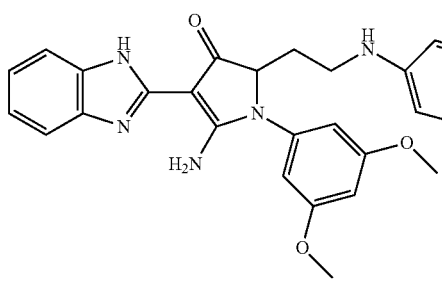
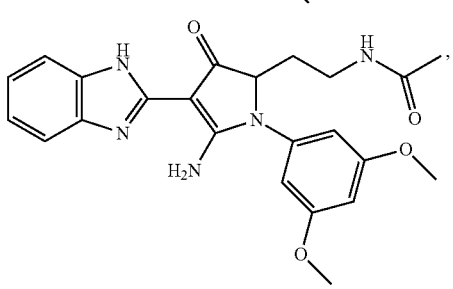
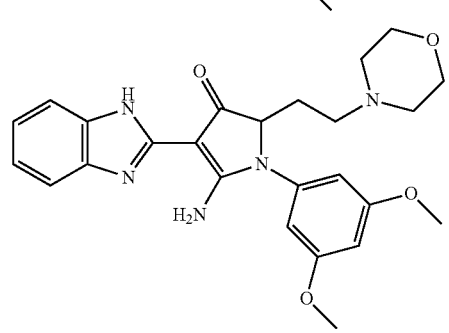

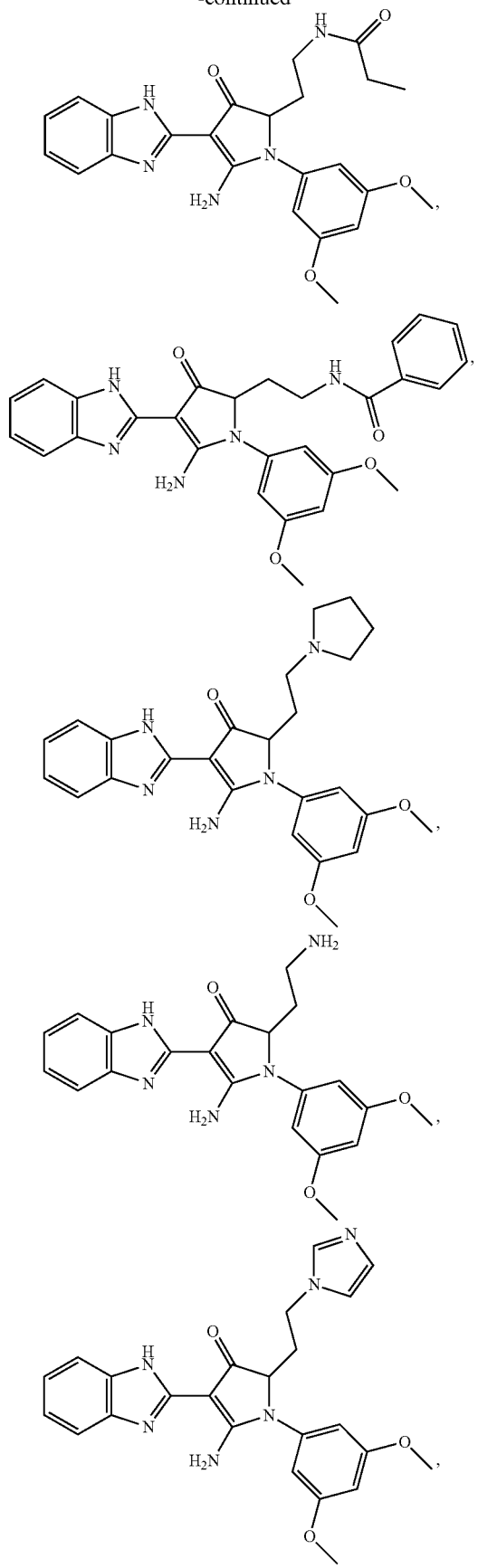
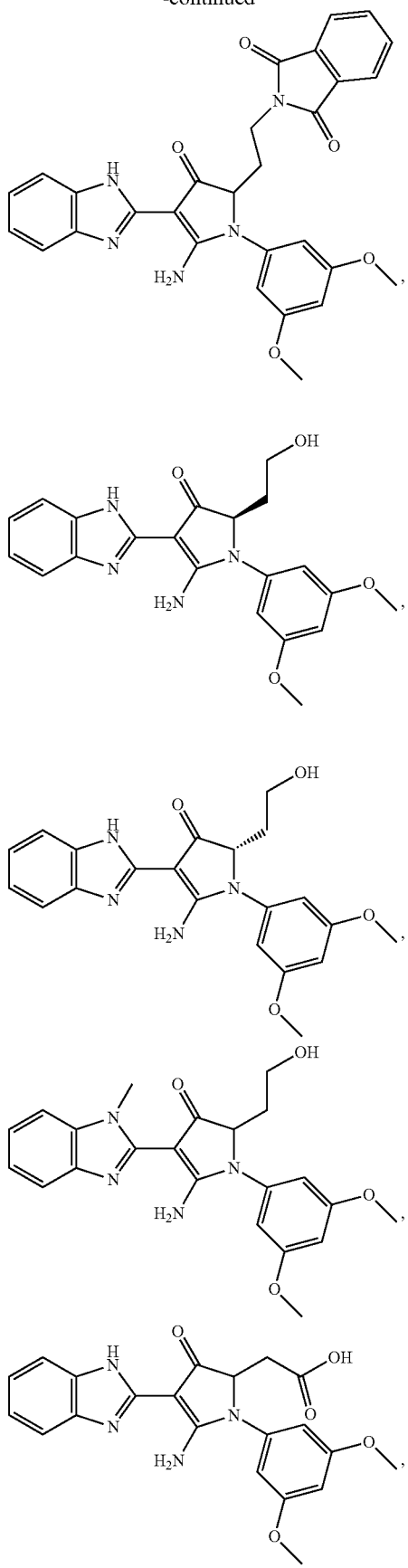

287
-continued
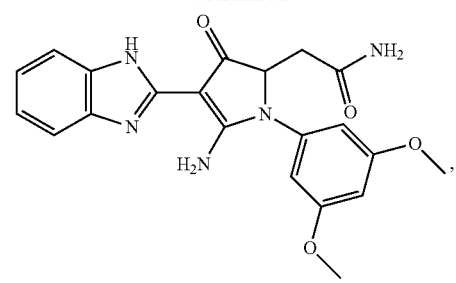
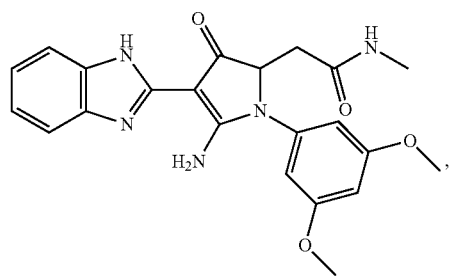
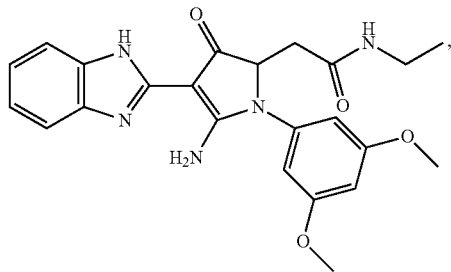
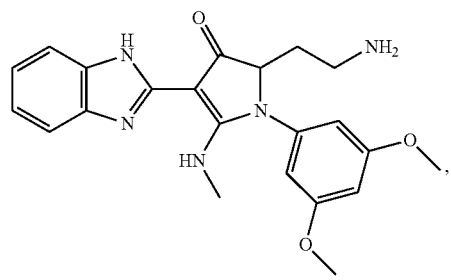
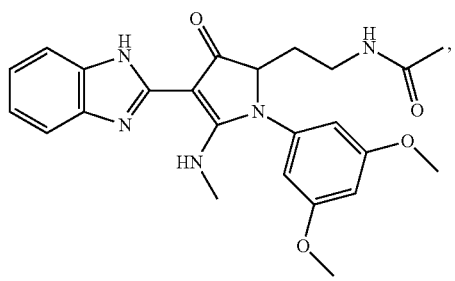
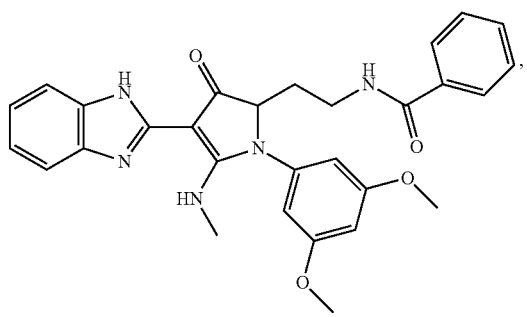
288
-continued
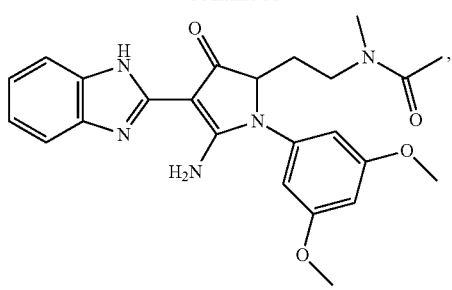
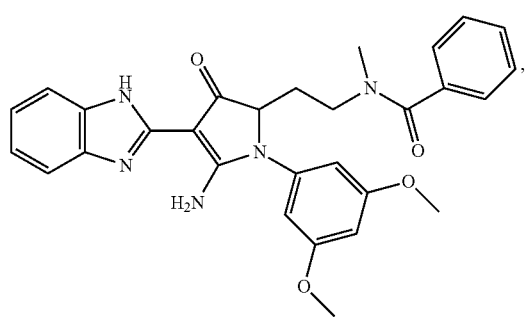
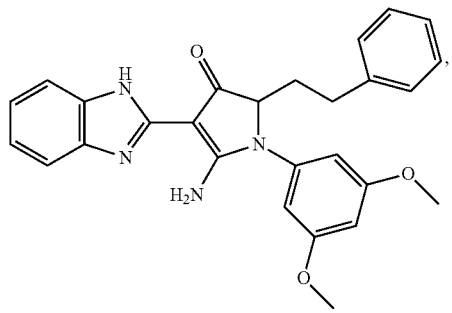
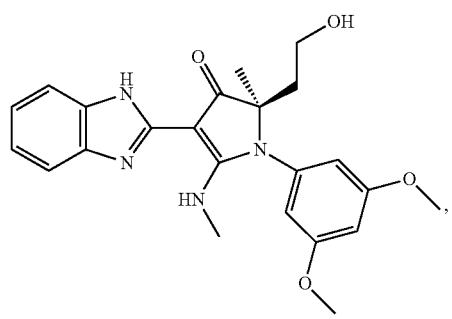
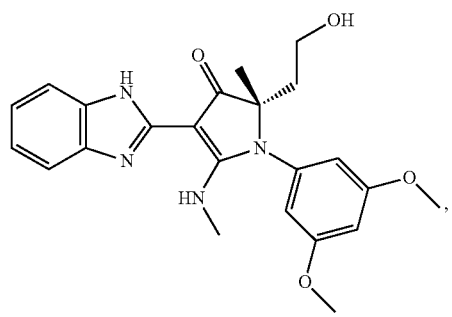

289
-continued
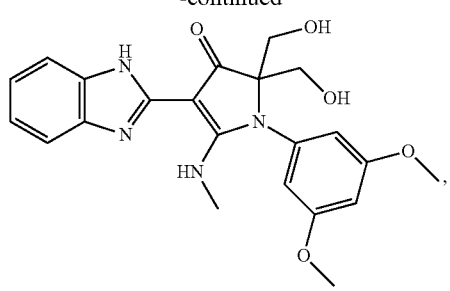
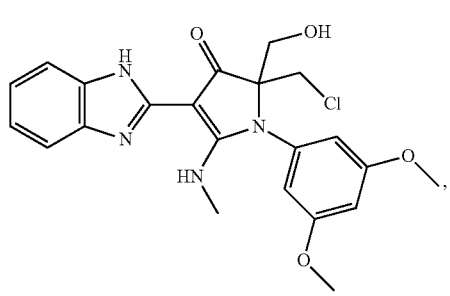
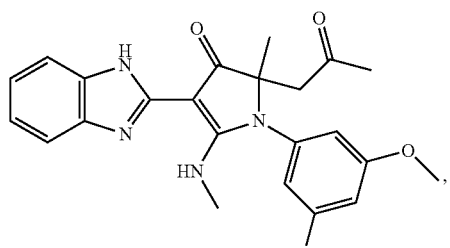
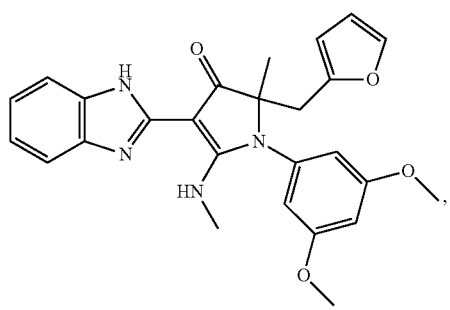
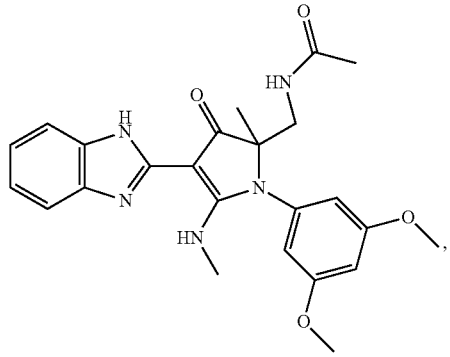
290
-continued
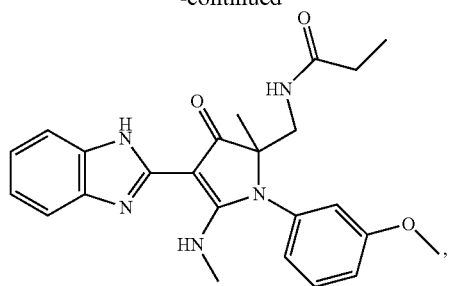
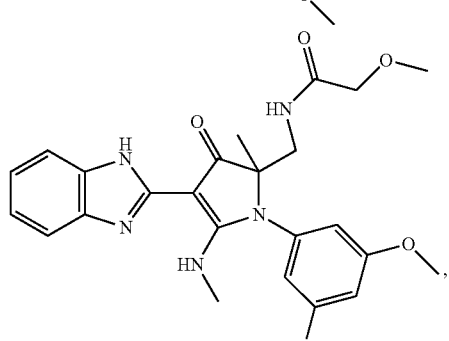
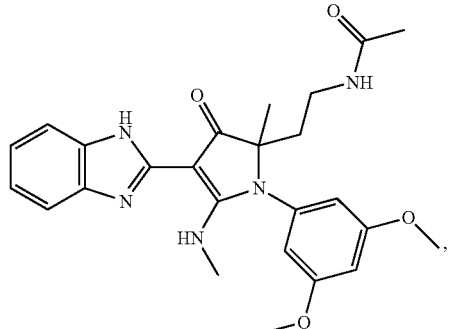
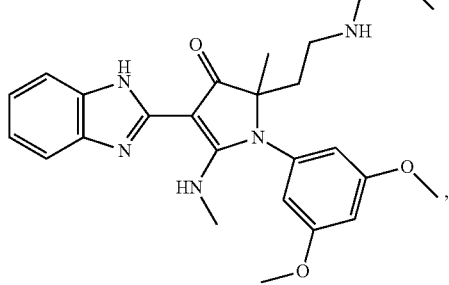
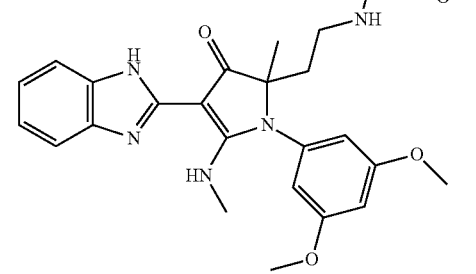

-continued
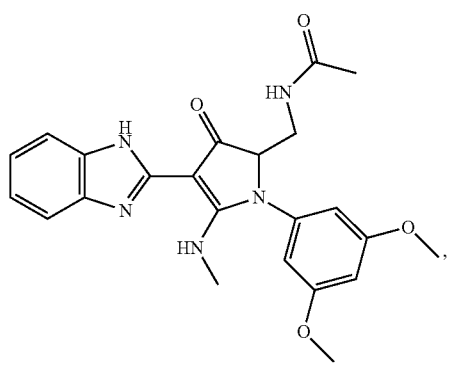
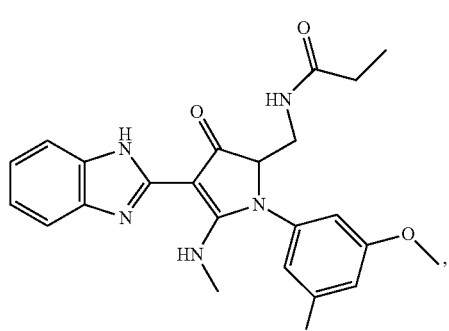
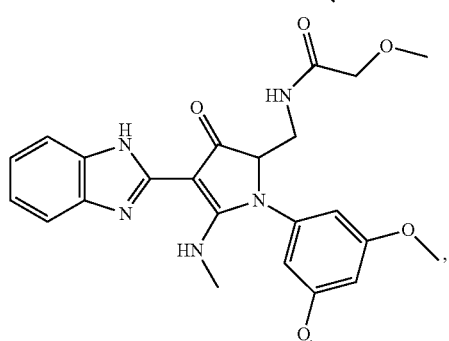
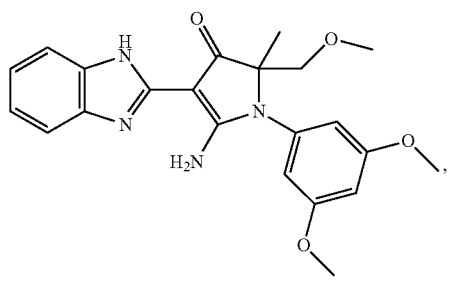
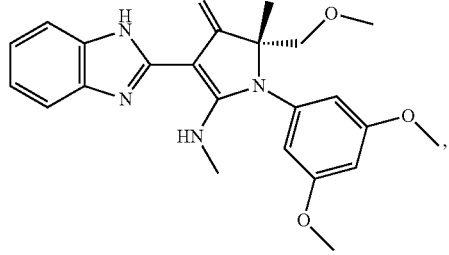
-continued
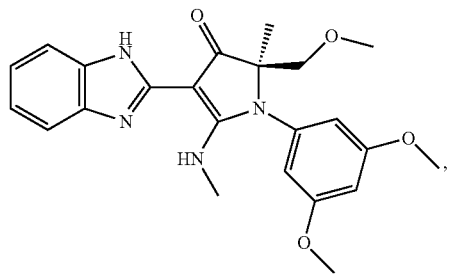
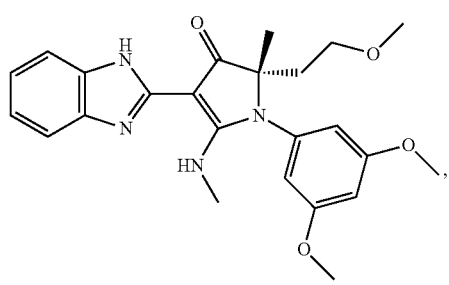
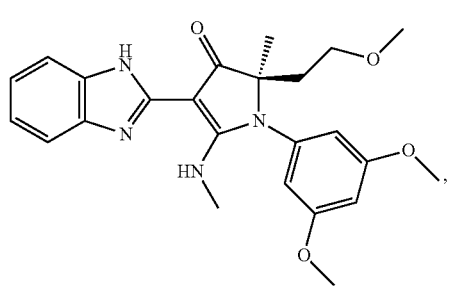
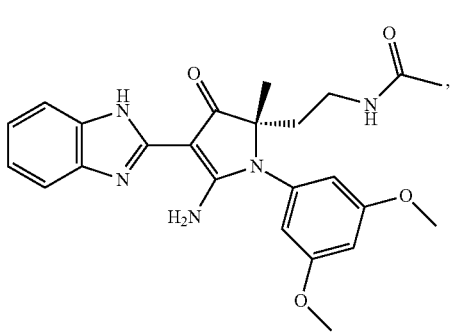
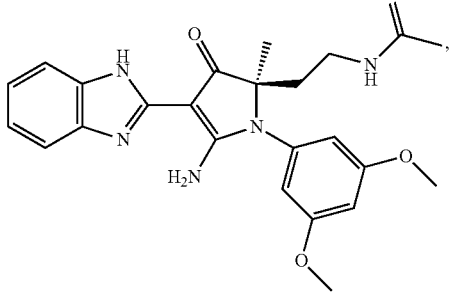

-continued
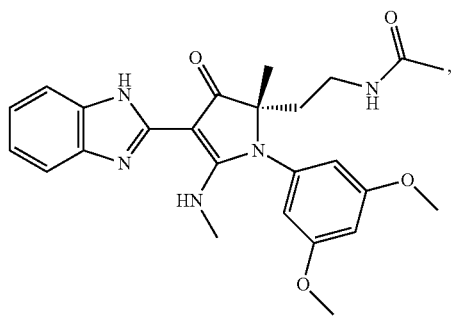
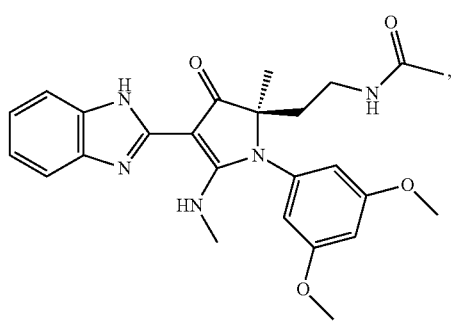
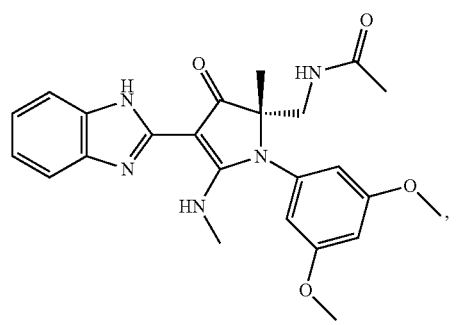
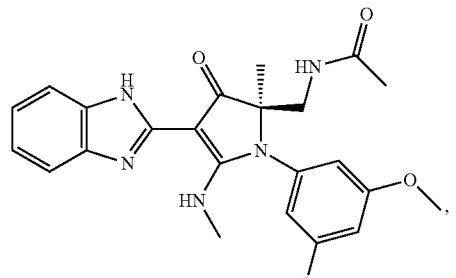
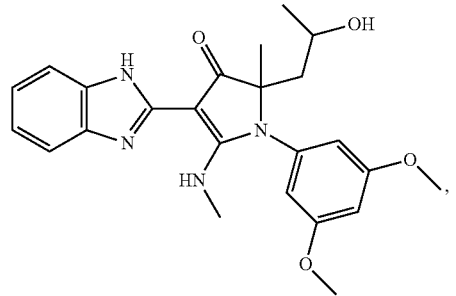
-continued
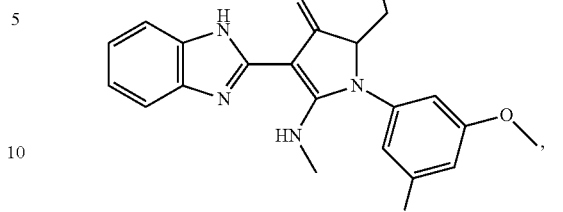
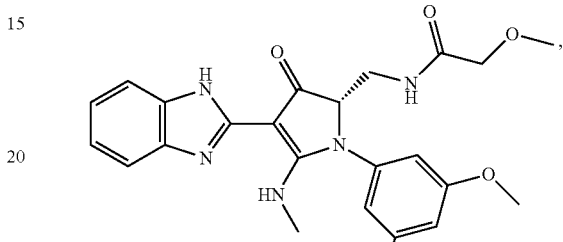
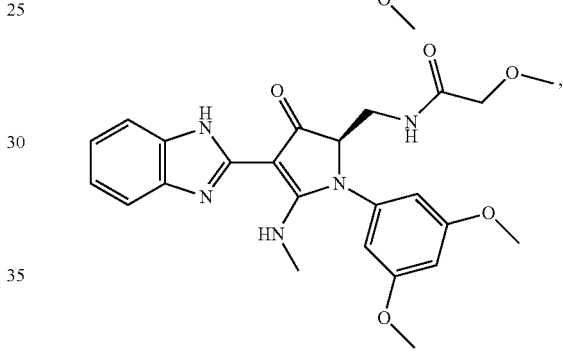
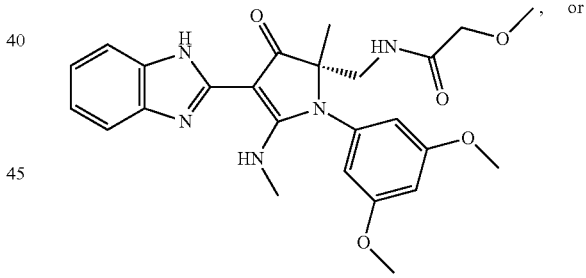, or
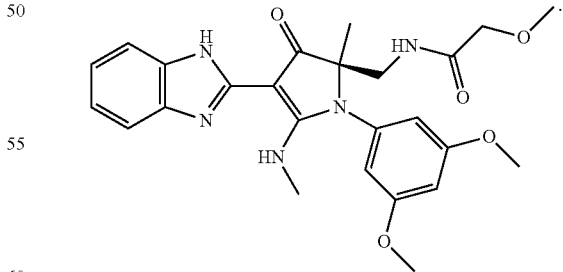
or a pharmaceutically acceptable salt thereof.
5. The compound of claim 1, or a pharmaceutically acceptable salt thereof, wherein one of $R^7$ and $R^8$ is $OR^3$, and the other is H or optionally substituted alkyl.

6. A compound selected from
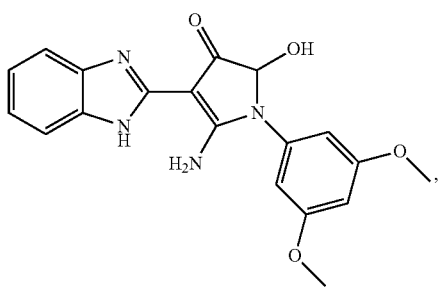
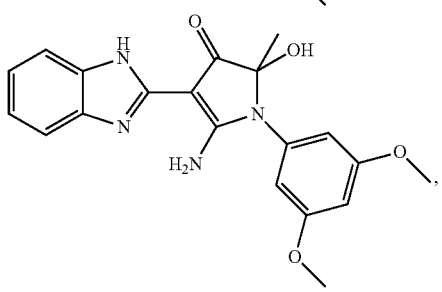
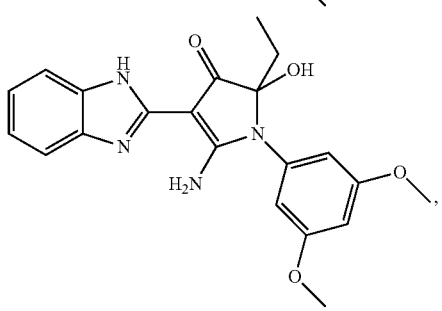
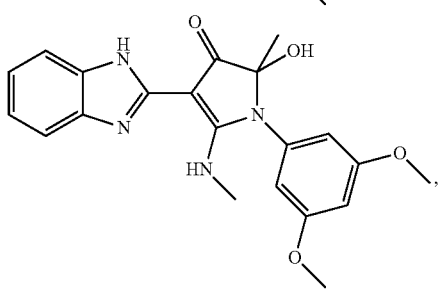
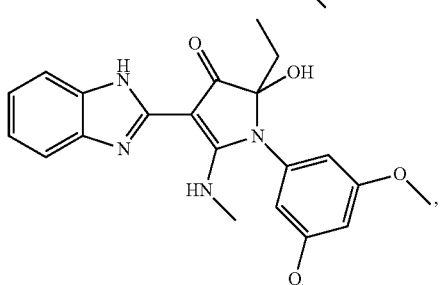
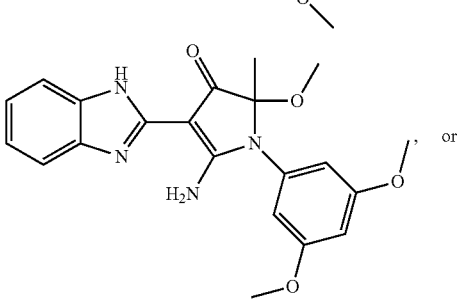
-continued
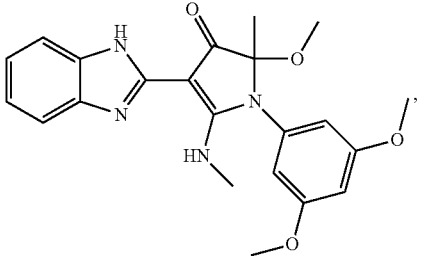
or a pharmaceutically acceptable salt thereof.
7. The compound of claim 1, or a pharmaceutically acceptable salt thereof, wherein one of $R^7$ and $R^8$ is optionally substituted aryl or optionally substituted heteroaryl, and the other is H or optionally substituted alkyl.
8. A compound selected from
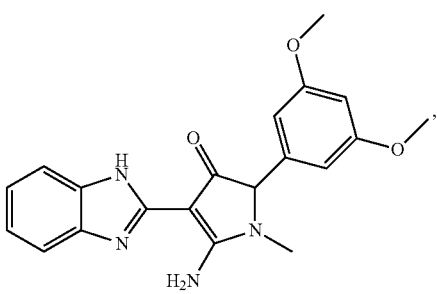
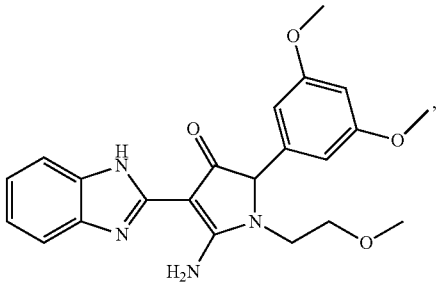
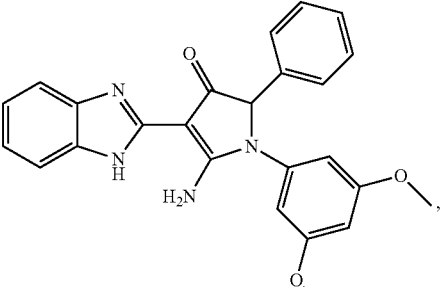
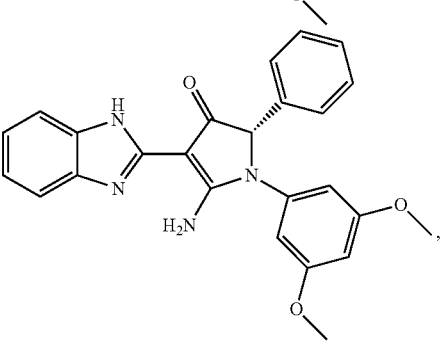

-continued
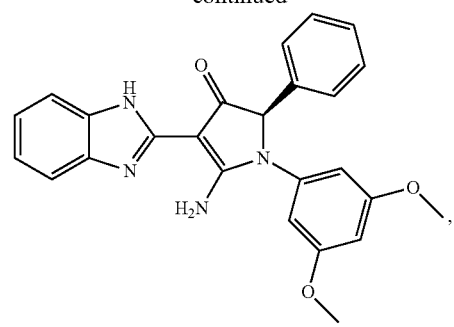
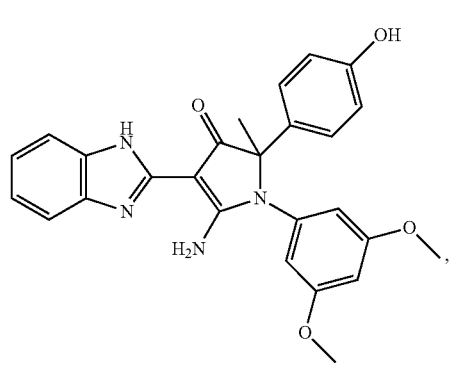
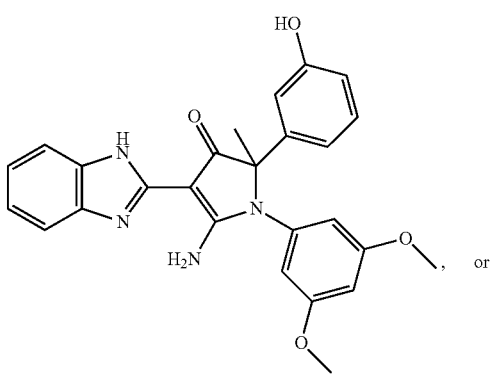
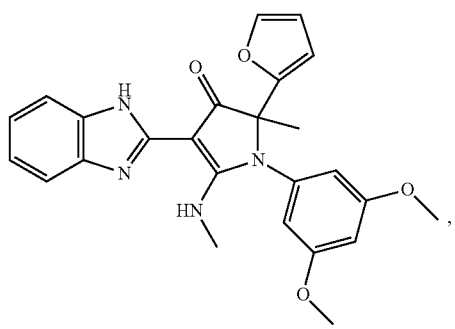
or a pharmaceutically acceptable salt thereof.
9. The compound of claim 1, or a pharmaceutically acceptable salt thereof, wherein one of $R^7$ and $R^8$ is C(O)OR$^3$ or C(O)R$^3$, and the other is H, OR$^3$, or optionally substituted alkyl; wherein R$^3$ can be the same or different.
10. A compound selected from
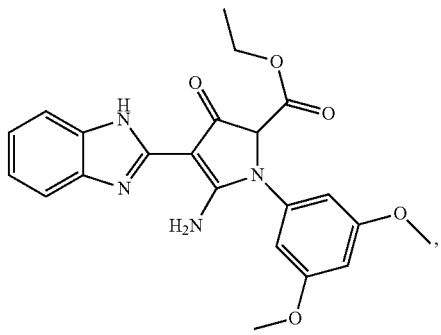
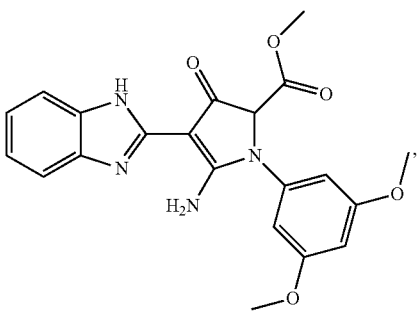
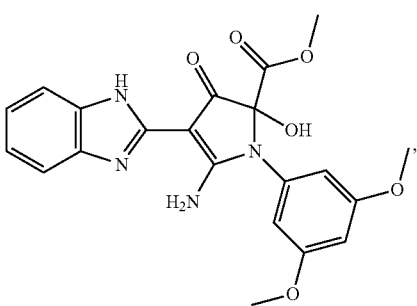
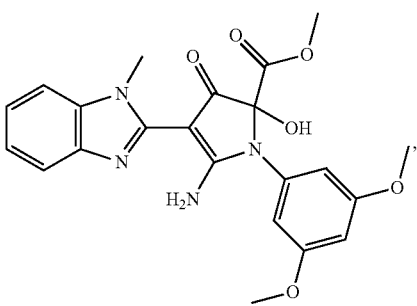
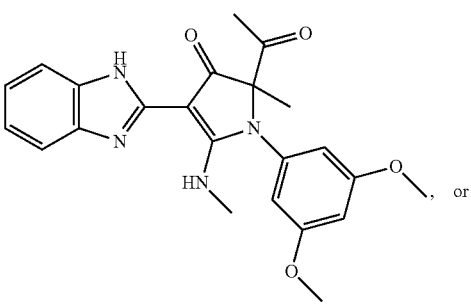
, or

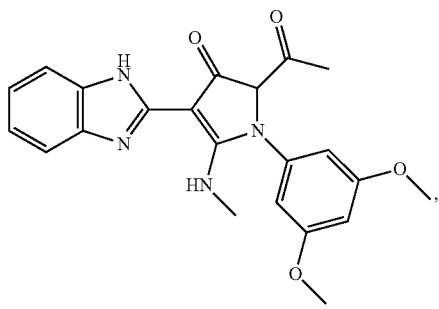 [SMILES: CNC1=C(c2nc3ccccc3[nH]2)C(=O)C(C(C)=O)N1c1cc(OC)cc(OC)c1]
or a pharmaceutically acceptable salt thereof.
11. The compound of claim 1, or a pharmaceutically acceptable salt thereof, wherein $R^7$ and $R^8$ together with the carbon atom to which they are attached form an optionally substituted 3- to 8-membered cycloalkyl or heterocyclyl ring.
12. A compound selected from
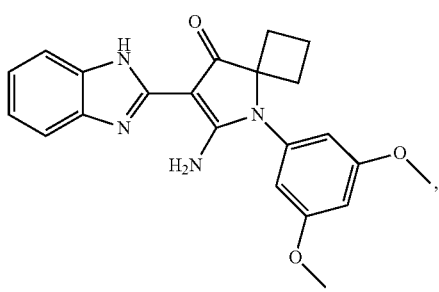
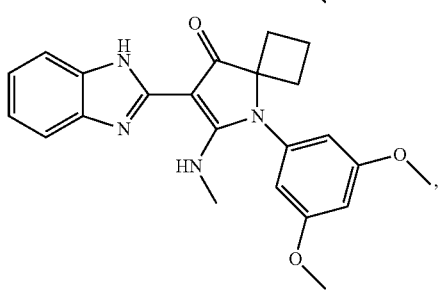
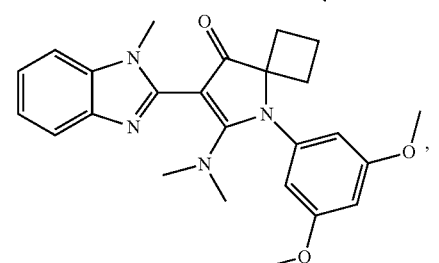
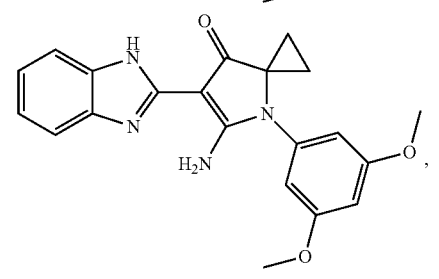
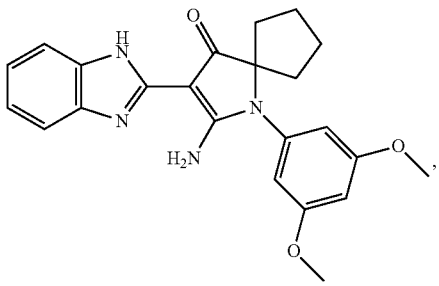
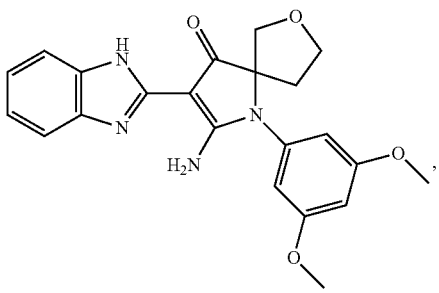
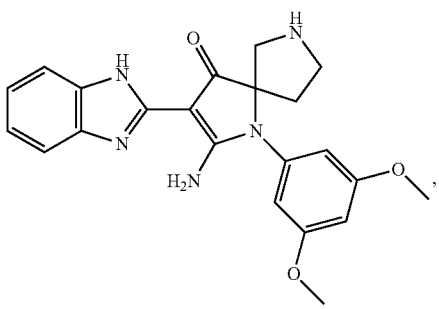
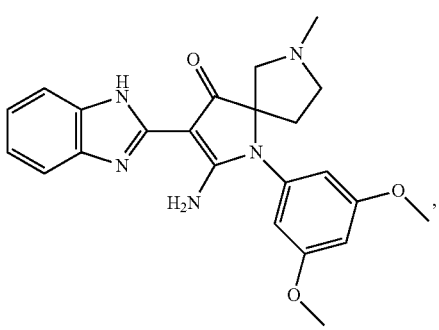
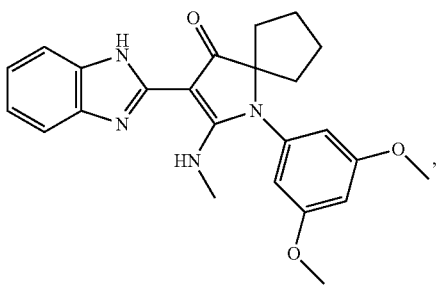

301
-continued
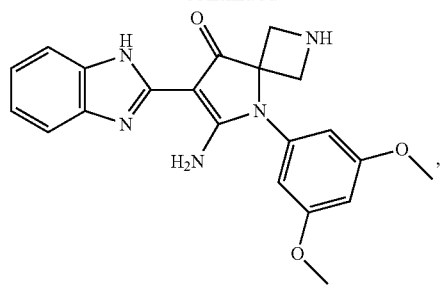
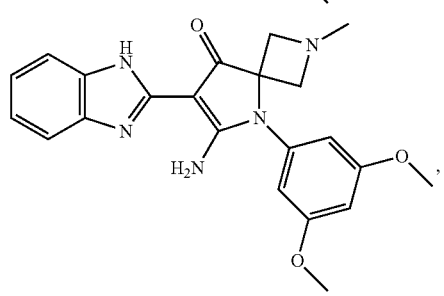
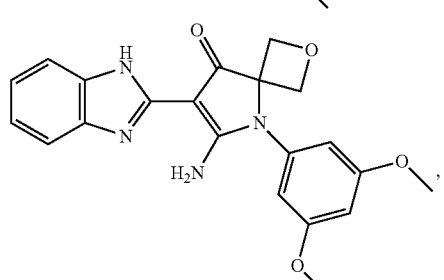
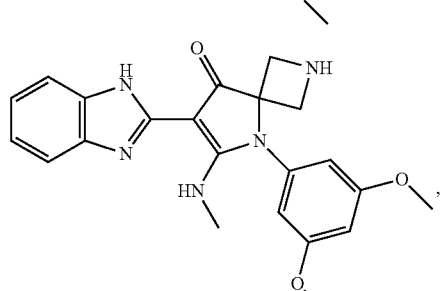
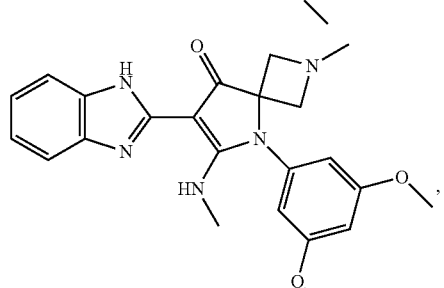
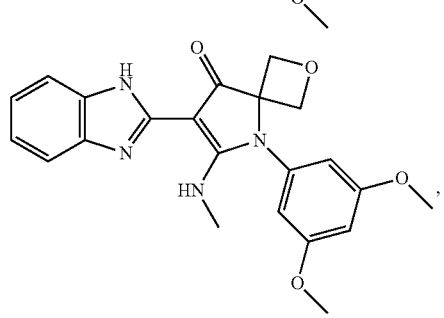
302
-continued
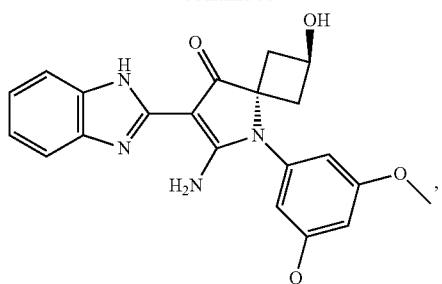
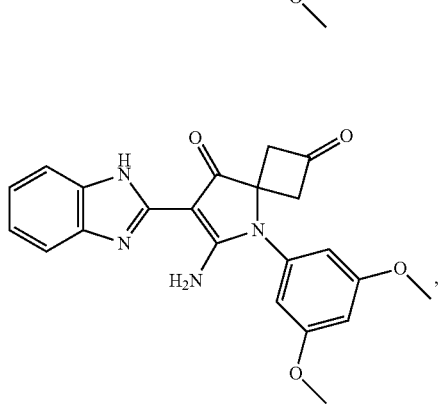
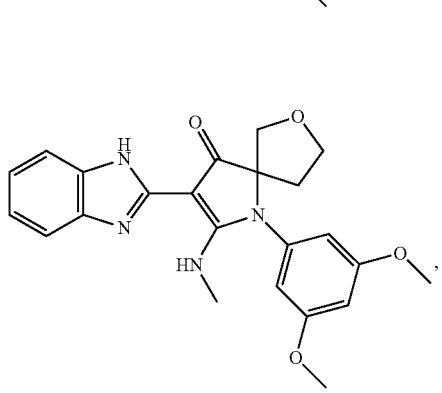
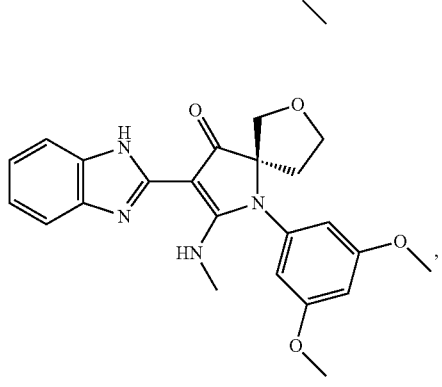
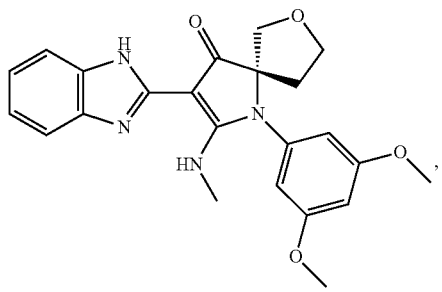

-continued
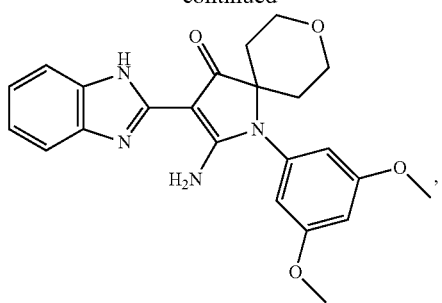
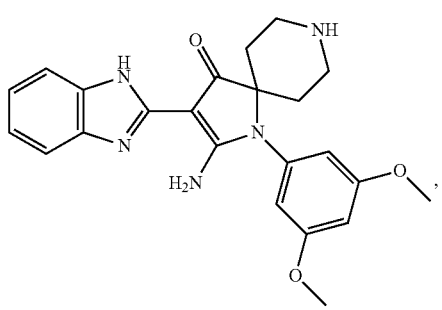
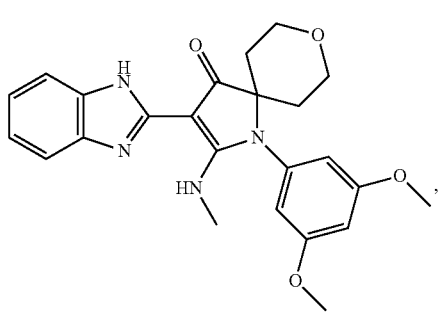
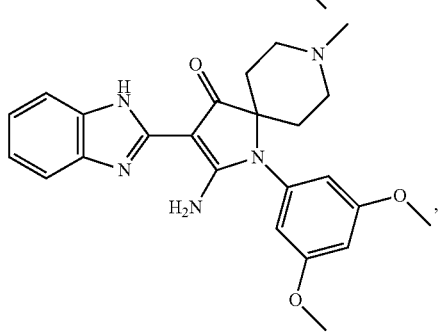
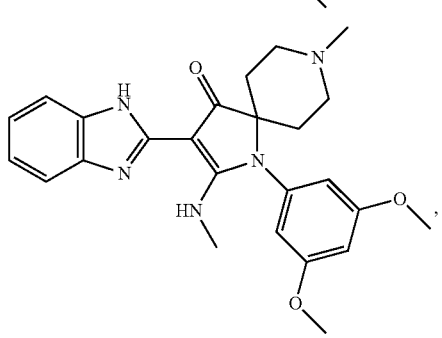
-continued
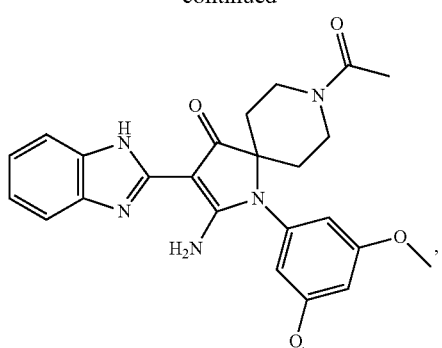
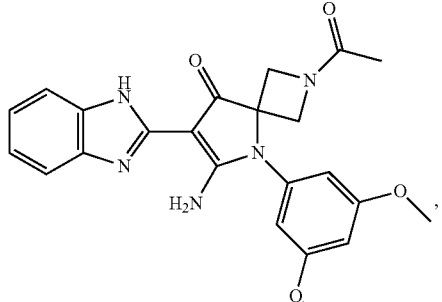
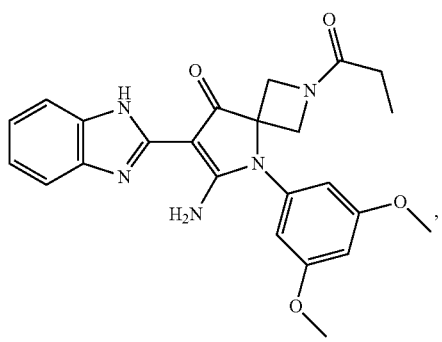
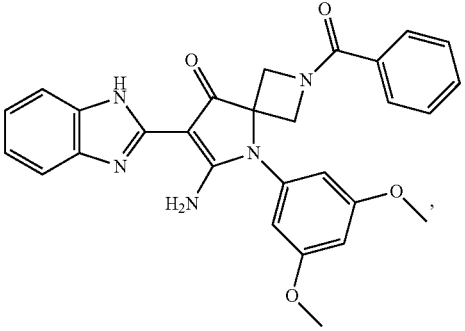
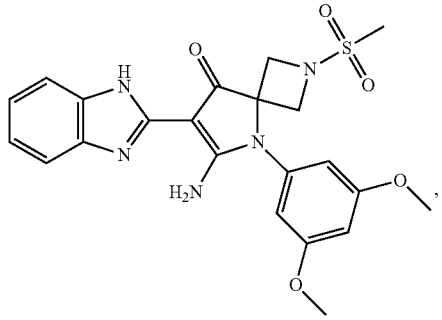

305
-continued
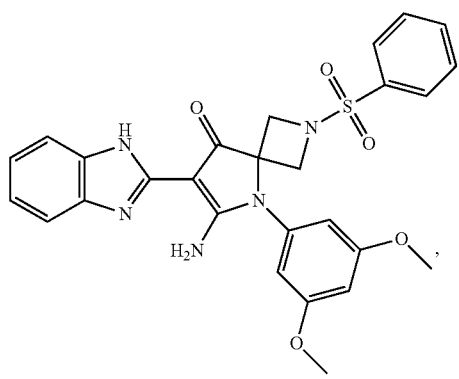
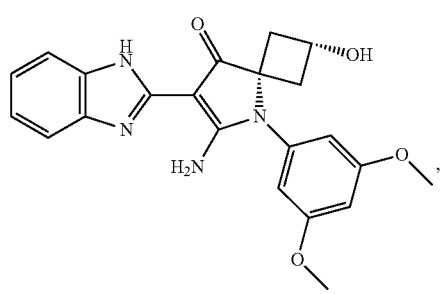
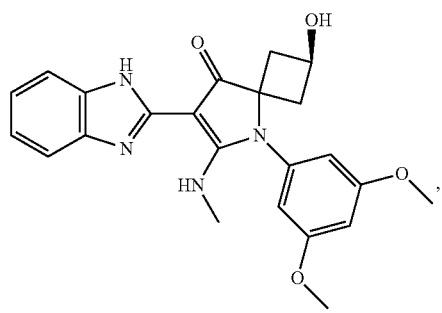
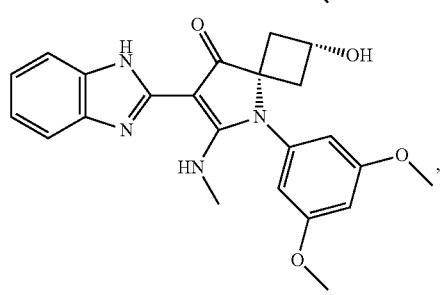
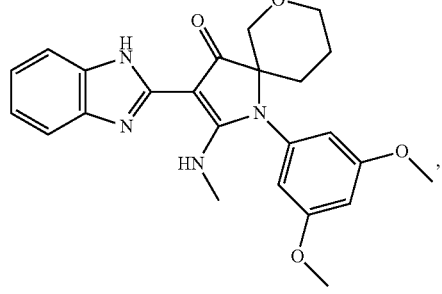
306
-continued
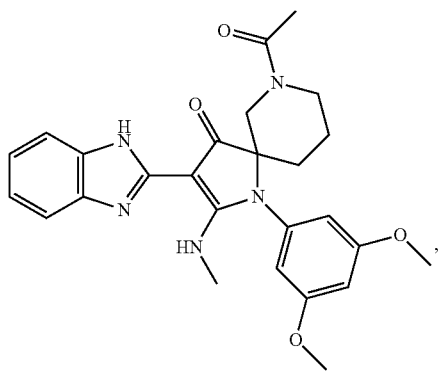
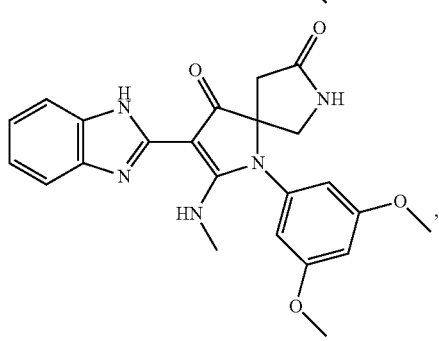
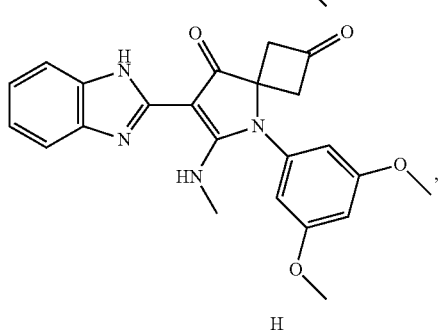
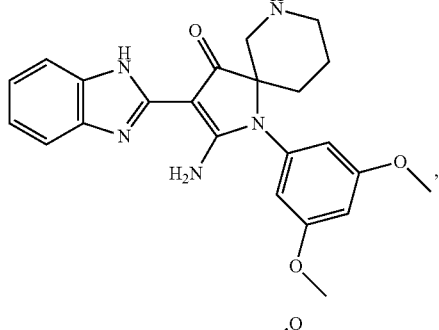
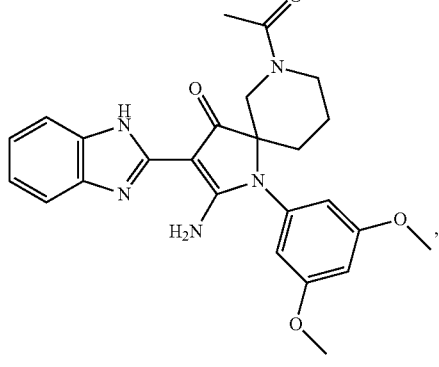

307

-continued

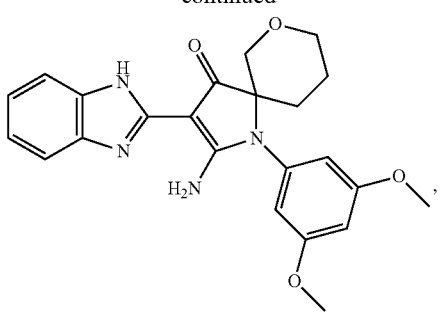

308

-continued

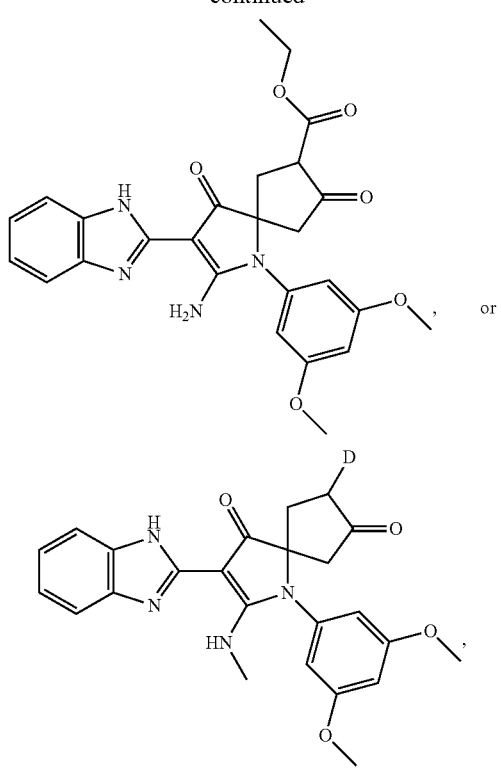

or a pharmaceutically acceptable salt thereof.

13. The compound of claim 1, or a pharmaceutically acceptable salt thereof, wherein $R^1$ is optionally substituted benzimidazolyl.

14. The compound of claim 1, or a pharmaceutically acceptable salt thereof, wherein $R^1$ is benzimidazolyl.

15. The compound of claim 1, or a pharmaceutically acceptable salt thereof, wherein $R^2$ is optionally substituted phenyl.

16. The compound of claim 1, or a pharmaceutically acceptable salt thereof, wherein $R^2$ is 3,5-dimethoxyphenyl.

17. The compound of claim 1, or a pharmaceutically acceptable salt thereof, wherein X is $CH_2$, $CHCH_3$, or $C(CH_3)_2$.

18. A compound selected from

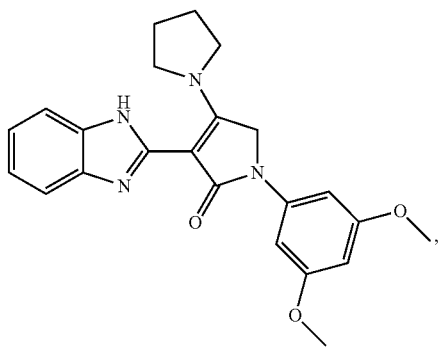

-continued

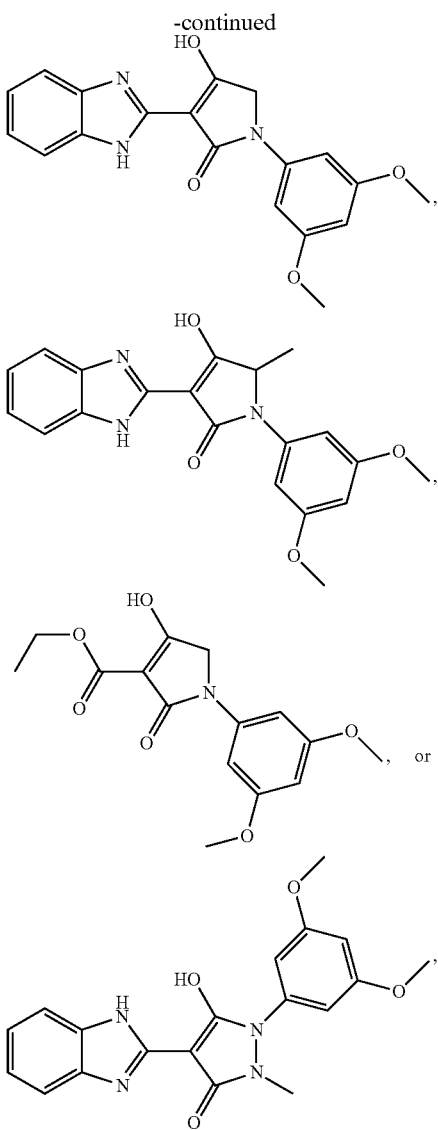

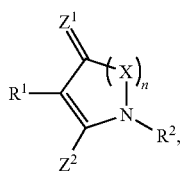

or a pharmaceutically acceptable salt thereof.

19. A pharmaceutical composition comprising a compound of claim 1, or a pharmaceutically acceptable salt thereof.

20. The pharmaceutical composition of claim 19, which further comprises one or more additional active agents.

21. A compound of formula (I):

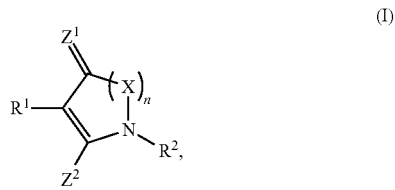

or a pharmaceutically acceptable salt thereof, wherein
$R^1$ is heteroaryl which is optionally substituted;
$R^2$ is aryl which is optionally substituted;
$Z^1$ is =O;
$Z^2$ is —$NR^3R^4$;
X is $CR^7R^8$;
n is 1;
$R^3$ is (i) hydrogen; or (ii) alkyl, alkenyl, heteroalkyl, cycloalkyl, heterocyclyl, aryl, heteroaryl, aralkyl, or heteroaralkyl, each of which is optionally substituted; or (iii) $R^3$ and $R^4$ together with the nitrogen atom to which they are attached form an optionally substituted 3- to 8-membered heterocyclyl or heteroaryl ring; or (iv) $R^4$ is OH and $R^3$ is hydrogen;
$R^4$ is (i) alkyl, alkenyl, heteroalkyl, cycloalkyl, heterocyclyl, aryl, heteroaryl, aralkyl, or heteroaralkyl, each of which is optionally substituted; or (ii) $R^3$ and $R^4$ together with the nitrogen atom to which they are attached form an optionally substituted 3- to 8-membered heterocyclyl or heteroaryl ring; or (iii) $R^4$ is OH and $R^3$ is hydrogen;
$R^7$ and $R^8$ together with the carbon atom to which they are attached form an optionally substituted 3- to 8-membered cycloalkyl or heterocyclyl ring; and
optionally (i) $Z^2$ and $R^1$ together with the atoms to which they are attached form an optionally substituted heterocyclyl, heteroaryl, aryl, or cycloalkyl ring; or (ii) $Z^2$ and $R^2$ together with the atoms to which they are attached form an optionally substituted heterocyclyl or heteroaryl ring.

22. A compound of formula (I):

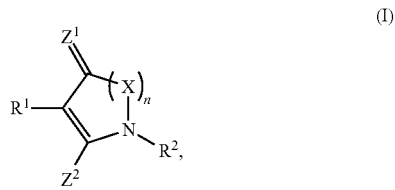

or a pharmaceutically acceptable salt thereof, wherein
$R^1$ is heteroaryl which is optionally substituted;
$R^2$ is 3,5-dimethoxyphenyl;
$Z^1$ is =O;
$Z^2$ is —$NR^3R^4$;
X is $CR^7R^8$;
n is 1;
$R^3$ is (i) hydrogen; or (ii) alkyl, alkenyl, heteroalkyl, cycloalkyl, heterocyclyl, aryl, heteroaryl, aralkyl, or heteroaralkyl, each of which is optionally substituted; or (iii) $R^3$ and $R^4$ together with the nitrogen atom to which they are attached form an optionally substituted 3- to 8-membered heterocyclyl or heteroaryl ring; or (iv) $R^4$ is OH and $R^3$ is hydrogen;
$R^4$ is (i) alkyl, alkenyl, heteroalkyl, cycloalkyl, heterocyclyl, aryl, heteroaryl, aralkyl, or heteroaralkyl, each of which is optionally substituted; or (ii) $R^3$ and $R^4$ together with the nitrogen atom to which they are attached form an optionally substituted 3- to 8-membered heterocyclyl or heteroaryl ring; or (iii) $R^4$ is OH and $R^3$ is hydrogen;
$R^7$ and $R^8$ are independently (i) hydrogen, halo, or cyano; or (ii) alkyl, alkenyl, heteroalkyl, alkoxyl, aminoalkyl, cycloalkyl, heterocyclyl, aryl, heteroaryl, aralkyl, or heteroaralkyl, each of which is optionally substituted; or (iii) $OR^3$, $C(O)OR^3$, —$C(O)NH_2$, —$C(O)NR^3R^4$, or $C(O)R^3$; or (iv) $R^7$ and $R^8$ together with the carbon atom to which they are attached form an optionally substituted 3- to 8-membered heterocyclyl, heteroaryl, aryl, or cycloalkyl ring; and optionally (i) $Z^2$ and $R^1$ together with the atoms to which they are attached form an optionally substituted heterocyclyl, heteroaryl, aryl, or cycloalkyl ring; or (ii) $R^7$ or $R^8$ together with the atoms to which they are attached form an optionally substituted heterocyclyl or heteroaryl ring.

* * * * *

UNITED STATES PATENT AND TRADEMARK OFFICE
CERTIFICATE OF CORRECTION

PATENT NO. : 9,580,409 B2  
APPLICATION NO. : 14/352294  
DATED : February 28, 2017  
INVENTOR(S) : Malcolm et al.

Page 1 of 2

It is certified that error appears in the above-identified patent and that said Letters Patent is hereby corrected as shown below:

Column 258, Line 35: Claim 2, Delete " 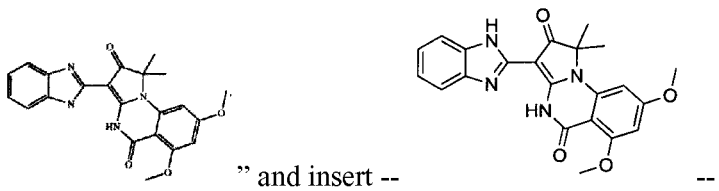 " and insert -- --

Column 259, Line 50 and 60: Claim 4, Delete " 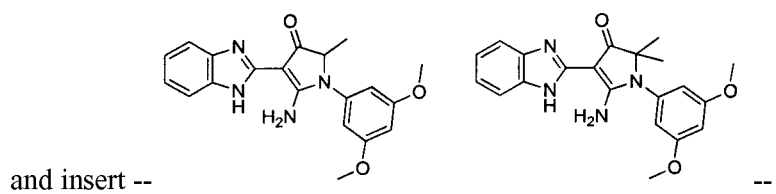 "

and insert -- 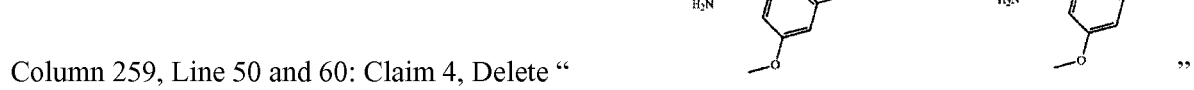 --

Column 270, Line 15: Claim 4, Delete "  " and insert -- --

Signed and Sealed this  
First Day of August, 2017

Joseph Matal  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 9,580,409 B2

Column 274, Line 5: Claim 4, Delete "  " and insert -- --

Column 309, Line 35: Claim 18, Delete " 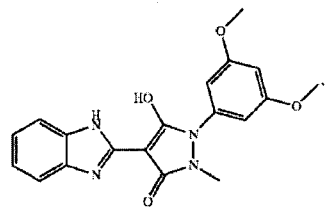 "

Column 311, Line 3: Claim 22, Delete "or (ii) $R^7$ or $R^8$" and insert -- or (ii) $R^2$ and $R^7$ or $R^8$ --